US009096615B2

(12) United States Patent
Lewis et al.

(10) Patent No.: US 9,096,615 B2
(45) Date of Patent: Aug. 4, 2015

(54) BRIDGED BICYCLIC AMINO THIAZINE DIOXIDE COMPOUNDS AS INHIBITORS OF BETA-SECRETASE AND METHODS OF USE THEREOF

(71) Applicant: AMGEN INC., Thousand Oaks, CA (US)

(72) Inventors: Richard T. Lewis, Framingham, MA (US); Jennifer R. Allen, Newbury Park, CA (US); James Brown, Moorpark, CA (US); Angel Guzman-Perez, Belmont, MA (US); Zihao Hua, Andover, MA (US); Ted Judd, Granada Hills, CA (US); Qingyian Liu, Camarillo, CA (US); Philip R. Olivieri, Charlestown, MA (US); Karina Romero, Arlington, MA (US); Laurie Schenkel, Boston, MA (US); John Stellwagen, Beverly, MA (US); Ryan White, Somerville, MA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 14/445,498

(22) Filed: Jul. 29, 2014

(65) Prior Publication Data
US 2015/0038497 A1    Feb. 5, 2015

Related U.S. Application Data

(60) Provisional application No. 61/859,923, filed on Jul. 30, 2013.

(51) Int. Cl.
*C07D 513/06* (2006.01)
*C07D 513/08* (2006.01)
*C07D 519/00* (2006.01)

(52) U.S. Cl.
CPC ............ *C07D 513/06* (2013.01); *C07D 513/08* (2013.01); *C07D 519/00* (2013.01)

(58) Field of Classification Search
CPC ..................... C07D 513/06; C07D 513/08
USPC ........................................ 514/224.2; 544/47
See application file for complete search history.

(56) References Cited

U.S. PATENT DOCUMENTS

| 5,441,870 | A | * | 8/1995 | Seubert et al. ................. 435/7.1 |
| 5,712,130 | A | * | 1/1998 | Hajko et al. .................... 435/123 |
| 5,942,400 | A | * | 8/1999 | Anderson et al. .............. 435/7.1 |
| 7,648,983 | B2 | | 1/2010 | Audia et al. |
| 8,158,620 | B2 | | 4/2012 | Suzuki et al. |
| 2010/0075957 | A1 | | 3/2010 | Tamura et al. |
| 2012/0022249 | A1 | | 1/2012 | Kobayashi et al. |
| 2012/0225858 | A1 | | 9/2012 | Hilpert et al. |
| 2012/0238557 | A1 | | 9/2012 | Masui et al. |
| 2012/0245157 | A1 | | 9/2012 | Masui et al. |

FOREIGN PATENT DOCUMENTS

| WO | 2006/081178 | A2 | 8/2006 |
| WO | 2011/005738 | A1 | 1/2011 |
| WO | 2012/138734 | A1 | 10/2012 |
| WO | 2012/139425 | A1 | 10/2012 |
| WO | 2012/162330 | A1 | 11/2012 |

(Continued)

OTHER PUBLICATIONS

International Search Report for analogous PCT Application No. /US2014/048610, mailed on Oct. 6, 2014.

(Continued)

*Primary Examiner* — Kahsay Habte
(74) *Attorney, Agent, or Firm* — Bernard P. Friedrichsen; G. Prabhakar Reddy

(57) ABSTRACT

The present invention provides a new class of compounds useful for the modulation of beta-secretase enzyme (BACE) activity. The compounds have a general Formula I:

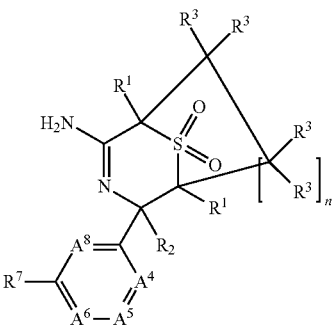

wherein variables $A^4$, $A^5$, $A^6$, $A^8$, $R^1$, $R^2$, $R^3$, $R^7$ and n of Formula I, independently, are defined herein. The invention also provides pharmaceutical compositions comprising the compounds, and corresponding uses of the compounds and compositions for treatment of disorders and/or conditions related to A-beta plaque formation and deposition, resulting from the biological activity of BACE. Such BACE mediated disorders include, for example, Alzheimer's Disease, cognitive deficits, cognitive impairments, schizophrenia and other central nervous system conditions. The invention further provides compounds of Formula II and sub-formula embodiments thereof, compounds of Formula III, intermediates and processes and methods useful for the preparation of compounds of Formulas I-III, and sub-Formulas thereof.

32 Claims, No Drawings

(56) References Cited

FOREIGN PATENT DOCUMENTS

| | | |
|---|---|---|
| WO | 2012/162334 A1 | 11/2012 |
| WO | 2013/004676 A1 | 1/2013 |
| WO | 2013/028670 A1 | 2/2013 |
| WO | 2013/030713 A1 | 3/2013 |
| WO | 2013/148851 A1 | 10/2013 |
| WO | 2013/164730 A1 | 11/2013 |
| WO | 2013/174781 A1 | 11/2013 |
| WO | 2013/182638 A1 | 12/2013 |
| WO | 2014/099768 A1 | 6/2014 |
| WO | 2014/099788 A1 | 6/2014 |
| WO | 2014/099794 A1 | 6/2014 |
| WO | 2014/150331 A1 | 9/2014 |
| WO | 2014/150340 A1 | 9/2014 |

OTHER PUBLICATIONS

Written Opinion for analogous PCT Application No. /US2014/048610, with International Search Report mailed on Oct. 6, 2014.
Yan, R et al., "Targeting the β secretase BACE1 for Alzheimer's Disease Therapy," Lancet Neurol (2014) 13: pp. 319-329.
Joachim et al., "The Seminal Role of β-Amyloid in the Pathogenesis of Alzheimer's Disease," Alz. Dis. Assoc. Dis., (1992) 6:1 pp. 7-34.
Selkoe, D. J. "The Molecular Pathology of Alzheimer's Disease" Neuron (1991), 6 pp. 487-498.
Seubert, P. et al., "Isolation and Quantification of Soluble Alzheimer's β-Peptide from Biological Fluids," Nature (1992) 359 pp. 325-327.
Citron, M. "β-Secretase Inhibition for the Treatment of Alzheimer's Disease-Promise and Challenge," Trends in Pharmacological Sciences (2004) 25(2) pp. 92-97.
Town, T. et al., "Blocking TGF- β-Smad2/3 Innate Immune Signalisng Mitigates Alzheimer-Like Pathology," Nature Medicine (2008) 14(6) pp. 681-687.
Sinha, S. et al., "Purification and Cloning of Amyloid Precursor Protein β-Secretase from Human Brain," Nature (1999) 402 pp. 537-540.
Sabbagh, M. N. et al., "β-Amyloid and Treatment Opportunities for Alzheimer's Disease," Alz. Dis. Rev. (1997) 3 pp. 1-19.
Cole, S.L. et al., "The Alzheimer's Disease β-Secretase Enzyme, BACE1," Molecular Neurodegeneration (2007) 2(22) pp. 1-25.
Luo, Y. et al., "Mice Deficient in BACE1, the Alzheimer's β-Secretase , have Normal Phenotype and Abolished β-Amyloid Generation," Nature Neuroscience, (2001) 4(3) pp. 231-232.
Malamas, M. S. et al., "Novel Pyrrolyl 2-Aminopyridines as Potent and Selective Human β-Secretase (BACE1) Inhibitors," Bioorganic & Medicinal Chemistry Letters (2010) vol. 20, pp. 2068-2073.
Malamas, M. S. et al., "Aminoimidazoles as Potent and Selective Human β-Secrete (BACE1) Inhibitors," J. Med. Chem. (2009).
Aisen, P. "Alzheimer's Disease Therapeutic Research: The Path Forward," Alzheimer's Research & Therapy (2009) vol. 1(1), pp. 1-6.
Lukiw, W. J. "Emerging Amyloid Beta (A β) Peptide Modulators for the Treatment of Alzheimer's Disease (AD)," Expert Opin. Emerging Drugs (2008) vol. 13(2), pp. 255-271.
Barrow, J. C. et al., "Discovery and X-ray Crystallographic Analysis of a Spiropiperidine Iminohydantoin Inhibitor of #-Secretase," J. Med. Chem. (2008) vol. 51(20), pp. 6259-6262.
Rauk, A. "The Chemistry of Alzheimer's Disease," Chem. Soc. Rev. (2009) vol. 38, pp. 2698-2715.
Sabbagh, M. N. "Drug Development for Alzheimer's Disease: Where Are We Now and Where Are We Headed?" Clinical Dev. (2009) vol. 7(3), pp. 167-185.
Vassar, R. et al., "The β-Secretase Enzyme in Health and Alzheimer's Disease: Regulation, Cell Biology, Function, and Therapeutic Potential," J. Neurosci. (2009) vol. 29(41), pp. 12787-12794.
Zhou, et. Al., "An efficient Synthesis of 2-Amino-4-(4-fluoro-3-(2-fluoropyridin-3yl)phenyl-4-(4-methoxy-3-methylphenyl)-1-methyl-1H-imidazol-5(4H)-one, a Potent BACE1 Inhibitor," ARKIVOC (2010) vol. vi, pp. 84-88.
Nowak, P. et al., "Discovery and Initial Optimization of 5,5'-Disubstituted Aminohydantoins as Potent β-Secretase (BACE1) Inhibitors," Bioorganic Medicinal Chemistry Letters (2009).
Malamas, M. S. et al., "Di-substituted Pyridinyl AMinohydrantoins as Potent and Highly Selective Human β-Secretase (BACE1) Inhibitors," Bioorganic Medicinal Chemistry Letters (2009).
Zhou, P. et al., "Pyridinyl Aminohydantoins as Small Molecule BACE1 Inhibitors," Bioorganic Medicinal Chemistry Letters (2010) vol. 20, pp. 2326-2329.
Malamas, M. S. et al., "Design and Synthesis of 5,5'-Disubstituted Aminohydantoins as Potent and Selective Human β-Secretase (VACE1) Inhibitors," J. Med. Chem (2009).
Saxena, U. "Alzheimer's Disease Amyloid Hypothesis at Crossroads: Where Do We Go from Here," Expert Opin. Ther. Targets (2010) vol. 14(12), pp. 1273-1277.
West, A. R. "Solid State Chemistry and Its Applications," Wiley, New York, (1988) pp. 358-365.
Jia, Q. et al., "Potential Therapeutic Strategies for Alzheimer's Disease Targeting or Beyond β-Amyloid: Insights from Clinical Trials," BioMcd Res. Intl. (2014) ID 837157, pp. 1-22.

* cited by examiner

BRIDGED BICYCLIC AMINO THIAZINE DIOXIDE COMPOUNDS AS INHIBITORS OF BETA-SECRETASE AND METHODS OF USE THEREOF

RELATED APPLICATIONS

This application claims the benefit of U.S. Provisional Patent Application Nos. 61/859,923, filed on Jul. 30, 2013, which specification is hereby incorporated herein by reference in its entirety.

FIELD OF THE INVENTION

The invention relates generally to pharmaceutically active compounds, pharmaceutical compositions and methods of use thereof, to treat beta-secretase mediated diseases and conditions, including, without limitation, Alzheimer's disease, plaque formation and associated central nervous system (CNS) disorders.

BACKGROUND OF THE INVENTION

Alzheimer's disease (AD) affects greater than 12 million people worldwide, and importantly, the number affected continues to grow. AD accounts for the majority of dementias clinically diagnosed after the age of 60. AD is generally characterized by the progressive decline of memory, reasoning, judgement and orientation. As the disease progresses, motor, sensory, and vocal abilities are affected until there is global impairment of multiple cognitive functions. The loss of cognitive function occurs gradually, typically leading to a diminished cognition of self, family and friends. Patients with severe cognitive impairment and/or diagnosed as end-stage AD are generally bedridden, incontinent, and dependent on custodial care. The AD patient eventually dies in about nine to ten years, on average, after initial diagnosis. Due to the incapacitating, generally humiliating and ultimately fatal effects of AD, there is a need to treat AD effectively upon diagnosis.

AD is characterized by two major physiological changes in the brain. The first change, beta amyloid plaque formation, supports the "amyloid cascade hypothesis" which conveys the thought that AD is caused by the formation of characteristic beta amyloid peptide (A-beta), or A-beta fragments thereof, deposits in the brain (commonly referred to as beta amyloid "plaques" or "plaque deposits") and in cerebral blood vessels (beta amyloid angiopathy). A wealth of evidence suggests that beta-amyloid and accompanying amyloid plaque formation is central to the pathophysiology of AD and is likely to play an early role in this intractable neurodegenerative disorder. The second change in AD is the formation of intraneuronal tangles, consisting of an aggregate form of the protein tau. Besides being found in patients with AD, intraneuronal tangles are also found in other dementia-inducing disorders. Joachim et al., *Alz. Dis. Assoc. Dis.*, 6:7-34 (1992).

Several lines of evidence indicate that progressive cerebral deposition of A-beta plays a seminal role in the pathogenesis of AD and can precede cognitive symptoms by years or even decades. Selkoe, *Neuron*, 6:487 (1991). Release of A-beta from neuronal cells grown in culture and the presence of A-beta in cerebrospinal fluid (CSF) of both normal individuals and AD patients has been demonstrated. Seubert et al., *Nature*, 359:325-327 (1992). Autopsies of AD patients have revealed large numbers of lesions comprising these 2 factors in areas of the human brain believed to be important for memory and cognition.

Smaller numbers of these lesions in a more restricted anatomical distribution are found in the brains of most aged humans who do not have clinical AD. Amyloid containing plaques and vascular amyloid angiopathy were also found in the brains of individuals with Down's Syndrome, Hereditary Cerebral Hemorrhage with Amyloidosis of the Dutch-type (HCHWA-D), and other neurodegenerative disorders.

It has been hypothesized that A-beta formation is a causative precursor or factor in the development of AD. More specifically, deposition of A-beta in areas of the brain responsible for cognitive factors is believed to be a major factor in the development of AD. Beta amyloid plaques are primarily composed of amyloid beta peptide (A-beta peptide). A-beta peptide is derived from the proteolytic cleavage of a large transmembrane amyloid precursor protein (APP), and is a peptide comprised of about 39-42 amino acid residues. A-beta 42 (42 amino acids long) is thought to be the major component of these plaque deposits in the brains of Alzheimer's Disease patients. Citron, *Trends in Pharmacological Sciences*, 25(2):92-97 (2004).

Similar plaques appear in some variants of Lewy body dementia and in inclusion body myositis, a muscle disease. Aβ also forms aggregates coating cerebral blood vessels in cerebral amyloid angiopathy. These plaques are composed of a tangle of regularly ordered fibrillar aggregates called amyloid fibers, a protein fold shared by other peptides such as prions associated with protein misfolding diseases. Research on laboratory rats suggest that the dimeric, soluble form of the peptide is a causative agent in the development of Alzheimer's and is the smallest synaptotoxic species of soluble amyloid beta oligomer. Shankar, G. M., *Nature Medicine* (Jun. 22, 2008) online doi 10:1038 nm 1782.

Several aspartyl proteases, including beta-secretase and gamma-secretase, are thought to be involved in the processing or cleavage of APP, resulting in the formation of A-beta peptide. Beta secretase (BACE, also commonly referred to as memapsin) is thought to first cleave APP to generate two fragments: (1) a first N-terminus fragment (beta APP) and (2) a second C-99 fragment, which is subsequently cleaved by gamma secretase to generate the A-beta peptide. APP has also found to be cleaved by alpha-secretase to produce alpha-sAPP, a secreted form of APP that does not result in beta-amyloid plaque formation. This alternate pathway precludes the formation of A-beta peptide. A description of the proteolytic processing fragments of APP is found, for example, in U.S. Pat. Nos. 5,441,870, 5,712,130 and 5,942,400.

BACE is an aspartyl protease enzyme comprising 501 amino acids and responsible for processing APP at the beta-secretase specific cleavage site. BACE is present in two forms, BACE 1 and BACE 2, designated as such depending upon the specific cleavage site of APP. Beta secretase is described in Sinha et al., *Nature*, 402:537-554 (1999) (p 510) and PCT application WO 2000/17369. It has been proposed that A-beta peptide accumulates as a result of APP processing by BACE. Moreover, in vivo processing of APP at the beta secretase cleavage site is thought to be a rate-limiting step in A-beta production. Sabbagh, M. et al., *Alz. Dis. Rev.* 3:1-19 (1997). Thus, inhibition of the BACE enzyme activity is desirable for the treatment of AD.

Studies have shown that the inhibition of BACE may be linked to the treatment of AD. The BACE enzyme is essential for the generation of beta-amyloid or A-beta.

BACE knockout mice do not produce beta-amyloid and are free from Alzheimer's associated pathologies including neuronal loss and certain memory deficits. Cole, S. L., Vasser, R., *Molecular Degeneration* 2:22, 2007. When crossed with transgenic mice that over express APP, the progeny of BACE deficient mice show reduced amounts of A-beta in brain extracts as compared with control animals (Luo et al., *Nature Neuroscience*, 4:231-232 (2001)). The fact that BACE initiates the formation of beta-amyloid, and the observation that BACE levels are elevated in this disease provide direct and compelling reasons to develop therapies directed at BACE inhibition thus reducing beta-amyloid and its associated toxicities. To this end, inhibition of beta secretase activity and a corresponding reduction of A-beta in the brain should provide a therapeutic method for treating AD and other beta amyloid or plaque related disorders.

Consequently, the approach of regulating or reducing the formation of A-beta peptide formation and deposition as a potential treatment for AD has received tremendous attention, support and commitment from both researchers and investors alike. A small molecule gamma-secretase inhibitor, LY450139 ("Semagacestat"), an A-beta lowering agent, is in phase II clinical trials for the treatment of Alzheimer's Disease. The pharmacokinetics of semagacestat in plasma, as well as the plasma and cerebral spinal fluid (CSF) A-Beta peptide levels as pharmacodynamic responses to semagacestat administration were evaluated in healthy human subjects in single and multiple doses, and pharmacokinetic and pharmacodynamic changes were also assessed in mild to moderate AD patients in two (2) clinical trials (*Expert Opin. Pharmacother.* (2009), 10 (10); *Clin. Neuropharmacol.* 2007; 30 (pgs 317-325); and *Neurology*, 2006, 66 (pgs 602-624)).

Additional approaches have been taken in attempts to treat AD and plaque-related disorders. One such approach to reduce the formation of plaque deposits in the brain involves the inhibition of and, therefore, the reduction of BACE activity. For example, each of the following PCT publications: WO2012139425 and WO2012162330 describe inhibitors of BACE, useful for treating AD and other beta-secretase mediated disorders. WO20121623303 describes tricyclic thiazine compounds as inhibitors of beta amyloid, formation having the general formula:

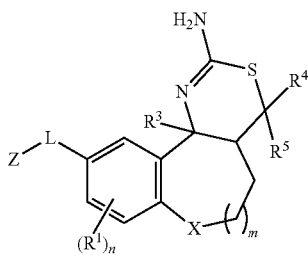

wherein X is selected from the group consisting of $CH_2$, O and $NR^2$.

The lysosomal aspartic protease Cathepsin D (CatD) is ubiquitously expressed in eukaryotic organisms. CatD activity is essential to accomplish the acid-dependent extensive or partial proteolysis of protein substrates within endosomal and lysosomal compartments therein delivered via endocytosis, phagocytosis or autophagocytosis. CatD may also act at physiological pH on small-size substrates in the cytosol and in the extracellular milieu. Mouse and fruit fly CatD knock-out models have highlighted the many or multiple pathophysiological roles of CatD in tissue homeostasis and organ development.

Inhibition of Cathepsin D has been implicated in the manifestation of undesirable side effects. For instance, the inhibition of Cathepsin D is believed to be linked to adverse retinal development and retinal atrophy. Particularly, in mice it was found that cathepsin D is essential for the metabolic maintenance of retinal photoreceptor cells and that its deficiency induces apoptosis of the cells, while the loss of INL neurons is mediated by nitrc oxide release from microglial cells. However, in the very same mice, it was also found that no atrophic change was detected in the retina of mice deficient in cathepsin B or L. *Mol. Cell. Neurosci*, 2003, February 22(2):146-161. Further, animal models of Cathepsin D (CatD) deficiency are characterized by a progressive and relentless neurodegenerative phenotype similar to that observed in Neuronal Ceroid Lipofuscinoses (NCL), a group of pediatric neurodegenerative diseases known collectively as Batten Disease. It has been shown that the targeted deletion of the pro-apoptotic molecule Bax prevents apoptotic markers but not neuronal cell death and neurodegeneration induced by CatD deficiency, which suggests that alterations in the macroautophagy-lysosomal degradation pathway can mediate neuronal cell death in NCL/Batten Disease in the absence of apoptosis. *Autophagy*, 2007, September-October; 3(5):474-476. Finally, an adverse effect of the inhibition of Cat D is evident from the data presented in *PLoS One*, 2011; 6(7): e21908, published Jul. 1, 2011. The authors of the PLoS One paper found that knock-down of cathepsin D affects the retinal pigment epithelium, impairs swim-bladder ontogenesis and causes premature death in zebrafish. The main phenotypic alterations produced by CatD knock-down in zebrafish were: 1. abnormal development of the eye and of retinal pigment epithelium; 2. absence of the swim-bladder; 3. skin hyper-pigmentation; 4. reduced growth and premature death. Rescue experiments confirmed the involvement of CatD in the developmental processes leading to these phenotypic alterations.

Moreover, such toxicity findings which, in view of the literature, may have played a role in the termination of a human Bace-mediated Alzheimer's Disease clinical trial. Eli Lilly terminated a phase I clinical trial of LY 2811376 after rat toxicology studies showed that a higher compound dose given for three months damaged the pigment epithelium of the rat's eye. The retinal layer had inclusions and extensive damage. The Ph I dosing trial was terminated and people brought in for eye assessments did not show any abnormalities. (Alzheimer's Research Forum News, Mar. 31, 2011 reporting on Martin Citron's presentation at the AD/PD Conference March 2011 in Barcelona, Spain)

Hence, it is desirable to provide compounds which modulate the activity of and are reasonably selective for BACE, while not suffering from undesirable side effects possibly due to intervention with or the reduction and/or direct or indirect inhibition of the expression and/or function of other proteins or biological pathways.

BRIEF DESCRIPTION OF THE INVENTION

The present invention provides a new class of compounds useful for the modulation of beta secretase activity, and as treatment of AD. Particularly, the compounds of the invention are useful for the regulation or reduction of the formation of A-beta peptide and, consequently, the regulation and/or reduction of formation of beta amyloid plaque both on the brain, as well as in the CNS. To this end, the compounds are useful for the treatment of AD and other beta secretase and/or plaque-related and/or mediated disorders. For example, the compounds are useful for the prophylaxis and/or treatment, acute and/or chronic, of AD and other diseases or conditions involving the deposition or accumulation of beta amyloid peptide, and formation of plaque, on the brain.

The compounds provided by the invention, including stereoisomers, tautomers, hydrates, solvates and pharmaceutically acceptable salts thereof, are generally defined by Formula I

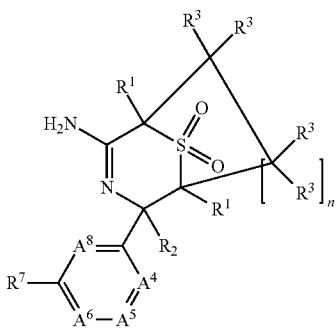

wherein each of $A^4$, $A^5$, $A^6$, $A^8$, $R^1$, $R^2$, $R^3$, $R^7$ and n of Formula I are defined below. The invention also provides procedures for making compounds of Formula I, and sub-Formulas thereof, as well as intermediates useful in such procedures.

The invention further provides pharmaceutical compositions comprising compounds of the invention, and uses of these compositions in the treatment of beta secretase mediated diseases. For example, and in one embodiment, the invention provides a pharmaceutical composition comprising an effective dosage amount of a compound of Formula I in association with at least one pharmaceutically acceptable excipient.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In embodiment A of the invention, there are provided compounds, including stereoisomers, tautomers, hydrates, solvates and pharmaceutically acceptable salts thereof, which are generally defined by Formula I:

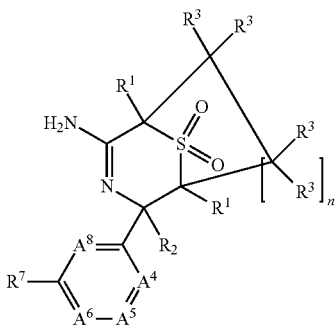

or a stereoisomer, tautomer, hydrate, solvate or pharmaceutically acceptable salt thereof, wherein
$A^4$ is $CR^4$ or N;
$A^5$ is $CR^5$ or N;
$A^6$ is $CR^6$ or N;
$A^8$ is $CR^8$ or N, provided that no more than one of $A^4$, $A^5$, $A^6$ and $A^8$ is N;
each $R^1$, independently, is H, F, Cl, $C_{1-4}$alkyl, $CH_2OC_{1-4}$alkyl, cyclopropyl or CN, wherein the $C_{1-4}$alkyl and $CH_2OC_{1-4}$alkyl are optionally substituted with 1-3 substituents of F;
$R^2$ is $C_{1-4}$alkyl, $CH_2OC_{1-4}$alkyl, $CH_2OH$, $CH_2CN$, $C_{3-6}$cycloalkyl or CN, wherein each of the $C_{1-4}$alkyl, $CH_2OC_{1-4}$alkyl and $C_{3-6}$cycloalkyl is optionally substituted with 1-4 substituents of F;
each $R^3$, independently, is H, halo, $C_{1-4}$alkyl, $OC_{1-4}$alkyl, $CH_2OC_{1-4}$alkyl, $CH_2OH$, $C_{1-4}$haloalkyl, cyclopropyl or CN, wherein each of the $OC_{1-4}$alkyl, $CH_2OC_{1-4}$alkyl and cyclopropyl is optionally substituted with 1-4 substituents of F;
each of $R^4$, $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;
$R^7$ is $-NH-R^9$, $-NHC(=O)-R^9$, $-C(=O)NH-R^9$, $-O-R^9$ or $-S-R^9$;
$R^9$ is acetyl, $C_{1-6}$-alkyl, $C_{2-4}$alkenyl, $C_{2-4}$alkynyl or a fully or partially unsaturated 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$;
each $R^{10}$, independently, is H, halo, haloalkyl, CN, OH, $NO_2$, $NH_2$, $SF_5$, acetyl, $-C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl, dioxolyl, $-NHC(O)R^{11}$— or $-C(O)NHR^{11}$—, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or oxetan-3yl;
$R^{11}$ is $C_{1-6}$alkyl, $C_{1-6}$alkoxyl or $C_{3-6}$cycloalkyl; and
n is 0, 1 or 2.

In embodiment A-a of the invention, there are provided compounds, including stereoisomers and pharmaceutically acceptable salts thereof, of embodiment A, wherein each $R^{10}$, independently, is H, halo, haloalkyl, CN, OH, $NO_2$, $NH_2$, $SF_5$, acetyl, $-C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl, dioxolyl, $-NHC(O)R^{11}$— or $-C(O)NHR^{11}$—, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, isobutyl, sec-butyl, tert-butyl, $C_{1-3}$alkylamino-, $C_{1-3}$dialkylamino, $C_{1-3}$thioalkoxyl, oxetan-3yl or a ring selected from oxazolyl, isoxazolyl, pyrazolyl, thiazolyl, isothiazolyl or oxadiazolyl wherein the ring is optionally substituted independently with 1-5 substituents of F, Cl, CN or $CH_3$.

In embodiment A-1 of the invention, there are provided compounds, including stereoisomers and pharmaceutically acceptable salts thereof, of embodiment A, wherein o is 1 or 2.

In embodiment A-2 of the invention, there are provided compounds, including stereoisomers and pharmaceutically acceptable salts thereof, of embodiments A and A-1, wherein
$A^4$ is $CR^4$;
$A^5$ is $CR^5$;
$A^6$ is $CR^6$; and
$A^8$ is $CR^8$.

In embodiment A-3 of the invention, there are provided compounds, including stereoisomers and pharmaceutically acceptable salts thereof, of embodiments A, A-1 and A-2, wherein each $R^1$, independently, is H, F, $CH_2OCH_3$, $CH_2F$ or $CH_3$.

In embodiment A-4 of the invention, there are provided compounds, including stereoisomers and pharmaceutically acceptable salts thereof, of embodiments A through A-3, wherein $R^2$ is $CH_3$, $CH_2F$ or $CHF_2$.

In embodiment A-5 of the invention, there are provided compounds, including stereoisomers and pharmaceutically acceptable salts thereof, of embodiments A through A-4, wherein $R^7$ is —NH—C(=O)—$R^9$, —C(=O)NH—$R^9$, —O—$R^9$ or —S—$R^9$;
or $R^7$ is

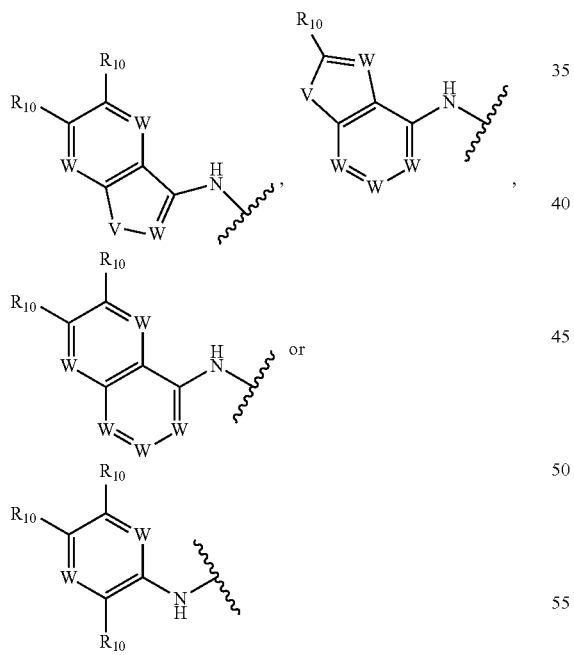

wherein V is $NR^{10}$, O or S; and
each W, independently, is CH, CF, CCl or N.

In embodiment A-6 of the invention, there are provided compounds, including stereoisomers and pharmaceutically acceptable salts thereof, of embodiments A through A-5, wherein $A^4$ is $CR^4$;
$A^5$ is $CR^5$ or N;
$A^6$ is $CR^6$;
$A^8$ is $CR^8$;

each $R^1$, independently, is H, F, Cl, $CF_3$, $CH_3$, $CH_2CH_3$, CN, $CH_2F$ or $CHF_2$;
$R^2$ is $CH_3$, $CH_2F$ or $CHF_2$;
each $R^3$, independently, is H, F, Cl, $CF_3$, $OCF_3$, $CH_3$, $CH_2CH_3$, CN, OH, $OCH_3$, $CH_2OCH_2F$ or $CH_2OCHF_2$; and
each of $R^4$, $R^5$, $R^6$ and $R^8$, independently, is H, F, Cl, $CF_3$, $OCF_3$, $CH_3$, $CH_2CH_3$, CN, OH, $OCH_3$, $SCH_3$, $NHCH_3$ or $C(O)CH_3$.

In embodiment A-7 of the invention, there are provided compounds, including stereoisomers and pharmaceutically acceptable salts thereof, of embodiments A through A-6, wherein $R^7$ is —NH—C(=O)—$R^9$ or

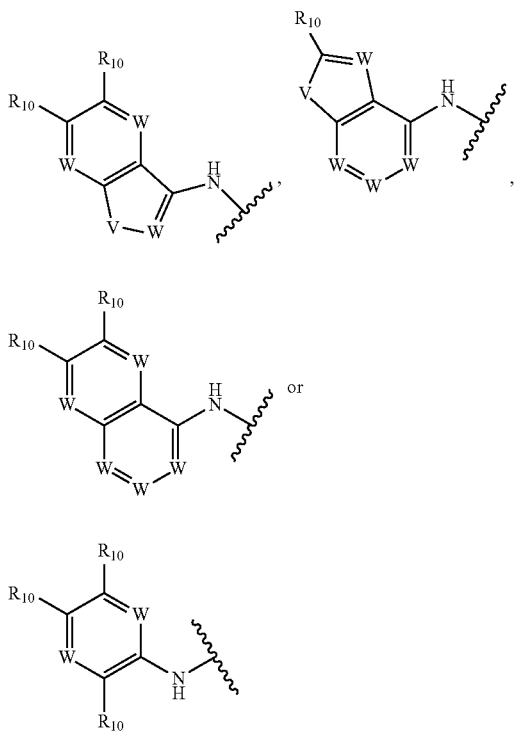

wherein V is $NR^{10}$, O or S; and
each W, independently, is CH, CF, CCl or N.

In embodiment A-8 of the invention, there are provided compounds, including stereoisomers and pharmaceutically acceptable salts thereof, of embodiments A through A-7, wherein $R^7$ is —NH—C(=O)—$R^9$.

In embodiment A-9 of the invention, there are provided compounds, including stereoisomers and pharmaceutically acceptable salts thereof, of embodiments A through A-7, wherein $R^7$ is

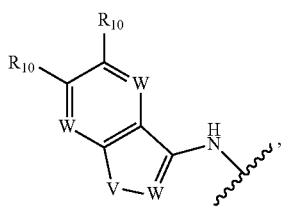

-continued

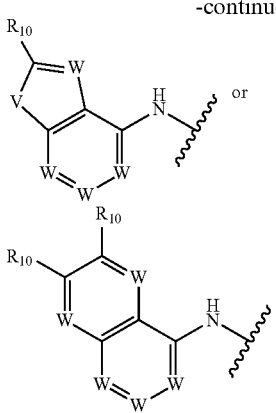

wherein V is NR[10], O or S; and
each W, independently, is CH, CF, CCl or N.

In embodiment A-10 of the invention, there are provided compounds, including stereoisomers and pharmaceutically acceptable salts thereof, of embodiments A through A-9, wherein
$A^4$ is $CR^4$;
$A^5$ is $CR^5$;
$A^6$ is $CR^6$; and
$A^8$ is $CR^8$; wherein each of $R^4$, $R^5$, $R^6$ and $R^8$, independently, is H, F, $CF_3$, $CF_2H$, $CH_2F$ or $CH_3$.

In embodiment A-11 of the invention, there are provided compounds, including stereoisomers and pharmaceutically acceptable salts thereof, of embodiments A through A-9, wherein
$A^4$ is $CR^4$ wherein $R^4$ is F, Cl or $CH_3$;
$A^5$ is $CR^5$ wherein $R^5$ is H, F, Cl or $CH_3$;
$A^6$ is CH; and
$A^8$ is CH.

In embodiment B of the invention, there are provided compounds, including stereoisomers, tautomers, hydrates, solvates and pharmaceutically acceptable salts thereof, which are generally defined by Formula II:

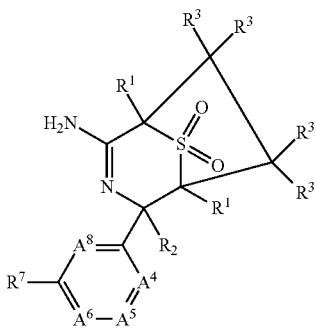

or a stereoisomer, tautomer, hydrate, solvate or pharmaceutically acceptable salt thereof, wherein
$A^4$ is $CR^4$ or N;
$A^5$ is $CR^5$ or N;
$A^6$ is $CR^6$ or N;
$A^8$ is $CR^8$ or N, provided that no more than one of $A^4$, $A^5$, $A^6$ and $A^8$ is N;
each $R^1$, independently, is H, F, Cl, $C_{1-4}$alkyl, $CH_2OC_{1-4}$alkyl, cyclopropyl or CN, wherein the $C_{1-4}$alkyl and $CH_2OC_{1-4}$alkyl are optionally substituted with 1-3 substituents of F;

$R^2$ is $C_{1-4}$alkyl, $CH_2OC_{1-4}$alkyl, $CH_2OH$, $CH_2CN$, $C_{3-6}$cycloalkyl or CN, wherein each of the $C_{1-4}$alkyl, $CH_2OC_{1-4}$alkyl and $C_{3-6}$cycloalkyl is optionally substituted with 1-4 substituents of F;

each $R^3$, independently, is H, halo, $C_{1-4}$alkyl, $OC_{1-4}$alkyl, $CH_2OC_{1-4}$alkyl, $CH_2OH$, $C_{1-4}$haloalkyl, cyclopropyl or CN, wherein each of the $OC_{1-4}$alkyl, $CH_2OC_{1-4}$alkyl and cyclopropyl is optionally substituted with 1-4 substituents of F;

each of $R^4$, $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;

$R^7$ is —NH—$R^9$ or —NHC(=O)—$R^9$;

$R^9$ is acetyl, $C_{1-6}$-alkyl, $C_{2-4}$alkenyl, $C_{2-4}$alkynyl or a fully or partially unsaturated 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$;

each $R^{10}$, independently, is H, halo, haloalkyl, CN, OH, $NO_2$, $NH_2$, $SF_5$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl, dioxolyl, —NHC(O)$R^{11}$— or —C(O)NH$R^{11}$—, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, isobutyl, sec-butyl, tert-butyl, $C_{1-3}$alkylamino-, $C_{1-3}$dialkylamino, $C_{1-3}$thioalkoxyl, oxetan-3yl or a ring selected from oxazolyl, isoxazolyl, pyrazolyl, thiazolyl, isothiazolyl or oxadiazolyl wherein the ring is optionally substituted independently with 1-5 substituents of F, Cl, CN or $CH_3$; and $R^{11}$ is $C_{1-6}$alkyl, $C_{1-6}$alkoxyl or $C_{3-6}$cycloalkyl.

In embodiment B-1 of the invention, there are provided compounds, including stereoisomers and pharmaceutically acceptable salts thereof, of embodiment B, wherein
$A^4$ is $CR^4$;
$A^5$ is $CR^5$;
$A^6$ is $CR^6$; and
A is $CR^8$.

In embodiment B-2 of the invention, there are provided compounds, including stereoisomers and pharmaceutically acceptable salts thereof, of embodiments B and B-1, wherein each $R^1$, independently, is H, F, $CH_2OCH_3$, $CH_2F$ or $CH_3$.

In embodiment B-3 of the invention, there are provided compounds, including stereoisomers and pharmaceutically acceptable salts thereof, of embodiments B, B-1 and B-2, wherein $R^2$ is $CH_3$, $CH_2F$ or $CHF_2$.

In embodiment B-4 of the invention, there are provided compounds, including stereoisomers and pharmaceutically acceptable salts thereof, of embodiments B through B-3, wherein $R^7$ is —NH—C(=O)—$R^9$ or —C(=O)NH—$R^9$;

or R[7] is

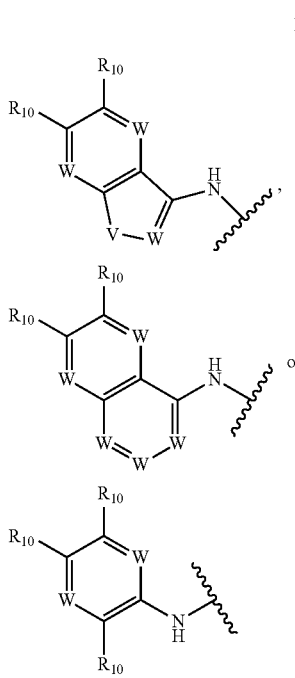

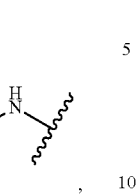

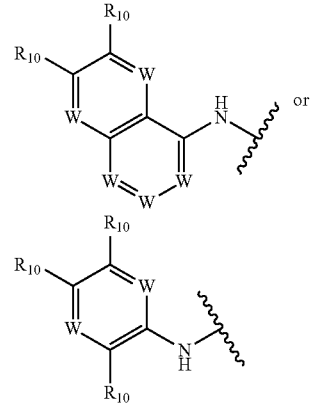

wherein V is NR[10], O or S; and
each W, independently, is CH, CF, CCl or N.

In embodiment B-5 of the invention, there are provided compounds, including stereoisomers and pharmaceutically acceptable salts thereof, of embodiments B through B-4, wherein A[4] is CR[4];

A[5] is CR[5] or N;

A[6] is CR[6];

A[8] is CR[8];

each R[1], independently, is H, F, Cl, CF$_3$, CH$_3$, CH$_2$CH$_3$, CN, CH$_2$F or CHF$_2$;

R[2] is CH$_3$, CH$_2$F or CHF$_2$;

each R[3], independently, is H, F, Cl, CF$_3$, OCF$_3$, CH$_3$, CH$_2$CH$_3$, CN, OH, OCH$_3$, CH$_2$OCH$_2$F or CH$_2$OCHF$_2$; and each of R[4], R[5], R[6] and R[8], independently, is H, F, Cl, CF$_3$, OCF$_3$, CH$_3$, CH$_2$CH$_3$, CN, OH, OCH$_3$, SCH$_3$, NHCH$_3$ or C(O)CH$_3$.

In embodiment B-6 of the invention, there are provided compounds, including stereoisomers and pharmaceutically acceptable salts thereof, of embodiments B through B-5, wherein R[7] is —NH—C(=O)—R[9] or

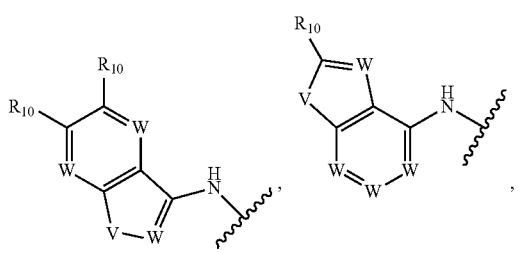

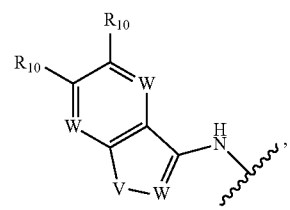

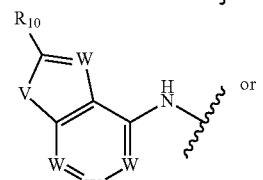

wherein V is NR[10], O or S; and
each W, independently, is CH, CF, CCl or N.

In embodiment B-7 of the invention, there are provided compounds, including stereoisomers and pharmaceutically acceptable salts thereof, of embodiments B through B-6, wherein R[7] is —NH—C(=O)—R[9].

In embodiment B-8 of the invention, there are provided compounds, including stereoisomers and pharmaceutically acceptable salts thereof, of embodiments B through B-6, wherein R[7] is

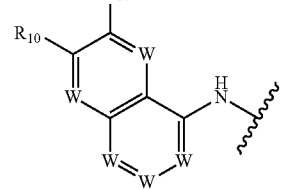

wherein V is NR[10] or S; and
each W, independently, is CH, CF, CCl or N.

In embodiment B-9 of the invention, there are provided compounds, including stereoisomers and pharmaceutically acceptable salts thereof, of embodiments B through B-8, wherein A[4] is CR[4];

A[5] is CR[5];

A[6] is CR[6]; and

A[8] is CR[8]; wherein each of R[4], R[5], R[6] and R[8], independently, is H, F, CF$_3$, CF$_2$H, CH$_2$F or CH$_3$.

In embodiment B-10 of the invention, there are provided compounds, including stereoisomers and pharmaceutically acceptable salts thereof, of embodiments B through B-9, wherein A[4] is CR[4] wherein R[4] is F, Cl or CH$_3$;

A⁵ is CR⁵ wherein R⁵ is H, F, Cl or CH₃;
A⁶ is CH; and
A⁸ is CH.

In embodiment B-A of the invention, there are provided compounds, including stereoisomers, tautomers, hydrates, solvates and pharmaceutically acceptable salts thereof, of embodiments A, A-1 through A-8, A-10, B, B-1 through B-7 and B-9-B-10, which are generally defined by Formula II-A:

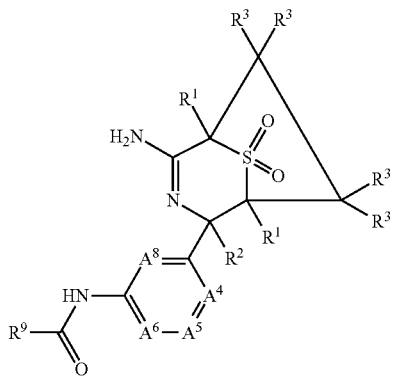

II-A wherein
A⁴ is CR⁴;
A⁵ is CR⁵ or N;
A⁶ is CR⁶;
A⁸ is CR⁸;
each R¹, independently, is H, F, Cl, CF₃, CH₃, CH₂CH₃, CH₂OCH₃, CN, CH₂F or CHF₂;
R² is CH₃, CH₂F or CHF₂;
each R³, independently, is H, F, Cl, CF₃, OCF₃, CH₃, CH₂CH₃, CN, OH, OCH₃, CH₂OCH₂F or CH₂OCHF₂;
each of R⁴, R⁵, R⁶ and R⁸, independently, is H, F, Cl, CF₃, OCF₃, CH₃, CH₂CH₃, CN, OH, OCH₃, SCH₃, NHCH₃ or C(O)CH₃;
R⁹ is acetyl, C₁₋₆-alkyl, C₂₋₄alkenyl, C₂₋₄alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, imidazo-pyridyl, cyclopropyl, cyclobutyl, cyclopentyl and cyclohexyl, wherein the C₁₋₆-alkyl, C₂₋₄alkenyl, C₂₋₄alkynyl and ring are optionally substituted, independently, with 1-5 substituents of R¹⁰; and
each R¹⁰, independently, is H, halo, haloalkyl, CN, OH, NO₂, NH₂, SF₅, acetyl, —C(O)NHCH₃, oxo, C₁₋₆alkyl, C₂₋₆alkenyl, C₂₋₆alkynyl, C₃₋₆cycloalkyl, C₁₋₆alkylamino-, C₁₋₆dialkylamino-, C₁₋₆alkoxyl, C₁₋₆thioalkoxyl, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the C₁₋₆alkyl, C₂₋₆alkenyl, C₂₋₆alkynyl, C₃₋₆cycloalkyl, C₁₋₆alkylamino-, C₁₋₆dialkylamino-, C₁₋₆alkoxyl, C₁₋₆thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO₂, NH₂, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, C₁₋₃alkylamino-, C₁₋₃dialkylamino, C₁₋₃thioalkoxyl or oxetan-3yl.

In embodiment B-A-a of the invention, there are provided compounds, including stereoisomers and pharmaceutically acceptable salts thereof, of embodiment B-A, wherein each R¹⁰, independently, is H, halo, haloalkyl, CN, OH, NO₂, NH₂, SF₅, acetyl, —C(O)NHCH₃, oxo, C₁₋₆alkyl, C₂₋₆alkenyl, C₂₋₆alkynyl, C₃₋₆cycloalkyl, C₁₋₆alkylamino-, C₁₋₆dialkylamino-, C₁₋₆alkoxyl, C₁₋₆thioalkoxyl, 2-propynyloxy, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl, dioxolyl, —NHC(O)R¹¹— or —C(O)NHR¹¹—, wherein each of the C₁₋₆alkyl, C₂₋₆alkenyl, C₂₋₆alkynyl, C₃₋₆cycloalkyl, C₁₋₆alkylamino-, C₁₋₆dialkylamino-, C₁₋₆alkoxyl, C₁₋₆thioalkoxyl, 2-propynyloxy, 2-butynyloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO₂, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, isobutyl, sec-butyl, tert-butyl, C₁₋₃alkylamino-, C₁₋₃dialkylamino, C₁₋₃thioalkoxyl, oxetan-3yl or a ring selected from oxazolyl, isoxazolyl, pyrazolyl, thiazolyl, isothiazolyl or oxadiazolyl wherein the ring is optionally substituted independently with 1-5 substituents of F, Cl, CN or CH₃.

In embodiment B-A-1 of the invention, there are provided compounds, including stereoisomers and pharmaceutically acceptable salts thereof, of embodiment B-A, wherein A⁴ is CR⁴;
A⁵ is CR⁵ or N;
A⁶ is CR⁶;
A⁸ is CR⁸; wherein each of R⁴, R⁵, R⁶ and R⁸, independently, is H, F, Cl, CF₃, OCF₃, CH₃, CN or OCH₃;
each R¹, independently, is H, F, CH₃, CF₃, CF₂H or CH₂F;
R² is CH₃, CH₂F or CHF₂;
each R³, independently, is H, F, CH₃, C₂H₅, CH₂F, CF₂H, CF₃ or CH₂CF₃;
R⁹ is a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, imidazo-pyridyl, cyclopropyl, cyclobutyl, cyclopentyl and cyclohexyl, wherein the ring is optionally substituted, independently, with 1-5 substituents of R¹⁰; and
each R¹⁰, independently, is H, halo, haloalkyl, CN, OH, NO₂, NH₂, SF₅, acetyl, —C(O)NHCH₃, oxo, C₁₋₆alkyl, C₂₋₆alkenyl, C₂₋₆alkynyl, C₃₋₆cycloalkyl, C₁₋₆alkylamino-, C₁₋₆dialkylamino-, C₁₋₆alkoxyl, C₁₋₆thioalkoxyl, 2-propynyloxy, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl, dioxolyl, —NHC(O)R¹¹— or —C(O)NHR¹¹—, wherein each of the C₁₋₆alkyl, C₂₋₆alkenyl, C₂₋₆alkynyl, C₃₋₆cycloalkyl, C₁₋₆alkylamino-, C₁₋₆dialkylamino-, C₁₋₆alkoxyl, C₁₋₆thioalkoxyl, 2-propynyloxy, 2-butynyloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO₂, NH₂, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, isobutyl, sec-butyl, tert-butyl, C₁₋₃alkylamino-, C₁₋₃dialkylamino, $C_{1-3}$thioalkoxyl, oxetan-3yl or a ring selected from oxazolyl, isoxazolyl, pyrazolyl, thiazolyl, isothiazolyl or oxadiazolyl wherein the ring is optionally substituted independently with 1-5 substituents of F, Cl, CN or $CH_3$; and $R^{11}$ is $C_{1-6}$alkyl, $C_{1-6}$alkoxyl or $C_{3-6}$cycloalkyl.

In embodiment B-A-2 of the invention, there are provided compounds, including stereoisomers and pharmaceutically acceptable salts thereof, of embodiments B-A and B-A-1, wherein $A^4$ is CH or CF;

$A^5$ is CH, CF or N;
$A^6$ is CH or CF;
$A^8$ is CH or CF;
each $R^1$, independently, is H, F, Cl, $CF_3$, $CH_3$, $CF_2H$ or $CH_2F$;
$R^2$ is $CH_3$ or $CH_2F$; and
each $R^3$, independently, is H, $CF_3$, $CH_3$, $CF_2H$ or $CH_2F$.

In embodiment B-B of the invention, there are provided compounds, including stereoisomers, tautomers, hydrates, solvates and pharmaceutically acceptable salts thereof, of embodiments A, A-1 through A-7, A-9 through A-11, B, B-1 through B-6 and B-8 through B-10, which are generally defined by Formula II-B:

II-B wherein
$A^4$ is $CR^4$;
$A^5$ is $CR^5$ or N;
$A^6$ is $CR^6$;
$A^8$ is $CR^8$;
each $R^1$, independently, is H, F, Cl, $CF_3$, $CH_3$, $CH_2CH_3$, $CH_2OCH_3$, CN, $CH_2F$ or $CHF_2$;
$R^2$ is $CH_3$, $CH_2F$ or $CHF_2$;
each $R^3$, independently, is H, F, Cl, $CF_3$, $OCF_3$, $CH_3$, $CH_2CH_3$, CN, OH, $OCH_3$, $CH_2OCH_2F$ or $CH_2OCHF_2$;
each of $R^4$, $R^5$, $R^6$ and $R^8$, independently, is H, F, Cl, $CF_3$, $OCF_3$, $CH_3$, $CH_2CH_3$, CN, OH, $OCH_3$, $SCH_3$, $NHCH_3$ or $C(O)CH_3$; and
each $R^{10}$, independently, is H, halo, haloalkyl, CN, OH, $NO_2$, $NH_2$, $SF_5$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or oxetan-3yl.

In embodiment B-B-a of the invention, there are provided compounds, including stereoisomers and pharmaceutically acceptable salts thereof, of embodiment B-B, wherein each $R^{10}$, independently, is H, halo, haloalkyl, CN, OH, $NO_2$, $NH_2$, $SF_5$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl, dioxolyl, —$NHC(O)R^{11}$— or —$C(O)NHR^{11}$—, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, isobutyl, sec-butyl, tert-butyl, $C_{1-3}$alkylamino-, $C_{1-3}$dialkylamino, $C_{1-3}$thioalkoxyl, oxetan-3yl or a ring selected from oxazolyl, isoxazolyl, pyrazolyl, thiazolyl, isothiazolyl or oxadiazolyl wherein the ring is optionally substituted independently with 1-5 substituents of F, Cl, CN or $CH_3$; and $R^{11}$ is $C_{1-6}$alkyl, $C_{1-6}$alkoxyl or $C_{3-6}$cycloalkyl.

In embodiment B-B-1 of the invention, there are provided compounds, including stereoisomers and pharmaceutically acceptable salts thereof, of embodiment B-B, wherein $A^4$ is CH or CF;

$A^5$ is CH, CF or N;
$A^6$ is CH or CF;
$A^8$ is CH or CF;
each $R^1$, independently, is H, F, Cl, $CF_3$, $CH_3$, $CF_2H$ or $CH_2F$;
$R^2$ is $CH_3$ or $CH_2F$; and
each $R^3$, independently, is H, $CF_3$, $CH_3$, $CF_2H$ or $CH_2F$.

In embodiment B-B-2 of the invention, there are provided compounds, including stereoisomers and pharmaceutically acceptable salts thereof, of embodiment B-B and B-B-1, wherein $A^4$ is CH or CF;

$A^5$ is CH or N;
$A^6$ is CH;
$A^8$ is CH;
each $R^1$, independently, is H, F, $CF_3$, $CH_3$, $CF_2H$ or $CH_2F$;
$R^2$ is $CH_3$ or $CH_2F$; and
each $R^3$, independently, is H, $CF_3$, $CH_3$, $CF_2H$ or $CH_2F$.

In embodiment B-C of the invention, there are provided compounds, including stereoisomers and pharmaceutically acceptable salts thereof, of embodiments A, A-1 through A-7, A-9 through A-10, B, B-1 through B-6, B-8 through B-9, B-A through B-A-2 and BB through B-B-2, having a formula II-C

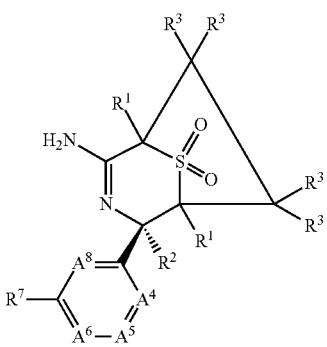

II-C wherein
A$^4$ is CR$^4$;
A$^5$ is CR$^5$ or N;
A$^6$ is CR$^6$;
A$^8$ is CR$^8$;
each R$^1$, independently, is H, F, Cl, CF$_3$, CH$_3$, CH$_2$CH$_3$, CH$_2$OCH$_3$, CN, CH$_2$F or CHF$_2$;
R$^2$ is CH$_3$, CH$_2$F or CHF$_2$;
each R$^3$, independently, is H, F, Cl, CF$_3$, OCF$_3$, CH$_3$, CH$_2$CH$_3$, CN, OH, OCH$_3$, CH$_2$OCH$_2$F or CH$_2$OCHF$_2$;
each of R$^4$, R$^5$, R$^6$ and R$^8$, independently, is H, F, Cl, CF$_3$, OCF$_3$, CH$_3$, CH$_2$CH$_3$, CN, OH, OCH$_3$, SCH$_3$, NHCH$_3$ or C(O)CH$_3$;
R$^7$ is —NH—C(=O)—R$^9$ or

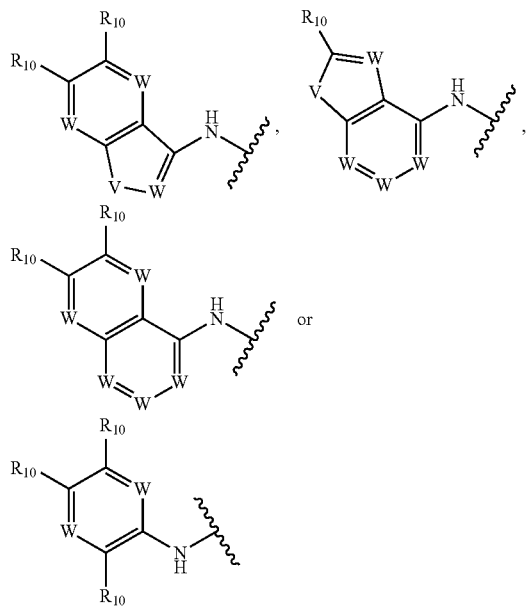

wherein V is NR$^{10}$, O or S; and
each W, independently, is CH, CF, CCl or N;
R$^9$ is acetyl, C$_{1-6}$-alkyl, C$_{2-4}$alkenyl, C$_{2-4}$alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, imidazopyridyl, cyclopropyl, cyclobutyl, cyclopentyl and cyclohexyl, wherein the C$_{1-6}$-alkyl, C$_{2-4}$alkenyl, C$_{2-4}$alkynyl and ring are optionally substituted, independently, with 1-5 substituents of R$^{10}$; and each R$^{10}$, independently, is H, halo, haloalkyl, CN, OH, NO$_2$, NH$_2$, SF$_5$, acetyl, —C(O)NHCH$_3$, oxo, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, 2-propynyloxy, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl, dioxolyl, —NHC(O)R$^{11}$— or —C(O)NHR$^{11}$—, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, 2-propynyloxy, 2-butynyloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO$_2$, NH$_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, isobutyl, sec-butyl, tert-butyl, C$_{1-3}$alkylamino-, C$_{1-3}$dialkylamino, C$_{1-3}$thioalkoxyl, oxetan-3yl or a ring selected from oxazolyl, isoxazolyl, pyrazolyl, thiazolyl, isothiazolyl or oxadiazolyl wherein the ring is optionally substituted independently with 1-5 substituents of F, Cl, CN or CH$_3$; and R$^{11}$ is C$_{1-6}$alkyl, C$_{1-6}$alkoxyl or C$_{3-6}$cycloalkyl.

In embodiment B-D of the invention, there are provided compounds, including stereoisomers and pharmaceutically acceptable salts thereof, of embodiments A, A-1 through A-7, A-9 through A-11, B, B-1 through B-6, B-8 through B-10, B-A through B-A-2 and B-B through B-B-2, having a formula II-C-1-A or Formula II-C-1-B

II-C-1-A

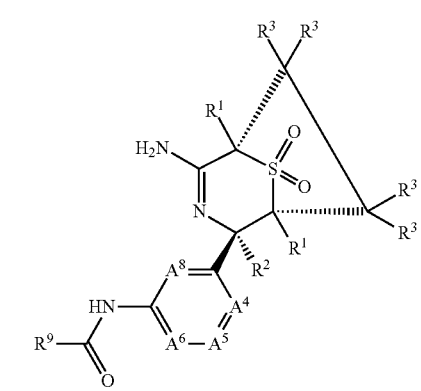

II-C-1-B

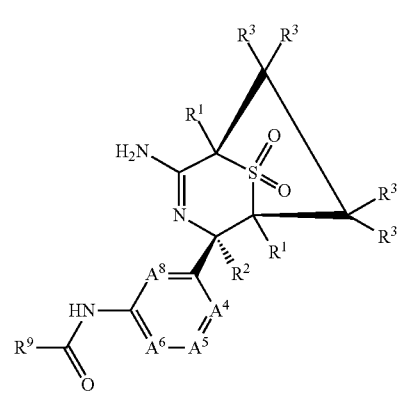

wherein $A^4$ is $CR^4$;

$A^5$ is $CR^5$ or N;

$A^6$ is $CR^6$;

$A^8$ is $CR^8$;

each $R^1$, independently, is H, F, Cl, $CF_3$, $CH_3$, $CH_2CH_3$, $CH_2OCH_3$, CN, $CH_2F$ or $CHF_2$;

$R^2$ is $CH_3$, $CH_2F$ or $CHF_2$;

each $R^3$, independently, is H, F, Cl, $CF_3$, $OCF_3$, $CH_3$, $CH_2CH_3$, CN, OH, $OCH_3$, $CH_2OCH_2F$ or $CH_2OCHF_2$;

each of $R^4$, $R^5$, $R^6$ and $R^8$, independently, is H, F, Cl, $CF_3$, $OCF_3$, $CH_3$, $CH_2CH_3$, CN, OH, $OCH_3$, $SCH_3$, $NHCH_3$ or $C(O)CH_3$;

$R^9$ is acetyl, $C_{1-6}$-alkyl, $C_{2-4}$alkenyl, $C_{2-4}$alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, imidazopyridyl, cyclopropyl, cyclobutyl, cyclopentyl and cyclohexyl, wherein the $C_{1-6}$-alkyl, $C_{2-4}$alkenyl, $C_{2-4}$alkynyl and ring are optionally substituted, independently, with 1-5 substituents of $R^{10}$; and each $R^{10}$, independently, is H, halo, haloalkyl, CN, OH, $NO_2$, $NH_2$, $SF_5$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-propynyloxy, 2-butynyloxy, isobutyl, sec-butyl, tert-butyl, $C_{1-3}$alkylamino-, $C_{1-3}$dialkylamino, $C_{1-3}$thioalkoxyl oxetan-3yl or a ring selected from oxazolyl, isoxazolyl, pyrazolyl, thiazolyl, isothiazolyl or oxadiazolyl wherein the ring is optionally substituted independently with 1-5 substituents of F, Cl, CN or $CH_3$.

In embodiment B-E of the invention, there are provided compounds, including stereoisomers and pharmaceutically acceptable salts thereof, of embodiments A, A-1 through A-7, A-9 through A-11, B, B-1 through B-6, B-8 through B-10, B-A through B-A-2, BB through B-B-2, B-C and B-D, having a formula II-C-2

II-C-2 wherein $A^4$ is $CR^4$;

$A^5$ is $CR^5$ or N;

$A^6$ is $CR^6$;

$A^8$ is $CR^8$;

each $R^1$, independently, is H, F, Cl, $CF_3$, $CH_3$, $CH_2CH_3$, $CH_2OCH_3$, CN, $CH_2F$ or $CHF_2$;

$R^2$ is $CH_3$, $CH_2F$ or $CHF_2$;

each $R^3$, independently, is H, F, Cl, $CF_3$, $OCF_3$, $CH_3$, $CH_2CH_3$, CN, OH, $OCH_3$, $CH_2OCH_2F$ or $CH_2OCHF_2$;

each of $R^4$, $R^5$, $R^6$ and $R^8$, independently, is H, F, Cl, $CF_3$, $OCF_3$, $CH_3$, $CH_2CH_3$, CN, OH, $OCH_3$, $SCH_3$, $NHCH_3$ or $C(O)CH_3$;

V is $NR^{10}$, O or S;

each W, independently, is CH, CF, CCl or N; and each $R^{10}$, independently, is H, halo, haloalkyl, CN, OH, $NO_2$, $NH_2$, $SF_5$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-propynyloxy, 2-butynyloxy, isobutyl, sec-butyl, tert-butyl, $C_{1-3}$alkylamino-, $C_{1-3}$dialkylamino, $C_{1-3}$thioalkoxyl oxetan-3yl or a ring selected from oxazolyl, isoxazolyl, pyrazolyl, thiazolyl, isothiazolyl or oxadiazolyl wherein the ring is optionally substituted independently with 1-5 substituents of F, Cl, CN or $CH_3$.

In embodiment B-E of the invention, there are provided compounds, including stereoisomers and pharmaceutically acceptable salts thereof, of embodiments A, A-1 through A-7, A-9 through A-11, B, B-1 through B-6, B-8 through B-10, B-A through B-A-2, BB through B-B-2, B-C and B-D, having a formula II-C-3

II-C-3

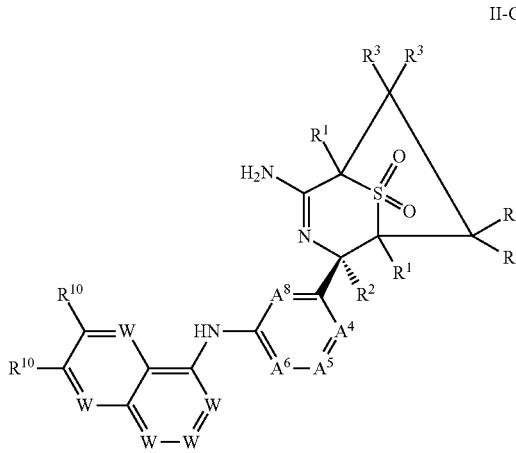

wherein

A⁴ is CR⁴;

A⁵ is CR⁵ or N;

A⁶ is CR⁶;

A⁸ is CR⁸;

each R¹, independently, is H, F, Cl, CF₃, CH₃, CH₂CH₃, CH₂OCH₃, CN, CH₂F or CHF₂;

R² is CH₃, CH₂F or CHF₂;

each R³, independently, is H, F, Cl, CF₃, OCF₃, CH₃, CH₂CH₃, CN, OH, OCH₃, CH₂OCH₂F or CH₂OCHF₂;

each of R⁴, R⁵, R⁶ and R⁸, independently, is H, F, Cl, CF₃, OCF₃, CH₃, CH₂CH₃, CN, OH, OCH₃, SCH₃, NHCH₃ or C(O)CH₃;

each W, independently, is CH, CF, CCl or N; and each R¹⁰, independently, is H, halo, haloalkyl, CN, OH, NO₂, NH₂, SF₅, acetyl, —C(O)NHCH₃, oxo, C₁₋₆alkyl, C₂₋₆alkenyl, C₂₋₆alkynyl, C₃₋₆cycloalkyl, C₁₋₆alkylamino-, C₁₋₆dialkylamino-, C₁₋₆alkoxyl, C₁₋₆thioalkoxyl, 2-propynyloxy, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the C₁₋₆alkyl, C₂₋₆alkenyl, C₂₋₆alkynyl, C₃₋₆cycloalkyl, C₁₋₆alkylamino-, C₁₋₆dialkylamino-, C₁₋₆alkoxyl, C₁₋₆thioalkoxyl, 2-propynyloxy, 2-butynyloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO₂, NH₂, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-propynyloxy, 2-butynyloxy, isobutyl, sec-butyl, tert-butyl, C₁₋₃alkylamino-, C₁₋₃dialkylamino, C₁₋₃thioalkoxyl oxetan-3yl or a ring selected from oxazolyl, isoxazolyl, pyrazolyl, thiazolyl, isothiazolyl or oxadiazolyl wherein the ring is optionally substituted independently with 1-5 substituents of F, Cl, CN or CH₃.

In embodiment B-F of the invention, there are provided compounds, including stereoisomers and pharmaceutically acceptable salts thereof, of embodiments A, A-1 through A-7, A-9 through A-10, B, B-1 through B-6, B-8 through B-9, B-A through B-A-2 and BB through B-B-2, having a formula II-D

II-D

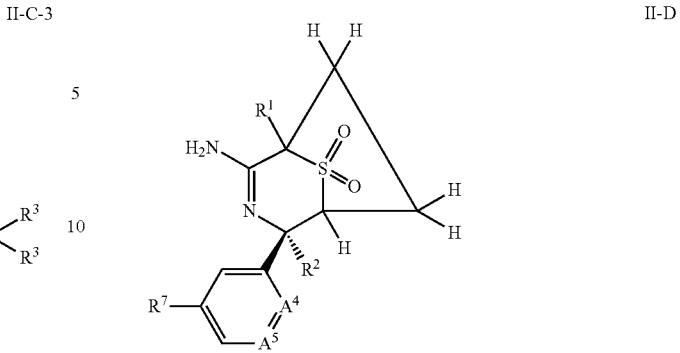

wherein

A⁴ is CR⁴ wherein R⁴ is F, Cl or CH₃;

A⁵ is CR⁵ or N, wherein R⁵ is H, F, Cl or CH₃;

R¹ is H, F, CF₃, CH₃, CH₂CH₃, CH₂OCH₃, CH₂F or CHF₂;

R² is CH₃, CH₂F or CHF₂;

R⁷ is —NH—C(=O)—R⁹ or

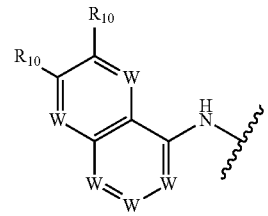

wherein each W, independently, is CH, CF, CCl or N;

R⁹ is a ring selected from phenyl, pyridyl, pyrimidyl, pyrazinyl, pyridazinyl, pyrazolyl, isoxazolyl, thiazolyl, furanyl, thienyl or pyrrolyl, wherein ring is optionally substituted, independently, with 1-5 substituents of R¹⁰; and each R¹⁰, independently, is H, halo, haloalkyl, CN, OH, NO₂, NH₂, SF₅, acetyl, —C(O)NHCH₃, oxo, C₁₋₆alkyl, C₂₋₆alkenyl, C₂₋₆alkynyl, C₃₋₆cycloalkyl, C₁₋₆alkylamino-, C₁₋₆dialkylamino-, C₁₋₆alkoxyl, C₁₋₆thioalkoxyl, 2-propynyloxy, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl, dioxolyl, —NHC(O)R¹¹— or —C(O)NHR¹¹—, wherein each of the C₁₋₆alkyl, C₂₋₆alkenyl, C₂₋₆alkynyl, C₃₋₆cycloalkyl, C₁₋₆alkylamino-, C₁₋₆dialkylamino-, C₁₋₆alkoxyl, C₁₋₆thioalkoxyl, 2-propynyloxy, 2-butynyloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO₂, NH₂, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, isobutyl, sec-butyl, tert-butyl, C₁₋₃alkylamino-, C₁₋₃dialkylamino, C₁₋₃thioalkoxyl, oxetan-3yl or a ring selected from oxazolyl, isoxazolyl, pyrazolyl, thiazolyl, isothiazolyl or oxadiazolyl wherein the ring is optionally substituted independently with 1-5 substituents of F, Cl, CN or CH₃; and R¹¹ is C₁₋₆alkyl, C₁₋₆alkoxyl or C₃₋₆cycloalkyl.

In embodiment C of the invention, there are provided compounds, including stereoisomers, tautomers, hydrates, solvates and pharmaceutically acceptable salts thereof, which are generally defined by Formula III:

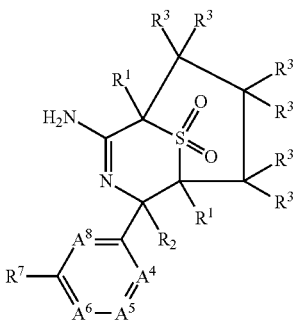

III wherein
or a stereoisomer, tautomer, hydrate, solvate or pharmaceutically acceptable salt thereof, wherein $A^4$ is $CR^4$ or N;

$A^5$ is $CR^5$ or N;

$A^6$ is $CR^6$ or N;

$A^8$ is $CR^8$ or N, provided that no more than one of $A^4$, $A^5$, $A^6$ and $A^8$ is N;

each $R^1$, independently, is H, F, Cl, $C_{1-4}$alkyl, $CH_2OC_{1-4}$alkyl, cyclopropyl or CN, wherein the $C_{1-4}$alkyl and $CH_2OC_{1-4}$alkyl are optionally substituted with 1-3 substituents of F;

$R^2$ is $C_{1-4}$alkyl, $CH_2OC_{1-4}$alkyl, $CH_2OH$, $CH_2CN$, $C_{3-6}$cycloalkyl or CN, wherein each of the $C_{1-4}$alkyl, $CH_2OC_{1-4}$alkyl and $C_{3-6}$cycloalkyl is optionally substituted with 1-4 substituents of F;

each $R^3$, independently, is H, halo, $C_{1-4}$alkyl, $OC_{1-4}$alkyl, $CH_2OC_{1-4}$alkyl, $CH_2OH$, $C_{1-4}$haloalkyl, cyclopropyl or CN, wherein each of the $OC_{1-4}$alkyl, $CH_2OC_{1-4}$alkyl and cyclopropyl is optionally substituted with 1-4 substituents of F;

each of $R^4$, $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;

$R^7$ is —NH—$R^9$, —NHC(=O)—$R^9$, —C(=O)NH—$R^9$, —O—$R^9$ or —S—$R^9$;

$R^9$ is acetyl, $C_{1-6}$-alkyl, $C_{2-4}$alkenyl, $C_{2-4}$alkynyl or a fully or partially unsaturated 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$;

each $R^{10}$, independently, is H, halo, haloalkyl, CN, OH, $NO_2$, $NH_2$, $SF_5$, acetyl, —C(O)NHCH$_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl, dioxolyl, —NHC(O)$R^{11}$— or —C(O)NH$R^{11}$—, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or oxetan-3yl; and $R^{11}$ is $C_{1-6}$alkyl, $C_{1-6}$alkoxyl or $C_{3-6}$cycloalkyl.

In embodiment C-1 of the invention, there are provided compounds, including stereoisomers and pharmaceutically acceptable salts thereof, of embodiment C, wherein $A^4$ is $CR^4$;

$A^5$ is $CR^5$;

$A^6$ is $CR^6$; and $A^8$ is $CR^8$.

In embodiment C-2 of the invention, there are provided compounds, including stereoisomers and pharmaceutically acceptable salts thereof, of embodiments C and C-1, wherein each $R^1$, independently, is H, F, $CH_2F$ or $CH_3$.

In embodiment C-3 of the invention, there are provided compounds, including stereoisomers and pharmaceutically acceptable salts thereof, of embodiments C, C-1 and C-2, wherein $R^2$ is $CH_3$, $CH_2F$ or $CHF_2$.

In embodiment C-4 of the invention, there are provided compounds, including stereoisomers and pharmaceutically acceptable salts thereof, of embodiments C through C-3, wherein $R^7$ is —NH—C(=O)—$R^9$ or —C(=O)NH—$R^9$; or $R^7$ is

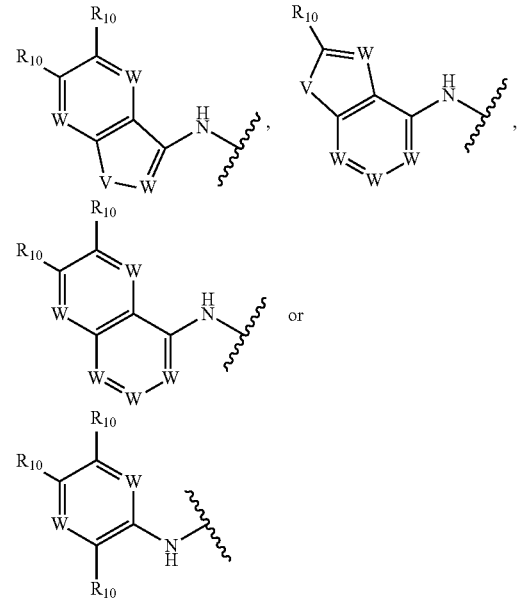

wherein V is $NR^{10}$, O or S; and
each W, independently, is CH, CF, CCl or N.

In embodiment C-5 of the invention, there are provided compounds, including stereoisomers and pharmaceutically acceptable salts thereof, of embodiments C through C-4, wherein $A^4$ is $CR^4$;

$A^5$ is $CR^5$ or N;

$A^6$ is $CR^6$;

$A^8$ is $CR^8$;

each $R^1$, independently, is H, F, Cl, $CF_3$, $CH_3$, $CH_2CH_3$, CN, $CH_2F$ or $CHF_2$;

$R^2$ is $CH_3$, $CH_2F$ or $CHF_2$;

each $R^3$, independently, is H, F, Cl, $CF_3$, $OCF_3$, $CH_3$, $CH_2CH_3$, CN, OH, $OCH_3$, $CH_2OCH_2F$ or $CH_2OCHF_2$; and each of $R^4$, $R^5$, $R^6$ and $R^8$, independently, is H, F, Cl, $CF_3$, $OCF_3$, $CH_3$, $CH_2CH_3$, CN, OH, $OCH_3$, $SCH_3$, $NHCH_3$ or $C(O)CH_3$.

In embodiment C-6 of the invention, there are provided compounds, including stereoisomers and pharmaceutically acceptable salts thereof, of embodiments C through C-5, wherein $R^7$ is —NH—C(=O)—$R^9$ or

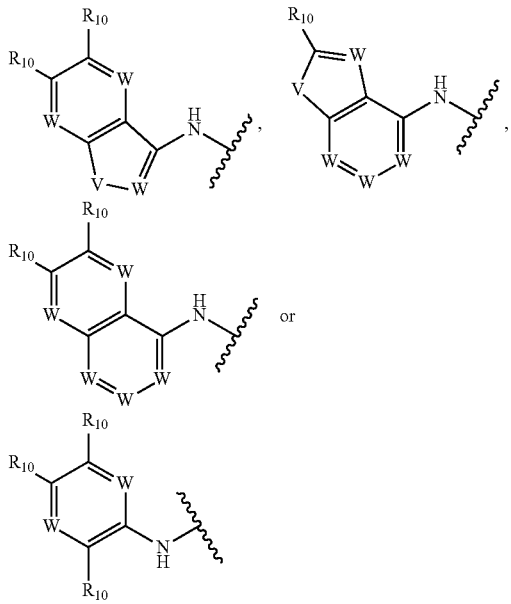

wherein V is $NR^{10}$, O or S; and
each W, independently, is CH, CF, CCl or N.

In embodiment C-7 of the invention, there are provided compounds, including stereoisomers and pharmaceutically acceptable salts thereof, of embodiments C through C-6, wherein $R^7$ is —NH—C(=O)—$R^9$.

In embodiment C-8 of the invention, there are provided compounds, including stereoisomers and pharmaceutically acceptable salts thereof, of embodiments C through C-6, wherein $R^7$ is

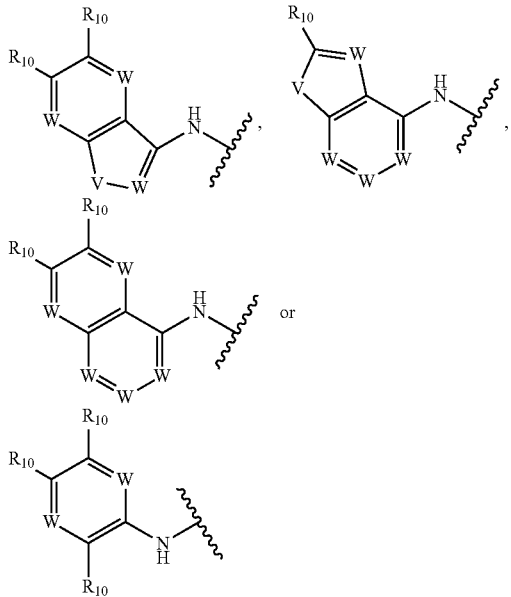

wherein V is $NR^{10}$ or S; and
each W, independently, is CH, CF, CCl or N.

In embodiment C-9 of the invention, there are provided compounds, including stereoisomers and pharmaceutically acceptable salts thereof, of embodiments C through C-8, wherein $A^4$ is $CR^4$;
$A^5$ is $CR^5$;
$A^6$ is $CR^6$; and
$A^8$ is $CR^8$; wherein each of $R^4$, $R^5$, $R^6$ and $R^8$, independently, is H, F, $CF_3$, $CF_2H$, $CH_2F$ or $CH_3$.

In embodiment C-A of the invention, there are provided compounds, including stereoisomers, tautomers, hydrates, solvates and pharmaceutically acceptable salts thereof, of embodiments A, A-1 through A-8, A-10, C, C-1 through C-7 and C-9, which are generally defined by Formula III-A:

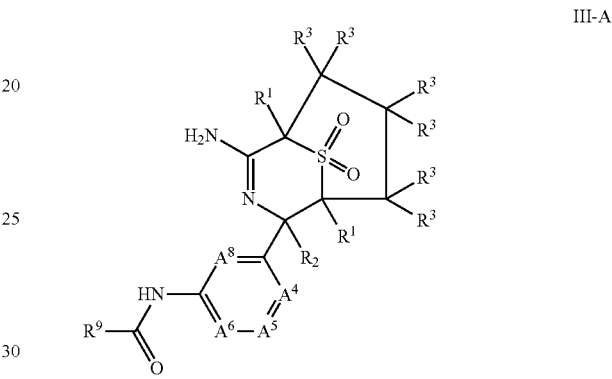

III-A wherein
$A^4$ is $CR^4$;
$A^5$ is $CR^5$ or N;
$A^6$ is $CR^6$;
$A^8$ is $CR^8$;
each $R^1$, independently, is H, F, Cl, $CF_3$, $CH_3$, $CH_2CH_3$, CN, $CH_2F$ or $CHF_2$;
$R^2$ is $CH_3$, $CH_2F$ or $CHF_2$;
each $R^3$, independently, is H, F, Cl, $CF_3$, $OCF_3$, $CH_3$, $CH_2CH_3$, CN, OH, $OCH_3$, $CH_2OCH_2F$ or $CH_2OCHF_2$;
each of $R^4$, $R^5$, $R^6$ and $R^8$, independently, is H, F, Cl, $CF_3$, $OCF_3$, $CH_3$, $CH_2CH_3$, CN, OH, $OCH_3$, $SCH_3$, $NHCH_3$ or $C(O)CH_3$;
$R^9$ is acetyl, $C_{1-6}$-alkyl, $C_{2-4}$alkenyl, $C_{2-4}$alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, imidazopyridyl, cyclopropyl, cyclobutyl, cyclopentyl and cyclohexyl, wherein the $C_{1-6}$-alkyl, $C_{2-4}$alkenyl, $C_{2-4}$alkynyl and ring are optionally substituted, independently, with 1-5 substituents of $R^{10}$; and
each $R^{10}$, independently, is H, halo, haloalkyl, CN, OH, $NO_2$, $NH_2$, $SF_5$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl, oxetan-3yl or a ring selected from oxazolyl, isoxazolyl, pyrazolyl, thiazolyl, isothiazolyl or oxadiazolyl wherein the ring is optionally substituted independently with 1-5 substituents of F, Cl, CN or $CH_3$.

In embodiment C-A-1 of the invention, there are provided compounds, including stereoisomers and pharmaceutically acceptable salts thereof, of embodiment C-A, wherein $A^4$ is $CR^4$;

$A^5$ is $CR^5$ or N;

$A^6$ is $CR^6$;

$A^8$ is $CR^8$; wherein each of $R^4$, $R^5$, $R^6$ and $R^8$, independently, is H, F, Cl, $CF_3$, $OCF_3$, $CH_3$, CN or $OCH_3$;

each $R^1$, independently, is H, F, $CH_3$, $CF_3$, $CF_2H$ or $CH_2F$;

$R^2$ is $CH_3$, $CH_2F$ or $CHF_2$;

each $R^3$, independently, is H, F, $CH_3$, $C_2H_5$, $CH_2F$, $CF_2H$, $CF_3$ or $CH_2CF_3$;

$R^9$ is a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, imidazo-pyridyl, cyclopropyl, cyclobutyl, cyclopentyl and cyclohexyl, wherein the ring is optionally substituted, independently, with 1-5 substituents of $R^{10}$; and each $R^{10}$, independently, is H, halo, haloalkyl, CN, OH, $NO_2$, $NH_2$, $SF_5$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or a ring selected from oxazolyl, isoxazolyl, pyrazolyl, thiazolyl, isothiazolyl or oxadiazolyl wherein the ring is optionally substituted independently with 1-5 substituents of F, Cl, CN or $CH_3$.

In embodiment C-A-2 of the invention, there are provided compounds, including stereoisomers, tautomers, hydrates, solvates and pharmaceutically acceptable salts thereof, of embodiments A, A-1 through A-8, A-11, C, C-1 through C-7 and C-9, which are generally defined by Formula III-A-1:

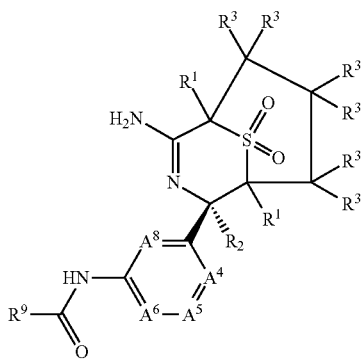

III-A-1 wherein
$A^4$ is $CR^4$;
$A^5$ is $CR^5$ or N;
$A^6$ is $CR^6$;
$A^8$ is $CR^8$;
each $R^1$, independently, is H, F, Cl, $CF_3$, $CH_3$, $CH_2CH_3$, CN, $CH_2F$ or $CHF_2$;
$R^2$ is $CH_3$, $CH_2F$ or $CHF_2$;
each $R^3$, independently, is H, F, Cl, $CF_3$, $OCF_3$, $CH_3$, $CH_2CH_3$, CN, OH, $OCH_3$, $CH_2OCH_2F$ or $CH_2OCHF_2$;
each of $R^4$, $R^5$, $R^6$ and $R^8$, independently, is H, F, Cl, $CF_3$, $OCF_3$, $CH_3$, $CH_2CH_3$, CN, OH, $OCH_3$, $SCH_3$, $NHCH_3$ or $C(O)CH_3$;
$R^9$ is acetyl, $C_{1-6}$-alkyl, $C_{2-4}$alkenyl, $C_{2-4}$alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, imidazo-pyridyl, cyclopropyl, cyclobutyl, cyclopentyl and cyclohexyl, wherein the $C_{1-6}$-alkyl, $C_{2-4}$alkenyl, $C_{2-4}$alkynyl and ring are optionally substituted, independently, with 1-5 substituents of $R^{10}$; and each $R^{10}$, independently, is H, halo, haloalkyl, CN, OH, $NO_2$, $NH_2$, $SF_5$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or a ring selected from oxazolyl, isoxazolyl, pyrazolyl, thiazolyl, isothiazolyl or oxadiazolyl wherein the ring is optionally substituted independently with 1-5 substituents of F, Cl, CN or $CH_3$.

In embodiment C-A-2 of the invention, there are provided compounds, including stereoisomers and pharmaceutically acceptable salts thereof, of embodiments C-A and C-A-1, wherein $A^4$ is CH or CF;

$A^5$ is CH, CF or N;
$A^6$ is CH or CF;
$A^8$ is CH or CF;
each $R^1$, independently, is H, F, Cl, $CF_3$, $CH_3$, $CF_2H$ or $CH_2F$;
$R^2$ is $CH_3$ or $CH_2F$; and
each $R^3$, independently, is H, $CF_3$, $CH_3$, $CF_2H$ or $CH_2F$.

In embodiment C-B of the invention, there are provided compounds, including stereoisomers, tautomers, hydrates, solvates and pharmaceutically acceptable salts thereof, of embodiments A, A-1 through A-7, A-9 through A-10, C, C-1 through C-6 and C-8 through C-9, which are generally defined by Formula III-B:

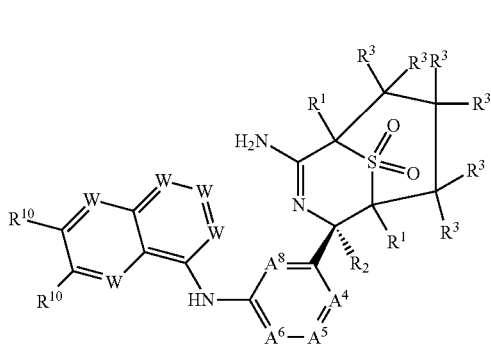

III-B wherein
$A^4$ is $CR^4$;
$A^5$ is $CR^5$ or N;
$A^6$ is $CR^6$;
$A^8$ is $CR^8$;
each $R^1$, independently, is H, F, Cl, $CF_3$, $CH_3$, $CH_2CH_3$, CN, $CH_2F$ or $CHF_2$;
$R^2$ is $CH_3$, $CH_2F$ or $CHF_2$;
each $R^3$, independently, is H, F, Cl, $CF_3$, $OCF_3$, $CH_3$, $CH_2CH_3$, CN, OH, $OCH_3$, $CH_2OCH_2F$ or $CH_2OCHF_2$;
each of $R^4$, $R^5$, $R^6$ and $R^8$, independently, is H, F, Cl, $CF_3$, $OCF_3$, $CH_3$, $CH_2CH_3$, CN, OH, $OCH_3$, $SCH_3$, $NHCH_3$ or $C(O)CH_3$;
each W, independently, is CH, CF, CCl or N; and
each $R^{10}$, independently, is H, halo, haloalkyl, CN, OH, $NO_2$, $NH_2$, $SF_5$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or a ring selected from oxazolyl, isoxazolyl, pyrazolyl, thiazolyl, isothiazolyl or oxadiazolyl wherein the ring is optionally substituted independently with 1-5 substituents of F, Cl, CN or $CH_3$.

In embodiment C-B-1 of the invention, there are provided compounds, including stereoisomers and pharmaceutically acceptable salts thereof, of embodiment C-B, wherein
$A^4$ is CH or CF;
$A^5$ is CH, CF or N;
$A^6$ is CH or CF;
$A^8$ is CH or CF;
each $R^1$, independently, is H, F, Cl, $CF_3$, $CH_3$, $CF_2H$ or $CH_2F$;
$R^2$ is $CH_3$ or $CH_2F$; and
each $R^3$, independently, is H, $CF_3$, $CH_3$, $CF_2H$ or $CH_2F$.

In embodiment C-B-2 of the invention, there are provided compounds, including stereoisomers and pharmaceutically acceptable salts thereof, of embodiment C-B and C-B-1, wherein $A^4$ is CH or CF;
$A^5$ is CH or N;
$A^6$ is CH;
$A^8$ is CH;
each $R^1$, independently, is H, F, $CF_3$, $CH_3$, $CF_2H$ or $CH_2F$;
$R^2$ is $CH_3$ or $CH_2F$; and
each $R^3$, independently, is H, $CF_3$, $CH_3$, $CF_2H$ or $CH_2F$.

In embodiment C-C of the invention, there are provided compounds, including stereoisomers and pharmaceutically acceptable salts thereof, of embodiments A, A-1 through A-7, A-9 through A-10, C, C-1 through C-6, C-8 through C-9, C-A through C-A-2 and C-B through C-B-2, having a formula III-C

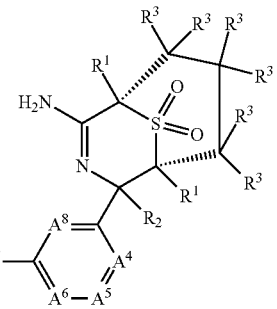

III-C wherein
$A^4$ is $CR^4$;
$A^5$ is $CR^5$ or N;
$A^6$ is $CR^6$;
$A^8$ is $CR^8$;
each $R^1$, independently, is H, F, Cl, $CF_3$, $CH_3$, $CH_2CH_3$, CN, $CH_2F$ or $CHF_2$;
$R^2$ is $CH_3$, $CH_2F$ or $CHF_2$;
each $R^3$, independently, is H, F, Cl, $CF_3$, $OCF_3$, $CH_3$, $CH_2CH_3$, CN, OH, $OCH_3$, $CH_2OCH_2F$ or $CH_2OCHF_2$;
each of $R^4$, $R^5$, $R^6$ and $R^8$, independently, is H, F, Cl, $CF_3$, $OCF_3$, $CH_3$, $CH_2CH_3$, CN, OH, $OCH_3$, $SCH_3$, $NHCH_3$ or $C(O)CH_3$;
$R^7$ is —NH—C(=O)—$R^9$ or

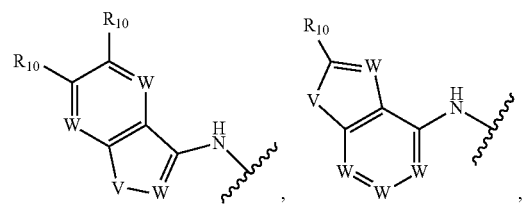

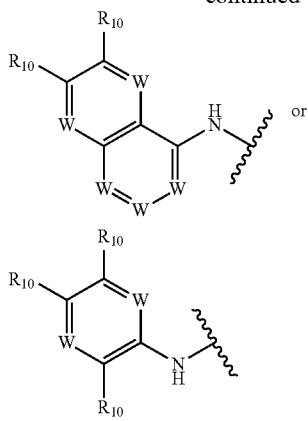

wherein V is NR$^{10}$, O or S; and each W, independently, is CH, CF, CCl or N;

R$^9$ is acetyl, C$_{1-6}$-alkyl, C$_{2-4}$alkenyl, C$_{2-4}$alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, imidazopyridyl, cyclopropyl, cyclobutyl, cyclopentyl and cyclohexyl, wherein the C$_{1-6}$-alkyl, C$_{2-4}$alkenyl, C$_{2-4}$alkynyl and ring are optionally substituted, independently, with 1-5 substituents of R$^{10}$; and each R$^{10}$, independently, is H, halo, haloalkyl, CN, OH, NO$_2$, NH$_2$, SF$_5$, acetyl, —C(O)NHCH$_3$, oxo, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO$_2$, NH$_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, C$_{1-3}$alkylamino-, C$_{1-3}$dialkylamino, C$_{1-3}$thioalkoxyl or oxetan-3yl.

In embodiment C-D of the invention, there are provided compounds, including stereoisomers and pharmaceutically acceptable salts thereof, of embodiments A, A-1 through A-7, A-9 through A-10, C, C-1 through C-6, C-8 through C-9, C-A through C-A-2 and BB through C-B-2, having a formula III-D

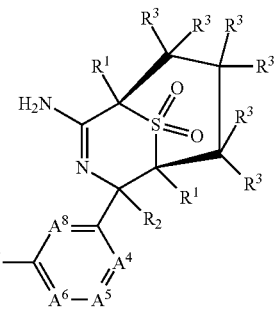

III-D wherein
A$^4$ is CR$^4$;
A$^5$ is CR$^5$ or N;
A$^6$ is CR$^6$;
A$^8$ is CR$^8$;
each R$^1$, independently, is H, F, Cl, CF$_3$, CH$_3$, CH$_2$CH$_3$, CN, CH$_2$F or CHF$_2$;
R$^2$ is CH$_3$, CH$_2$F or CHF$_2$;
each R$^3$, independently, is H, F, Cl, CF$_3$, OCF$_3$, CH$_3$, CH$_2$CH$_3$, CN, OH, OCH$_3$, CH$_2$OCH$_2$F or CH$_2$OCHF$_2$;
each of R$^4$, R$^5$, R$^6$ and R$^8$, independently, is H, F, Cl, CF$_3$, OCF$_3$, CH$_3$, CH$_2$CH$_3$, CN, OH, OCH$_3$, SCH$_3$, NHCH$_3$ or C(O)CH$_3$;
R$^7$ is —NH—C(=O)—R$^9$ or
wherein V is NR$^{10}$, O or S; and
each W, independently, is CH, CF, CCl or N;

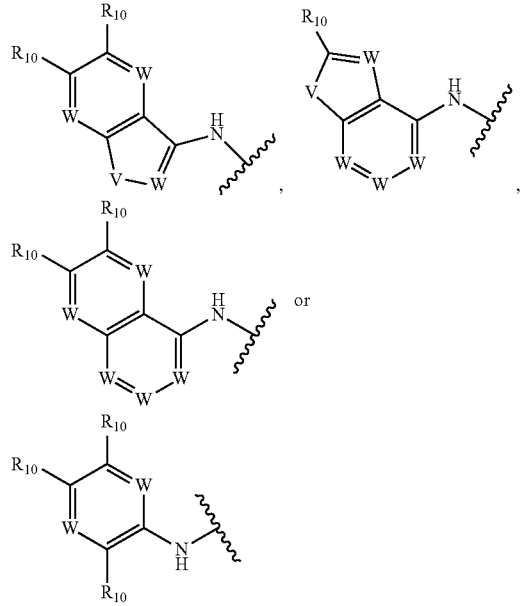

R$^9$ is acetyl, C$_{1-6}$-alkyl, C$_{2-4}$alkenyl, C$_{2-4}$alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, imidazopyridyl, cyclopropyl, cyclobutyl, cyclopentyl and cyclohexyl, wherein the $C_{1-6}$-alkyl, $C_{2-4}$alkenyl, $C_{2-4}$alkynyl and ring are optionally substituted, independently, with 1-5 substituents of $R^{10}$; and each $R^{10}$, independently, is H, halo, haloalkyl, CN, OH, $NO_2$, $NH_2$, $SF_5$, acetyl, —C(O)NHCH$_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or oxetan-3yl.

Similarly, the invention provides compounds of sub-formulas II-B-1 and II-B-2, respectively, as described below:

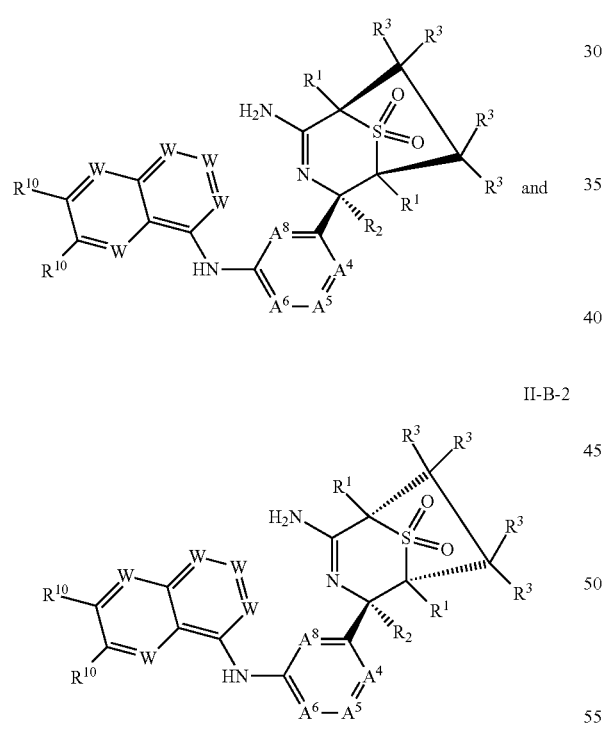

wherein each of the variables listed in II-A-1, II-A-2, II-B-1 and II-B-2, respectively, are as defined hereinabove and below with respect to Formulas II, II-A and II-B, individually or in conjunction with any of the above or below embodiments, including those described in embodiments A, A-1 to A-11, B, B-1 to B-10, B-A, B-A-1, B-A-2, B-B, B-B-1, B-B-2, B-C, B-D, B-E, D, D-1 to D-4, E, E-1 to E-8, F, F-1 to F-7, G, G-1 to G-3, H, H-1 to H-5, I, I-1 to I-5, J, J-1 to J-5, K, K-1 to K-5, L, L-1 to L-8, M, M-1 to M-9, N, N-1, O, P and P-1 to P-2 described herein.

Similarly, the invention provides compounds of sub-formulas III-A-1, III-A-2, III-B-1 and III-B-2, respectively, as described below.

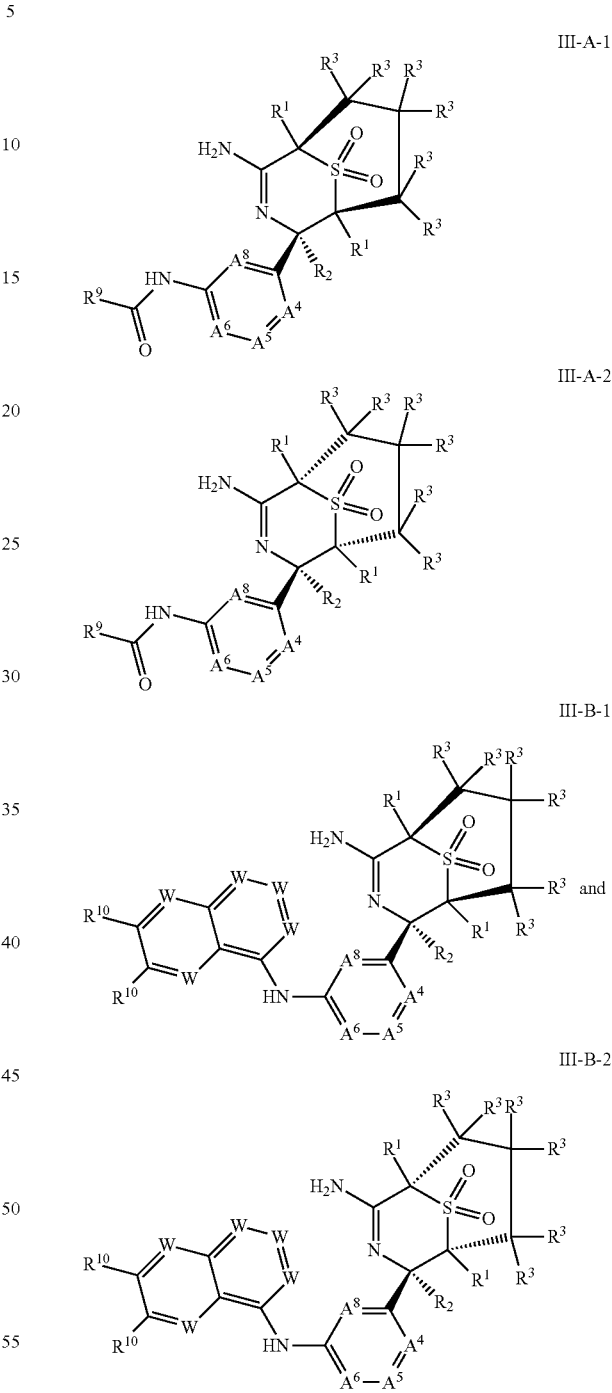

wherein each of the variables listed in III-A-1, III-A-2, III-B-1 and III-B-2, respectively, are as defined hereinabove and below with respect to Formulas III, III-A and III-B, individually or in conjunction with any of the above or below embodiments, including those described in embodiments A, A-1 to A-11, C, C-1 to C-9, C-A, C-A-1, C-A-2, C-B, C-B-1, C-B-2, C-C, C-D, C-E, D, D-1 to D-4, E, E-1 to E-8, F, F-1 to F-7, G, G-1 to G-3, H, H-1 to H-5, I, I-1 to I-5, J, J-1 to J-5, K, K-1 to K-5, L, L-1 to L-8, M, M-1 to M-9, N, N-1, O and Q-1 to Q-2 described herein.

The present invention contemplates that the various different embodiments of Formulas I, II and III, and sub-Formulas thereof, described herein, may comprise the following embodiments with respect to individual variables of $A^4$, $A^5$, $A^6$, $A^8$, $R^1$, $R^2$, $R^3$, $R^7$, $R^9$, $R^{10}$, V, W and o, where applicable, as described below. Hence, these embodiments with respect to individual variables $A^4$, $A^5$, $A^6$, $A^8$, $R^1$, $R^2$, $R^3$, $R^7$, $R^9$, $R^{10}$, V, W and o, where applicable, may be applied "in conjunction with any of the other {above and below}embodiments" to create various embodiments of general Formulas I, II and III, and each sub-formula thereof, which are not literally or identically described herein. More specifically, the term "in conjunction with any of the above or below embodiments" includes embodiments A, A-1 to A-10, B, B-1 to B-9, B-A, B-A-1, B-A-2, B-B, B-B-1, B-B-2, B-C, B-D, B-E, C, C-1 to C-9, C-A, C-A-1, C-A-2, C-B, C-B-1, C-B-2, C-C, C-D, C-E, D, D-1 to D-4, E, E-1 to E-8, F, F-1 to F-7, G, G-1 to G-3, H, H-1 to H-5, I, I-1 to I-5, J, J-1 to J-5, K, K-1 to K-5, L, L-1 to L-8, M, M-1 to M-9, N, N-1, O, P and P-1 to P-2 described herein, as it applies to general Formulas I, II and III, and sub-formulas thereof, also described herein (above and below).

In another embodiment D, the invention includes compounds of Formula I, wherein n is 0, 1 or 2, in conjunction with any of the above or below embodiments.

In another embodiment D-1, the invention includes compounds of Formula I, wherein n is 1 or 2, in conjunction with any of the above or below embodiments.

In another embodiment D-2, the invention includes compounds of Formula I, wherein n is 2, in conjunction with any of the above or below embodiments.

In another embodiment D-3, the invention includes compounds of Formula I, wherein n is 1, in conjunction with any of the above or below embodiments.

In another embodiment D-4, the invention includes compounds of Formula I, wherein n is 0, in conjunction with any of the above or below embodiments.

In another embodiment E, the invention includes compounds wherein each $R^1$, independently, is H, F, Cl, $C_{1-4}$alkyl, $CH_2OC_{1-4}$alkyl, cyclopropyl or CN, wherein the $C_{1-4}$alkyl and $CH_2OC_{1-4}$alkyl are optionally substituted with 1-3 substituents of F;

In another embodiment E-1, the invention includes compounds wherein each $R^1$, independently, is H, F, Cl, $CH_3$, $CH_2CH_3$, $CH_2OCH_3$, cyclopropyl or CN, wherein the $CH_3$, $CH_2CH_3$ and $CH_2OCH_3$ are optionally substituted with 1-3 substituents of F, in conjunction with any of the above or below embodiments.

In another embodiment E-2, the invention includes compounds wherein each $R^1$, independently, is H, F, $CH_2OCH_3$, $CH_2F$ or $CH_3$, in conjunction with any of the above or below embodiments.

In another embodiment E-3, the invention includes compounds wherein each $R^1$, independently, is H, F, Cl, $CF_3$, $CH_3$, $CH_2CH_3$, $CH_2OCH_3$, CN, $CH_2F$ or $CHF_2$, in conjunction with any of the above or below embodiments.

In another embodiment E-4, the invention includes compounds wherein one $R^1$ is $CH_3$, $CH_2OCH_3$ or $CH_2F$ and the other $R^1$ is H, in conjunction with any of the above or below embodiments.

In another embodiment E-5, the invention includes compounds wherein each $R^1$, independently, is $CH_2F$ in conjunction with any of the above or below embodiments.

In another embodiment E-6, the invention includes compounds wherein each $R^1$, independently, is $CH_3$, in conjunction with any of the above or below embodiments.

In another embodiment F, the invention includes compounds wherein $R^2$ is $C_{1-4}$alkyl, $CH_2OC_{1-4}$alkyl, $CH_2OH$, $CH_2CN$, $C_{3-6}$cycloalkyl or CN, wherein each of the $C_{1-4}$alkyl, $CH_2OC_{1-4}$alkyl and $C_{3-6}$cycloalkyl is optionally substituted with 1-4 substituents of F, in conjunction with any of the above or below embodiments.

In another embodiment F-1, the invention includes compounds wherein $R^2$ is $CH_3$, $CH_2F$ or $CHF_2$, in conjunction with any of the above or below embodiments.

In another embodiment F-2, the invention includes compounds wherein $R^2$ is $CH_3$ or $CH_2F$, in conjunction with any of the above or below embodiments.

In another embodiment F-3, the invention includes compounds wherein $R^2$ is $CH_3$, $CF_3$ or $CH_2F$, in conjunction with any of the above or below embodiments.

In another embodiment F-5, the invention includes compounds wherein $R^2$ is $CF_3$ or $CH_3$, in conjunction with any of the above or below embodiments.

In another embodiment F-6, the invention includes compounds wherein $R^2$ is $CH_3$, in conjunction with any of the above or below embodiments.

In another embodiment F-7, the invention includes compounds wherein $R^2$ is $CH_2F$, in conjunction with any of the above or below embodiments.

In another embodiment G, the invention includes compounds wherein each $R^3$, independently, is H, halo, $C_{1-4}$alkyl, $OC_{1-4}$alkyl, $CH_2OC_{1-4}$alkyl, $CH_2OH$, $C_{1-4}$haloalkyl, cyclopropyl or CN, wherein each of the $OC_{1-4}$alkyl, $CH_2OC_{1-4}$alkyl and cyclopropyl is optionally substituted with 1-4 substituents of F, in conjunction with any of the above or below embodiments.

In another embodiment G-1, the invention includes compounds wherein each $R^3$, independently, is H, F, Cl, $CF_3$, $OCF_3$, $CH_3$, $CH_2CH_3$, CN, OH, $OCH_3$, $CH_2OCH_2F$ or $CH_2OCHF_2$, in conjunction with any of the above or below embodiments.

In another embodiment G-2, the invention includes compounds wherein each $R^3$, independently, is H, F, $CH_3$, $C_2H_5$, $CH_2F$, $CF_2H$, $CF_3$ or $CH_2CF_3$, in conjunction with any of the above or below embodiments.

In another embodiment G-3, the invention includes compounds wherein each $R^3$, independently, is H or F, in conjunction with any of the above or below embodiments.

In another embodiment H, the invention includes compounds wherein $A^4$ is $CR^4$ wherein $R^4$ is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl, in conjunction with any of the above or below embodiments.

In another embodiment H-1, the invention includes compounds wherein $A^4$ is $CR^4$ wherein $R^4$ is H, F, Cl, $CF_3$, $OCF_3$, $CH_3$, $CH_2CH_3$, CN, OH, $OCH_3$, $SCH_3$, $NHCH_3$ or $C(O)CH_3$, in conjunction with any of the above or below embodiments.

In another embodiment H-2, the invention includes compounds wherein $A^4$ is $CR^4$ wherein $R^4$ is H, F, $CF_3$, $CF_2H$, $CH_2F$ or $CH_3$, in conjunction with any of the above or below embodiments.

In another embodiment H-3, the invention includes compounds wherein $A^4$ is $CR^4$ wherein $R^4$ is H or F, in conjunction with any of the above or below embodiments.

In another embodiment H-4, the invention includes compounds wherein $A^4$ is $CR^4$ wherein $R^4$ is F, in conjunction with any of the above or below embodiments.

In another embodiment I, the invention includes compounds wherein $A^5$ is $CR^5$ wherein $R^5$ is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl, in conjunction with any of the above or below embodiments.

In another embodiment I-1, the invention includes compounds wherein $A^5$ is $CR^5$ wherein $R^5$ is H, F, Cl, $CF_3$, $OCF_3$, $CH_3$, $CH_2CH_3$, CN, OH, $OCH_3$, $SCH_3$, $NHCH_3$ or $C(O)CH_3$, in conjunction with any of the above or below embodiments.

In another embodiment I-2, the invention includes compounds wherein $A^5$ is $CR^5$ wherein $R^5$ is H, F, $CF_3$, $CF_2H$, $CH_2F$ or $CH_3$, in conjunction with any of the above or below embodiments.

In another embodiment I-3, the invention includes compounds wherein $A^5$ is $CR^5$ wherein $R^5$ is H or F, in conjunction with any of the above or below embodiments.

In another embodiment I-4, the invention includes compounds wherein $A^5$ is $CR^5$ wherein $R^5$ is F, in conjunction with any of the above or below embodiments.

In another embodiment I-5, the invention includes compounds wherein $A^5$ is N, in conjunction with any of the above or below embodiments.

In another embodiment J, the invention includes compounds wherein $A^6$ is $CR^6$ wherein $R^6$ is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl, in conjunction with any of the above or below embodiments.

In another embodiment J-1, the invention includes compounds wherein $A^6$ is $CR^6$ wherein $R^6$ is H, F, Cl, $CF_3$, $OCF_3$, $CH_3$, $CH_2CH_3$, CN, OH, $OCH_3$, $SCH_3$, $NHCH_3$ or $C(O)CH_3$, in conjunction with any of the above or below embodiments.

In another embodiment J-2, the invention includes compounds wherein $A^6$ is $CR^6$ wherein $R^6$ is H, F, $CF_3$, $CF_2H$, $CH_2F$ or $CH_3$, in conjunction with any of the above or below embodiments.

In another embodiment J-3, the invention includes compounds wherein $A^6$ is $CR^6$ wherein $R^5$ is H or F, in conjunction with any of the above or below embodiments.

In another embodiment J-4, the invention includes compounds wherein $A^6$ is $CR^6$ wherein $R^6$ is F, in conjunction with any of the above or below embodiments.

In another embodiment J-5, the invention includes compounds wherein $A^6$ is N, in conjunction with any of the above or below embodiments.

In another embodiment K, the invention includes compounds wherein $A^8$ is $CR^8$ wherein $R^8$ is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl, in conjunction with any of the above or below embodiments.

In another embodiment K-1, the invention includes compounds wherein $A^8$ is $CR^8$ wherein $R^8$ is H, F, Cl, $CF_3$, $OCF_3$, $CH_3$, $CH_2CH_3$, CN, OH, $OCH_3$, $SCH_3$, $NHCH_3$ or $C(O)CH_3$, in conjunction with any of the above or below embodiments.

In another embodiment K-2, the invention includes compounds wherein $A^8$ is $CR^8$ wherein $R^8$ is H, F, $CF_3$, $CF_2H$, $CH_2F$ or $CH_3$, in conjunction with any of the above or below embodiments.

In another embodiment K-3, the invention includes compounds wherein $A^8$ is $CR^8$ wherein $R^8$ is H or F, in conjunction with any of the above or below embodiments.

In another embodiment K-4, the invention includes compounds wherein $A^8$ is $CR^8$ wherein $R^8$ is F, in conjunction with any of the above or below embodiments.

In another embodiment K-5, the invention includes compounds wherein $A^8$ is N, in conjunction with any of the above or below embodiments.

In another embodiment L, the invention includes compounds wherein no more than one of $A^4$, $A^5$, $A^6$ and $A^8$ is N, in conjunction with any of the above or below embodiments.

In another embodiment L-1, the invention includes compounds wherein no more than one of $A^5$ and $A^6$ is N, in conjunction with any of the above or below embodiments.

In another embodiment L-2, the invention includes compounds wherein $A^4$ is $CR^4$, $A^5$ is $CR^5$ or N, $A^6$ is $CR^6$ and $A^8$ is $CR^8$ or N, in conjunction with any of the above or below embodiments.

In another embodiment L-3, the invention includes compounds wherein $A^4$ is $CR^4$, $A^5$ is $CR^5$, $A^6$ is $CR^6$ and $A^8$ is $CR^8$, in conjunction with any of the above or below embodiments.

In another embodiment L-4, the invention includes compounds wherein $A^4$ is $CR^4$ or N;

$A^5$ is $CR^5$ or N;

$A^6$ is $CR^6$ or N;

$A^8$ is $CR^8$ or N, provided that no more than one of $A^4$, $A^5$, $A^6$ and $A^8$ is N; and each of $A^4$, $R^5$, $R^6$ and $R^8$, independently, is H, F, Cl, $CF_3$, $OCF_3$, $CH_3$, $CH_2CH_3$, CN, OH, $OCH_3$, $SCH_3$, $NHCH_3$ or $C(O)CH_3$, in conjunction with any of the above or below embodiments.

In another embodiment L-5, the invention includes compounds wherein $A^4$ is $CR^4$;

$A^5$ is $CR^5$;

$A^6$ is $CR^6$; and $A^8$ is $CR^8$; wherein each of $R^4$, $R^5$, $R^6$ and $R^8$, independently, is H, F, $CF_3$, $CF_2H$, $CH_2F$ or $CH_3$, in conjunction with any of the above or below embodiments.

In another embodiment L-6, the invention includes compounds wherein $A^4$ is $CR^4$; $A^5$ is $CR^5$ or N; $A^6$ is $CR^6$; and $A^8$ is $CR^8$, wherein each of $R^4$, $R^5$, $R^6$ and $R^8$, independently, is H, F, Cl, $CF_3$, $OCF_3$, $CH_3$, CN or $OCH_3$, in conjunction with any of the above or below embodiments.

In another embodiment L-7, the invention includes compounds wherein $A^4$ is CH or CF; $A^5$ is CH, CF or N; $A^6$ is CH or CF; and $A^8$ is CH or CF, in conjunction with any of the above or below embodiments.

In another embodiment L-8, the invention includes compounds wherein $A^4$ is CH or CF; $A^5$ is CH or N; $A^6$ is CH; and $A^8$ is CH, in conjunction with any of the above or below embodiments.

In another embodiment M-1, the invention includes compounds wherein $R^7$ is $-NH-R^9$, $-NH-C(=O)-R^9$ or

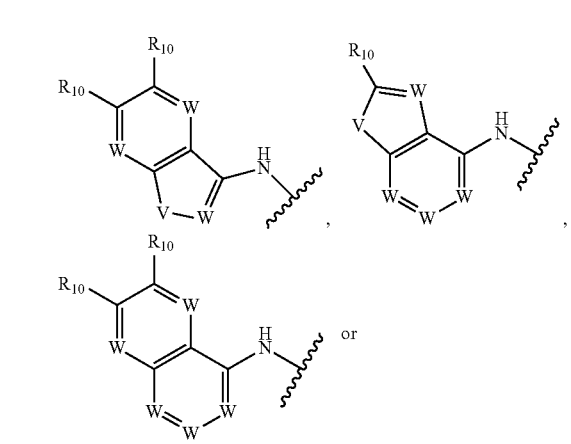

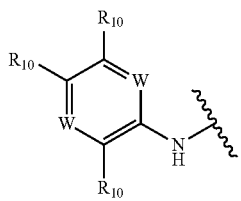

wherein V is NR¹⁰, O or S; and each W, independently, is CH, CF, CCl or N, in conjunction with any of the above or below embodiments.

In another embodiment M-2, the invention includes compounds wherein R⁷ is —NH—C(=O)—R⁹ or

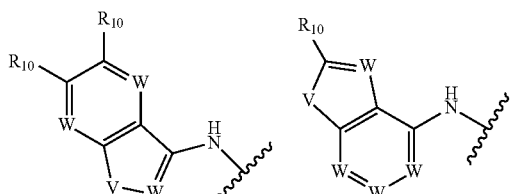

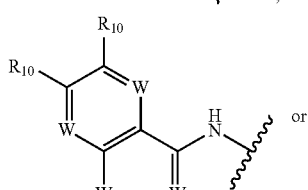
or

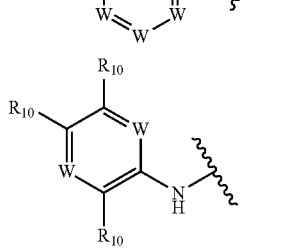

wherein V is NR¹⁰, O or S; and each W, independently, is CH, CF, CCl or N, in conjunction with any of the above or below embodiments.

In another embodiment M-3, the invention includes compounds wherein R⁷ is —NH—C(=O)—R⁹, in conjunction with any of the above or below embodiments.

In another embodiment M-4, the invention includes compounds wherein R⁷ is —NH—R⁹, in conjunction with any of the above or below embodiments.

In another embodiment M-5, the invention includes compounds wherein R⁷ is

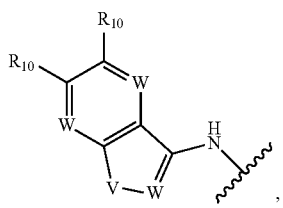

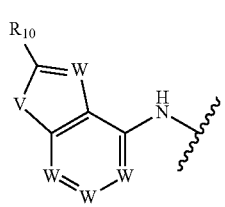 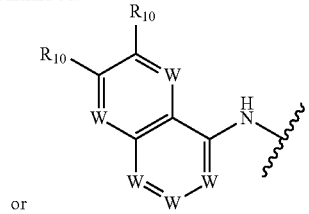
or wherein V is NR¹⁰, O or S; and each W, independently, is CH, CF, CCl or N, in conjunction with any of the above or below embodiments.

In another embodiment M-6, the invention includes compounds wherein R⁷ is selected from the group consisting of

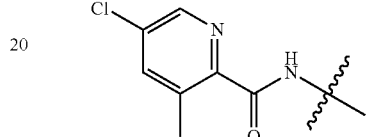

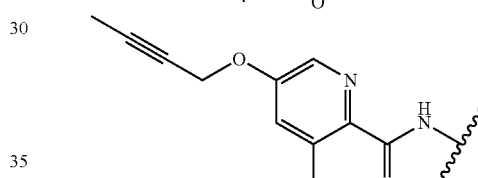

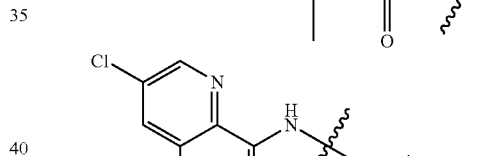
and in conjunction with any of the above or below embodiments.

In another embodiment M-8, the invention includes compounds wherein R⁷ is —NH—C(=O)—R⁹, wherein R⁹ is a fully or partially unsaturated 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of R¹⁰, in conjunction with any of the above or below embodiments.

In another embodiment N, the invention includes compounds wherein R⁹ is acetyl, $C_{1-6}$-alkyl, $C_{2-4}$alkenyl, $C_{2-4}$alkynyl or a fully or partially unsaturated 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$, in conjunction with any of the above or below embodiments.

In another embodiment N-1, the invention includes compounds wherein each $R^9$, independently, is a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, imidazo-pyridyl, cyclopropyl, cyclobutyl, cyclopentyl and cyclohexyl, wherein the $C_{1-6}$-alkyl, $C_{2-4}$alkenyl, $C_{2-4}$alkynyl and ring are optionally substituted, independently, with 1-5 substituents of $R^{10}$, in conjunction with any of the above or below embodiments.

In another embodiment O, the present invention provides compounds, and solvates, tautomers, hydrates, stereoisomers and pharmaceutically acceptable salts thereof, as defined by Formulas I, II, II-A to II-E, III-A to III-E, II-A-1, II-A-2, II-B-1, II-B-2, III-A-1, III-A-2, III-B-1 or III-B-2, wherein
$A^4$ is CH or CF;
$A^5$ is CH, CF or N;
$A^6$ is CH or CF;
$A^8$ is CH or CF;
one $R^1$ is H, F, Cl, $CF_3$, $CH_3$, $CF_2H$, $CH_2F$ or $CH_2OCH_3$ and the other $R^1$ is H;
$R^2$ is $CH_3$ or $CH_2F$; and
each $R^3$, independently, is H, $CF_3$, $CH_3$, $CF_2H$ or $CH_2F$, in conjunction with any of the above or below embodiments.

In another embodiment P, the present invention provides compounds, and solvates, tautomers, hydrates, stereoisomers and pharmaceutically acceptable salts thereof, as defined by Formulas I and II and each sub-Formula thereof, wherein
$R^7$ is —NH—C(=O)—$R^9$ or

[structure showing a bicyclic ring with $R_{10}$ substituents and W atoms, and an NH group]

wherein each W, independently, is CH, CF, CCl or N, in conjunction with any of the above or below embodiments.

In another embodiment P-1, the invention includes compounds of Formula II-A, II-B, II-C, II-D or II-E, or a sub-formula thereof, wherein
$A^4$ is CH or CF;
$A^5$ is CH, CF or N;
$A^6$ is CH or CF;
$A^8$ is CH or CF;
one $R^1$ is H, F, Cl, $CF_3$, $CH_3$, $CF_2H$, $CH_2F$ or $CH_2OCH_3$ and the other $R^1$ is H;
$R^2$ is $CH_3$ or $CH_2F$; and
each $R^3$, independently, is H, $CF_3$, $CH_3$, $CF_2H$ or $CH_2F$;
$R^9$ is a ring selected from phenyl, pyridyl, pyrimidyl, pyrazinyl, pyridazinyl, pyrazolyl, isoxazolyl, thiazolyl, furanyl, thienyl, pyrrolyl, wherein the ring is optionally substituted, independently, with 1-5 substituents of $R^{10}$; and
each $R^{10}$, independently, is H, halo, haloalkyl, CN, OH, $NO_2$, $NH_2$, $SF_5$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl, dioxolyl or —C(O)$NHCH_3$, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, isobutyl, sec-butyl, tert-butyl, $C_{1-3}$alkylamino-, $C_{1-3}$dialkylamino, $C_{1-3}$thioalkoxyl, oxetan-3yl or a ring selected from oxazolyl, isoxazolyl, pyrazolyl, thiazolyl, isothiazolyl or oxadiazolyl wherein the ring is optionally substituted independently with 1-5 substituents of F, Cl, CN or $CH_3$.

In embodiment P-2, the invention includes compounds of Formula II-A-a,

II-A-a

[chemical structure showing the II-A-a compound with $R^1$, $R^2$, $R^{10}$ substituents, $H_2N$, $SO_2$, and F groups]

wherein
$A^9$ is $CR^{10}$ or N;
$R^1$ is H, F, $CF_3$, $CH_3$, $CH_2CH_3$, $CH_2OCH_3$, $CH_2F$ or $CHF_2$;
R is $CH_3$, $CH_2F$ or $CHF_2$; and
each $R^{10}$, independently, is H, F, Cl, Br, CN, OH, $NO_2$, $NH_2$, acetyl, —C(O)$NHCH_3$, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy or 2-butynyloxy, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy or 2-butynyloxy, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, isobutyl, sec-butyl, tert-butyl, $C_{1-3}$alkylamino-, $C_{1-3}$dialkylamino, $C_{1-3}$thioalkoxyl, oxetan-3yl or a ring selected from oxazolyl, isoxazolyl, pyrazolyl, thiazolyl, isothiazolyl or oxadiazolyl wherein the ring is optionally substituted independently with 1-5 substituents of F, Cl, CN or $CH_3$.

In embodiment P-3, the invention includes compounds of embodiment P-2 wherein $A^9$ is CH or N; and $R^1$ is H, $CH_3$, $CH_2OCH_3$, $CH_2F$ or $CHF_2$.

In embodiment P-4, the invention includes compounds of Formula II-A-b,

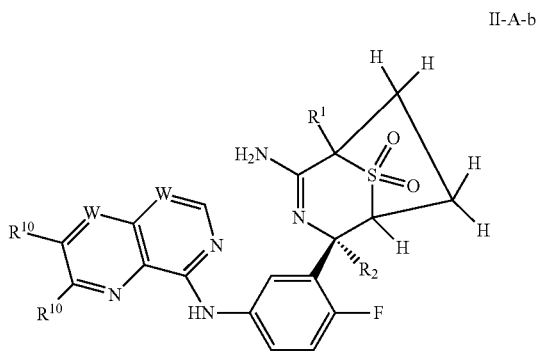

II-A-b wherein
$R^1$ is H, F, $CF_3$, $CH_3$, $CH_2CH_3$, $CH_2OCH_3$, $CH_2F$ or $CHF_2$;
R is $CH_3$, $CH_2F$ or $CHF_2$;
each W, independently, is CH, CF, CCl, $CCH_3$ or N; and
each $R^{10}$, independently, is H, F, Cl, Br, CN, OH, $NO_2$, $NH_2$, acetyl, —C(O)$NHCH_3$, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy or 2-butynyloxy, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy or 2-butynyloxy, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, isobutyl, sec-butyl, tert-butyl, $C_{1-3}$alkylamino-, $C_{1-3}$dialkylamino, $C_{1-3}$thioalkoxyl, oxetan-3yl or a ring selected from oxazolyl, isoxazolyl, pyrazolyl, thiazolyl, isothiazolyl or oxadiazolyl wherein the ring is optionally substituted independently with 1-5 substituents of F, Cl, CN or $CH_3$.

In embodiment P-5, the invention includes compounds of embodiment P-4 wherein each W is CH or N provided no more than one W is N; and one $R^{10}$ is H and the other $R^{10}$ is as defined in P-4.

All of the possible embodiments described herein for the various A, R, V, W, X and Y groups of the compounds of Formula I may be applied, as appropriate, to compounds of Formula II and any sub-formulas thereof, as well as to a compound of Formulas III-A, III-B, III-C and III-D.

In another embodiment, the invention provides each of the Exemplary compounds, and stereoisomers, tautomers, solvates, pharmaceutically acceptable salts, derivatives or prodrugs thereof, and related intermediates, described herein.

In another embodiment, the invention provides the exemplified compounds described herein, and pharmaceutically acceptable salt forms of each thereof.

In another embodiment, the invention provides one or more of the compounds, or a pharmaceutically acceptable salt thereof, of Formulas I, II and III, and sub-formulas thereof, as exemplified and/or specifically disclosed or described herein.

In another embodiment, the invention provides a compound of Formula I, II, II-A, II-B, II-C, II-C-1-A, II-C-1-B, II-C-2, II-C-3 or II-D, or a sub-Formula thereof, or a stereoisomer, tautomer or pharmaceutically acceptable salt thereof, selected from N-(3-((1R,2R,5S)-4-amino-2-methyl-8,8-dioxido-8-thia-3-azabicyclo[3.2.1]oct-3-en-2-yl)-4-fluorophenyl)-5-chloro-3-methyl-2-pyridinecarboxamide;

N-(3-((1S,2R,5R)-4-amino-2,5-dimethyl-8,8-dioxido-8-thia-3-azabicyclo[3.2.1]oct-3-en-2-yl)-4-fluorophenyl)-5-chloro-3-methyl-2-pyridinecarboxamide;

N-(3-((1R,2S,5S)-4-amino-2,5-dimethyl-8,8-dioxido-8-thia-3-azabicyclo[3.2.1]oct-3-en-2-yl)-4-fluorophenyl)-5-chloro-3-methyl-2-pyridinecarboxamide;

N-(3-((1S,2R,5R)-4-amino-2,5-dimethyl-8,8-dioxido-8-thia-3-azabicyclo[3.2.1]oct-3-en-2-yl)-4-fluorophenyl)-5-(difluoromethoxy)-3-methyl-2-pyridinecarboxamide;

N-(3-((1R,2R,5S)-4-amino-2,5-dimethyl-8,8-dioxido-8-thia-3-azabicyclo[3.2.1]oct-3-en-2-yl)-4-fluorophenyl)-5-chloro-3-methyl-2-pyridinecarboxamide;

N-(3-((1S,2R,5R)-4-amino-2,5-dimethyl-8,8-dioxido-8-thia-3-azabicyclo[3.2.1]oct-3-en-2-yl)-4-fluorophenyl)-3-methyl-5-(trifluoromethyl)-2-pyridinecarboxamide;

N-(3-((1S,2R,5R)-4-amino-2,5-dimethyl-8,8-dioxido-8-thia-3-azabicyclo[3.2.1]oct-3-en-2-yl)-4-fluorophenyl)-6-chloro-3-methylimidazo[1,2-a]pyridine-2-carboxamide;

N-(3-((1S,2R,5R)-4-amino-2,5-dimethyl-8,8-dioxido-8-thia-3-azabicyclo[3.2.1]oct-3-en-2-yl)-4-fluorophenyl)-3-chloro-5-fluoro-1,7-naphthyridin-8-amine;

N-(3-((1R,2R,5S)-4-amino-2,5-dimethyl-8,8-dioxido-8-thia-3-azabicyclo[3.2.1]oct-3-en-2-yl)-4-fluorophenyl)-6-chloro-3-methylimidazo[1,2-a]pyridine-2-carboxamide;

N-(3-((1R,2R,5S)-4-amino-2,5-dimethyl-8,8-dioxido-8-thia-3-azabicyclo[3.2.1]oct-3-en-2-yl)-4-fluorophenyl)-3-methyl-5-(trifluoromethyl)-2-pyridinecarboxamide;

N-(3-((1S,2R,5R)-4-amino-1,2,5-trimethyl-8,8-dioxido-8-thia-3-azabicyclo[3.2.1]oct-3-en-2-yl)-4-fluorophenyl)-5-chloro-3-methyl-2-pyridinecarboxamide;

N-(3-((1R,2R,5S)-4-amino-1,2,5-trimethyl-8,8-dioxido-8-thia-3-azabicyclo[3.2.1]oct-3-en-2-yl)-4-fluorophenyl)-5-chloro-3-methyl-2-pyridinecarboxamide;

N-(3-((1R,2R,5S)-4-amino-2,5-dimethyl-8,8-dioxido-8-thia-3-azabicyclo[3.2.1]oct-3-en-2-yl)-4-fluorophenyl)-3-chloro-5-fluoro-1,7-naphthyridin-8-amine;

N-(3-((1S,2R,5R)-4-amino-2,5-dimethyl-8,8-dioxido-8-thia-3-azabicyclo[3.2.1]oct-3-en-2-yl)-4-fluorophenyl)-5-fluoro-3-methoxy-1,7-naphthyridin-8-amine; and N-(3-((1S,2R,5R)-4-amino-2,5-dimethyl-8,8-dioxido-8-thia-3-azabicyclo[3.2.1]oct-3-en-2-yl)-4-fluorophenyl)-5-methoxy-2-pyrazinecarboxamide.

In another embodiment, the invention provides a compound of Formula I, II, II-A, II-B, II-C, II-C-1-A, II-C-1-B, II-C-2, II-C-3 or II-D, or a sub-Formula thereof, or a stereoisomer, tautomer or pharmaceutically acceptable salt thereof, selected from 4-((3-((1S,2R,5R)-4-amino-5-(fluoromethyl)-2-methyl-8,8-dioxido-8-thia-3-azabicyclo[3.2.1]oct-3-en-2-yl)-4-fluorophenyl)amino)pyrido[3,2-d]pyrimidine-7-carbonitrile;

N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-2-methoxypyrido[3,4-b]pyrazin-5-amine;

N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-methoxy-3-methyl-2-pyridinecarboxamide;

N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-(2-propyn-1-yloxy)-2-pyridinecarboxamide;

N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-3-methoxy-1,7-naphthyridin-8-amine;

N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-3-methyl-5-(2-propyn-1-yloxy)-2-pyrazinecarboxamide;

N-(3-((1S,2R,5R)-4-amino-2,5-dimethyl-8,8-dioxido-8-thia-3-azabicyclo[3.2.1]oct-3-en-2-yl)-4-fluorophenyl)-5-methoxy-2-pyrazinecarboxamide;

N-(3-((1S,2R,5R)-4-amino-2,5-dimethyl-8,8-dioxido-8-thia-3-azabicyclo[3.2.1]oct-3-en-2-yl)-4-fluorophenyl)-5-(1-propyn-1-yl)-2-pyridinecarboxamide;

N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-methoxy-3-methyl-2-pyrazinecarboxamide;

N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-chloro-2-pyridinecarboxamide;

N-(3-((1S,2R,5R)-4-amino-2,5-dimethyl-8,8-dioxido-8-thia-3-azabicyclo[3.2.1]oct-3-en-2-yl)-4-fluorophenyl)-5-fluoro-3-methoxy-1,7-naphthyridin-8-amine;

N-(3-((1S,2R,5R)-4-amino-2,5-dimethyl-8,8-dioxido-8-thia-3-azabicyclo[3.2.1]oct-3-en-2-yl)-4-fluorophenyl)-5-methoxy-3-methyl-2-pyrazinecarboxamide;

N-(3-((1S,2R,5R)-4-amino-2,5-dimethyl-8,8-dioxido-8-thia-3-azabicyclo[3.2.1]oct-3-en-2-yl)-4-fluorophenyl)-2-methoxypyrido[3,4-b]pyrazin-5-amine;

N-(3-((1S,2R,5R)-4-amino-2,5-dimethyl-8,8-dioxido-8-thia-3-azabicyclo[3.2.1]oct-3-en-2-yl)-4-fluorophenyl)-5-(2-butyn-1-yloxy)-2-pyrazinecarboxamide;

N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-chloro-3-methyl-2-pyridinecarboxamide;

N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-3-methyl-5-(trifluoromethyl)-2-pyridinecarboxamide;

N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-cyano-3-methyl-2-pyridinecarboxamide;

N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-7-methoxypyrido[3,2-d]pyrimidin-4-amine;

N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-7-chloropyrido[3,2-d]pyrimidin-4-amine;

8-((3-((1S,2R,5R)-4-amino-5-(fluoromethyl)-2-methyl-8,8-dioxido-8-thia-3-azabicyclo[3.2.1]oct-3-en-2-yl)-4-fluorophenyl)amino)-1,7-naphthyridine-3-carbonitrile;

N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-(difluoromethoxy)-3-methyl-2-pyridinecarboxamide;

N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-(difluoromethyl)-3-methyl-2-pyridinecarboxamide;

N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-2-(1,3-oxazol-2-ylmethoxy)pyrido[3,4-b]pyrazin-5-amine;

N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-3,5-dichloro-2-pyridinecarboxamide;

N-(3-((1S,2R,5R)-4-amino-2,5-dimethyl-8,8-dioxido-8-thia-3-azabicyclo[3.2.1]oct-3-en-2-yl)-4-fluorophenyl)-7-(trifluoromethyl)pyrido[3,2-d]pyrimidin-4-amine;

N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-7-(trifluoromethyl)pyrido[3,2-d]pyrimidin-4-amine;

N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-(difluoromethyl)-2-pyrazinecarboxamide;

N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-(trifluoromethyl)-2-pyridinecarboxamide;

N-(3-((1S,2R,5R)-4-amino-2,5-dimethyl-8,8-dioxido-8-thia-3-azabicyclo[3.2.1]oct-3-en-2-yl)-4-fluorophenyl)-7-methoxypyrido[3,2-d]pyrimidin-4-amine;

N-(3-((1S,2R,5R)-4-amino-2,5-dimethyl-8,8-dioxido-8-thia-3-azabicyclo[3.2.1]oct-3-en-2-yl)-4-fluorophenyl)-2-(1,3-oxazol-2-ylmethoxy)pyrido[3,4-b]pyrazin-5-amine; and N-(3-((1S,2R,5R)-4-amino-2,5-dimethyl-8,8-dioxido-8-thia-3-azabicyclo[3.2.1]oct-3-en-2-yl)-4-fluorophenyl)-2-((5-methyl-1,3-oxazol-2-yl)methoxy)pyrido[3,4-b]pyrazin-5-amine.

In another embodiment, the invention provides a compound of Formula I, III, III-A, III-B, III-C, III-D or III-E, or a sub-Formula thereof, or a stereoisomer, tautomer or pharmaceutically acceptable salt thereof, selected from N-(3-((1R,2R,5R)-4-amino-2-methyl-9,9-dioxido-9-thia-3-azabicyclo[3.3.1]non-3-en-2-yl)-4-fluorophenyl)-5-chloro-3-methyl-2-pyridinecarboxamide;

N-(3-((1R,2R,5R)-4-amino-2-methyl-9,9-dioxido-9-thia-3-azabicyclo[3.3.1]non-3-en-2-yl)-4-fluorophenyl)-5-(difluoromethoxy)-3-methyl-2-pyridinecarboxamide;

N-(3-((1S,2R,5S)-4-amino-2-methyl-9,9-dioxido-9-thia-3-azabicyclo[3.3.1]non-3-en-2-yl)-4-fluorophenyl)-5-chloro-3-methyl-2-pyridinecarboxamide;

N-(3-((1R,2R,5R)-4-amino-2-methyl-9,9-dioxido-9-thia-3-azabicyclo[3.3.1]non-3-en-2-yl)-4-fluorophenyl)-2-methoxypyrido[3,4-b]pyrazin-5-amine;

N-(3-((1S,2R,5R)-4-amino-2,5-dimethyl-9,9-dioxido-9-thia-3-azabicyclo[3.3.1]non-3-en-2-yl)-4-fluorophenyl)-2-methoxypyrido[3,4-b]pyrazin-5-amine;

N-(3-((1R,2R,5S)-4-amino-2,5-dimethyl-9,9-dioxido-9-thia-3-azabicyclo[3.3.1]non-3-en-2-yl)-4-fluorophenyl)-2-methoxypyrido[3,4-b]pyrazin-5-amine;

N-(3-((1S,2R,5R)-4-amino-2,5-dimethyl-9,9-dioxido-9-thia-3-azabicyclo[3.3.1]non-3-en-2-yl)-4-fluorophenyl)-5-chloro-3-methyl-2-pyridinecarboxamide;

N-(3-((1R,2R,5S)-4-amino-2,5-dimethyl-9,9-dioxido-9-thia-3-azabicyclo[3.3.1]non-3-en-2-yl)-4-fluorophenyl)-5-chloro-3-methyl-2-pyridinecarboxamide;

N-(3-((1S,2R,5R)-4-amino-2,5-dimethyl-9,9-dioxido-9-thia-3-azabicyclo[3.3.1]non-3-en-2-yl)-4-fluorophenyl)-5-(difluoromethoxy)-3-methyl-2-pyridinecarboxamide;

N-(3-((1R,2R,5S)-4-amino-2,5-dimethyl-9,9-dioxido-9-thia-3-azabicyclo[3.3.1]non-3-en-2-yl)-4-fluorophenyl)-5-(difluoromethoxy)-3-methyl-2-pyridinecarboxamide;

N-(3-((1S,2R,5R)-4-amino-1-fluoro-2,5-dimethyl-9,9-dioxido-9-thia-3-azabicyclo[3.3.1]non-3-en-2-yl)-4-fluorophenyl)-5-chloro-3-methyl-2-pyridinecarboxamide;

N-(3-((1S,2R,5R)-4-amino-1-fluoro-2,5-dimethyl-9,9-dioxido-9-thia-3-azabicyclo[3.3.1]non-3-en-2-yl)-4-fluorophenyl)-5-(difluoromethoxy)-3-methyl-2-pyridinecarboxamide;

N-(3-((1R,2R,5S)-4-amino-1-fluoro-2,5-dimethyl-9,9-dioxido-9-thia-3-azabicyclo[3.3.1]non-3-en-2-yl)-4-fluorophenyl)-5-chloro-3-methyl-2-pyridinecarboxamide;

N-(3-((1R,2R,5S)-4-amino-1-fluoro-2,5-dimethyl-9,9-dioxido-9-thia-3-azabicyclo[3.3.1]non-3-en-2-yl)-4-fluorophenyl)-5-(difluoromethoxy)-3-methyl-2-pyridinecarboxamide;

N-(3-((1S,2R,5R)-4-amino-1,2,5-trimethyl-9,9-dioxido-9-thia-3-azabicyclo[3.3.1]non-3-en-2-yl)-4-fluorophenyl)-5-chloro-3-methyl-2-pyridinecarboxamide;

N-(3-((1R,2R,5S)-4-amino-1,2,5-trimethyl-9,9-dioxido-9-thia-3-azabicyclo[3.3.1]non-3-en-2-yl)-4-fluorophenyl)-5-chloro-3-methyl-2-pyridinecarboxamide;

N-(3-((1S,2R,5R)-4-amino-1,2,5-trimethyl-9,9-dioxido-9-thia-3-azabicyclo[3.3.1]non-3-en-2-yl)-4-fluorophenyl)-5-(difluoromethoxy)-3-methyl-2-pyridinecarboxamide;

N-(3-((1R,2R,5S)-4-amino-1,2,5-trimethyl-9,9-dioxido-9-thia-3-azabicyclo[3.3.1]non-3-en-2-yl)-4-fluorophenyl)-5-(difluoromethoxy)-3-methyl-2-pyridinecarboxamide;

N-(3-((1S,2R,5R)-4-amino-1,2,5-trimethyl-9,9-dioxido-9-thia-3-azabicyclo[3.3.1]non-3-en-2-yl)-4-fluorophenyl)-5-methoxy-2-pyrazinecarboxamide; and N-(3-((1R,2R,5S)-4-amino-1,2,5-trimethyl-9,9-dioxido-9-thia-3-azabicyclo[3.3.1]non-3-en-2-yl)-4-fluorophenyl)-5-methoxy-2-pyrazinecarboxamide.

In another embodiment, the invention provides a compound of Formula I, or a stereoisomer, tautomer or pharmaceutically acceptable salt thereof, selected from

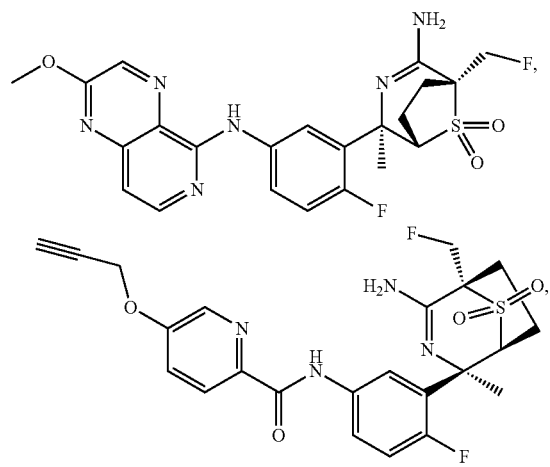

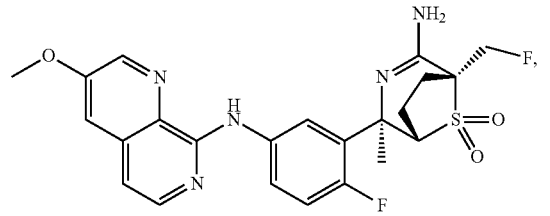

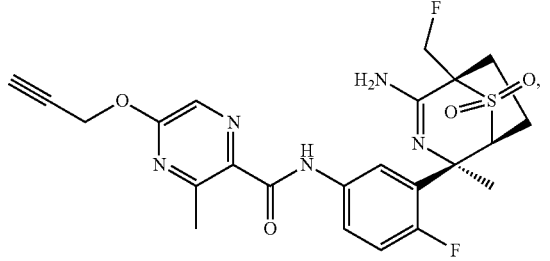

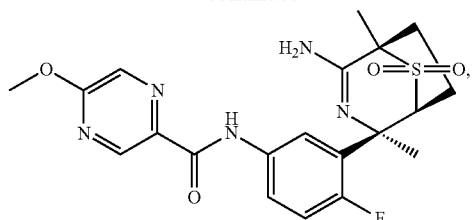

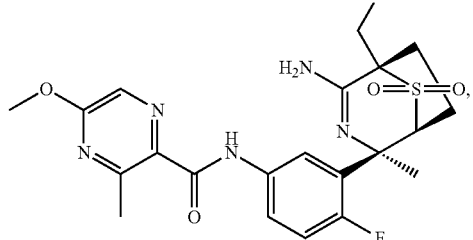

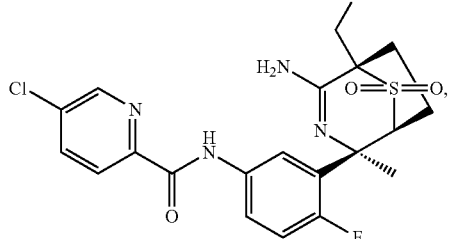

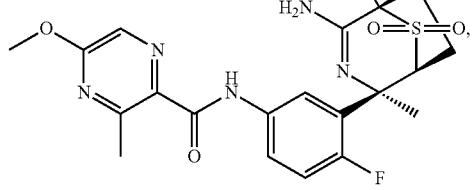

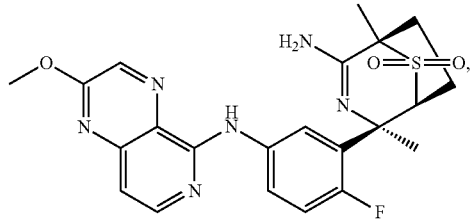

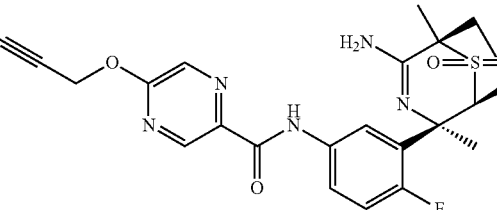

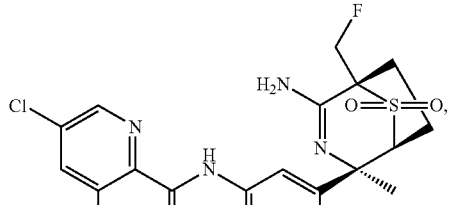

-continued

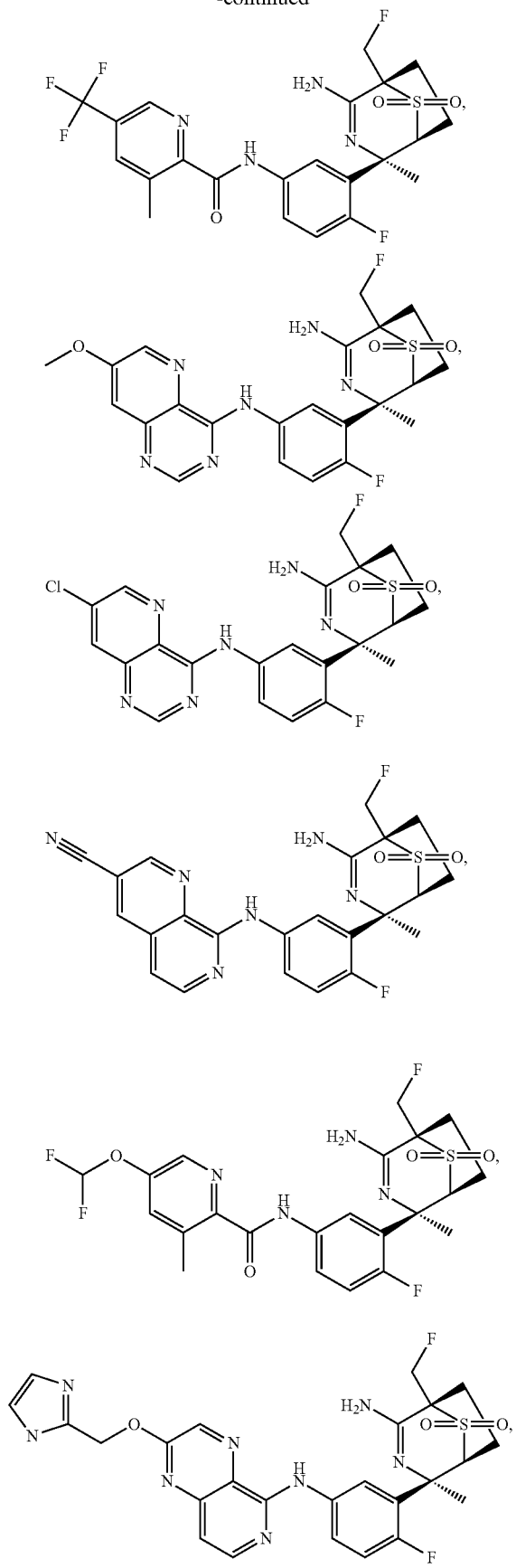

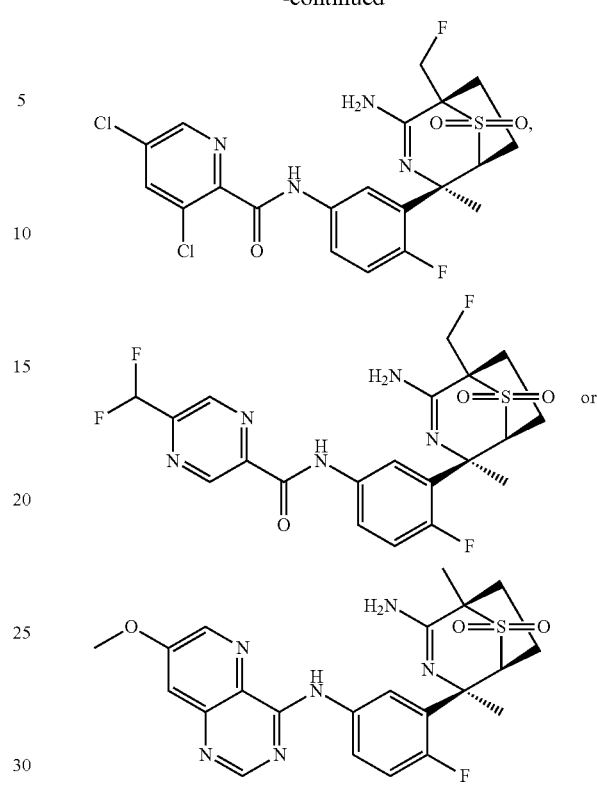

In another embodiment, the invention provides the compound, or a tautomer or pharmaceutically acceptable salt thereof, of

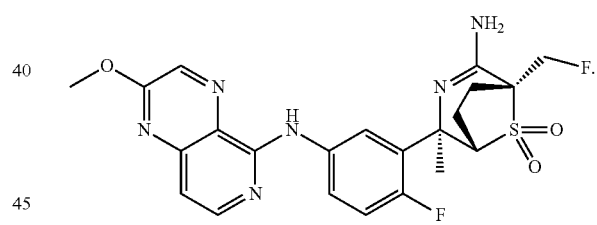

In another embodiment, the invention provides the compound, or a tautomer or pharmaceutically acceptable salt thereof, of

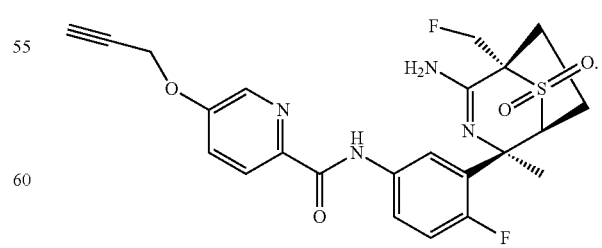

In another embodiment, the invention provides the compound, or a tautomer or pharmaceutically acceptable salt thereof, of In another embodiment, the invention provides the compound, or a tautomer or pharmaceutically acceptable salt thereof, of

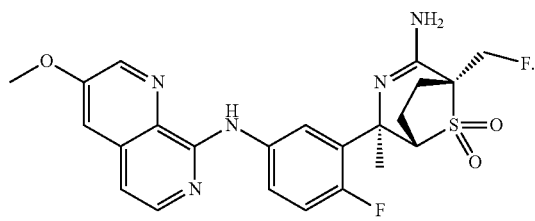 [SMILES: COc1cnc2c(Nc3ccc(F)c([C@@]4(C)N=C(N)[C@@]5(CF)CC[C@@H]4S5(=O)=O)c3)nccc2c1]

In another embodiment, the invention provides the compound, or a tautomer or pharmaceutically acceptable salt thereof, of

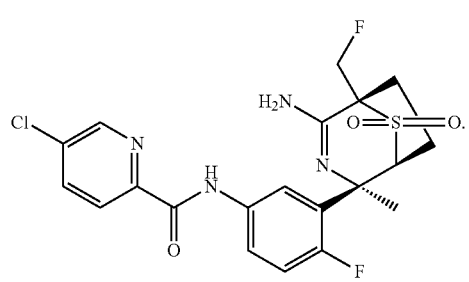

In another embodiment, the invention provides the compound, or a tautomer or pharmaceutically acceptable salt thereof, of

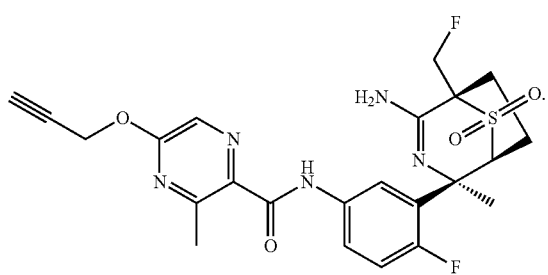 [SMILES: C#CCOc1cnc(C(=O)Nc2ccc(F)c([C@@]3(C)N=C(N)[C@@]4(CF)CC[C@@H]3S4(=O)=O)c2)c(C)n1]

In another embodiment, the invention provides the compound, or a tautomer or pharmaceutically acceptable salt thereof, of

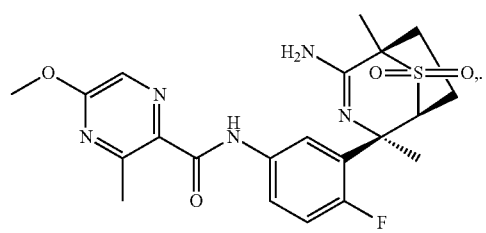

In another embodiment, the invention provides the compound, or a tautomer or pharmaceutically acceptable salt thereof, of

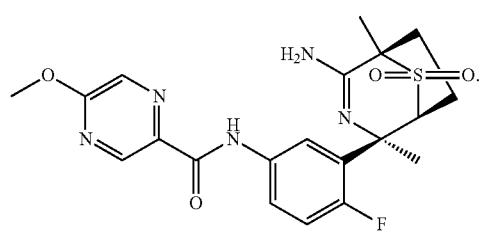 [SMILES: COc1cnc(C(=O)Nc2ccc(F)c([C@@]3(C)N=C(N)[C@@]4(C)CC[C@@H]3S4(=O)=O)c2)cn1]

In another embodiment, the invention provides the compound, or a tautomer or pharmaceutically acceptable salt thereof, of

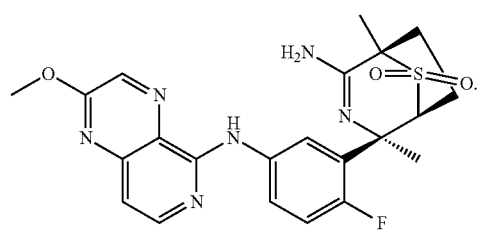

In another embodiment, the invention provides the compound, or a tautomer or pharmaceutically acceptable salt thereof, of

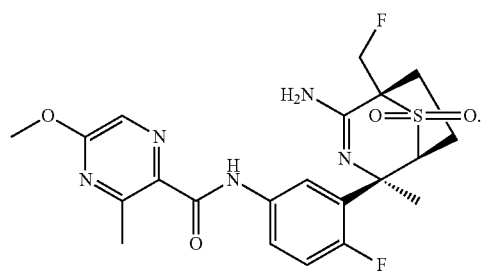 [SMILES: COc1cnc(C(=O)Nc2ccc(F)c([C@@]3(C)N=C(N)[C@@]4(CF)CC[C@@H]3S4(=O)=O)c2)c(C)n1]

In another embodiment, the invention provides the compound, or a tautomer or pharmaceutically acceptable salt thereof, of

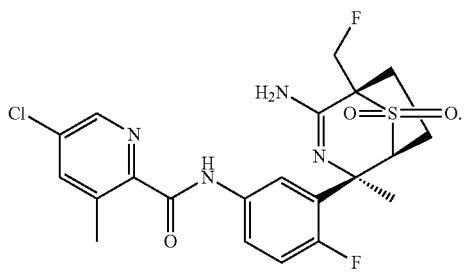 [SMILES: Cc1cc(Cl)cnc1C(=O)Nc1ccc(F)c([C@@]2(C)N=C(N)[C@@]3(CF)CC[C@@H]2S3(=O)=O)c1]

In another embodiment, the invention provides the compound, or a tautomer or pharmaceutically acceptable salt thereof, of

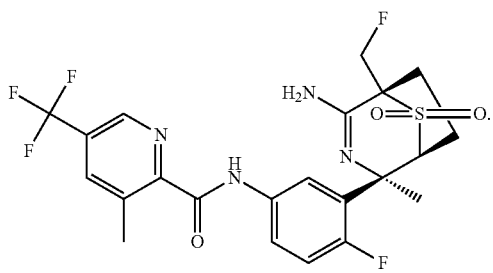 [SMILES: Cc1cc(C(F)(F)F)cnc1C(=O)Nc1ccc(F)c([C@@]2(C)N=C(N)[C@@]3(CF)CC[C@@H]2S3(=O)=O)c1]

In another embodiment, the invention provides the compound, or a tautomer or pharmaceutically acceptable salt thereof, of

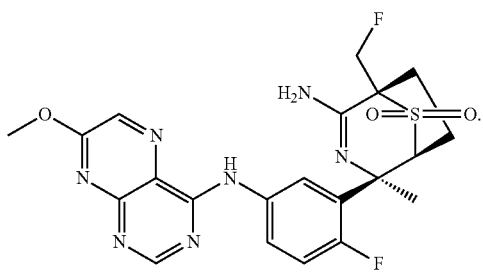 [SMILES: COc1cnc2c(Nc3ccc(F)c([C@@]4(C)N=C(N)[C@@]5(CF)CC[C@@H]4S5(=O)=O)c3)ncnc2n1]

In another embodiment, the invention provides the compound, or a tautomer or pharmaceutically acceptable salt thereof, of

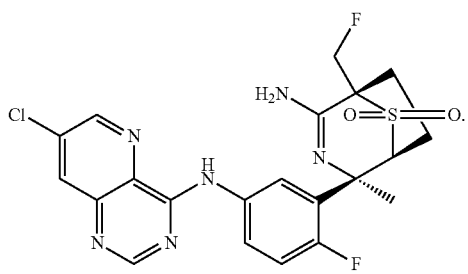 [SMILES: C[C@]1(c2cc(Nc3ncnc4cc(Cl)cnc34)ccc2F)N=C(N)[C@@]2(CF)CC[C@@H]1S2(=O)=O]

In another embodiment, the invention provides the compound, or a tautomer or pharmaceutically acceptable salt thereof, of In another embodiment, the invention provides the compound, or a tautomer or pharmaceutically acceptable salt thereof, of

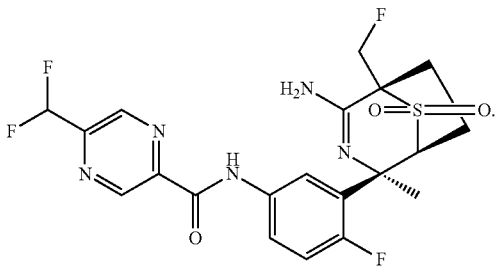 [SMILES: C[C@]1(c2cc(NC(=O)c3cnc(C(F)F)cn3)ccc2F)N=C(N)[C@@]2(CF)CC[C@@H]1S2(=O)=O]

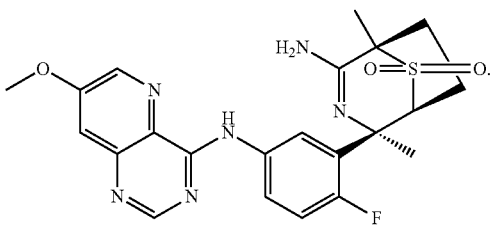 [SMILES: COc1cnc2c(Nc3ccc(F)c([C@@]4(C)N=C(N)[C@@]5(C)CC[C@@H]4S5(=O)=O)c3)ncnc2c1]

Definitions

The following definitions should assist in understanding the metes and bounds of the invention.

The term "A through A-10" with reference to embodiments is intended to mean the same as the term "A, A-1 through A-10", both terms of which are intended to encompass each embodiment listed therein, individually, beginning with embodiment A, and including each of embodiments A-1, A-2, A-3, A-4, A-5, A-6, A-7, A-8, A-9 and A-10. Similarly, language with respect to other embodiments, including embodiments B, C, etc. mean the same as with embodiment A.

The term "comprising" is meant to be open ended, i.e., all encompassing and non-limiting. It may be used herein synonymously with "having." Comprising is intended to include each and every indicated or recited component or element(s) while not excluding any other components or elements.

The term "$C_{\alpha\text{-}\beta}$alkyl", when used either alone or within other terms such as "haloalkyl" and "alkylamino", embraces linear or branched radicals having $\alpha$ to $\beta$ number of carbon atoms (such as $C_1$-$C_{10}$; $C_1$-$C_6$; or $C_1$-$C_4$). Unless otherwise specified, one or more carbon atoms of the "alkyl" radical may be substituted, such as with a cycloalkyl moiety. Examples of "alkyl" radicals include methyl, cyclopropylmethyl, cyclobutylmethyl, cyclopentylmethyl, ethyl, cyclopropylethyl, cyclobutylethyl, cyclopentylethyl, n-propyl, isopropyl, n-butyl, cyclopropylbutyl, isobutyl, sec-butyl, tert-butyl, pentyl, isoamyl, hexyl and the like.

The term "$C_{\alpha\text{-}\beta}$alkenyl", when used alone or in combination, embraces linear or branched radicals having at least one carbon-carbon double bond in a moiety having a number of carbon atoms in the range from $\alpha$ and $\beta$. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "$C_{\alpha\text{-}\beta}$alkynyl", when used alone or in combination, denotes linear or branched radicals having at least one carbon-carbon triple bond in a moiety having a number of carbon atoms in the range from $\alpha$ and $\beta$. Examples of alkynyl radicals include "lower alkynyl" radicals having two to about six carbon atoms and, for example, lower alkynyl radicals having two to about four carbon atoms. Examples of such radicals include, without limitation, ethynyl, propynyl (propargyl), butynyl, and the like.

The term "$C_{\alpha\text{-}\beta}$-alkyl", "$C_{\alpha\text{-}\beta}$-alkenyl" and "$C_{\alpha\text{-}\beta}$-alkynyl", when used with other terms such as "wherein 1, 2 or 3 carbon atoms of said $C_{\alpha\text{-}\beta}$-alkyl, $C_{\alpha\text{-}\beta}$-alkenyl or $C_{2\alpha\text{-}\beta}$-alkynyl is optionally replaced with a heteroatom selected from O, S, S(O), S(O)$_2$ and N" embraces linear or branched radicals wherein one or more of the carbon atoms may be replaced with a heteroatom. Examples of such "alkyl" radicals include —O-methyl, —O-ethyl, —CH$_2$—O—CH$_3$, —CH$_2$CH$_2$—O—CH$_3$, —NH—CH$_2$, —CH$_2$CH$_2$—N(CH$_3$)—CH$_3$, —S—(CH$_2$)$_3$CH$_2$, —CH$_2$CH$_2$—S—CH$_3$ and the like. Accordingly, such radicals also include radicals encompassed by —OR$^7$ where R$^7$ may be defined as a $C_{\alpha\text{-}\beta}$-alkyl. Examples of such "alkenyl" radicals include —NH—CH$_2$CH=CH$_2$, —S—CH$_2$CH$_2$CH=CHCH$_3$ and the like. Similar examples exist for such "alkynyl" radicals, as appreciated by those skilled in the art.

The term "$C_{\alpha\text{-}\beta}$alkoxyl" or "—OC$_{\alpha\text{-}\beta}$alkyl" when used alone or in combination, embraces linear or branched oxygen-containing alkyl radicals each having $\alpha$ to $\beta$ number of carbon atoms (such as $C_1$-$C_{10}$). The terms "alkoxy" and "alkoxyl", when used alone or in combination, embraces linear or branched oxygen-containing radicals each having alkyl and substituted alkyl portions of one or more carbon atoms. Examples of such radicals include methoxy, ethoxy, propoxy, butoxy, tert-butoxy and neopentoxy. Alkoxy radicals may be further substituted with one or more halo atoms, such as fluoro, chloro or bromo, to provide "haloalkoxy" radicals or with other substitution. Examples of such radicals include fluoromethoxy, chloromethoxy, trifluoromethoxy, trifluoroethoxy, fluoroethoxy and fluoropropoxy.

The term "aryl", when used alone or in combination, means a carbocyclic aromatic moiety containing one, two or even three rings wherein such rings may be attached together in a fused manner. Every ring of an "aryl" multi-ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. The "aryl" group may be substituted, such as with 1 to 5 substituents including lower alkyl, hydroxyl, halo, haloalkyl, nitro, cyano, alkoxy and lower alkylamino, and the like. Phenyl substituted with —O—CH$_2$—O— or —O—CH$_2$—CH$_2$—O— forms an aryl benzodioxolyl substituent.

The term "$C_{\alpha\text{-}\beta}$-cycloalkyl", also referred to herein as "carbocyclic", when used alone or in combination, denotes a partially or fully saturated ring radical having a number of carbon atoms in the range from $\alpha$ and $\beta$. The "cycloalkyl" may contain one ("monocyclic"), two ("bicyclic") or even three ("tricyclic") rings wherein such rings may be attached together in a fused manner and each formed from carbon atoms. Examples of saturated carbocyclic radicals include saturated 3 to 6-membered monocyclic groups such as cyclopropane, cyclobutane, cyclopentane and cyclohexane. Cycloalkyls may be substituted as described herein.

The terms "ring" and "ring system" refer to a ring comprising the delineated number of atoms, the atoms being carbon or, where indicated, a heteroatom such as nitrogen, oxygen or sulfur. Where the number of atoms is not delineated, such as a "monocyclic ring system" or a "bicyclic ring system", the numbers of atoms are 3-8 for a monocyclic and 6-12 for a bicyclic ring. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

The terms "partially or fully saturated or unsaturated" and "saturated or partially or fully unsaturated" with respect to each individual ring, refer to the ring either as fully aromatic (fully unsaturated), partially aromatic (or partially saturated) or fully saturated (containing no double or triple bonds therein). If not specified as such, then it is contemplated that each ring (monocyclic) in a ring system (if bicyclic or tricyclic) may either be fully aromatic, partially aromatic or fully saturated, and optionally substituted with up to 5 substituents. This includes carbocyclics, heterocyclics, aryl and heteroaryl rings.

The term "halo", when used alone or in combination, means halogens such as fluorine (F), chlorine (Cl), bromine (Br) or iodine (I) atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—, —O—S— or —S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, azaquinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The terms "heterocycle" or "heterocyclic", when used alone or in combination, means a partially or fully saturated ring moiety containing one, two or even three rings wherein such rings may be attached together in a fused manner, formed from carbon atoms and including one or more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocycle" also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and fully saturated heterocyclyls include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted" refers to a single ring of 3-, 4-, 5-, 6-, 7- or 8-atom membered or a 6-, 7-, 8-, 9-, 10-, 11 or 12-atom membered bicyclic ring system comprising the delineated number of atoms, the atoms being carbon or, where indicated, a heteroatom such as nitrogen (N), oxygen (O) or sulfur (S). Where the number of atoms is not delineated, such as a "monocyclic ring system" or a "bicyclic ring system", the numbers of atoms are 3-8 for a monocyclic and 6-12 for a bicyclic ring. The ring or ring system may contain substitutents thereon, attached at any atom that allows a stable compound to be formed. A bicyclic ring is intended to include fused ring systems as well as spiro-fused rings. This phrase encompasses carbocyclics, heterocyclics, aryl and heteroaryl rings.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N,N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The term "carbonyl", whether used alone or with other terms, such as "aminocarbonyl", denotes —(C=O)—. "Carbonyl" is also used herein synonymously with the term "oxo".

The term "alkylthio" or "thioalkoxy" embraces radicals containing a linear or branched alkyl radical, of one to ten carbon atoms, attached to a divalent sulfur atom. An example of "alkylthio" or "thioalkoxy" is methylthio, ($CH_3S$—).

The term "Formula I" includes any sub formulas, such as Formulas II and III. Similar with Formulas II and III, in that they include sub-formulas where described.

The term "pharmaceutically-acceptable" when used with reference to a compound of Formulas I-III is intended to refer to a form of the compound that is safe for administration. For example, a salt form, a solvate, a hydrate, a prodrug or derivative form of a compound of Formulas I-III, which has been approved for mammalian use, via oral ingestion or other routes of administration, by a governing body or regulatory agency, such as the Food and Drug Administration (FDA) of the United States, is pharmaceutically acceptable.

Included in the compounds of Formulas I-III are the pharmaceutically acceptable salt forms of the free-base compounds. The term "pharmaceutically-acceptable salts" embraces salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I-III may be prepared from an inorganic acid or from an organic acid. Examples of such inorganic acids are hydrochloric, hydrobromic, hydroiodic, hydrofluoric, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, 3-hydroxybutyric, salicylic, galactaric and galacturonic acid. Suitable pharmaceutically-acceptable base addition salts of compounds of Formulas I-III include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I-III.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Additional examples of such salts can be found in Berge et al., J. Pharm. Sci., 66:1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "pharmaceutically-acceptable derivative" as used herein, denotes a derivative which is pharmaceutically acceptable.

The compound(s) of Formulas I-III may be used to treat a subject by administering the compound(s) as a pharmaceutical composition. To this end, the compound(s) can be combined with one or more excipients, including without limitation, carriers, diluents or adjuvants to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies. Accordingly, this term is not limited to a single dose, but may comprise multiple dosages required to bring about a therapeutic or prophylactic response in the subject. For example, "effective dosage amount" is not limited to a single capsule or tablet, but may include more than one capsule or tablet, which is the dose prescribed by a qualified physician or medical care giver to the subject.

The term "leaving group" (also denoted as "LG") generally refers to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

GENERAL SYNTHETIC PROCEDURES

The present invention further comprises procedures for the preparation of compounds of Formulas I-III and sub-formulas thereof. The compounds of Formulas I-III, including sub-formulas thereof, can be synthesized according to the procedures described in the following Schemes 1a, 1b, 2, 3a and 3b, wherein the substituents are as defined for Formulas I-III above, except where further noted. The synthetic methods described below are merely exemplary, and the compounds of the invention may also be synthesized by alternate routes utilizing alternative synthetic strategies, as appreciated by persons of ordinary skill in the art.

The following list of abbreviations used throughout the specification represent the following and should assist in understanding the invention:
ACN, MeCN—acetonitrile
Aq., aq.—aqueous
Ar—argon (gas)
BOC—tert-butoxycarbonyl
BOP—benzotriazol-1-yl-oxy Hexafluorophosphate
BuLi—Butyllithium
$Cs_2CO_3$—cesium carbonate
$CHCl_3$—chloroform
$CH_2Cl_2$, DCM—dichloromethane, methylene chloride
Cu(1)I—copper(1) iodide DCC—dicyclohexylcarbodiimide
DEA—diethylamine
DIC—1,3-diisopropylcarbodiimide
DIEA, DIPEA—diisopropylethylamine
DME—dimethoxyethane
DMF—dimethylformamide
DMAP—4-dimethylaminopyridine
DMSO—dimethylsulfoxide
EDC, EDCI—1-(3-dimethylaminopropyl)-3-ethylcarbodiimide
$Et_2O$—diethyl ether
EtOAc—ethyl acetate
FC—flash (column) chromatography
g, gm—gram
h, hr—hour
$H_2$—hydrogen (gas)
$H_2O$—water
HATU—O-(7-azabenzotriazol-1-yl)-N,N,N',N'-tetramethyluroniumhexafluorophosphate
HBr—hydrobromic acid
HCl—hydrochloric acid
HOBt—1-hydroxybenzotriazole hydrate
HOAc—acetic acid
HPLC—high pressure liquid chromatography
IPA, IpOH—isopropyl alcohol
$K_2CO_3$—potassium carbonate
KI—potassium iodide
LG—leaving group
LDA—Lithium diisopropylamide
LiOH—lithium hydroxide
$MgSO_4$—magnesium sulfate
MS—mass spectrum
MeOH—methanol
$N_2$—nitrogen (gas)
$NaCNBH_3$—sodium cyanoborohydride
$Na_2CO_3$—sodium carbonate
$NaHCO_3$—sodium bicarbonate
NaH—sodium hydride
NaI—sodium iodide
$NaBH_4$—sodium borohydride
NaOH—sodium hydroxide
$Na_2SO_4$—sodium sulfate
$NH_4Cl$—ammonium chloride
$NH_4OH$—ammonium hydroxide
$P(t-bu)_3$—tri(tert-butyl)phosphine
$Ph_3P$—triphenylphosphine
Pd/C—palladium on carbon
$Pd(PPh_3)_4$—palladium(0)triphenylphosphine tetrakis
$Pd(dppf)Cl_2$—palladium(1,1-bisdiphenylphosphinoferrocene) II chloride
$Pd(PhCN)_2Cl_2$—palladium di-cyanophenyl dichloride
$Pd(OAc)_2$—palladium acetate
$Pd_2(dba)_3$—tris(dibenzylideneacetone)dipalladium
PyBop—benzotriazol-1-yl-oxy-tripyrrolidino-phosphonium hexafluorophosphate
RCM—ring-closing metathesis
RT, rt—room temperature
RBF, rbf—round bottom flask
TLC, tlc—thin layer chromatography
TBAF—Tetrabutylammonium fluoride
TBTU—O-benzotriazol-1-yl-N,N,N,N'-tetramethyluronium tetrafluoroborate
TEA, $Et_3N$—triethylamine
TFA—trifluoroacetic acid
THF—tetrahydrofuran
UV—ultraviolet light

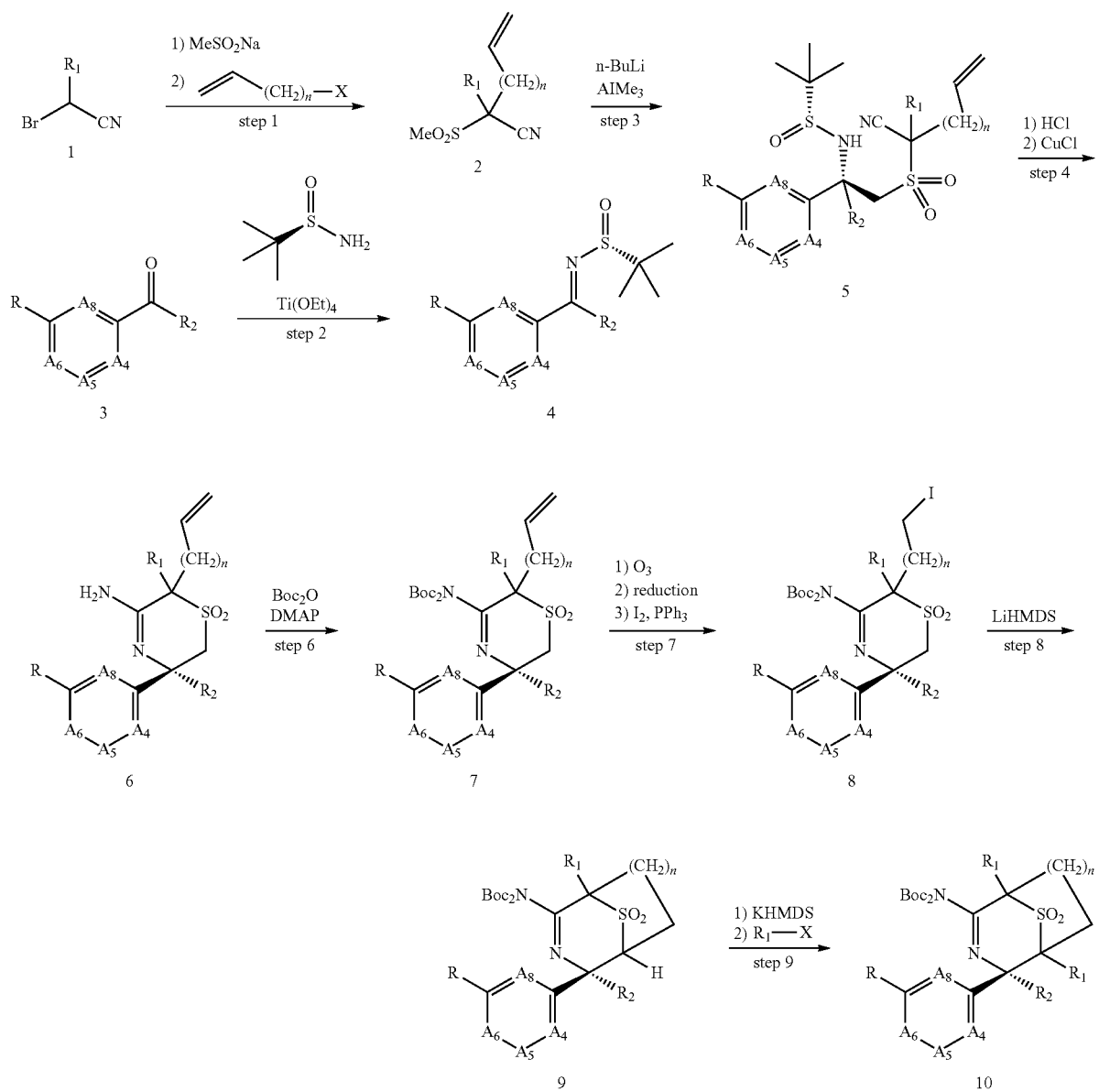

Scheme 1-A

Scheme 1-A describes an exemplary method for preparing intermediate 10, enroute to preparing compounds of Formulas I, II and III, wherein $R^7$ is designated as R above and n can be either 1 or 2. Beginning with starting material 1 (commercially purchased or prepared), one of ordinary skill in the art may react it with sodium methanesulfinate to afford the methylsulfonyl intermediate (not shown. This intermediate can then be treated with a desired halo-substituted olefin as shown, such as a bromo-butene for example, in the presence of an appropriate base, such as cesium carbonate or other suitable basem to provide the olefin adduct 2. In addition, intermediate 3 (may be commercially purchased or prepared by known methods in the literature) can be reacted with a suitable titanium reagent and t-butyl sulfonamide to provide intermediate 4 shown above. Intermediate 2 can be reacted with intermediate 4 in the presence of a suitably strong base, such as a lithium base and trimethyl aluminum to afford adduct 5. Ring closure product 6 of adduct 5 can be accomplished in the presence of a suitable acid, such as HCl, and a suitable catalyst, such as the copper catalyst shown above in scheme 1. The amine of intermediate 6 can be boc protected by conventional methods or as shown, to provide intermediate 7. The olefin group of boc-intermediate 7 can be ozonolylated and reduced, and converted to the corresponding iodine intermediate 8 as shown. Treatment of intermediate 8 with a strong base, such as the lithium hexamethyl disilazide base as whon, will afford the bridged ring closured adduct 9. The proton aalpha to the sulfonyl group can be deprotonated using a strong base, and the desired R1 group can be installed at this position to afford product 10 as shown in scheme 1. Additional methods of preparing intermediates can also be found in the intermediate experimentals 1-14 described hereinbelow.

Scheme 1-B

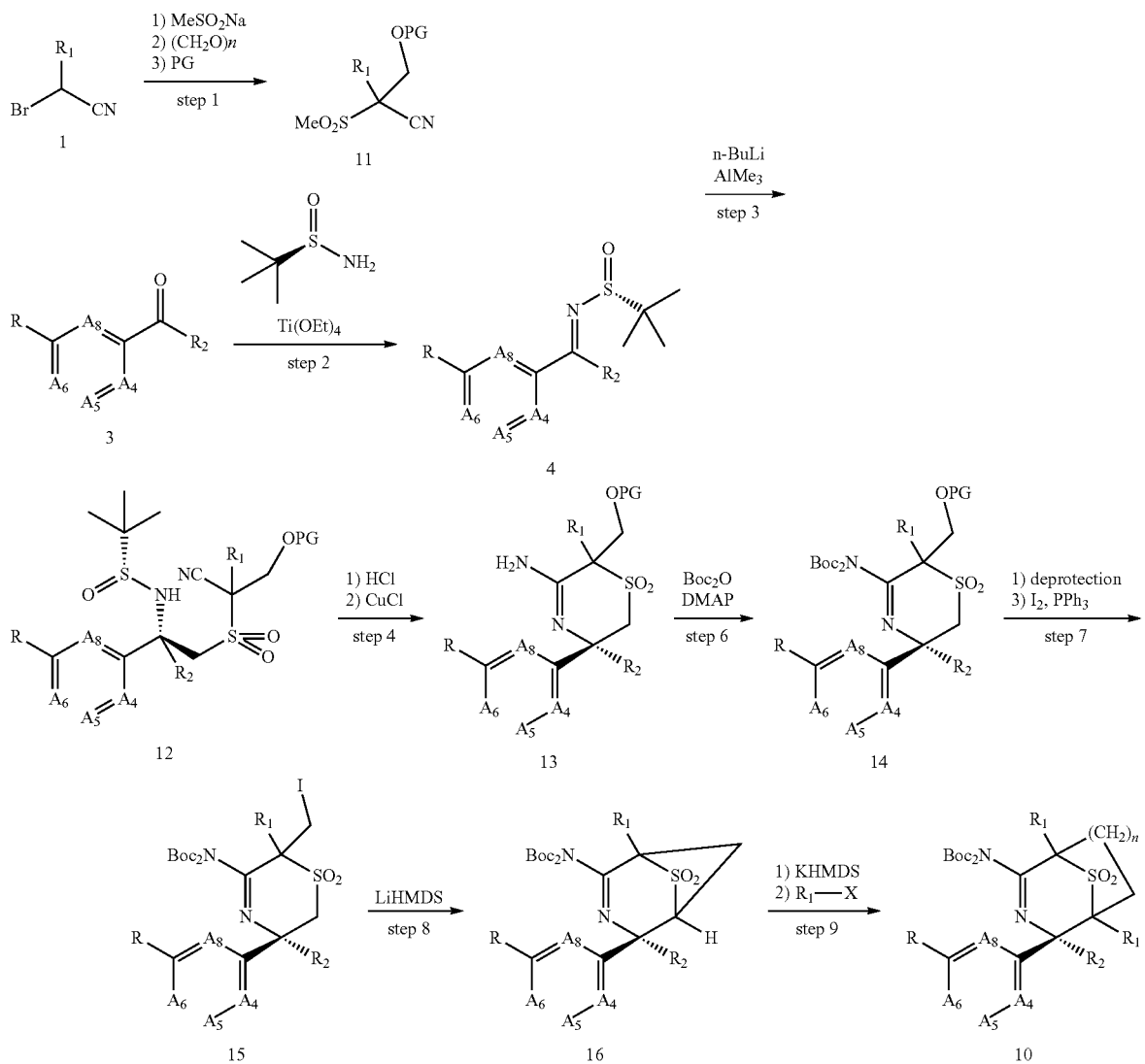

Scheme 1-B describes an exemplary, alternative method for preparing stereospecific, boc-protected compounds 10 of Formulas I, II and III, wherein $R^7$ is designated as R above and n can be either 1 or 2. Beginning with compound 1 (See Scheme 1 above) one of ordinary skill in the art may generate the corresponding OPG sulfone intermediate 12 via techniques and reagents such as those described in scheme 1 above, under suitable conditions. Similarly, intermediate 13 can be generated using conditions as described hereinabove in scheme 1 to close the ring. Ring closed intermediate 13 can be boc protected as shown in scheme 1, then boc-amino-intermediate 14 can be converted to the corresponding iodide 15 as shown, with a strong base, such as LiHMDS, under suitable conditions to effect ring closed intermediate 16 (the bridge of intermediate 16 is only one carbon. The present invention also includes bridges of 2 or 3 carbons, as taught herein). The desired $R^1$ group can be installed similar to that taught in scheme 1, to provide intermediate 10 above. Scheme 3 and 4 herein further reveal how one may prepared desired $R^7$-substituted compounds of Formulas I, II, III and sub-Formulas thereof.

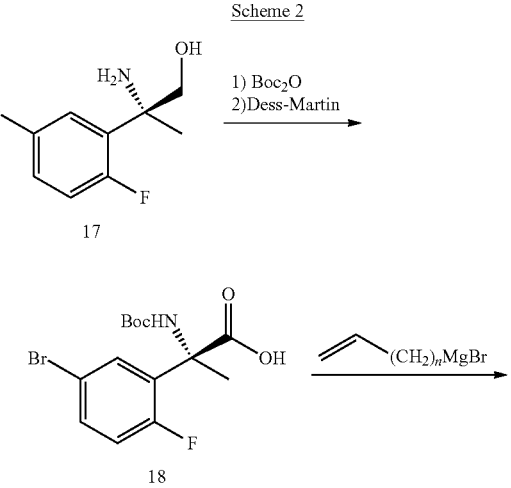

Scheme 2

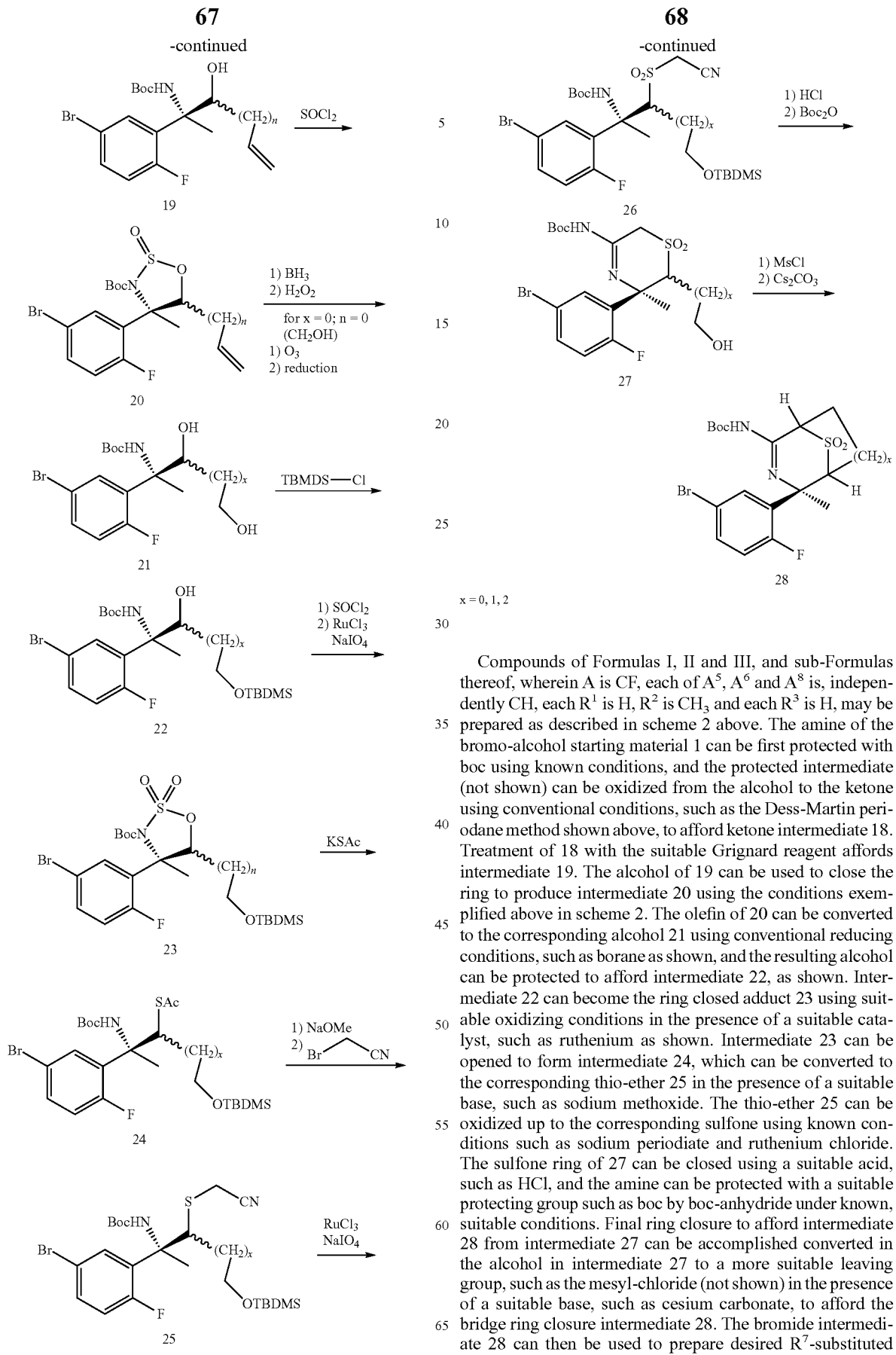

Compounds of Formulas I, II and III, and sub-Formulas thereof, wherein A is CF, each of $A^5$, $A^6$ and $A^8$ is, independently CH, each $R^1$ is H, $R^2$ is $CH_3$ and each $R^3$ is H, may be prepared as described in scheme 2 above. The amine of the bromo-alcohol starting material 1 can be first protected with boc using known conditions, and the protected intermediate (not shown) can be oxidized from the alcohol to the ketone using conventional conditions, such as the Dess-Martin periodane method shown above, to afford ketone intermediate 18. Treatment of 18 with the suitable Grignard reagent affords intermediate 19. The alcohol of 19 can be used to close the ring to produce intermediate 20 using the conditions exemplified above in scheme 2. The olefin of 20 can be converted to the corresponding alcohol 21 using conventional reducing conditions, such as borane as shown, and the resulting alcohol can be protected to afford intermediate 22, as shown. Intermediate 22 can become the ring closed adduct 23 using suitable oxidizing conditions in the presence of a suitable catalyst, such as ruthenium as shown. Intermediate 23 can be opened to form intermediate 24, which can be converted to the corresponding thio-ether 25 in the presence of a suitable base, such as sodium methoxide. The thio-ether 25 can be oxidized up to the corresponding sulfone using known conditions such as sodium periodiate and ruthenium chloride. The sulfone ring of 27 can be closed using a suitable acid, such as HCl, and the amine can be protected with a suitable protecting group such as boc by boc-anhydride under known, suitable conditions. Final ring closure to afford intermediate 28 from intermediate 27 can be accomplished converted in the alcohol in intermediate 27 to a more suitable leaving group, such as the mesyl-chloride (not shown) in the presence of a suitable base, such as cesium carbonate, to afford the bridge ring closure intermediate 28. The bromide intermediate 28 can then be used to prepare desired $R^7$-substituted compounds of Formulas I, II, III and sub-Formulas thereof, using methods known in the art, or by the techniques described hereinbelow in schemes 3 and 4.

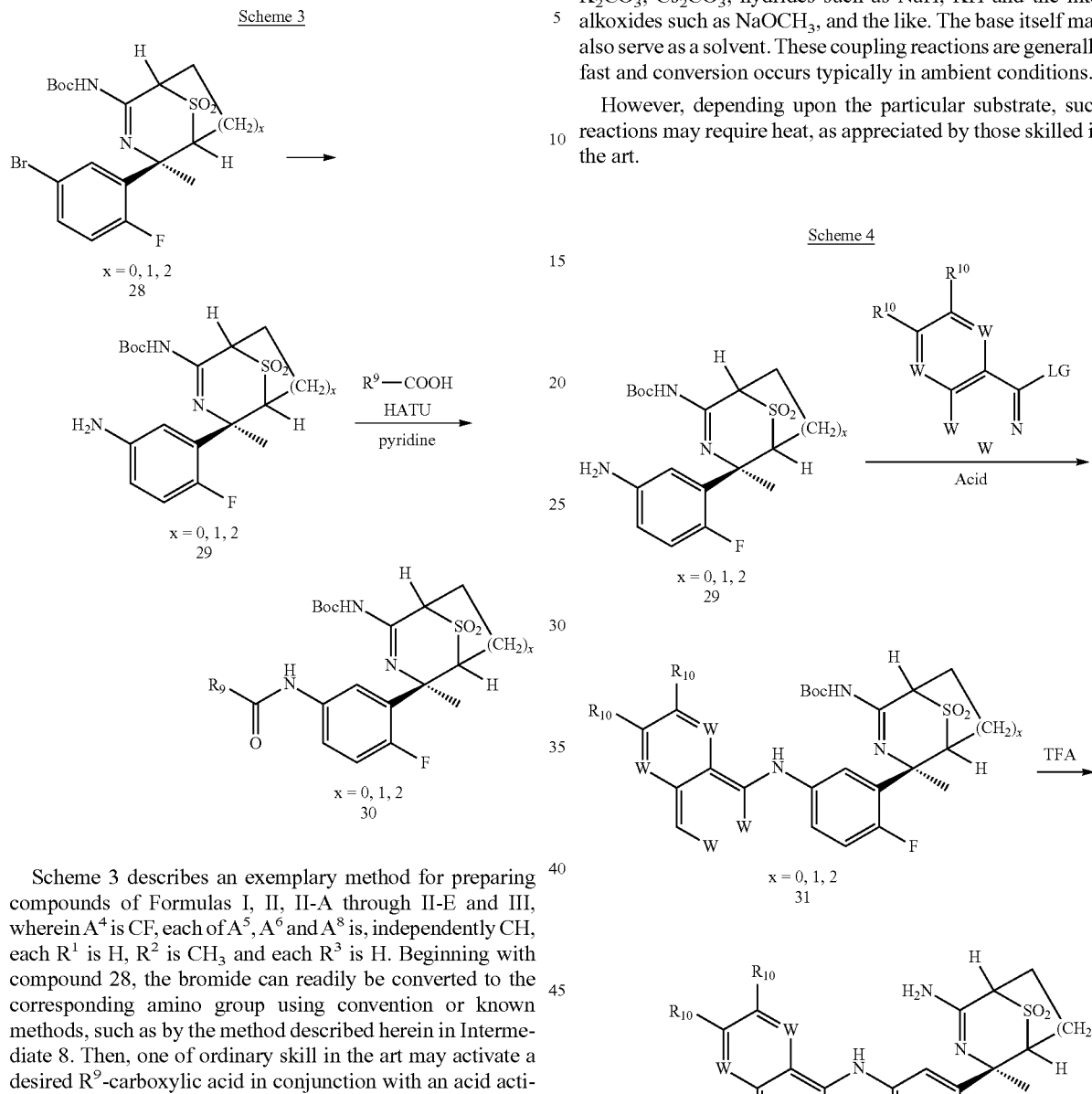

Scheme 3 describes an exemplary method for preparing compounds of Formulas I, II, II-A through II-E and III, wherein $A^4$ is CF, each of $A^5$, $A^6$ and $A^8$ is, independently CH, each $R^1$ is H, $R^2$ is $CH_3$ and each $R^3$ is H. Beginning with compound 28, the bromide can readily be converted to the corresponding amino group using convention or known methods, such as by the method described herein in Intermediate 8. Then, one of ordinary skill in the art may activate a desired $R^9$-carboxylic acid in conjunction with an acid activating reagent, such as HATU, DCC, TATU, DMTMM and the like known in the art and commonly used acid activating agents/reagents (see Example 3-28 and 32 described herein) and react it in the presence of amine 29 to afford the desired boc-protected amide-linked adduct 30. Compound 30 can be deprotected using known conditions (not shown), such as with an acid, like TFA, to afford final compounds of Formula I, II, II-A and III.

Acid activating agents convert the OH of the acid into a strong leaving group "LG." Suitable leaving groups include halides, such as an iodide, bromide, chloride or fluoride. The LG may also be a non-halide moiety such as an alkylsulfonate or other known groups which generally form an electrophilic species ($E^+$). Coupling reactions generally occur more readily in one or a combination of solvents and a base. Suitable solvents include, without limitation, generally non-nucleophilic, anhydrous solvents such as toluene, $CH_2Cl_2$, THF, DMF, N,N-dimethylacetamide, pyridine and the like. The solvent may range in polarity, as appreciated by those skilled in the art. Suitable bases include, for example, tertiary amine bases such as DIEA, TEA, carbonate bases such as $Na_2CO_3$, $K_2CO_3$, $Cs_2CO_3$, hydrides such as NaH, KH and the like, alkoxides such as $NaOCH_3$, and the like. The base itself may also serve as a solvent. These coupling reactions are generally fast and conversion occurs typically in ambient conditions.

However, depending upon the particular substrate, such reactions may require heat, as appreciated by those skilled in the art.

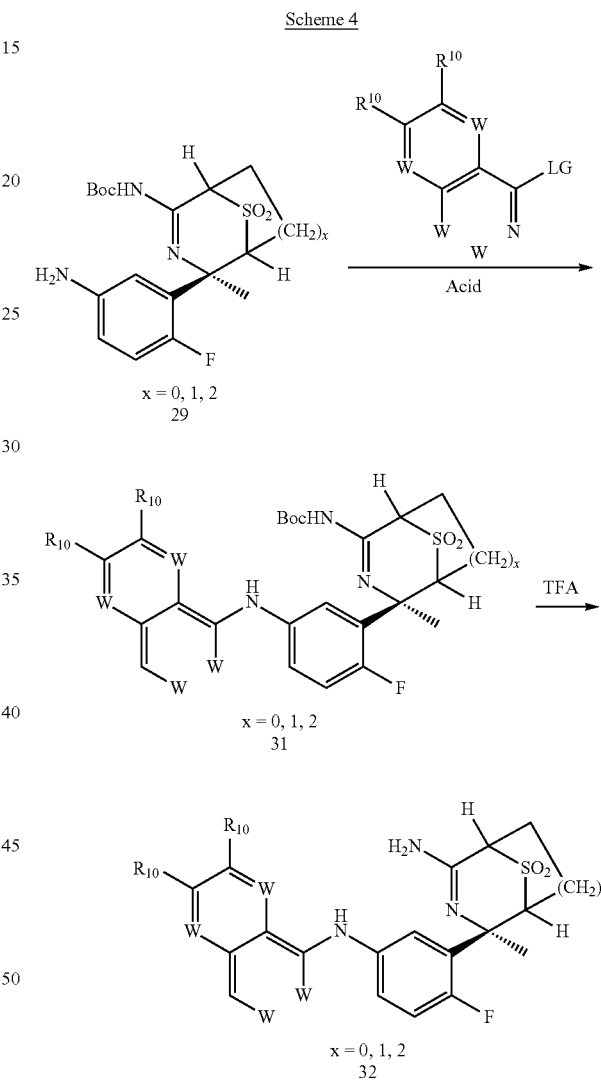

Similarly, and as shown in scheme 4, desired compounds 32 of Formulas I, II and III can be prepared by treatment from intermediate amine 29 (see scheme 3) with a desired bicyclic $R^9$ group having a suitable leaving group, such as a chloride (Cl) or other aromatic leaving group, in the presence of a suitable acid, such as in the presence of sulfuric acid. This allows coupling of the bicyclic heteroaromatic $R^9$ group to the amine to form boc-protected intermediate 31. Intermediate 31 can then be treated with acid, such as TFA, to afford the desired amine-linked compounds of Formulas I, II and III, and sub-formulas thereof.

EXAMPLES

The Examples, described herein below, represent various exemplary starting materials, intermediates and compounds of Formulas I-III, which should assist in a better understanding and appreciation of the scope of the present invention and of the various methods which may be used to synthesize compounds of Formulas I-III. It should be appreciated that the general methods above and specific examples below are illustrative only, for the purpose of assistance and of understanding the present invention, and should not be construed as limiting the scope of the present invention in any manner.

Chromatography:

Unless otherwise indicated, crude product-containing residues were purified by passing the crude material or concentrate through either a Biotage or Isco brand silica gel column (pre-packed or individually packed with SiO$_2$) and eluting the product off the column with a solvent gradient as indicated. For example a description of (330 g SiO$_2$, 0-40% EtOAc/Hexane) means the product was obtained by elution from the column packed with 330 gms of silica, with a solvent gradient of 0% to 40% EtOAc in Hexanes.

Preparative HPLC Method:

Where so indicated, the compounds described herein were purified via reverse phase HPLC using one of the following instruments: Shimadzu, Varian, Gilson; utilizing one of the following two HPLC columns: (a) a Phenomenex Luna or (b) a Gemini column (5 micron or 10 micron, C18, 150×50 mm)

A typical run through the instrument included: eluting at 45 ml/min with a linear gradient of 10% (v/v) to 100% MeCN (0.1% v/v TFA) in water (0.1% TFA) over 10 minutes; conditions can be varied to achieve optimal separations.

Proton NMR Spectra:

Unless otherwise indicated, all $^1$H NMR spectra were run on a Bruker series 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method (commonly referred to as an ESI MS) utilizing a PE SCIEX API 150EX MS instrument or an Agilent 1100 series LC/MSD system. Compounds having an isotopic atom, such as bromine and the like, are generally reported according to the detected isotopic pattern, as appreciated by those skilled in the art.

The compounds disclosed and described herein have been named using either (1) the naming convention provided with Chem-Draw Ultra 11.0 software, available in Chem Office, or (2) by the ISIS database software (Advanced Chemistry Design Labs or ACD software).

Intermediate 1

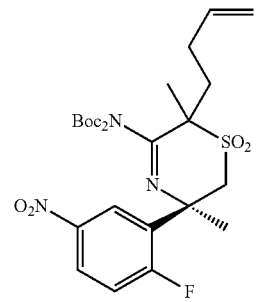

Synthesis of Imidodicarbonic acid, 2-[(5R)-2-(but-3-en-1-yl)-5-(2-fluoro-5-nitrophenyl)-2,5-dimethyl-1,1-dioxido-5,6-dihydro-2H-1,4-thiazin-3-yl]-, 1,3-bis(1,1-dimethylethyl) ester Step 1: (+/−)-2-(Methylsulfonyl)propanenitrile To a suspension of sodium methanesulfinate (8.44 g, 83 mmol) in DMF (127 mL) was added 2-bromopropionitrile (5.5 mL, 63.6 mmol). The reaction was stirred at 40° C. After 16 hours, the reaction mixture was diluted with water (1 L) and extracted with ethyl acetate. The combined organic layers were washed with water and brine and concentrated to provide the title compound (8.5 g, quantitative yield).

Step 2: (+/−)-2-Methyl-2-(methylsulfonyl)hex-5-enenitrile

To a solution of 2-(methylsulfonyl)propanenitrile (8.47 g, 63.6 mmol) in ACN (200 mL) was added cesium carbonate (26.9 g, 83 mmol) and 4-bromo-1-butene (7.75 mL, 76 mmol). The reaction was stirred at ambient temperature. After 16 hours, the reaction mixture was filtered to remove inorganic salts, concentrated, and partitioned between water and ethyl acetate. The organic layer was washed with water and brine, dried over anhydrous magnesium sulfate, filtered, and concentrated to provide the title compound (11.1 g, 93% yield).

Step 3: (R)—N-((2R)-1-((2-cyanohex-5-en-2-yl)sulfonyl)-2-(2-fluoro-5-nitrophenyl)propan-2-yl)-2-methylpropane-2-sulfinamide To a solution of 2-methyl-2-(methylsulfonyl)hex-5-enenitrile (9.91 g, 52.9 mmol) in THF (100 mL) at −78° C. was added a 2.8 N solution of n-buLi in heptane (18.76 mL, 52.9 mmol), and the mixture was stirred for 30 minutes at −78° C. Separately, a solution of (R,E)-N-(1-(2-fluoro-5-nitrophenyl)ethylidene)-2-methylpropane-2-sulfinamide (10.1 g, 35.3 mmol) in THF (76 mL) was stirred for 10 minutes at −78° C. and then added to the sulfone anion via cannula, and the reaction was stirred at −78° C. for 3 hours. After 3 hours, the reaction was quenched with the addition of saturated aqueous ammonium chloride and allowed to warm to RT. The reaction mixture was partitioned between water and ethyl acetate. The organic layer was concentrated and purified by column chromatography, eluting with 30-70% ethyl acetate in heptane, to provide the title compound as an approximately 1:1 mixture of diastereomers (8.17 g, 48.9% yield).

Step 4: (3R)-5-amino-6-(but-3-en-1-yl)-3-(2-fluoro-5-nitrophenyl)-3,6-dimethyl-3,6-dihydro-2H-1,4-thiazine 1,1-dioxide To a solution of (R)—N-((2R)-1-((2-cyanohex-5-en-2-yl)sulfonyl)-2-(2-fluoro-5-nitrophenyl)propan-2-yl)-2-methyl-propane-2-sulfinamide (8.17 g, 17.2 mmol) in ethanol (100 mL) was added 4 N HCl in 1,4-dioxane (12.9 mL, 51.8 mmol). The reaction was stirred at ambient temperature for 30 minutes, and then concentrated at reduced pressure to about half of the initial volume. To the reaction was added cuprous chloride (1.8 g, 18 mmol). The flask was sealed and stirred at 85° C. for two hours. The reaction mixture was concentrated, and the residue was resuspended in EtOH (100 mL) and stirred at 85° C. for another 3 hours. The reaction mixture was concentrated and partitioned between water and ethyl acetate; the aqueous layer was neutralized with saturated aqueous sodium bicarbonate and extracted with ethyl acetate. The combined organic layers were filtered through a pad of silica gel (eluting with ethyl acetate) and concentrated to provide the title compound as an approximately 1:1 mixture of diastereomers (7.24 g, quantitative yield).

Step 5: Imidodicarbonic acid, 2-[(5R)-2-(but-3-en-1-yl)-5-(2-fluoro-5-nitrophenyl)-2,5-dimethyl-1,1-dioxido-5,6-dihydro-2H-1,4-thiazin-3-yl]-, 1,3-bis(1,1-dimethylethyl) ester To a solution of (3R)-5-amino-6-(but-3-en-1-yl)-3-(2-fluoro-5-nitrophenyl)-3,6-dimethyl-3,6-dihydro-2H-1,4-thiazine 1,1-dioxide (6.4 g, 17.3 mmol) in DCM (87 mL) was added N,N-diisopropylethylamine (7.53 mL, 43.3 mmol), di-tert-butyl dicarbonate (9.45 g, 43.3 mmol), and N,N-dimethylpyridin-4-amine (1.27 g, 10.4 mmol). The reaction was stirred at ambient temperature for 16 hours, diluted with DCM, and washed with water (adjusted to pH-8 with HOAc). The resulting emulsion was filtered through Celite, and the organic layer was concentrated. The crude product was purified by column chromatography, eluting with 20-60% ethyl acetate in heptane, to provide the title compound as an approximately 1:1 mixture of diastereomers (6.8 g, 68.9% yield). LC/MS (ESI⁺) m/z=592.2 D (M+Na).

Intermediates 2A and 2B

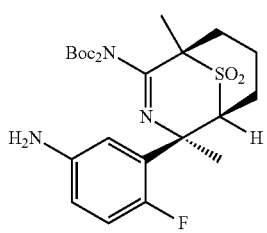

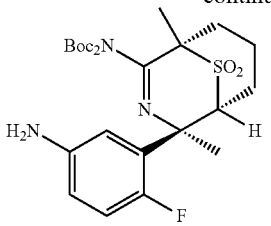

Synthesis of imidodicarbonic acid, 2-[(1R,4R,5S)-4-(5-amino-2-fluorophenyl)-1,4-dimethyl-9,9-dioxido-9-thia-3-azabicyclo[3.3.1]non-2-en-2-yl]-, 1,3-bis(1,1-dimethylethyl) ester and imidodicarbonic acid, 2-[(1S,4R,5R)-4-(5-amino-2-fluorophenyl)-1,4-dimethyl-9,9-dioxido-9-thia-3-azabicyclo[3.3.1]non-2-en-2-yl]-, 1,3-bis(1,1-dimethylethyl) ester Step 1: Imidodicarbonic acid, 2-[(5R)-5-(2-fluoro-5-nitrophenyl)-2-(3-hydroxypropyl)-2,5-dimethyl-1,1-dioxido-5,6-dihydro-2H-1,4-thiazin-3-yl]-, 1,3-bis(1,1-dimethylethyl) ester To a solution of Intermediate 1 (0.84 g, 1.475 mmol) in DCM (9.6 mL) and methanol (4.80 mL) was added sodium bicarbonate (0.248 g, 2.95 mmol), and the mixture was cooled to −78° C. Ozone was bubbled through the stirred reaction until the reaction mixture turned light blue, and then purged with nitrogen until the color dissipated. To the reaction was added sodium borohydride (0.112 g, 2.95 mmol), and the reaction was stirred at −78° C. for 15 minutes and then allowed to warm slowly to 0° C. After stirring at 0° C. for 30 minutes, the reaction was partitioned between water and DCM; the organic layer was dried over anhydrous magnesium sulfate, filtered, and concentrated to provide the title compound as an approximately 1:1 mixture of diastereomers (0.85 g, quantitative yield).

Step 2: Imidodicarbonic acid, 2-[(5R)-5-(2-fluoro-5-nitrophenyl)-2-(3-(4-methylbenzenesulfonyloxy)-propyl)-2,5-dimethyl-1,1-dioxido-5,6-dihydro-2H-1,4-thiazin-3-yl]-, 1,3-bis(1,1-dimethylethyl) ester To a solution of imidodicarbonic acid, 2-[((5R)-5-(2-fluoro-5-nitrophenyl)-2-(3-hydroxypropyl)-2,5-dimethyl-1,1-dioxido-5,6-dihydro-2H-1,4-thiazin-3-yl]-, 1,3-bis(1,1-dimethylethyl) ester (0.9 g, 1.569 mmol) in DCM (15 mL) was added triethylamine (0.262 mL, 1.88 mmol) and p-toluenesulfonyl chloride (0.329 g, 1.73 mmol). The reaction was stirred at RT. After 16 hours, 4-(N,N-dimethylamino)pyridine (0.019 g, 0.157 mmol) was added, and the reaction was stirred at ambient temperature for an additional six hours. The reaction mixture was washed with water and purified by column chromatography on silica gel, eluting with 20-80% ethyl acetate in heptane, to provide the title compound as a mixture of diastereomers (0.87 g, 1.195 mmol, 76% yield).

Step 3: Imidodicarbonic acid, 2-[(1R,4R,5S)-4-(5-nitro-2-fluorophenyl)-1,4-dimethyl-9,9-dioxido-9-thia-3-azabicyclo[3.3.1]non-2-en-2-yl]-, 1,3-bis(1,1-dimethylethyl) ester and imidodicarbonic acid, 2-[(1S,4R,5R)-4-(5-nitro-2-fluorophenyl)-1,4-dimethyl-9,9-dioxido-9-thia-3-azabicyclo[3.3.1]non-2-en-2-yl]-, 1,3-bis(1,1-dimethylethyl) ester To a −78° C. solution of imidodicarbonic acid, 2-[((5R)-5-(2-fluoro-5-nitrophenyl)-2-(3-(4-methylbenzenesulfonyloxy)-propyl)-2,5-dimethyl-1,1-dioxido-5,6-dihydro-2H-1,4-thiazin-3-yl]-, 1,3-bis(1,1-dimethylethyl) ester (0.87 g, 1.195 mmol) in THF (10 mL) was added a 1 N solution of potassium bis(trimethylsilyl)amide in THF (1.79 mL, 1.79 mmol). The reaction was stirred at −78° C. for one hour, quenched with the addition of saturated aqueous ammonium chloride, and warmed to ambient temperature. The reaction mixture was partitioned between water and ethyl acetate, and the crude product was purified by column chromatography on silica gel, eluting with 20-80% ethyl acetate in heptane, to provide the title compounds as a mixture of diastereomers (0.6 g, 90% yield).

Step 4: Imidodicarbonic acid, 2-[(1R,4R,5S)-4-(5-amino-2-fluorophenyl)-1,4-dimethyl-9,9-dioxido-9-thia-3-azabicyclo[3.3.1]non-2-en-2-yl]-, 1,3-bis(1,1-dimethylethyl) ester and imidodicarbonic acid, 2-[(1S,4R,5R)-4-(5-amino-2-fluorophenyl)-1,4-dimethyl-9,9-dioxido-9-thia-3-azabicyclo[3.3.1]non-2-en-2-yl]-, 1,3-bis(1,1-dimethylethyl) ester To a suspension of imidodicarbonic acid, 2-[(1R,4R,5S)-4-(5-nitro-2-fluorophenyl)-1,4-dimethyl-9,9-dioxido-9-thia-3-azabicyclo[3.3.1]non-2-en-2-yl]-, 1,3-bis(1,1-dimethylethyl) ester and imidodicarbonic acid, 2-[(1S,4R,5R)-4-(5-nitro-2-fluorophenyl)-1,4-dimethyl-9,9-dioxido-9-thia-3-azabicyclo[3.3.1]non-2-en-2-yl]-, 1,3-bis(1,1-dimethylethyl) ester (350 mg, 0.630 mmol) in THF (8 mL) was added 10 wt % palladium on carbon (134 mg, 0.126 mmol). A balloon filled with hydrogen was installed, and the reaction vessel was evacuated and backfilled with hydrogen twice. The reaction was stirred at ambient temperature under a hydrogen atmosphere. After 16 hours, the reaction mixture was diluted with THF and filtered through a Celite plug, which was washed with methanol. The filtrate was concentrated and purified by column chromatography on silica gel, eluting with 0-60% ethyl acetate in DCM, to provide the title compound (300 mg, 91% yield). LC/MS (ESI+) m/z=548.2 D (M+Na).

Intermediate 3

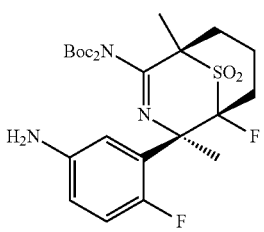

Synthesis of imidodicarbonic acid, 2-[(1R,4R,5S)-4-(5-amino-2-fluorophenyl)-5-fluoro-1,4-dimethyl-9,9-dioxido-9-thia-3-azabicyclo[3.3.1]non-2-en-2-yl]-, 1,3-bis(1,1-dimethylethyl) ester Step 1: Imidodicarbonic acid, 2-[(5R)-2-(but-3-en-1-yl)-6-fluoro-5-(2-fluoro-5-nitrophenyl)-2,5-dimethyl-1,1-dioxido-5,6-dihydro-2H-1,4-thiazin-3-yl]-, 1,3-bis(1,1-dimethylethyl) ester To a solution of Intermediate 1 (1.0 g, 1.76 mmol) in THF (11.7 mL) at −78° C. was added a 1.0-N solution of lithium bis(trimethylsilyl)amide in THF (1.84 mL, 1.84 mmol). The reaction was stirred at −78° C. for 50 minutes, and then a solution of N-fluorobenzenesulfonimide (0.664 g, 2.11 mmol) in THF (0.5 mL) was added. The reaction was stirred at −78° C. for 30 minutes, and then allowed to warm to ambient temperature. After 90 minutes, the reaction was quenched with saturated aqueous ammonium chloride and partitioned between water and ethyl acetate. The organic layer was concentrated and purified by column chromatography on silica gel, eluting with 20-60% ethyl acetate in heptane, to provide the title compound (0.89 g, 86% yield) as a mixture of diastereomers.

Step 2: Imidodicarbonic acid, 2-[(1R,4R,5S)-4-(5-amino-2-fluorophenyl)-5-fluoro-1,4-dimethyl-9,9-dioxido-9-thia-3-azabicyclo[3.3.1]non-2-en-2-yl]-, 1,3-bis(1,1-dimethylethyl) ester In a series of reactions analogous to those described in Intermediate 2, Steps 1-4, imidodicarbonic acid, 2-[(5R)-2-(but-3-en-1-yl)-6-fluoro-5-(2-fluoro-5-nitrophenyl)-2,5-dimethyl-1,1-dioxido-5,6-dihydro-2H-1,4-thiazin-3-yl]-, 1,3-bis(1,1-dimethylethyl) ester was converted to the title compound. LC/MS (ESI+) m/z=566.3 D (M+Na).

Intermediate 4

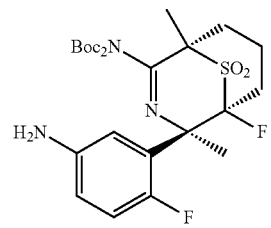

Synthesis of Imidodicarbonic acid, 2-[(1S,4R,5R)-4-(5-amino-2-fluorophenyl)-5-fluoro-1,4-dimethyl-9,9-dioxido-9-thia-3-azabicyclo[3.3.1]non-2-en-2-yl]-, 1,3-bis(1,1-dimethylethyl) ester Imidodicarbonic acid, 2-[(1S,4R,5R)-4-(5-amino-2-fluorophenyl)-5-fluoro-1,4-dimethyl-9,9-dioxido-9-thia-3-azabicyclo[3.3.1]non-2-en-2-yl]-, 1,3-bis(1,1-dimethylethyl) ester. The title compound was also isolated from the reaction described in Intermediate 3, Step 2. LC/MS (ESI+) m/z=566.2 D (M+Na).

Intermediates 5A and 5B

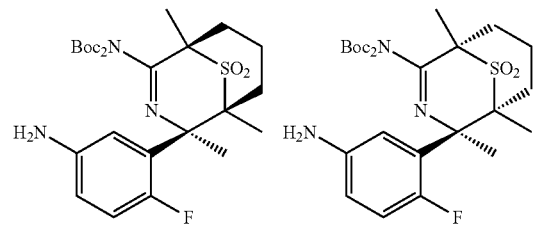

Synthesis of Imidodicarbonic acid, 2-[(1R,4R,5S)-4-(5-amino-2-fluorophenyl)-1,4,5-trimethyl-9,9-dioxido-9-thia-3-azabicyclo[3.3.1]non-2-en-2-yl]-, 1,3-bis(1,1-dimethylethyl) ester and imidodicarbonic acid, 2-[(1S,4R,5R)-4-(5-amino-2-fluorophenyl)-1,4,5-trimethyl-9,9-dioxido-9-thia-3-azabicyclo[3.3.1]non-2-en-2-yl]-, 1,3-bis(1,1-dimethylethyl) ester Step 1: Imidodicarbonic acid, 2-[(5R)-2-(but-3-en-1-yl)-5-(2-fluoro-5-nitrophenyl)-2,5,6-trimethyl-1,1-dioxido-5,6-dihydro-2H-1,4-thiazin-3-yl]-, 1,3-bis(1,1-dimethylethyl) ester To a solution of Intermediate 1 (1.0 g, 1.76 mmol) in THF (11.7 mL) was added a 1.0-N solution of lithium bis(trimethylsilyl)amide in THF (1.84 mL, 1.84 mmol). The reaction was stirred at −78° C. for 45 minutes, and then iodomethane (0.131 mL, 2.11 mmol) was added. The reaction was stirred at −78° C. for 30 minutes, and then allowed to warm to RT. After 1 hour, the reaction was quenched with saturated aqueous ammonium chloride and partitioned between water and ethyl acetate. The organic layer was concentrated and purified by column chromatography on silica gel, eluting with 20-60% EtOAc in heptane, to provide the title compound (1.02 g, 100% yield) as a mixture of diastereomers.

Step 2: Imidodicarbonic acid, 2-[(5R)-5-(2-fluoro-5-nitrophenyl)-2-(3-hydroxypropyl)-2,5,6-trimethyl-1,1-dioxido-5,6-dihydro-2H-1,4-thiazin-3-yl]-, 1,3-bis(1,1-dimethylethyl) ester In a sequence of reactions analogous to those described in Intermediate 2, Step 1, imidodicarbonic acid, 2-[(5R)-2-(but-3-en-1-yl)-5-(2-fluoro-5-nitrophenyl)-2,5,6-trimethyl-1,1-dioxido-5,6-dihydro-2H-1,4-thiazin-3-yl]-, 1,3-bis(1,1-dimethylethyl) ester was converted to the title compound in 96% yield.

Step 3: Imidodicarbonic acid, 2-[(5R)-5-(2-fluoro-5-nitrophenyl)-2-(3-iodopropyl)-2,5,6-trimethyl-1,1-dioxido-5,6-dihydro-2H-1,4-thiazin-3-yl]-, 1,3-bis(1,1-dimethylethyl) ester To a solution of imidazole (0.337 g, 4.95 mmol) and triphenylphosphine (0.520 g, 1.981 mmol) in DCM (8 mL) at 0° C. was added iodine (0.503 g, 1.981 mmol). The reaction was stirred at 0° C. for 2 minutes, and then a solution of imidodicarbonic acid, 2-[(5R)-5-(2-fluoro-5-nitrophenyl)-2-(3-hydroxypropyl)-2,5,6-trimethyl-1,1-dioxido-5,6-dihydro-2H-1,4-thiazin-3-yl]-, 1,3-bis(1,1-dimethylethyl) ester (0.97 g, 1.651 mmol) in DCM (1 mL) was added. The ice-bath was removed, and the reaction was allowed to warm to ambient temperature. After 20 minutes, the reaction was washed with saturated aqueous sodium bisulfite and concentrated. The crude product was purified by column chromatography on silica gel, eluting with 20-60% ethyl acetate in heptane, to provide the title compound (0.85 g, 73.8% yield) as a mixture of diastereomers.

Step 4: Imidodicarbonic acid, 2-[(1R,4R,5S)-4-(5-amino-2-fluorophenyl)-1,4,5-trimethyl-9,9-dioxido-9-thia-3-azabicyclo[3.3.1]non-2-en-2-yl]-, 1,3-bis(1,1-dimethylethyl) ester and imidodicarbonic acid, 2-[(1S,4R,5R)-4-(5-amino-2-fluorophenyl)-1,4,5-trimethyl-9,9-dioxido-9-thia-3-azabicyclo[3.3.1]non-2-en-2-yl]-, 1,3-bis(1,1-dimethylethyl) ester In a sequence of reactions analogous to those described in Intermediate 2, Step 3-4, imidodicarbonic acid, 2-[(5R)-5-(2-fluoro-5-nitrophenyl)-2-(3-iodopropyl)-2,5,6-trimethyl-1,1-dioxido-5,6-dihydro-2H-1,4-thiazin-3-yl]-, 1,3-bis(1,1-dimethylethyl) ester was converted to the title compounds. LC/MS (ESI$^+$) m/z=562.3 D (M+Na).

Intermediate 6

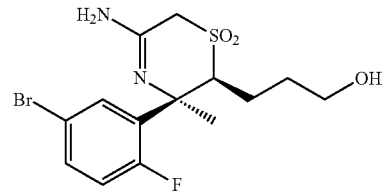 [SMILES: C[C@]1(c2cc(Br)ccc2F)N=C(N)CS(=O)(=O)[C@H]1CCCO]

Synthesis of (2S,3R)-5-Amino-3-(5-bromo-2-fluorophenyl)-2-(3-hydroxypropyl)-3-methyl-3,6-dihydro-2H-1,4-thiazine 1,1-dioxide Step 1: (R)-tert-Butyl (2-(5-bromo-2-fluorophenyl)-1-oxopropan-2-yl)carbamate To a solution of (R)-tert-butyl (2-(5-bromo-2-fluorophenyl)-1-hydroxypropan-2-yl)carbamate (18.6 g, 53.4 mmol) in DCM (200 mL) at 0° C. was added Dess-Martin periodinane (24.9 g, 58.8 mmol) portionwise. The mixture was stirred at 0° C. for 10 minutes and at ambient temperature for 90 minutes. After 90 minutes, the reaction was quenched with the addition of saturated aqueous sodium bicarbonate and saturated aqueous sodium bisulfite. Ether (50 mL) was added, and the reaction was stirred for 30 minutes at ambient temperature. The layers were separated, and the aqueous layer was extracted with ether. The combined organic layers were dried over anhydrous magnesium sulfate, filtered, and concentrated. The crude product was purified by column chromatography on silica gel, eluting with 20-80% ethyl acetate in heptane, to provide the title compound (14.6 g, 79% yield).

Step 2: tert-Butyl ((2R)-2-(5-bromo-2-fluorophenyl)-3-hydroxyhex-5-en-2-yl)carbamate To a solution of (R)-tert-butyl (2-(5-bromo-2-fluorophenyl)-1-oxopropan-2-yl)carbamate (8.8 g, 25.4 mmol) in THF (100 mL) at 0° C. was added a 2-N solution of allylmagnesium chloride in THF (25.4 mL, 50.8 mmol) dropwise. The mixture was stirred at 0° C. for 15 minutes and at RT for 30 minutes. After 30 minutes, the reaction mixture was concentrated and partitioned between water and ethyl acetate; the organic layer was washed with brine, dried over anhydrous magnesium sulfate, filtered, and concentrated to provide the title compound (9.6 g, 97% yield) as a mixture of diastereomers.

Step 3: (4R)-tert-Butyl 5-allyl-4-(5-bromo-2-fluorophenyl)-4-methyl-1,2,3-oxathiazolidine-3-carboxylate 2-oxide A solution of tert-butyl ((2R)-2-(5-bromo-2-fluorophenyl)-3-hydroxyhex-5-en-2-yl)carbamate (7.7 g, 19.8 mmol) in DCM (66 mL) was added dropwise to pre-cooled mixture of pyridine (8.09 mL, 99 mmol) and thionyl chloride (2.89 mL, 39.7 mmol) at 0° C. The mixture was allowed to warm to RT. After 2 hours, the reaction mixture was partitioned between water and DCM. The aqueous layer was extracted with DCM, and the combined organic layers were concentrated and purified by column chromatography on silica gel, eluting with 0-80% ethyl acetate in DCM, to provide the title compound (7.85 g, 91% yield) as a mixture of diastereomers.

Step 4: (4R)-tert-Butyl 4-(5-bromo-2-fluorophenyl)-5-(3-hydroxypropyl)-4-methyl-1,2,3-oxathiazolidine-3-carboxylate 2-oxide To a solution of (4R)-tert-butyl 5-allyl-4-(5-bromo-2-fluorophenyl)-4-methyl-1,2,3-oxathiazolidine-3-carboxylate 2-oxide (0.2 g, 0.46 mmol) in THF (2 mL) at 0° C. was added a 1-M solution of borane in THF (0.55 mL, 0.55 mmol). The mixture was allowed to warm to ambient temperature. After stirring for 2 hours, a 3 N aqueous solution of NaOH (0.92 mL, 2.8 mmol) and 30% hydrogen peroxide in water (0.28 mL, 2.8 mmol) were added dropwise. The reaction was stirred at ambient temperature for 2 hours, and then partitioned between water and ethyl acetate. The organic layer was concentrated, and the crude product was purified by column chromatography on silica gel, eluting with 0-100% ethyl acetate in DCM, to provide the title compound (2.8 g, 42.2% yield) as a mixture of diastereomers.

Step 5: tert-Butyl ((2R)-2-(5-bromo-2-fluorophenyl)-6-((tert-butyldimethylsilyl)oxy)-3-hydroxyhexan-2-yl)carbamate To a solution of (4R)-tert-butyl 4-(5-bromo-2-fluorophenyl)-5-(3-hydroxypropyl)-4-methyl-1,2,3-oxathiazolidine-3-carboxylate 2-oxide (84 mg, 0.207 mmol) and imidazole (15.48 mg, 0.227 mmol) in DCM (2 mL) was added tert-butyldimethylchlorosilane (0.227 mL, 0.227 mmol). The mixture was stirred at ambient temperature. After 1 hour, the reaction mixture was partitioned between ethyl acetate and saturated aqueous sodium bicarbonate. The organic layer was dried over anhydrous magnesium sulfate, filtered, and concentrated to provide the title compound (0.15 g, quantitative yield) as a mixture of diastereomers.

Step 6: (4R)-tert-Butyl 4-(5-bromo-2-fluorophenyl)-5-(3-((tert-butyldimethylsilyl)oxy)propyl)-4-methyl-1,2,3-oxathiazolidine-3-carboxylate 2,2-dioxide A solution of tert-butyl ((2R)-2-(5-bromo-2-fluorophenyl)-6-((tert-butyldimethylsilyl)oxy)-3-hydroxyhexan-2-yl)carbamate (3.6 g, 6.92 mmol) in DCM (25 mL) was added dropwise to pre-cooled mixture of pyridine (2.8 mL, 34.6 mmol) and thionyl chloride (1.0 mL, 13.8 mmol) at 0° C. The mixture was stirred at RT for 1 hour, and then partitioned between water and DCM. The aqueous layer was extracted with DCM, and the combined organic layers were washed with aqueous copper sulfate, water, and brine, and concentrated. The residue was redissolved in ACN (20 mL), and sodium meta-periodate (1.48 g, 6.92 mmol) was added, followed by a solution of ruthenium (III) chloride hydrate (0.078 g, 0.346 mmol) in water (10 mL). The reaction was stirred at ambient temperature. After 20 minutes, the reaction was partitioned between water and DCM; the organic layer was filtered through a silica-gel pad (eluting with DCM) and concentrated to the title compound (2.75 g, 68.3% yield) as a mixture of diastereomers.

Step 7: S-((9R)-9-(5-Bromo-2-fluorophenyl)-2,2,3,3,9,13,13-heptamethyl-11-oxo-4,12-dioxa-10-aza-3-silatetradecan-8-yl)ethanethioate To a solution of (4R)-tert-butyl 4-(5-bromo-2-fluorophenyl)-5-(3-((tert-butyldimethylsilyl)oxy)propyl)-4-methyl-1,2,3-oxathiazolidine-3-carboxylate 2,2-dioxide (1.66 g, 2.85 mmol) in DMF (15 mL) was added potassium thioacetate (3.25 g, 28.5 mmol). The reaction was stirred at 80° C. After 90 minutes, the reaction mixture was partitioned between water and 1:1 ethyl acetate/heptane. The organic layer was concentrated, and the crude product was purified by column chromatography on silica gel, eluting with 5-50% ethyl acetate in heptanes, to provide the title compound (1.1 g, 66.7% yield) as a mixture of diastereomers.

Step 8: (R)-tert-Butyl (2-(5-bromo-2-fluorophenyl)-6-((tert-butyldimethylsilyl)oxy)-3-((cyanomethyl)thio)hexan-2-yl)carbamate To a solution of (R)—S-(9-(5-bromo-2-fluorophenyl)-2,2,3,3,9,13,13-heptamethyl-11-oxo-4,12-dioxa-10-aza-3-silatetradecan-8-yl)ethanethioate (1.1 g, 1.9 mmol) in methanol (10 mL) was added a 0.5-M solution of sodium methoxide in methanol (3.8 mL, 1.9 mmol). The mixture was stirred at ambient temperature for 10 minutes, and then 2-bromoacetonitrile (0.16 mL, 2.28 mmol) was added. The reaction was stirred at ambient temperature for another 40 minutes and concentrated. The crude product was purified by column chromatography on silica gel, eluting with 5-50% ethyl acetate in heptane, to provide the title compound (0.55 g, 50.3% yield) as a mixture of diastereomers.

Step 9: (R)-tert-Butyl (2-(5-bromo-2-fluorophenyl)-6-((tert-butyldimethylsilyl)oxy)-3-((cyanomethyl)sulfonyl)hexan-2-yl)carbamate To a solution of (R)-tert-butyl (2-(5-bromo-2-fluorophenyl)-6-((tert-butyldimethylsilyl)oxy)-3-((cyanomethyl)thio)hexan-2-yl)carbamate (0.55 g, 0.955 mmol) in ACN (5 mL) at 0° C. was added sodium periodate (0.409 g, 1.911 mmol), followed by a solution of ruthenium (III) chloride hydrate (4.3 mg, 0.019 mmol) in water (2.500 mL). The mixture was stirred at 0° C. for 5 minutes, and then diluted with water, quenched with aqueous sodium thiosulfate, and extracted with DCM. The organic layer was passed through a silica-gel pad and concentrated to provide the title compound (0.534 g, 92% yield) as a mixture of diastereomers.

Step 10: (2S,3R)-5-amino-3-(5-bromo-2-fluorophenyl)-2-(3-hydroxypropyl)-3-methyl-3,6-dihydro-2H-1,4-thiazine 1,1-dioxide To a solution of (R)-tert-butyl (2-(5-bromo-2-fluorophenyl)-6-((tert-butyldimethylsilyl)oxy)-3-((cyanomethyl)sulfonyl)hexan-2-yl)carbamate (0.534 g, 0.879 mmol) in 1,4-dioxane (5 mL) was added a 4-N solution of hydrochloric acid in 1,4-dioxane (2.2 mL, 8.8 mmol). The reaction mixture was stirred at 90° C. for 2 hours, concentrated, and partitioned between ethyl acetate and saturated aqueous sodium bicarbonate. The organic layer was concentrated, and the crude product was purified by column chromatography on silica gel, eluting with 0-10% methanol in DCM, to provide the title compound (140 mg, 40.5% yield). LC/MS (ESI$^+$) m/z=393.0, 395.0 D (M+H; two bromine isotopes).

Intermediate 7

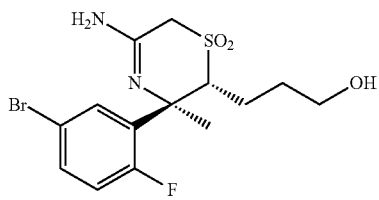 [SMILES: C[C@]1(c2cc(Br)ccc2F)N=C(N)CS(=O)(=O)[C@@H]1CCCO]

Synthesis of (2R,3R)-5-Amino-3-(5-bromo-2-fluorophenyl)-2-(3-hydroxypropyl)-3-methyl-3,6-dihydro-2H-1,4-thiazine 1,1-dioxide The title compound was also isolated from the reaction described in Intermediate 6, Step 10 (60 mg, 17.4% yield). LC/MS (ESI+) m/z=393.0, 395.0 D (M+H; two bromine isotopes).

Intermediate 8

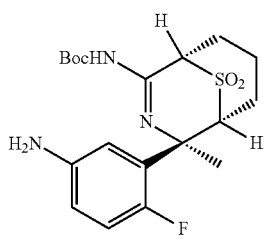 [SMILES: CC(C)(C)OC(=O)NC1=N[C@](C)(c2cc(N)ccc2F)[C@H]2CCC[C@@H]1S2(=O)=O]

Synthesis of tert-Butyl ((1S,4R,5R)-4-(5-amino-2-fluorophenyl)-4-methyl-9,9-dioxido-9-thia-3-azabicyclo[3.3.1]non-2-en-2-yl)carbamate Step 1: tert-Butyl ((5R,6R)-5-(5-bromo-2-fluorophenyl)-6-(3-hydroxypropyl)-5-methyl-1,1-dioxido-5,6-dihydro-2H-1,4-thiazin-3-yl)carbamate To a solution of Intermediate 7 (140 mg, 0.356 mmol) in 1,4-dioxane (2 mL) was added a solution of sodium bicarbonate (35.9 mg, 0.427 mmol) in water (0.4 mL), followed by di-tert-butyl dicarbonate (93 mg, 0.427 mmol). The mixture was stirred at RT for 16 hours, and then partitioned between water and EtOAc. The organic layer was concentrated to provide the title compound (200 mg, quantitative yield).

Step 2: 3-((2R,3R)-3-(5-Bromo-2-fluorophenyl)-5-((tert-butoxycarbonyl)amino)-3-methyl-1,1-dioxido-3,6-dihydro-2H-1,4-thiazin-2-yl)propyl methanesulfonate To a solution of tert-butyl ((5R,6R)-5-(5-bromo-2-fluorophenyl)-6-(3-hydroxypropyl)-5-methyl-1,1-dioxido-5,6-dihydro-2H-1,4-thiazin-3-yl)carbamate (175 mg, 0.355 mmol) in DCM (3 mL) was added pyridine (0.087 mL, 1.064 mmol), followed by methanesulfonyl chloride (0.041 mL, 0.532 mmol). The mixture was stirred at RT for 16 hours, and then partitioned between water and ethyl acetate. The organic layer was concentrated to provide the title compound (220 mg, quantitative yield).

Step 3: tert-Butyl ((1S,4R,5R)-4-(5-bromo-2-fluorophenyl)-4-methyl-9,9-dioxido-9-thia-3-azabicyclo[3.3.1]non-2-en-2-yl)carbamate To a solution of 3-((2R,3R)-3-(5-bromo-2-fluorophenyl)-5-((tert-butoxycarbonyl)amino)-3-methyl-1,1-dioxido-3,6-dihydro-2H-1,4-thiazin-2-yl)propyl methanesulfonate (200 mg, 0.350 mmol) in acetonitrile (5 mL) was added cesium carbonate (342 mg, 1.050 mmol). The mixture was stirred at RT for 48 hours, and then partitioned between water and ethyl acetate. The organic layer was concentrated, and the crude product was purified by column chromatography on silica gel, eluting with 20-80% ethyl acetate in heptane, to provide the title compound (166 mg, 100% yield).

Step 4: tert-Butyl ((1S,4R,5R)-4-(5-amino-2-fluorophenyl)-4-methyl-9,9-dioxido-9-thia-3-azabicyclo[3.3.1]non-2-en-2-yl)carbamate A microwave vial was charged with copper (I) iodide (12.8 mg, 0.067 mmol), sodium azide (65 mg, 1.01 mmol), (+)-sodium L-ascorbate (13 mg, 0.067 mmol), and tert-butyl ((1S,4R,5R)-4-(5-bromo-2-fluorophenyl)-4-methyl-9,9-dioxido-9-thia-3-azabicyclo[3.3.1]non-2-en-2-yl)carbamate (160 mg, 0.337 mmol). Water (1 mL), ethanol (2.3 mL), and trans-N,N'-dimethyl-1,2-cyclohexanediamine (0.021 mL, 0.135 mmol), were added, the vial was capped, and the reaction was irradiated at 50° C. for 60 minutes. The reaction mixture was partitioned between water and ethyl acetate. The organic layer was passed through a silica-gel pad (eluting with ethyl acetate), and the filtrate was concentrated. The residue was redissolved in THF (3 mL) and water (1 mL), and a 1-M solution of trimethylphosphine in THF (0.34 mL, 0.34 mmol) was added. The reaction was stirred for 45 minutes at ambient temperature, and then partitioned between water and ethyl acetate. The organic layer was washed with brine, dried over anhydrous magnesium sulfate, filtered, and concentrated. The crude product was purified by column chromatography on silica gel, eluting with 50-100% ethyl acetate in heptane, to provide the title compound (96 mg, 69.4% yield). LC/MS (ESI+) m/z=412.1 D (M+H).

Intermediate 9

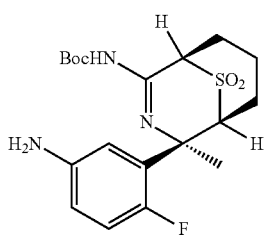 [SMILES: CC(C)(C)OC(=O)NC1=N[C@](C)(c2cc(N)ccc2F)[C@@H]2CCC[C@H]1S2(=O)=O]

Synthesis of tert-Butyl ((1R,4R,5S)-4-(5-amino-2-fluorophenyl)-4-methyl-9,9-dioxido-9-thia-3-azabicyclo[3.3.1]non-2-en-2-yl)carbamate The titled compound was prepared in a series of reactions analogous to those described in Intermediate 7, Steps 1-4, using Intermediate 5. LC/MS (ESI$^+$) m/z=412.1 D (M+H).

Intermediate 10

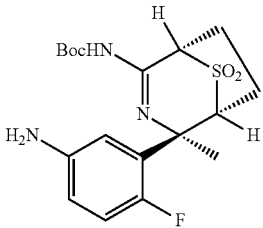 [SMILES: CC(C)(C)OC(=O)NC1=N[C@](C)(c2cc(N)ccc2F)[C@H]2CC[C@@H]1S2(=O)=O]

Synthesis of tert-Butyl ((1S,4R,5R)-4-(5-amino-2-fluorophenyl)-4-methyl-8,8-dioxido-8-thia-3-azabicyclo[3.2.1]oct-2-en-2-yl)carbamate Step 1: (2R,3R)-5-Amino-3-(5-bromo-2-fluorophenyl)-2-(3-hydroxyethyl)-3-methyl-3,6-dihydro-2H-1,4-thiazine 1,1-dioxide In a series of reactions analogous to those described in Intermediate 6, Steps 1-10, (R)-tert-butyl (2-(5-bromo-2-fluorophenyl)-1-oxopropan-2-yl)carbamate and vinylmagnesium bromide were converted to the title compound.

Step 2: tert-Butyl ((1S,4R,5R)-4-(5-amino-2-fluorophenyl)-4-methyl-8,8-dioxido-8-thia-3-azabicyclo[3.2.1]oct-2-en-2-yl)carbamate In a series of reactions analogous to those described in Intermediate 8, Steps 1-4, (2R,3R)-5-amino-3-(5-bromo-2-fluorophenyl)-2-(3-hydroxyethyl)-3-methyl-3,6-dihydro-2H-1,4-thiazine 1,1-dioxide was converted to the title compound. LC/MS (ESI$^+$) m/z=398.1 D (M+H).

Intermediate 11

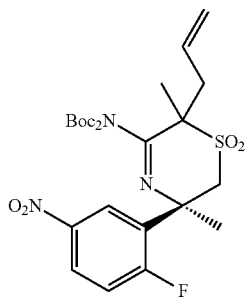

Synthesis of Imidodicarbonic acid, 2-[(5R)-2-allyl-5-(2-fluoro-5-nitrophenyl)-2,5-dimethyl-1,1-dioxido-5,6-dihydro-2H-1,4-thiazin-3-yl)]-, 1,3-bis(1,1-dimethylethyl) ester Step 1: (+/−)-2-Methyl-2-(methylsulfonyl)pent-4-enenitrile In an analogous reaction to that described for Intermediate 1, step 2, 2-(methylsulfonyl)propanenitrile and allyl bromide were converted into the title.

Step 2: (R)—N-((2R)-1-((2-Cyanopent-4-en-2-yl)sulfonyl)-2-(2-fluoro-5-nitrophenyl)propan-2-yl)-2-methylpropane-2-sulfinamide To a solution of 2-methyl-2-(methylsulfonyl)pent-4-enenitrile (0.91 g, 5.24 mmol) in THF (14 mL) at −78° C. was added a 2.7-N solution of n-butyllithium in heptane (1.94 mL, 5.24 mmol) dropwise. The reaction was stirred at −78° C. for 30 minutes. In a separate flask, a solution of (R,E)-N-(1-(2-fluoro-5-nitrophenyl)ethylidene)-2-methylpropane-2-sulfinamide (1 g, 3.49 mmol) in THF (15 mL) was cooled to −78° C. and added to the n-butyllithium solution via cannula. The reaction was stirred at −78° C. for 5 hours, quenched with saturated ammonium chloride, and then warmed to 0° C. The reaction mixture was diluted with water and stirred at RT for 20 minutes, and then partitioned between water and ethyl acetate. The organic layer was washed with brine, dried over anhydrous sodium sulfate, filtered, and concentrated. The crude product was purified by column chromatography on silica gel, eluting with 0-30% (3:1 ethyl acetate:ethanol, 2% ammonium hydroxide) in heptanes, to provide the title compound (0.88 g, 55% yield). LC/MS (ESI$^+$) m/z=460.1 (M+H).

Step 3: (3R)-6-Allyl-5-amino-3-(2-fluoro-5-nitrophenyl)-3,6-dimethyl-3,6-dihydro-2H-1,4-thiazine 1,1-dioxide To a solution of (R)—N-((2R)-1-((2-cyanopent-4-en-2-yl)sulfonyl)-2-(2-fluoro-5-nitrophenyl)propan-2-yl)-2-methylpropane-2-sulfinamide (0.88 g, 1.92 mmol) in dichloromethane (4.8 mL) and methanol (1.6 mL) was added a 4-N solution of hydrochloric acid in dioxane (2.9 mL, 11.5 mmol) and the reaction was stirred at RT for 2 hours. The reaction was then concentrated, diluted with toluene, and reconcentrated. The residue was redissolved in ethanol (12 mL) and transferred to a pressure vessel. To this solution was added copper (I) chloride (0.20 g, 2.0 mmol) and the flask was sealed and stirred at 85° C. for 4 hours. After cooling to ambient temperature, the reaction was partitioned between water and ethyl acetate. The organic layer was washed with brine, dried over anhydrous sodium sulfate, filtered, and concentrated, to provide the title compound (0.680 g, quantitative yield). The isolated product was used in the next step without further purification. LC/MS (ESI$^+$) m/z=356.1 (M+H).

Step 4: Imidodicarbonic acid, 2-[(5R)-2-allyl-5-(2-fluoro-5-nitrophenyl)-2,5-dimethyl-1,1-dioxido-5,6-dihydro-2H-1,4-thiazin-3-yl)]-, 1,3-bis(1,1-dimethylethyl) ester To a solution of (3R)-6-allyl-5-amino-3-(2-fluoro-5-nitrophenyl)-3,6-dimethyl-3,6-dihydro-2H-1,4-thiazine 1,1-dioxide (0.68 g, 1.9 mmol) in DCM (6.4 mL) was added di-tert-butyl dicarbonate (0.877 g, 4.0 mmol), N,N-diisopropylethylamine (0.70 mL, 4.0 mmol), and N,N- dimethylpyridin-4-amine (0.070 g, 0.574 mmol), and the reaction was stirred at ambient temperature for 1.5 hours. The reaction was partitioned between water and ethyl acetate; the organic layer was washed with brine, dried over anhydrous sodium sulfate, filtered, and concentrated. The crude product was purified by column chromatography on silica gel, eluting with 0-50% ethyl acetate in heptanes, to provide the title compound (0.60 g, 56.4% yield). LC/MS (ESI) m/z=578.2 (M+Na).

Intermediate 12

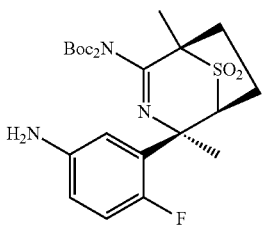

Synthesis of Imidodicarbonic acid, 2-[(1R,4R,5S)-4-(5-amino-2-fluorophenyl)-1,4-dimethyl-8,8-dioxido-8-thia-3-azabicyclo[3.2.1]oct-2-en-2-yl)]-, 1,3-bis(1,1-dimethylethyl) ester Step 1: Imidodicarbonic acid, 2-[(5R)-5-(2-fluoro-5-nitrophenyl)-2,5-dimethyl-1,1-dioxido-2-(2-oxoethyl)-5,6-dihydro-2H-1,4-thiazin-3-yl)]-, 1,3-bis(1,1-dimethylethyl) ester A solution of Intermediate 11 (3.1 g, 5.58 mmol) in dichloromethane (18.60 mL) was cooled to −78° C. and an ozone/oxygen mixture was bubbled through the solution until the reaction turned blue. Nitrogen was then bubbled through the reaction until blue color disappeared. Triphenylphosphine (1.76 g, 6.70 mmol) was added and the mixture was stirred for 10 min at −78° C. and then allowed to reach room temperature. The solution was concentrated, and the crude product was purified by column chromatography on silica gel, eluting with 10-80% ethyl acetate in heptanes, to provide the title compound (3.0 g, 96% yield). LC/MS (ESI+) m/z=580.1 (M+Na).

Step 2: Imidodicarbonic acid, 2-[(5R)-5-(2-fluoro-5-nitrophenyl)-2-(2-hydroxyethyl)-2,5-dimethyl-1,1-dioxido-5,6-dihydro-2H-1,4-thiazin-3-yl)]-, 1,3-bis(1,1-dimethylethyl) ester To a solution of imidodicarbonic acid, 2-[(5R)-5-(2-fluoro-5-nitrophenyl)-2,5-dimethyl-1,1-dioxido-2-(2-oxoethyl)-5,6-dihydro-2H-1,4-thiazin-3-yl)]-, 1,3-bis(1,1-dimethylethyl) ester (3.0 g, 5.38 mmol) in THF (18 mL) at 0° C. was added a 1 M solution of borane tetrahydrofuran complex in THF (8.07 mL, 8.07 mmol) dropwise. The mixture was stirred for 10 min at 0° C., and then carefully quenched with aqueous saturated ammonium chloride. The reaction was partitioned between water and ethyl acetate. The organic layer was washed with water, brine, and concentrated to afford the title compound (2.58 g, 86% yield) which was used without further purification for the next step. LC/MS (ESI+) m/z=582.2 (M+Na).

Step 3: 2-((5R)-3-((1,1-Bis-tert-butoxycarbonyl)amino)-5-(2-fluoro-5-nitrophenyl)-2,5-dimethyl-1,1-dioxido-5,6-dihydro-2H-1,4-thiazin-2-yl)ethyl 4-methylbenzenesulfonate To a solution of imidodicarbonic acid, 2-[(5R)-5-(2-fluoro-5-nitrophenyl)-2-(2-hydroxyethyl)-2,5-dimethyl-1,1-dioxido-5,6-dihydro-2H-1,4-thiazin-3-yl)]-, 1,3-bis(1,1-dimethylethyl) ester (2.58 g, 4.61 mmol) in DCM (15 mL) was added triethylamine (1.29 mL, 9.22 mmol), p-toluenesulfonyl chloride (1.76 g, 9.22 mmol) and N,N-dimethylpyridin-4-amine (0.28 g, 2.3 mmol). The reaction was stirred at RT for 1 hour, and partitioned between water and dichloromethane. The organic layer was washed with brine, dried over anhydrous sodium sulfate, filtered, and concentrated. The crude product was purified by column chromatography on silica gel, eluting with 0-50% ethyl acetate in heptanes, to provide the title compound (2.15 g, 65.3% yield). LC/MS (ESI+) m/z=736.2 (M+Na).

Step 4: Imidodicarbonic acid, 2-[(4R)-4-(2-fluoro-5-nitrophenyl)-1,4-dimethyl-8,8-dioxido-8-thia-3-azabicyclo[3.2.1]oct-2-en-2-yl)]-, 1,3-bis(1,1-dimethylethyl) ester To a solution of 2-((5R)-3-((1,1-bis tert-butoxycarbonyl)amino)-5-(2-fluoro-5-nitrophenyl)-2,5-dimethyl-1,1-dioxido-5,6-dihydro-2H-1,4-thiazin-2-yl)ethyl 4-methylbenzenesulfonate (2.15 g, 3.01 mmol) in THF (25 mL) at −78° C. was added a 1-M solution of lithium bis(trimethylsilyl)amide in THF (4.5 mL, 4.5 mmol). The reaction was stirred at −78° C. for 1.5 hours, quenched with the addition of saturated aqueous ammonium chloride, and warmed to RT. The reaction was partitioned between water and ethyl acetate, and the organic layer was washed with brine, dried over anhydrous sodium sulfate, filtered, and concentrated to provide the title compound (1.5 g, 92% yield). The crude product was used in the next reaction without further purification. LC/MS (ESI+) m/z=564.2 (M+Na).

Step 5: Imidodicarbonic acid, 2-[(1R,4R,5S)-4-(5-amino-2-fluorophenyl)-1,4-dimethyl-8,8-dioxido-8-thia-3-azabicyclo[3.2.1]oct-2-en-2-yl)]-, 1,3-bis(1,1-dimethylethyl) ester A RBF was charged with imidodicarbonic acid, 2-[(4R)-4-(2-fluoro-5-nitrophenyl)-1,4-dimethyl-8,8-dioxido-8-thia-3-azabicyclo[3.2.1]oct-2-en-2-yl)]-, 1,3-bis(1,1-dimethylethyl) ester (1.5 g, 2.77 mmol) and palladium on carbon (10% by weight) (0.295 g, 0.277 mmol). Ethyl acetate was added (6.9 mL) followed by addition of methanol (6.9 mL), and the flask was purged with nitrogen. It was then evacuated and filled with hydrogen, and the reaction was stirred at RT under a hydrogen atmosphere for 4 hours. The mixture was filtered through Celite and washed with a methanol/ethyl acetetate mixture. The filtrate was concentrated and purified by reversed-phase HPLC on an 18×100 mm Waters xBridge C18 column, 10-micron pore size. The flow rate was 40 mL/min, eluting with 25-100% (1% TFA in acetonitrile) in (1% TFA in water). The product fractions were combined, neutralized with aqueous sodium carbonate, and extracted into EtOAc. The organic layer was washed with aqueous sodium carbonate, dried over anhydrous sodium sulfate, filtered, and concentrated to provide the title compound (266 mg, 0.52 mmol) as a white solid. LC/MS (ESI⁺) m/z=534.2 (M+Na).

Intermediate 13

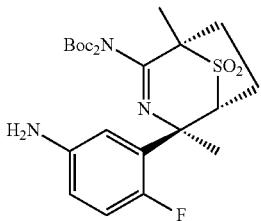

Synthesis of Imidodicarbonic acid, 2-[(1S,4R,5R)-4-(5-amino-2-fluorophenyl)-1,4-dimethyl-8,8-dioxido-8-thia-3-azabicyclo[3.2.1]oct-2-en-2-yl)]-, 1,3-bis(1,1-dimethylethyl) ester The title compound (120 mg, 0.235 mmol) was also isolated from the reaction described in Intermediate 12, Step 5. LC/MS (ESI⁺) m/z=534.2 (M+Na).

Intermediates 14A and 14B

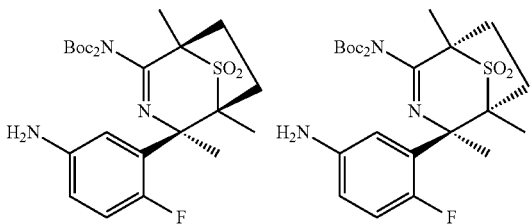

Synthesis of Imidodicarbonic acid, 2-[(1R,4R,5S)-4-(5-amino-2-fluorophenyl)-1,4,5-trimethyl-8,8-dioxido-8-thia-3-azabicyclo[3.2.1]oct-2-en-2-yl]-, 1,3-bis(1,1-dimethylethyl) ester and imidodicarbonic acid, 2-[(1S,4R,5R)-4-(5-amino-2-fluorophenyl)-1,4,5-trimethyl-8,8-dioxido-8-thia-3-azabicyclo[3.2.1]oct-2-en-2-yl]-, 1,3-bis(1,1-dimethylethyl) ester Step 1: (R)—N-((2R)-1-((2-Cyanopent-4-en-2-yl)sulfonyl)-2-(2-fluoro-5-nitrophenyl)propan-2-yl)-2-methylpropane-2-sulfinamide To a solution of 2-methyl-2-(methylsulfonyl)pent-4-enenitrile (7.8 g, 45.0 mmol) in 2-methyltetrahydrofuran (40 mL) under nitrogen at −75° C. was added a 1.6-M solution of n-butyllithium in hexane (28.9 mL, 46.2 mmol) dropwise. The mixture was stirred at −75° C. for 30 minutes. Separately, a solution of (R,E)-N-(1-(2-fluoro-5-nitrophenyl)ethylidene)-2-methylpropane-2-sulfinamide (6.79 g, 23.70 mmol) in toluene was cooled to −35 to −40° C. and a 2.0 M solution of trimethylaluminum in toluene (11.85 mL, 23.70 mmol) was added dropwise. The resulting mixture was stirred for 15 min and transferred via cannula to the first solution. The reaction mixture was stirred at −75° C. for 2 hrs, and then quenched with brine (50 mL) and water (50 mL) and warmed to RT. The mixture was extracted with ethyl acetate. The combined organic extracts were washed with brine, dried over anhydrous sodium sulfate, filtered, and concentrated. The crude product was purified by silica-gel column chromatography, eluting with 10% to 60% ethyl acetate in hexane, to provide the title compound (9.3 g, 20.24 mmol, 85% yield) as light-yellow solid.

Step 2: Imidodicarbonic acid, 2-[(5R)-2-allyl-5-(2-fluoro-5-nitrophenyl)-2,5-dimethyl-1,1-dioxido-5,6-dihydro-2H-1,4-thiazin-3-yl)]-, 1,3-bis(1,1-dimethylethyl) ester Following the sequence of reactions described in Intermediate 11, Steps 3-4, (R)—N-((2R)-1-((2-cyanopent-4-en-2-yl)sulfonyl)-2-(2-fluoro-5-nitrophenyl)propan-2-yl)-2-methylpropane-2-sulfinamide was converted to the title compound.

Step 3: Imidodicarbonic acid, 2-[(5R)-5-(2-fluoro-5-nitrophenyl)-2,5,6-trimethyl-1,1-dioxido-2-(2-oxoethyl)-5,6-dihydro-2H-1,4-thiazin-3-yl)]-, 1,3-bis(1,1-dimethylethyl) ester To a solution of imidodicarbonic acid, 2-[(5R)-2-allyl-5-(2-fluoro-5-nitrophenyl)-2,5-dimethyl-1,1-dioxido-5,6-dihydro-2H-1,4-thiazin-3-yl)]-, 1,3-bis(1,1-dimethylethyl) ester (2.01 g, 3.62 mmol) in THF (24 mL) at −78° C. was added a 1-M solution of lithium bis(trimethylsilyl)amide in THF (3.80 mL, 3.80 mmol) and the solution was stirred at −78° C. for 45 minutes. Iodomethane (0.270 mL, 4.34 mmol) was added and the mixture was stirred at −78° C. for 30 minutes. The reaction was quenched with water and extracted with ethyl acetate. The combined extracts were washed with brine, dried and concentrated. The residue was redissolved in DCM (30 mL) and cooled to −78° C. A flow of ozone/oxygen mixture was bubbled through the solution until the reaction turned blue. Nitrogen was then bubbled through the reaction until blue color disappeared. Triphenylphosphine (1.13 g, 4.30 mmol) was added and the mixture was stirred for 5 minutes at −78° C. and then allowed to warm to ambient temperature. The mixture was concentrated and purified by silica-gel column chromatography, eluting with 10-70% ethyl acetate in heptanes, to provide the title compound (1.929 g, 94% yield).

Step 4: 2-((5R)-3-(bis(tert-butoxycarbonyl)amino)-5-(2-fluoro-5-nitrophenyl)-2,5,6-trimethyl-1,1-dioxido-5,6-dihydro-2H-1,4-thiazin-2-yl)ethyl 4-methylbenzenesulfonate To a solution of imidodicarbonic acid, 2-[(5R)-5-(2-fluoro-5-nitrophenyl)-2,5,6-trimethyl-1,1-dioxido-2-(2-oxoethyl)-5,6-dihydro-2H-1,4-thiazin-3-yl)]-, 1,3-bis(1,1-dimethylethyl) ester (1.929 g, 3.37 mmol) in THF (17 mL) at 0° C. was added a 1 M solution of borane tetrahydrofuran complex in THF (5.06 mL, 5.06 mmol) dropwise. The mixture was stirred for 10 minutes at 0° C. The reaction was carefully quenched with saturated aqueous ammonium chloride, diluted with water, and extracted with ethyl acetate. The organic layer was washed with water and brine, dried over anhydrous sodium sulfate, filtered, and concentrated. The residue was redissolved in dichloromethane (34 mL), and triethylamine (0.940 mL, 6.75 mmol), p-toluenesulfonyl chloride (1.286 g, 6.75 mmol) and N,N-dimethylpyridin-4-amine (0.206 g, 1.687 mmol) were added. The mixture was stirred at RT for 16 hours and then concentrated. The crude product was purified by silica-gel column chromatography, eluting with 5-50% ethyl acetate in heptanes, to provide the title (2.24 g, 91% yield).

Step 5: Imidodicarbonic acid, 2-[(4R)-4-(2-fluoro-5-nitrophenyl)-1,4,5-trimethyl-8,8-dioxido-8-thia-3-azabicyclo[3.2.1]oct-2-en-2-yl]-, 1,3-bis(1,1-dimethylethyl) ester To a solution of 2-((5R)-3-(bis(tert-butoxycarbonyl) amino)-5-(2-fluoro-5-nitrophenyl)-2,5,6-trimethyl-1,1-dioxido-5,6-dihydro-2H-1,4-thiazin-2-yl)ethyl 4-methylbenzenesulfonate (0.52 g, 0.714 mmol) in THF (4.8 mL) at −78° C. was added a 1 M solution of potassium bis(trimethylsilyl) amide in THF (0.93 mL, 0.93 mmol). The reaction was stirred at −78° C. for 30 minutes, and then quenched with saturated aqueous ammonium chloride and warmed to RT. The reaction mixture was partitioned between water and ethyl acetate. The organic layer was concentrated and purified by silica-gel column chromatography, eluting with 5-50% ethyl acetate in heptane, to provide the title compound (0.26 g, 65.5% yield).

Step 6: Imidodicarbonic acid, 2-[(1R,4R,5S)-4-(5-amino-2-fluorophenyl)-1,4,5-trimethyl-8,8-dioxido-8-thia-3-azabicyclo[3.2.1]oct-2-en-2-yl]-, 1,3-bis(1,1-dimethylethyl) ester and imidodicarbonic acid, 2-[(1S,4R,5R)-4-(5-amino-2-fluorophenyl)-1,4,5-trimethyl-8,8-dioxido-8-thia-3-azabicyclo[3.2.1]oct-2-en-2-yl]-, 1,3-bis(1,1-dimethylethyl) ester To a solution of imidodicarbonic acid, 2-[(4R)-4-(2-fluoro-5-nitrophenyl)-1,4,5-trimethyl-8,8-dioxido-8-thia-3-azabicyclo[3.2.1]oct-2-en-2-yl]-, 1,3-bis(1,1-dimethylethyl) ester (0.26 g, 0.468 mmol) in ethyl acetate (2.3 mL) was added 10% (w/w) palladium on carbon (0.050 g, 0.047 mmol). A hydrogen balloon was installed, the flask was evacuated and filled with hydrogen, and the reaction mixture was stirred at RT under hydrogen atmosphere for 17 hours. The reaction mixture was filtered through Celite and the filter cake was washed with ethyl acetate. The filtrate was concentrated and purified by silica-gel column chromatography, eluting with 0.5% to 5% methanol in DCM, to provide the title compounds (0.218 g, 89% yield).

Intermediate 15

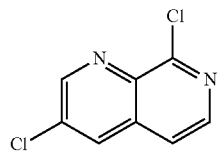

Synthesis of 3,8-Dichloro-1,7-naphthyridine

Step 1: 3-Bromo-5-chloropicolinonitrile

A microwave vial was charged with copper (I) cyanide (1.089 g, 12.16 mmol), 2,3-dibromo-5-chloropyridine (3 g, 11.06 mmol), and propionitrile (15 mL). The vial was capped and irradiated in a microwave reactor at 150° C. for 2.5 hours. The solution was concentrated, diluted with DCM (25 mL), and filtered. The filtrate was concentrated, and the residue was purified by silica gel chromatography, eluting with 0-30% EtOAc in heptanes, to afford the title compound (2 g, 9.20 mmol). MS m/z=219 (M+H).

Step 2: 5-Chloro-3-((trimethylsilyl)ethynyl)picolinonitrile

A pressure vessel was charged with triethylamine (7.65 mL, 55.2 mmol), ethynyltrimethylsilane (2.32 mL, 16.6 mmol), copper (I) iodide (0.263 g, 1.380 mmol), palladium (0) tetrakis(triphenylphosphine) (0.558 g, 0.483 mmol), 3-bromo-5-chloropicolinonitrile (3.0 g, 13.8 mmol), and N,N-dimethylformamide (50 ml). The vessel was flushed with argon, sealed, stirred at ambient temperature for 15 minutes, and then heated at 50° C. for 4 hours. The solution was diluted with water and extracted with ethyl acetate. The combined organic layers were concentrated, and the residue was purified by silica-gel chromatography, eluting 0-50% ethyl acetate in hexane, to afford the title compound (1.3 g, 5.5 mmol). MS m/z=235 (M+H).

Step 3: 5-Chloro-3-(2,2-dimethoxyethyl)picolinonitrile

A pressure vessel was charged with 5-chloro-3-((trimethylsilyl)ethynyl)picolinonitrile (2 g, 8.52 mmol) and sodium methoxide (0.5 M in methanol, 42.6 mL, 21.30 mmol), sealed, and stirred at 55° C. for one hour. The solution was concentrated, and the residue was purified via silica gel chromatography, eluting with 10% methanol in DCM to afford the title compound (1.7 g, 7.50 mmol). MS m/z=227 (M+H).

Step 4: 3-Chloro-1,7-naphthyridin-8(7H)-one

To a solution of 5-chloro-3-(2,2-dimethoxyethyl)picolinonitrile (1.7 g, 7.50 mmol) in acetone (50 mL) and water (150 mL) was added aqueous saturated sodium carbonate (37.5 mL, 113 mmol) and 30% aqueous hydrogen peroxide (38.3 mL, 375 mmol). The reaction was stirred at RT for one hour, concentrated to remove most of the acetone, and extracted with dichloromethane. The combined organic layers were concentrated.

To a solution of this intermediate (1.8 g, 7.36 mmol) in benzene (20 mL) was added p-toluenesulfonic acid (0.350 g, 1.839 mmol) and the reaction was sonicated for 10 minutes. The solution was stirred overnight at 80° C. and concentrated. The crude product was purified via silica gel, eluting with 0-100% (80/20/1 ethyl acetate/methanol/ammonium hydroxide) in ethyl acetate, to the title intermediate (1.1 g, 6.1 mmol). MS m/z=181 (M+H).

Step 5: 3,8-Dichloro-1,7-naphthyridine

A suspension of -chloro-1,7-naphthyridin-8(7H)-one (250 mg, 1.384 mmol) in phosphorus oxychloride (1.94 mL, 20.8 mmol) was stirred at 95° C. for one hour. The solution was concentrated to afford the title compound (276 mg, 1.39 mmol). MS m/z=199 (M+H).

Intermediate 16

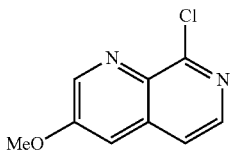

Synthesis of 8-Chloro-3-methoxy-1,7-naphthridine

Step 1: 3-chloro-5-methoxypicolinonitrile

To a solution of 3,5-dichloropicolinonitrile (22.5 g, 130 mmol) in DMF (500 mL) at 0° C. was added sodium methoxide (6.67 g, 124 mmol) slowly. The reaction was stirred for 5 minutes at 0° C., then allowed to warm to RT and stir for 30 minutes. The solution was partitioned between water and EtOAc. The organic layer was washed with water and concentrated. The crude product was purified via silica gel chromatography, eluting with 0-75% ethyl acetate in heptanes, to afford a 1:1 ratio of the desired isomer 3-chloro-5-methoxypicolinonitrile and 5-chloro-3-methoxypicolinonitrile (7.0 g, 41.5 mmol). The material was used without further purification. MS m/z=169 (M+H).

Step 2: 5-Methoxy-3-((triethylsilyl)ethynyl)picolinonitrile

A sealed vessel was charged with bis(acetonitrile)palladium (II) chloride (0.154 g, 0.593 mmol), dicyclohexyl(2',4',6'-triisopropyl-[1,1'-biphenyl]-2-yl)phosphine (0.848 g, 1.780 mmol), cesium carbonate (25.1 g, 77 mmol), the product of Intermediate 9, step 1 (5 g, 29.7 mmol), and ACN (60 mL). The vessel was flushed with argon, sealed, and stirred at RT for 25 minutes. To the reaction was added triethyl(ethynyl)silane (5.41 g, 38.6 mmol), and the vessel was resealed and stirred at 90° C. for 3 hours. The solution was concentrated, and the residue was purified via silica gel chromatography, eluting with 0-50% ethyl acetate in heptanes, to afford the title compound (3.8 g, 13.9 mmol). MS m/z=273 (M+H).

Step 3: 3-(2,2-Dimethoxyethyl)-5-methoxypicolinonitrile

A pressure vessel was charged with 5-methoxy-3-((triethylsilyl)ethynyl)picolinonitrile (3.8 g, 13.95 mmol) and sodium methoxide (0.5 M in methanol, 69.7 mL, 34.9 mmol). The vessel was sealed and stirred at 55° C. for 2 hours. The reaction was concentrated to afford the title intermediate (3.1 g, 13.95 mmol).

Step 4: 8-chloro-3-methoxy-1,7-naphthyridine

Using an analogous sequence of reactions to those described in Intermediate 8, steps 4-5, 3-(2,2-dimethoxyethyl)-5-methoxypicolinonitrile (3.4 g, 15.30 mmol) was converted to the title compound (552 mg, 2.84 mmol). MS m/z=195 (M+H).

Intermediate 17

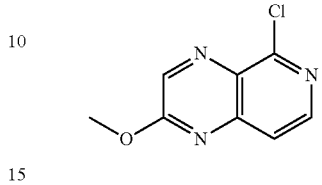

Synthesis of 5-Chloro-2-methoxypyrido[3,4-b]pyrazine

Step 1: 5-Chloropyrido[3,4-b]pyrazin-2(1H)-one

A suspension 2-chloropyridine-3,4-diamine (2.5 g, 17.41 mmol) and a 50% solution of ethyl glyoxalate in toluene (3.45 mL, 17.41 mmol) in ethanol (34.8 mL) was stirred at reflux for 24 hours. The solution was cooled to −20° C. for 16 hours, and the resulting precipitate was collected by vacuum filtration and rinsed with ethanol. The crude product was purified via reverse-phase HPLC, eluting with 5-50% acetonitrile/0.1% trifluoroacetic acid in water/0.1% trifluoroacetic acid, to afford the title compound (570 mg, 3.14 mmol). MS m/z=182 (M+H).

Step 2: 2,5-Dichloropyrido[3,4-b]pyrazine

A suspension of 5-chloropyrido[3,4-b]pyrazin-2(1H)-one (0.57 g, 3.14 mmol) in phosphorus oxychloride (10.24 mL, 110 mmol) was stirred at 110° C. for two hours, and then concentrated. The residue was dissolved in dichloromethane, washed with saturated sodium bicarbonate, dried over anhydrous sodium sulfate, filtered, and concentrated to afford the title compound (580 mg, 2.90 mmol). MS m/z=200 (M+H).

Step 3: 5-Chloro-2-methoxypyrido[3,4-b]pyrazine

To a solution of 2,5-dichloropyrido[3,4-b]pyrazine (580 mg, 2.90 mmol) in N,N-dimethylformamide (10 mL) was added a 0.5-M solution of sodium methoxide in methanol (6.09 mL, 3.04 mmol), and the reaction was stirred at room temperature for 5 minutes. The solution was diluted with water and extracted with ethyl acetate. The organic layer was dried with sodium sulfate, filtered and concentrated to afford the title compound (550 mg, 2.81 mmol). MS m/z=196 (M+H).

Intermediate 18

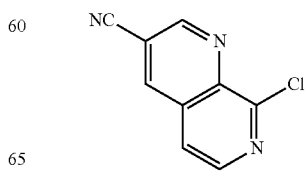

Synthesis of 8-Chloro-1,7-naphthyridine-3-carbonitrile

A screw-cap vial was charged with 3-chloro-1,7-naphthyridin-8(7H)-one (100 mg, 0.554 mmol), zinc cyanide (52.7 μl, 0.831 mmol), 2-dicyclohexylphosphino-2',6'-dimethoxybiphenyl (45.5 mg, 0.111 mmol), tris(dibenzylideneacetone)dipalladium(0) (40.6 mg, 0.044 mmol), DMF (2.74 mL) and water (28 μL). The vial was purged with argon, sealed, and stirred at 110° C. for 1 hour. The mixture was filtered through a pad of Celite, which was rinsed with methanol and dimethylsulfoxide. The combined filtrates were concentrated, and a few drops of water were added. The resulting solids were collected by vacuum filtration, rinsed with water and dried.

The solids were suspended in toluene (3.5 mL), and phosphorus oxychloride (98 μL, 1.052 mmol) and DIPEA (122 μL, 0.701 mmol) were added. The reaction was stirred at 120° C. for 1.5 hours, cooled to RT, diluted with EtOAc, and washed with 2 M aqueous sodium carbonate. The organic portion was dried over anhydrous sodium sulfate, filtered and concentrated. The crude material was purified by silica gel chromatography, eluting with 5-50% EtOAc in heptanes, to provide the title compound (50 mg, 0.264 mmol) as a white solid. LC/MS (ESI$^+$) m/z=190 (M+H).

Intermediate 19

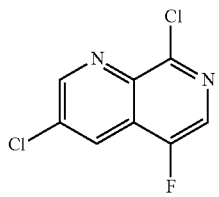 [SMILES: Fc1cnc(Cl)c2ncc(Cl)cc12]

Synthesis of 3,8-Dichloro-5-fluoro-1,7-naphthyridine

Step 1: 3-chloro-5-fluoro-6-methoxy-6,7-dihydro-1,7-naphthyridin-8(5H)-one

A pressure bottle was charged with 3-chloro-1,7-naphthyridin-8(7H)-one (15 g, 83 mmol), methanol (34.6 mL), ACN (173 mL) and 1-chloromethyl-4-fluoro-1,4-diazoniabicyclo[2.2.2]octane bis(tetrafluoroborate) (30.9 g, 87 mmol), and the mixture was heated at 45° C. for 15 hours. Water and ethyl acetate were added, and the layers were separated. The aqueous portion was extracted twice with ethyl acetate and once with DCM, and the combined organic layers were dried with anhydrous sodium sulfate, filtered and concentrated. The crude solid was triturated with a minimum amount of ethyl acetate and filtered. The title intermediate was isolated as an off-white solid (15.34 g, 80%) as a 3:1 mixture of diastereomers.

Step 2: 3,8-dichloro-5-fluoro-1,7-naphthyridine

A vial was charged with 3-chloro-5-fluoro-6-methoxy-6,7-dihydro-1,7-naphthyridin-8(5H)-one (7.5 g, 32.5 mmol), acetonitrile (130 mL) and phosphorus oxychloride (9.09 mL, 98 mmol), and the mixture was stirred at 75° C. for 15 hours. The mixture was concentrated, and the crude material was purified by silica gel chromatography, eluting with 0-50% ethyl acetate in heptanes, to provide the title compound (5.57 g, 25.7 mmol, 79% yield) as a white solid. LC/MS (ESI$^+$) m/z=217 (M+H).

Intermediate 20

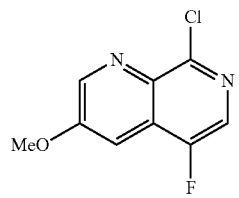 [SMILES: COc1cnc2c(Cl)ncc(F)c2c1]

Synthesis of 8-Chloro-5-fluoro-3-methoxy-1,7-naphthyridine

Using an analogous sequence of reactions to those described for Intermediate 19, 3-ethoxy-1,7-naphthyridin-8(7H)-one was converted to the title compound. LC/MS (ESI$^+$) m/z=213 (M+H).

Intermediate 21

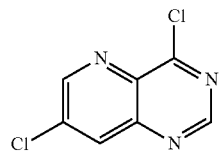

Synthesis of 4,7-Dichloropyrido[3,2-d]pyrimidine

Step 1: 3-Amino-5-chloropicolinamide

To a suspension of 5-chloro-2-cyano-3-nitropyridine (1.274 mL, 10.9 mmol) in water (22 mL) was added 28% aqueous ammonium hydroxide (3.94 mL, 28.3 mmol), and the reaction was stirred at RT for 20 minutes. Sodium hydrosulfite (2.68 mL, 32.7 mmol) was added, and the reaction mixture was stirred at RT for 70 minutes. The yellow precipitate was collected by vacuum filtration to provide the title compound (1.097 g, 6.39 mmol) as yellow solid. $^1$H-NMR (400 MHz, DMSO-d$_6$): δ 7.88 (br. s, 1 H), δ 7.73 (s, 1 H), δ 7.39 (br. s, 1 H), δ 7.23 (s, 1 H), δ 7.06 (br. s, 2 H). LC/MS (ESI$^+$) m/z=172 (M+H).

Step 2: 7-Chloropyrido[3,2-d]pyrimidin-4(1H)-one

A suspension of 3-amino-5-chloropicolinamide (1.1 g, 6.41 mmol) in triethyl orthoformate (15.99 mL, 96 mmol) was stirred at 155° C. for 22 hours. After cooling to RT, the yellow precipitate was collected by vacuum filtration and washed with hexanes to yield the title intermediate (1.03 g, 5.67 mmol) as a yellow solid. $^1$H NMR (400 MHz, DMSO-d$_6$) δ ppm 8.20 (s, 1 H) 8.27 (d, J=2.35 Hz, 1 H) 8.80 (d, J=2.25 Hz, 1 H) 12.68 (br. s., 1 H). LC/MS (ESI$^+$) m/z=182 (M+H).

Step 3: 4,7-Dichloropyrido[3,2-d]pyrimidine

To a mixture of 7-chloropyrido[3,2-d]pyrimidin-4(1H)-one (250 mg, 1.377 mmol) in toluene (12 mL) were added DIPEA (0.73 mL, 4.20 mmol) and phosphorus oxychloride (0.391 mL, 4.27 mmol), and the reaction was stirred at reflux for 1 hour. After cooling to RT, the reaction mixture was concentrated to provide the title compound. LC/MS (ESI⁺) m/z=200 (M+H).

Intermediate 22

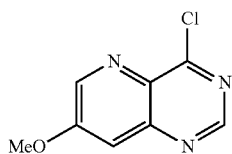

Synthesis of 4-Chloro-7-methoxypyrido[3,2-d]pyrimidine

Step 1: 7-Methoxypyrido[3,2-d]pyrimidin-4(1H)-one

A microwave vial was charged with 7-chloropyrido[3,2-d]pyrimidin-4(1H)-one (110 mg, 0.606 mmol), a 0.5 M solution of sodium methoxide in methanol (3.65 mL, 1.817 mmol) and sodium methoxide (327 mg, 6.06 mmol). The vial was capped and irradiated in a microwave reactor at 145° C. for 30 minutes. The reaction was neutralized with saturated aqueous ammonium chloride (3 mL), concentrated, and diluted with cold water. The resulting precipitate was collected by vacuum filtration and dried in vacuo to provide the title compound (107 mg, 0.604 mmol) as pink solid. $^1$H NMR (400 MHz, DMSO-$d_6$) δ ppm 3.95 (s, 3 H) 7.49 (d, J=2.74 Hz, 1 H) 8.11 (s, 1 H) 8.47 (d, J=2.74 Hz, 1 H). LC/MS (ESI⁺) m/z=178 (M+H).

Step 2: 4-Chloro-7-methoxypyrido[3,2-d]pyrimidine

Using an analogous reaction to that described for Intermediate 21, step 3, 7-methoxypyrido[3,2-d]pyrimidin-4(1H)-one was converted to the title compound. LC/MS (ESI⁺) m/z=196 (M+H).

Intermediate 23

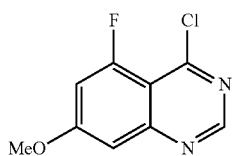 [SMILES: COc1cc(F)c2c(Cl)ncnc2c1]

Synthesis of 4-Chloro-5-fluoro-7-methoxyquinazoline

Step 1: 2-Amino-6-fluoro-4-methoxybenzonitrile

Ammonia gas was bubbled through a solution of 2,6-difluoro-4-methoxybenzonitrile (1.0 g, 5.91 mmol) in dimethylsulfoxide (11.83 mL) for 10 minutes. The reaction was then sealed and stirred at 90° C. for 24 hours. The reaction mixture was cooled to ambient temperature and concentrated in vacuo to afford a tan residue. The residue was triturated with water, collected be vacuum filtration, and dried in vacuo to afford the title intermediate (0.9 g, 5.42 mmol) as a white solid. LC/MS (ESI⁺) m/z=167 (M+H).

Step 2: 5-Fluoro-7-methoxyquinazolin-4-ol

To a mixture of formic acid (11.43 mL, 298 mmol) and sulfuric acid (0.866 mL, 16.25 mmol) was added 2-amino-6-fluoro-4-methoxybenzonitrile (0.9 g, 5.42 mmol) in portions. The reaction mixture was stirred at 100° C. for 1 hour, cooled to ambient temperature, and poured into 80 mL of an ice-water mixture. The resulting precipitate was collected by vacuum filtration and dried in vacuo to provide the title intermediate (0.8 g, 4.12 mmol) as an off-white solid. LC/MS (ESI⁺) m/z=195 (M+H).

Step 3: 4-Chloro-5-fluoro-7-methoxyquinazoline

To a suspension of 5-fluoro-7-methoxyquinazolin-4-ol (0.125 g, 0.644 mmol) in thionyl chloride (1.410 mL, 19.31 mmol) was added N,N-dimethylformamide (0.028 mL, 0.361 mmol). The reaction was stirred at 80° C. for 6 hours and concentrated in vacuo. The residue was suspended in saturated aqueous sodium bicarbonate and extracted with dichloromethane. The organic layer was concentrated in vacuo to generate the title compound (0.13 g, 0.611 mmol) as a yellow solid. LC/MS (ESI⁺) m/z=213 (M+H).

Intermediate 24

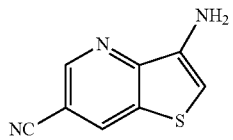 [SMILES: N#Cc1cnc2c(N)csc2c1]

Synthesis of 3-Aminothieno[3,2-b]pyridine-6-carbonitrile

Step 1: Sodium (E)-2-cyano-3,3-dimethoxyprop-1-en-1-olate

To a suspension of NaH (60% dispersion in mineral oil, 2.52 g, 63.0 mmol) in diethylether (75 mL) was added 3,3-dimethoxypropanenitrile (6.17 mL, 55.0 mmol) followed by methyl formate (6.74 mL, 110 mmol). The solution was stirred for 3 days at RT. The resulting solid was collected by vacuum filtration and washed with ether to afford sodium (E)-2-cyano-3,3-dimethoxyprop-1-en-1-olate (4.2 g, 25.4 mmol).

Step 2: 3-Aminothieno[3,2-b]pyridine-6-carbonitrile

To a solution of sodium (E)-2-cyano-3,3-dimethoxyprop-1-en-1-olate (1012 mg, 6.13 mmol) in methanol (12 mL) was added concentrated hydrochloric acid (503 µL 6.13 mmol). The solution was stirred for 5 minutes, and then a solution of thiophene-3,4-diamine (700 mg, 6.13 mmol) in methanol (12 mL) was added. The solution was stirred at reflux for 3 hours, and then a solution of concentrated HCl (1.0 mL) in methanol (2 mL) was added. The reaction was stirred at reflux for an additional two hours, quenched with TEA (3 mL), and concentrated. The crude product was purified via silica gel chromatography, eluting with 0-100% ethyl acetate in heptanes, to provide the title compound (250 mg, 1.427 mmol). MS m/z=176 (M+H).

Intermediate 25

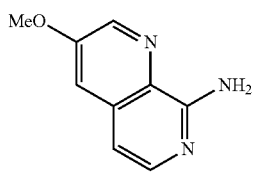 [SMILES: COc1cnc2c(N)nccc2c1]

Synthesis of 3-Methoxy-1,7-naphthyridin-8-amine

Step 1: 3-Methoxy-N-(4-methoxybenzyl)-1,7-naphthyridin-8-amine

To a solution of 8-chloro-3-methoxy-1,7-naphthyridine (1 g, 5.14 mmol) in N,N-dimethylformamide (10.28 mL) was added potassium carbonate (1.42 g, 10.28 mmol) followed by 4-methoxybenzylamine (1.47 ml, 11.3 mmol). The reaction was stirred at 100° C. for 24 hours and then concentrated to generate a brown residue. This was partitioned between ethyl acetate and water. The organic layer was concentrated and purified by silica-gel chromatography, eluting with 1-5% methanol in DCM, to provide the title compound (1.37 g, 4.63 mmol) as a tan solid. LC/MS (ESI$^+$) m/z=296 (M+H).

Step 2: 3-methoxy-1,7-naphthyridin-8-amine

To a solution of N-(4-methoxybenzyl)-1,7-naphthyridin-8-amine (340 mg, 1.15 mmol) in 1,2-dichloroethane (5.80 mL) was added TFA (2.67 mL, 34.5 mmol). The reaction was stirred at 75° C. for 8 hours and then concentrated. The residue was partitioned between DCM and aqueous sodium bicarbonate. The organic layer was concentrated and purified by silica-gel chromatography, eluting with 50-100% EtOAc in DCM, to provide the title compound (171.7 mg, 0.98 mmol) as an off-white solid. LC/MS (ESI$^+$) m/z=176 (M+H).

Intermediate 26

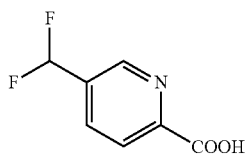

Synthesis of 5-(Difluoromethyl)picolinic acid

Step 1: 5-Formylpicolinonitrile

A suspension of 2-bromo-5-formylpyridine (940 mg, 5.05 mmol) and copper (I) cyanide (233 µL, 7.58 mmol) in DMF (8.4 mL) was stirred at 120° C. for 1.5 hours, cooled to RT, and partitioned between water and EtOAc. The solids were removed from the aqueous layer by filtration, and the filtrate was extracted with ethyl acetate. The combined organic layers were washed with brine, dried over anhydrous magnesium sulfate, filtered and concentrated. The crude product was purified by silica-gel chromatography, eluting with a gradient of 40%-60% (40% ethyl acetate in heptane) in heptane, to provide the title compound (236 mg, 1.786 mmol) as white solid. LC/MS (ESI$^+$) m/z=133 (M+H).

Step 2: 5-(Difluoromethyl)picolinonitrile

To a solution of 5-formylpicolinonitrile (74 mg, 0.560 mmol) in toluene (0.25 mL) was added bis(2-methoxyethyl)aminosulfur trifluoride (0.258 mL, 1.400 mmol), and the reaction was stirred at RT overnight. The reaction mixture was carefully quenched with saturated aqueous sodium bicarbonate, diluted with water, and extracted with DCM. The organic layer was washed with brine, dried over anhydrous magnesium sulfate, filtered, and concentrated. The crude material was purified by silica-gel chromatography, eluting with a gradient of 40% to 60% (40% ethyl acetate/heptane) in heptane, to provide the title compound (48 mg, 0.311 mmol) as white solid. LC/MS (ESI$^+$) m/z=155 (M+H).

Step 3: 5-(difluoromethyl)picolinic acid

A suspension of 5-(difluoromethyl)picolinonitrile (48 mg, 0.311 mmol) in 12 N aqueous hydrochloric acid (4.3 mL, 140 mmol) was stirred at 110° C. for 1.5 hours. After cooling to ambient temperature, the reaction mixture was concentrated and treated with DIPEA (2 mL). The mixture was concentrated and dried in vacuo to provide the title compound in quantitative yield. LC/MS (ESI$^+$) m/z=174 (M+H).

Intermediate 27

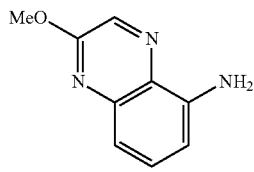

Synthesis of 2-Methoxyquinoxalin-5-amine

To a suspension of 5-aminoquinoxalin-2(1H)-one (440 mg, 2.73 mmol) in methanol (1 mL), DCM (8 mL) and acetonitrile (8 mL), at 0° C., was added TEA (1.14 mL, 8.19 mmol), followed by (trimethylsilyl)diazomethane (2 mL, 4.10 mmol; 2.0M in hexanes). The reaction mixture was allowed to warm to RT and stirred for additional 3 hours. The suspension was filtered, and the filtrate was concentrated under reduced pressure. The crude product was purified by silica gel chromatography, eluting with 10%-50% ethyl acetate in hexane, to provide the title compound (167 mg, 0.953 mmol) as a light-yellow powder. LC/MS (ESI$^+$) m/z=176 (M+H).

General amidation procedures: The following two (2) methods may be used to couple the amine core intermediates (see examples and intermediates 1-17; note that the bromide needs to be converted to the corresponding amine to be used in the methods below).

Method A: HATU Procedure

To a solution of the aniline (1 equivalent) and the carboxylic acid (1.1 equivalent) in DCM were added triethylamine (1.5 eq) and 1-[bis(dimethylamino)methylene]-1H-1,2,3-triazolo[4,5-b]pyridinium 3-oxide hexafluorophosphate (HATU, 1.1 equivalent). The reaction mixture was stirred at RT for 3 hours, diluted with DCM, and washed with water and brine. The organic layer was concentrated.

The residue was redissolved in DCM, and TFA (up to 10 equivalents) was added. The reaction is stirred at RT for 1 hour, diluted with DCM, and washed with saturated aqueous sodium bicarbonate and brine, and concentrated. The crude product was purified by silica-gel chromatography to provide the title compound.

Method B: DMTMM Procedure

To a solution of the aniline (1 equivalent) and the carboxylic acid (1.1 equivalent) in 2:1 tetrahydrofuran/methanol is added 4-(4,6-dimethoxy-1,3,5-triazin-2-yl)-4-methylmorpholinium chloride (DMTMM, 1.5 equivalents). After about ten minutes, water and saturated aqueous sodium bicarbonate is added, and the mixture is extracted with DCM. The organic extract is washed with brine and concentrated.

The residue is redissolved in DCM, and TFA (up to 10 equivalents) is added. The reaction is stirred at RT for 1 hour, diluted with dichloromethane, and washed with saturated aqueous sodium bicarbonate and brine, and concentrated. The crude product is purified by silica-gel chromatography to provide the title compound.

Note for purposes of Table 2 and for Methods C and D described hereinbelow, the aniline intermediates use in Method A and Method B are designated as intermediate R, while the carboxylic acid intermediates are designated as intermediate L.

Example 1

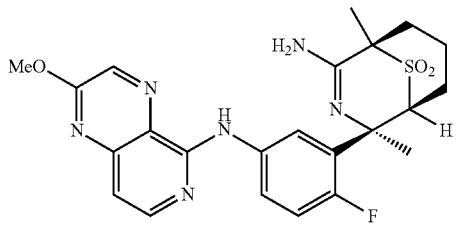 [SMILES: COc1cnc2c(Nc3ccc(F)c([C@@]4(C)N=C(N)[C@@]5(C)CCC[C@@H]4S5(=O)=O)c3)nccc2n1]

Synthesis of (1R,4R,5S)-2-Amino-4-(2-fluoro-5-((2-methoxypyrido[3,4-b]pyrazin-5-yl)amino)phenyl)-1,4-dimethyl-9-thia-3-azabicyclo[3.3.1]non-2-ene 9,9-dioxide To a solution of Intermediates 2A and 2B (75 mg, 0.143 mmol) and 5-chloro-2-methoxypyrido[3,4-b]pyrazine (27.9 mg, 0.143 mmol) in 2-propanol (1.5 mL) was added concentrated sulfuric acid (7.6 μL, 0.143 mmol). The reaction was stirred for 20 minutes at 100° C. After 30 minutes, the reaction mixture was diluted with DCM, washed with saturated aqueous sodium bicarbonate, and concentrated. The residue was redissolved in DCM (2 mL), and TFA (0.220 mL, 2.85 mmol) was added. The reaction was stirred at ambient temperature for one hour, diluted with DCM, and washed with saturated aqueous sodium bicarbonate. The organic layer was purified by silica-gel column chromatography, eluting with 0-10% methanol in DCM, to provide the title compound (23 mg, 33% yield). $^{1}$H-NMR (400 MHz, DMSO-$d_{6}$): δ ppm 9.43 (s, 1 H), 8.55 (s, 1 H), 8.21-8.25 (m, 2 H), 8.12-8.16 (m, 1 H), 7.14 (dd, J=11.7, 8.9 Hz, 1 H), 7.06 (d, J=5.9 Hz, 1 H), 5.99 (s, 2 H), 4.07 (s, 3 H), 3.56 (s, 1 H), 2.04-2.14 (m, 1 H), 1.91-1.98 (m, 2 H), 1.72 (s, 3 H), 1.38-1.58 (m, 6 H). LC/MS (ESI$^{+}$) m/z=485.1 D (M+H).

Example 2

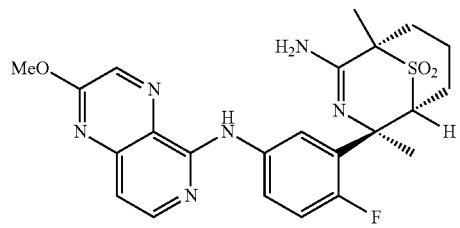 [SMILES: COc1cnc2c(Nc3ccc(F)c([C@@]4(C)N=C(N)[C@]5(C)CCC[C@H]4S5(=O)=O)c3)nccc2n1]

Synthesis of (1S,4R,5R)-2-Amino-4-(2-fluoro-5-((2-methoxypyrido[3,4-b]pyrazin-5-yl)amino)phenyl)-1,4-dimethyl-9-thia-3-azabicyclo[3.3.1]non-2-ene 9,9-dioxide The title compound was also isolated from the reaction described in Example 1 (10 mg, 14% yield). $^{1}$H-NMR (400 MHz, DMSO-$d_{6}$): δ ppm 9.17 (s, 1 H), 8.56 (s, 1 H), 8.24 (d, J=5.8 Hz, 2 H), 8.03-8.07 (m, 1 H), 7.80-7.85 (m, 1 H), 7.05-7.10 (m, 2 H), 6.11 (bs, 2 H), 4.08 (s, 3 H), 3.62 (bs, 1 H), 2.37-2.46 (m, 1 H), 2.22-2.30 (m, 1 H), 2.00-2.06 (m, 2 H), 1.76 (s, 3 H), 1.57-1.67 (m, 5 H). LC/MS (ESI$^{+}$) m/z=485.1 D (M+H).

Example 3

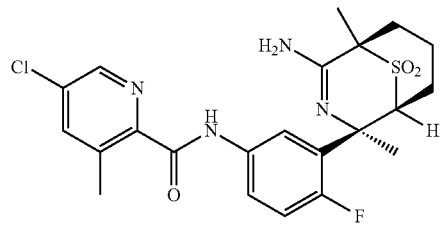 [SMILES: Cc1cc(Cl)cnc1C(=O)Nc1ccc(F)c([C@@]2(C)N=C(N)[C@@]3(C)CCC[C@@H]2S3(=O)=O)c1]

Synthesis of N-(3-((1S,2R,5R)-4-Amino-2,5-dimethyl-9,9-dioxido-9-thia-3-azabicyclo[3.3.1]non-3-en-2-yl)-4-fluorophenyl)-5-chloro-3-methylpicolinamide To a solution of Intermediates 2A and 2B (150 mg, 0.285 mmol) and 5-chloro-3-methylpyridine-2-carboxylic acid (49 mg, 0.285 mmol) in methanol (1 mL) and THF (2 mL) was added 4-(4,6-dimethoxy-1,3,5-triazin-2-yl)-4-methylmorpholin-4-ium chloride (88 mg, 0.300 mmol). The reaction was stirred at RT. After 3 hours, the reaction mixture was partitioned between water and ethyl acetate; the organic layer was dried over anhydrous magnesium sulfate, filtered, and concentrated. The residue was redissolved in DCM (5 mL), and TFA (0.44 mL, 5.71 mmol) was added. The reaction was stirred at RT for 2.5 hours, washed with saturated aqueous sodium bicarbonate and brine, and concentrated. The crude product was purified by silica-gel column chromatography, eluting with 2-10% methanol in DCM, to provide the title compound (56 mg, 41% yield). ¹H-NMR (400 MHz, DMSO-d₆): δ ppm 10.54 (s, 1 H), 8.57 (d, J=2.3 Hz, 1 H), 8.02-8.06 (m, 2 H), 7.85-7.89 (m, 1 H), 7.16 (dd, J=11.7, 8.8 Hz, 1 H), 5.96 (s, 2 H), 3.57 (s, 1 H), 2.57 (s, 3 H), 2.03-2.14 (m, 1 H), 1.89-1.96 (m, 2 H), 1.70 (s, 3 H), 1.50-1.53 (m, 1 H), 1.48 (s, 3 H), 1.21-1.35 (m, 2 H). LC/MS (ESI⁺) m/z=479.1 D (M+H).

Example 4

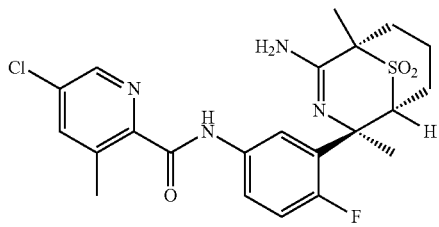

Synthesis of N-(3-((1R,2R,5S)-4-Amino-2,5-dimethyl-9,9-dioxido-9-thia-3-azabicyclo[3.3.1]non-3-en-2-yl)-4-fluorophenyl)-5-chloro-3-methylpicolinamide The title compound was also isolated from the reaction described in Example 3 (41 mg, 30% yield). ¹H-NMR (400 MHz, DMSO-d₆): δ ppm 10.43 (s, 1 H), 8.56 (d, J=1.8 Hz, 1 H), 8.00 (d, J=1.6 Hz, 1 H), 7.81-7.85 (m, 1 H), 7.53 (dd, J=7.5, 2.7 Hz, 1 H), 7.08 (dd, J=12.3, 8.9 Hz, 1 H), 6.07 (s, 2 H), 3.59 (s, 1 H), 2.53 (s, 3 H), 2.36-2.44 (m, 1 H), 2.18-2.30 (m, 1 H), 1.98-2.05 (m, 2 H), 1.59-1.67 (m, 2 H), 1.57 (s, 3 H), 1.41 (s, 3 H). LC/MS (ESI⁺) m/z=479.1 D (M+H).

Example 5

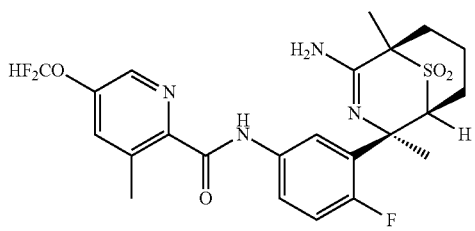

Synthesis of N-(3-((1S,2R,5R)-4-Amino-2,5-dimethyl-9,9-dioxido-9-thia-3-azabicyclo[3.3.1]non-3-en-2-yl)-4-fluorophenyl)-5-(difluoromethoxy)-3-methylpicolinamide In a sequence of reactions analogous to those described in Example 3, Intermediates 2A and 2B (150 mg, 0.285 mmol) and 5-(difluoromethoxy)-methylpyridine-2-carboxylic acid (58 mg, 0.285 mmol) were combined to provide the title compound (35 mg, 24% yield). ¹H-NMR (400 MHz, DMSO-d₆): δ ppm 10.50 (s, 1 H), 8.42 (d, J=2.5 Hz, 1 H), 8.05 (dd, J=7.2, 2.7 Hz, 1 H), 7.86-7.90 (m, 1 H), 7.72 (d, J=2.3 Hz, 1 H), 7.44 (t, J=73.0 Hz, 1 H), 7.16 (dd, J=11.8, 8.8 Hz, 1 H), 5.96 (s, 2 H), 3.57 (s, 1 H), 2.61 (s, 3 H), 2.05-2.12 (m, 1 H), 1.92-1.94 (m, 2 H), 1.70 (s, 3 H), 1.48-1.55 (m, 1 H), 1.48 (s, 3 H), 1.14-1.35 (m, 2 H). LC/MS (ESI⁺) m/z=511.1 D (M+H).

Example 6

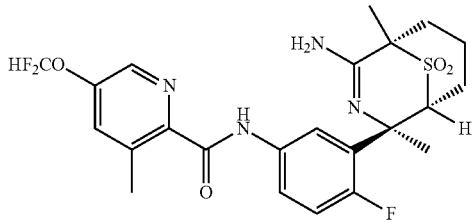

Synthesis of N-(3-((1R,2R,5S)-4-Amino-2,5-dimethyl-9,9-dioxido-9-thia-3-azabicyclo[3.3.1]non-3-en-2-yl)-4-fluorophenyl)-5-(difluoromethoxy)-3-methylpicolinamide The title compound was also isolated from the reaction described in Example 5 (39 mg, 26% yield). ¹H-NMR (400 MHz, DMSO-d₆): δ ppm 10.39 (s, 1 H), 8.41 (d, J=2.5 Hz, 1 H), 7.81-7.85 (m, 1 H), 7.70 (d, J=2.3 Hz, 1 H), 7.54 (dd, J=7.5, 2.7 Hz, 1H), 7.43 (t, J=73.1 Hz, 1 H), 7.08 (dd, J=12.3, 8.8 Hz, 1 H), 6.07 (s, 2 H), 3.59 (bs, 1 H), 2.57 (s, 3 H), 2.18-2.44 (m, 2 H), 1.98-2.05 (m, 2 H), 1.59-1.68 (m, 2 H), 1.57 (s, 3 H), 1.41 (s, 3 H). LC/MS (ESI⁺) m/z=511.1 D (M+H).

Example 7

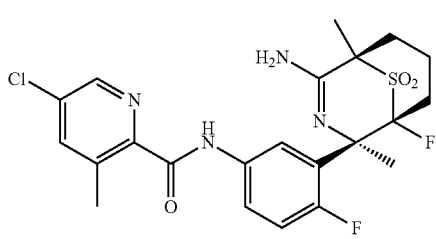

Synthesis of N-(3-((1S,2R,5R)-4-Amino-1-fluoro-2,5-dimethyl-9,9-dioxido-9-thia-3-azabicyclo[3.3.1]non-3-en-2-yl)-4-fluorophenyl)-5-chloro-3-methylpicolinamide In a sequence of reactions analogous to those described in Example 3, Intermediate 3 (64 mg, 0.118 mmol) and 5-chloro-3-methyl-pyridine-2-carboxylic acid (0.015 mL, 0.118 mmol) were combined to provide the title compound (45 mg, 77% yield). ¹H-NMR (400 MHz, DMSO-d₆): δ ppm 10.61 (s, 1 H), 8.58 (d, J=1.9 Hz, 1 H), 8.03-8.06 (m, 2 H), 7.91-7.96 (m, 1 H), 7.17 (dd, J=11.7, 8.8 Hz, 1 H), 6.20 (s, 2 H), 2.57 (s, 3 H), 2.14-2.21 (m, 1 H), 1.94-2.03 (m, 2 H), 1.76

(d, J=3.1 Hz, 3 H), 1.58-1.66 (m, 2 H), 1.55 (s, 3 H), 1.37-1.46 (m, 1 H). LC/MS (ESI+) m/z=497.1 D (M+H).

Example 8

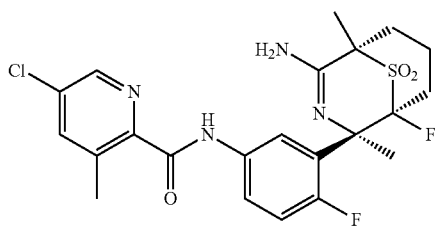 [SMILES: Cc1cc(Cl)cnc1C(=O)Nc1ccc(F)c([C@@]2(C)N=C(N)[C@]3(C)CCC[C@H]2S3(=O)=O)c1]

Synthesis of N-(3-((1R,2R,5S)-4-Amino-1-fluoro-2,5-dimethyl-9,9-dioxido-9-thia-3-azabicyclo[3.3.1]non-3-en-2-yl)-4-fluorophenyl)-5-chloro-3-methylpicolinamide In a sequence of reactions analogous to those described in Example 3, Intermediate 4 (40 mg, 0.074 mmol) and 5-chloro-3-methyl-pyridine-2-carboxylic acid (12.6 mg, 0.074 mmol) were combined to provide the title compound (12 mg, 33% yield). $^1$H-NMR (400 MHz, DMSO-d$_6$): δ ppm 10.42 (s, 1 H), 8.56 (d, J=2.2 Hz, 1 H), 8.00 (d, J=1.9 Hz, 1 H), 7.88-7.91 (m, 1 H), 7.40-7.43 (m, 1 H), 7.02 (dd, J=12.4, 8.9 Hz, 1 H), 6.25 (s, 2 H), 2.60-2.68 (m, 1 H), 2.51 (s, 3 H), 2.28-2.40 (m, 1 H), 2.01-2.10 (m, 2 H), 1.67-1.89 (m, 5 H), 1.55 (s, 3 H), 1.37-1.46 (m, 1 H). LC/MS (ESI+) m/z=497.1 D (M+H).

Example 9

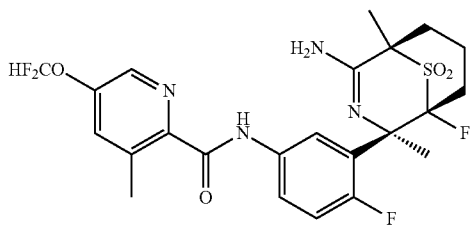

Synthesis of N-(3-((1S,2R,5R)-4-Amino-1-fluoro-2,5-dimethyl-9,9-dioxido-9-thia-3-azabicyclo[3.3.1]non-3-en-2-yl)-4-fluorophenyl)-5-(difluoromethoxy)-3-methylpicolinamide In a sequence of reactions analogous to those described in Example 3, Intermediate 3 (64 mg, 0.118 mmol) and 5-(difluoromethoxy)-3-methylpicolinic acid (23.92 mg, 0.118 mmol) were combined to provide the title compound (39 mg, 63% yield). $^1$H-NMR (400 MHz, DMSO-d$_6$): δ ppm 10.57 (s, 1 H), 8.43 (d, J=2.4 Hz, 1 H), 8.03-8.06 (m, 1 H), 7.92-7.96 (m, 1 H), 7.72 (d, J=2.2 Hz, 1 H), 7.44 (t, J=73.1 Hz, 1H), 7.17 (dd, J=11.8, 8.8 Hz, 1 H), 6.20 (s, 2 H), 2.60 (s, 3 H), 2.13-2.24 (m, 1 H), 1.93-2.04 (m, 2 H), 1.76 (d, J=3.1 Hz, 3 H), 1.59-1.68 (m, 2 H), 1.55 (s, 3 H), 1.37-1.46 (m, 1 H). LC/MS (ESI+) m/z=529.1 D (M+H).

Example 10

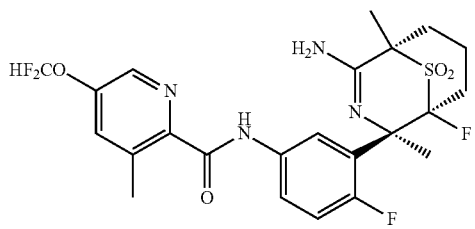

Synthesis of N-(3-((1R,2R,5S)-4-Amino-1-fluoro-2,5-dimethyl-9,9-dioxido-9-thia-3-azabicyclo[3.3.1]non-3-en-2-yl)-4-fluorophenyl)-5-(difluoromethoxy)-3-methylpicolinamide In a sequence of reactions analogous to those described in Example 3, Intermediate 4 (40 mg, 0.074 mmol) and 5-(difluoromethoxy)-3-methylpicolinic acid (14.95 mg, 0.074 mmol) were combined to provide the title compound (15 mg, 39% yield). $^1$H-NMR (400 MHz, DMSO-d$_6$): δ ppm 10.38 (s, 1 H), 8.42 (d, J=2.5 Hz, 1 H), 7.88-7.92 (m, 1 H), 7.72 (d, J=2.2 Hz, 1 H), 7.42 (t, J=73.1 Hz, 1 H), 7.40-7.44 (m, 1H), 7.03 (dd, J=12.2, 8.9 Hz, 1 H), 6.25 (s, 2 H), 2.60-2.68 (m, 1 H), 2.55 (s, 3 H), 2.29-2.40 (m, 1 H), 2.04-2.09 (m, 1 H), 1.67-1.89 (m, 6 H), 1.52 (s, 3 H). LC/MS (ESI+) m/z=529.2 D (M+H).

Example 11

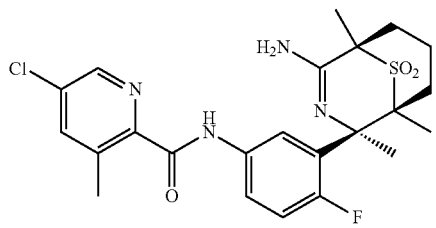 [SMILES: Cc1cc(Cl)cnc1C(=O)Nc1ccc(F)c([C@@]2(C)N=C(N)[C@@]3(C)CCC[C@]2(C)S3(=O)=O)c1]

Synthesis of N-(3-((1S,2R,5R)-4-Amino-1,2,5-trimethyl-9,9-dioxido-9-thia-3-azabicyclo[3.3.1]non-3-en-2-yl)-4-fluorophenyl)-5-chloro-3-methylpicolinamide In a sequence of reactions analogous to those described in Example 3, Intermediates 5A and 5B (100 mg, 0.185 mmol) and 5-chloro-3-methyl-pyridine-2-carboxylic acid (31.8 mg, 0.185 mmol) were combined to provide the title compound (14 mg, 15% yield). $^1$H-NMR (400 MHz, DMSO-d$_6$): δ ppm 10.63 (s, 1 H), 8.58 (d, J=1.9 Hz, 1 H), 8.02-8.05 (m, 2 H), 7.89-7.93 (m, 1 H), 7.15 (dd, J=12.8, 8.8 Hz, 1 H), 5.92 (s, 2

H), 2.54 (s, 3 H), 2.00-2.20 (m, 2 H), 1.71-1.87 (m, 6 H), 1.50 (s, 3 H), 1.46 (d, J=3.4 Hz, 3 H). LC/MS (ESI⁺) m/z=493.1 D (M+H).

Example 12

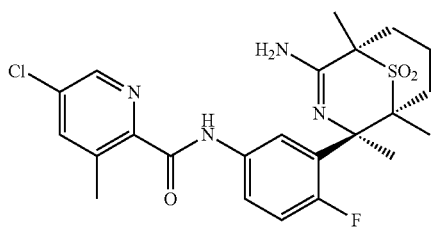 [SMILES: Cc1cc(Cl)cnc1C(=O)Nc1ccc(F)c([C@@]2(C)N=C(N)[C@]3(C)CCC[C@@]2(C)S3(=O)=O)c1]

Synthesis of N-(3-((1R,2R,5S)-4-Amino-1,2,5-trimethyl-9,9-dioxido-9-thia-3-azabicyclo[3.3.1]non-3-en-2-yl)-4-fluorophenyl)-5-chloro-3-methylpicolinamide The title compound was also isolated from the reaction described in Example 11 (16 mg, 18% yield). ¹H-NMR (400 MHz, DMSO-d₆): δ ppm 10.36 (s, 1 H), 8.57 (d, J=2.3 Hz, 1 H), 8.00 (d, J=1.6 Hz, 1 H), 7.88-7.91 (m, 1 H), 7.29-7.33 (m, 1 H), 7.00 (dd, J=12.8, 8.8 Hz, 1 H), 5.95 (s, 2 H), 2.51 (s, 3 H), 2.21-2.29 (m, 1 H), 1.90-2.10 (m, 4 H), 1.58-1.79 (m, 6 H), 1.50 (s, 3 H), 1.46-1.56 (m, 1 H). LC/MS (ESI⁺) m/z=493.1 D (M+H).

Example 13

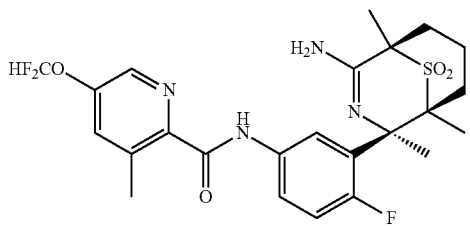

Synthesis of N-(3-((1S,2R,5R)-4-Amino-1,2,5-trimethyl-9,9-dioxido-9-thia-3-azabicyclo[3.3.1]non-3-en-2-yl)-4-fluorophenyl)-5-(difluoromethoxy)-3-methylpicolinamide In a sequence of reactions analogous to those described in Example 3, Intermediates 5A and 5B (100 mg, 0.185 mmol) and 5-(difluoromethoxy)-3-methylpicolinic acid (37.6 mg, 0.185 mmol) were combined to provide the title compound (26 mg, 27% yield). ¹H-NMR (400 MHz, DMSO-d₆): δ ppm 10.61 (s, 1 H), 8.43 (d, J=2.4 Hz, 1 H), 8.02-8.06 (m, 1 H), 7.92-7.96 (m, 1 H), 7.72 (d, J=2.2 Hz, 1H), 7.43 (t, J=73.1 Hz, 1 H), 7.18 (bs, 1 H), 5.93 (s, 2 H), 2.58 (s, 3 H), 1.96-2.12 (m, 3 H), 1.69-1.89 (m, 6 H), 1.44-1.58 (m, 6 H). LC/MS (ESI⁺) m/z=525.2 D (M+H).

Example 14

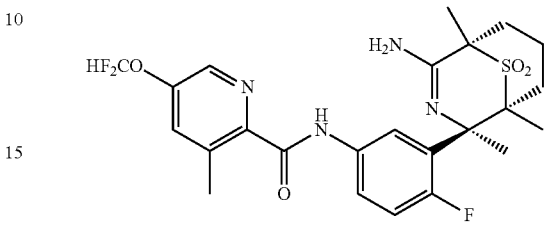

Synthesis of N-(3-((1R,2R,5S)-4-Amino-1,2,5-trimethyl-9,9-dioxido-9-thia-3-azabicyclo[3.3.1]non-3-en-2-yl)-4-fluorophenyl)-5-(difluoromethoxy)-3-methylpicolinamide The title compound was also isolated from the reaction described in Example 13 (7 mg, 7% yield). ¹H-NMR (400 MHz, DMSO-d₆): δ ppm 10.33 (s, 1 H), 8.42 (d, J=2.4 Hz, 1 H), 7.89-7.93 (m, 1 H), 7.70 (d, J=2.2 Hz, 1 H), 7.41 (t, J=73.1 Hz, 1 H), 7.31 (bs, 1 H), 7.01 (dd, J=12.8, 8.9 Hz, 1 H), 5.96 (s, 2 H), 2.55 (s, 3 H), 2.22-2.31 (m, 1 H), 1.88-2.11 (m, 4 H), 1.53-1.80 (m, 7 H), 1.51 (s, 3 H). LC/MS (ESI⁺) m/z=525.2 D (M+H).

Example 15

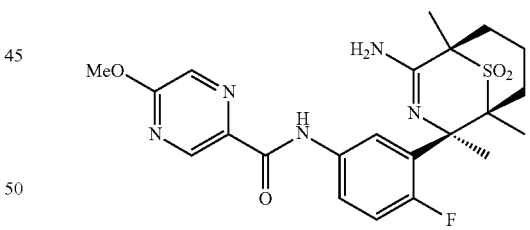

Synthesis of N-(3-((1S,2R,5R)-4-Amino-1,2,5-trimethyl-9,9-dioxido-9-thia-3-azabicyclo[3.3.1]non-3-en-2-yl)-4-fluorophenyl)-5-methoxypyrazine-2-carboxamide In a sequence of reactions analogous to those described in Example 3, Intermediates 5A and 5B (100 mg, 0.185 mmol) and 5-methoxypyrazine-2-carboxylic acid (28.6 mg, 0.185 mmol) were combined to provide the title compound (19 mg, 21% yield). ¹H-NMR (400 MHz, DMSO-d₆): δ ppm 10.63 (s, 1 H), 8.89 (d, J=1.4 Hz, 1 H), 8.42 (d, J=1.3 Hz, 1 H), 8.21-8.23 (m, 1 H), 7.86-7.89 (m, 1 H), 7.15 (dd, J=12.8, 8.8

Hz, 1 H), 5.93 (s, 2 H), 4.02 (s, 3 H), 1.70-2.06 (m, 8 H), 1.50 (s, 3 H), 1.47 (d, J=3.3 Hz, 3 H). LC/MS (ESI⁺) m/z=476.1 D (M+H).

Example 16

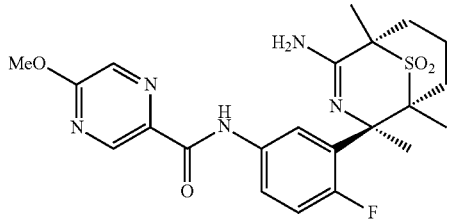 [SMILES: COc1cnc(C(=O)Nc2ccc(F)c([C@@]3(C)N=C(N)[C@]4(C)CCC[C@@]3(C)S4(=O)=O)c2)cn1]

Synthesis of N-(3-((1R,2R,5S)-4-Amino-1,2,5-trimethyl-9,9-dioxido-9-thia-3-azabicyclo[3.3.1]non-3-en-2-yl)-4-fluorophenyl)-5-methoxypyrazine-2-carboxamide The title compound was also isolated from the reaction described in Example 15 (24 mg, 27% yield). ¹H-NMR (400 MHz, DMSO-$d_6$): δ ppm 10.16 (s, 1 H), 8.87 (d, J=1.4 Hz, 1 H), 8.42 (d, J=1.3 Hz, 1 H), 7.80-7.84 (m, 1 H), 7.48-7.53 (m, 1 H), 7.00 (dd, J=12.8, 8.8 Hz, 1 H), 5.95 (s, 2 H), 4.02 (s, 3 H), 2.23-2.30 (m, 1 H), 1.90-2.08 (m, 4 H), 1.57-1.82 (m, 7 H), 1.50 (s, 3 H). LC/MS (ESI⁺) m/z=476.1 D (M+H).

Example 17

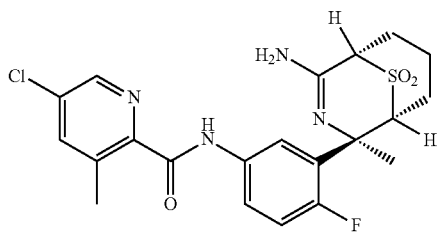 [SMILES: Cc1cc(Cl)cnc1C(=O)Nc1ccc(F)c([C@@]2(C)N=C(N)[C@@H]3CCC[C@H]2S3(=O)=O)c1]

Synthesis of N-(3-((1R,2R,5S)-4-Amino-2-methyl-9,9-dioxido-9-thia-3-azabicyclo[3.3.1]non-3-en-2-yl)-4-fluorophenyl)-5-chloro-3-methylpicolinamide In a sequence of reactions analogous to those described in Example 3, Intermediate 8 (30 mg, 0.073 mmol) and 5-chloro-3-methyl-pyridine-2-carboxylic acid (13.76 mg, 0.080 mmol) were combined to provide the title compound (26 mg, 77% yield). ¹H-NMR (400 MHz, CDCl₃): δ ppm 9.94 (s, 1 H), 8.36 (d, J=1.8 Hz, 1 H), 7.93-7.97 (m, 1 H), 7.62 (d, J=1.6 Hz, 1 H), 7.38 (dd, J=7.2, 2.7 Hz, 1 H), 7.00 (dd, J=12.2, 8.9 Hz, 1 H), 4.80 (bs, 2 H), 3.73-3.78 (m, 1 H), 3.46 (bs, 1 H), 2.41-2.57 (m, 3 H), 2.20-2.29 (m, 1 H), 1.72 (s, 3 H), 1.62-1.69 (m, 2 H). LC/MS (ESI⁺) m/z=465.1 D (M+H).

Example 18

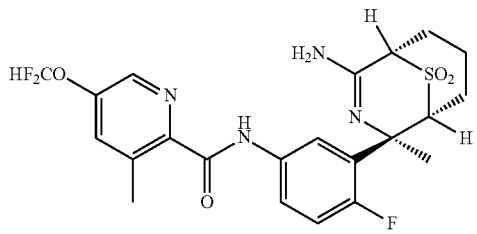

Synthesis of N-(3-((1R,2R,5S)-4-Amino-2-methyl-9,9-dioxido-9-thia-3-azabicyclo[3.3.1]non-3-en-2-yl)-4-fluorophenyl)-5-(difluoromethoxy)-3-methylpicolinamide In a sequence of reactions analogous to those described in Example 3, Intermediate 8 (30 mg, 0.073 mmol) and 5-(difluoromethoxy)-3-methylpicolinic acid (16.29 mg, 0.080 mmol) were combined to provide the title compound (24 mg, 66% yield). ¹H-NMR (400 MHz, CDCl₃): δ ppm 9.98 (s, 1 H), 8.22 (d, J=2.2 Hz, 1 H), 7.91-7.95 (m, 1 H), 7.39 (dd, J=7.2, 2.7 Hz, 1 H), 7.35 (d, J=2.0 Hz, 1 H), 7.01 (dd, J=12.1, 8.8 Hz, 1 H), 6.59 (t, J=72.3 Hz, 1 H), 4.89 (bs, 2 H), 3.77 (bs, 1 H), 3.40 (bs, 1 H), 2.40-2.56 (m, 3 H), 2.18-2.27 (m, 1 H), 1.72 (s, 3 H), 1.62-1.70 (m, 2 H). LC/MS (ESI⁺) m/z=497.1 D (M+H).

Example 19

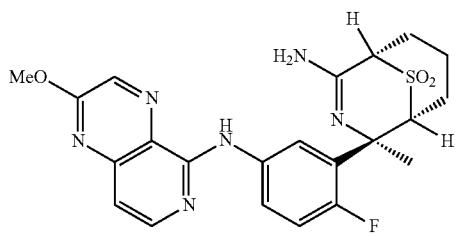 [SMILES: COc1cnc2c(Nc3ccc(F)c([C@@]4(C)N=C(N)[C@@H]5CCC[C@H]4S5(=O)=O)c3)nccc2n1]

Synthesis of N-(3-((1R,2R,5S)-4-Amino-2-(2-fluoro-5-((2-methoxypyrido[3,4-b]pyrazin-5-yl)amino)phenyl)-2-methyl-9-thia-3-azabicyclo[3.3.1]non-3-ene 9,9-dioxide To a suspension of Intermediate 8 (35 mg, 0.085 mmol) and 5-chloro-2-methoxypyrido[3,4-b]pyrazine (16.64 mg, 0.085 mmol) in 2-propanol (0.9 mL) was added concentrated sulfuric acid (4.5 μL, 0.085 mmol). The reaction was stirred for 20 minutes at 100° C., and then partitioned between saturated aqueous sodium bicarbonate and DCM. The organic layer was concentrated and purified by silica-gel column chromatography, eluting with 0-10% methanol in DCM, to provide the title compound (20 mg, 50.0% yield). ¹H-NMR (400 MHz, CDCl₃): δ ppm 8.58 (s, 1 H), 8.25 (s, 1 H), 8.20 (d, J=5.9 Hz, 1 H), 8.14-8.18 (m, 1 H), 7.45-7.50 (m, 1 H), 6.99 (d, J=5.9 Hz, 1 H), 6.90-6.95 (m, 1 H), 4.09 (s, 3 H), 3.81-3.88

(m, 1 H), 3.73 (bs, 1 H), 2.43-2.61 (m, 3 H), 2.26-2.34 (m, 1 H), 1.76 (s, 3 H), 1.65-1.74 (m, 2 H). LC/MS (ESI+) m/z=471.1 D (M+H).

Example 20

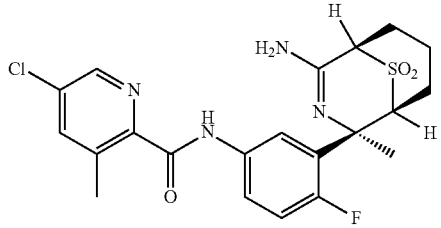 [SMILES: Cc1cc(Cl)cnc1C(=O)Nc1ccc(F)c([C@@]2(C)N=C(N)[C@H]3CCC[C@@H]2S3(=O)=O)c1]

Synthesis of N-(3-((1S,2R,5R)-4-Amino-2-methyl-9,9-dioxido-9-thia-3-azabicyclo[3.3.1]non-3-en-2-yl)-4-fluorophenyl)-5-chloro-3-methylpicolinamide In a sequence of reactions analogous to those described in Example 3, Intermediate 9 (12 mg, 0.029 mmol) and 5-chloro-3-methyl-pyridine-2-carboxylic acid (5.50 mg, 0.032 mmol) were combined to provide the title compound (8 mg, 59% yield). $^1$H-NMR (400 MHz, CDCl$_3$): δ ppm 10.06 (s, 1 H), 8.38 (d, J=2.0 Hz, 1 H), 8.02-8.06 (m, 1 H), 7.75 (dd, J=6.8, 2.6 Hz, 1 H), 7.65 (d, J=1.7 Hz, 1 H), 7.08 (dd, J=11.5, 8.8 Hz, 1 H), 5.18 (bs, 2 H), 3.71 (bs, 1 H), 3.57 (bs, 1 H), 2.40-2.52 (m, 1 H), 2.6-2.37 (m, 2 H), 1.91 (s, 3 H), 1.70-1.79 (m, 1 H), 1.18-1.36 (m, 2 H). LC/MS (ESI+) m/z=465.1 D (M+H).

Example 21

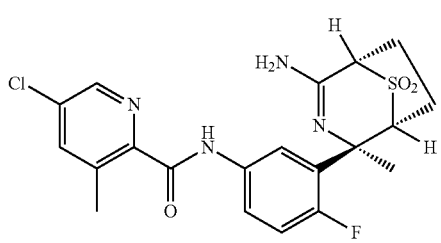 [SMILES: Cc1cc(Cl)cnc1C(=O)Nc1ccc(F)c([C@@]2(C)N=C(N)[C@@H]3CC[C@H]2S3(=O)=O)c1]

Synthesis of N-(3-((1R,2R,5S)-4-Amino-2-methyl-8,8-dioxido-8-thia-3-azabicyclo[3.2.1]oct-3-en-2-yl)-4-fluorophenyl)-5-chloro-3-methylpicolinamide In a sequence of reactions analogous to those described in Example 3, Intermediate 10 (25 mg, 0.063 mmol) and 5-chloro-3-methyl-pyridine-2-carboxylic acid (10.79 mg, 0.063 mmol) were combined to provide the title compound (16 mg, 57% yield). $^1$H-NMR (400 MHz, CDCl$_3$): δ ppm 9.99 (s, 1 H), 8.37 (d, J=1.9 Hz, 1 H), 7.99-8.03 (m, 1 H), 7.62 (d, J=1.7 Hz, 1 H), 7.44 (dd, J=7.1, 2.7 Hz, 1 H), 7.03 (dd, J=12.0, 8.9 Hz, 1 H), 5.44 (bs, 2 H), 3.88 (bs, 1 H), 3.67 (bs, 1 H), 2.78 (s, 3 H), 2.44-2.54 (m, 3 H), 2.22-2.33 (m, 1 H), 1.70 (s, 3 H). LC/MS (ESI+) m/z=451.1 D (M+H).

Example 22

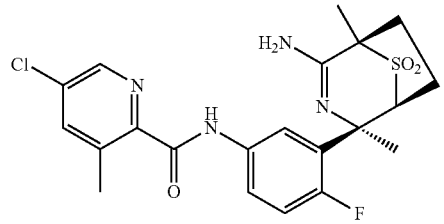 [SMILES: Cc1cc(Cl)cnc1C(=O)Nc1ccc(F)c([C@@]2(C)N=C(N)[C@@]3(C)CC[C@@H]2S3(=O)=O)c1]

Synthesis of N-(3-((1S,2R,5R)-4-Amino-2,5-dimethyl-8,8-dioxido-8-thia-3-azabicyclo[3.2.1]oct-3-en-2-yl)-4-fluorophenyl)-5-chloro-3-methylpicolinamide To a solution of Intermediate 12 (100 mg, 0.195 mmol) in N,N-dimethylformamide (1.0 mL) was added 5-chloro-3-methylpicolinic acid (43.6 mg, 0.254 mmol), (O-(7-azabenzotriazol-1-yl)-N,N,N',N'-tetramethyluronium hexafluorophosphate) (111 mg, 0.293 mmol), and pyridine (0.047 mL, 0.586 mmol). The reaction was stirred at ambient temperature for 2 hours, and then partitioned between water and ethyl acetate. The organic layer was washed with brine, dried over anhydrous sodium sulfate, filtered, and concentrated. The residue was redissolved in DCM (0.5 mL) and TFA (0.301 mL, 3.91 mmol) was added. The reaction was stirred at RT for an hour. The reaction was quenched with saturated aqueous sodium carbonate, and partitioned between water and ethyl acetate. The organic layer was washed with brine, dried over anhydrous sodium sulfate, filtered, and concentrated. The crude product was purified by silica-gel column chromatography, eluting with 0-50% (3:1 ethyl acetate:ethanol, 2% ammonium hydroxide) in heptanes, to provide the title compound (62 mg, 68.2% yield). $^1$H NMR (400 MHz, DMSO-d$_6$) ppm 1.28-1.34 (m, 1 H) 1.46 (s, 3 H) 1.68-1.72 (m, 1H) 1.74 (s, 3 H) 1.87-2.09 (m, 2 H) 2.57 (s, 3 H) 3.68 (d, J=5.77 Hz, 1 H) 6.03 (br. s., 2 H) 7.17 (dd, J=11.74, 8.90 Hz, 1 H) 7.72-7.81 (m, 1 H) 7.81-7.89 (m, 1 H) 8.03 (dd, J=2.25, 0.68 Hz, 1 H) 8.52-8.61 (m, 1 H) 10.54 (s, 1 H). LC/MS (ESI+) m/z=465.1 (M+H).

Example 23

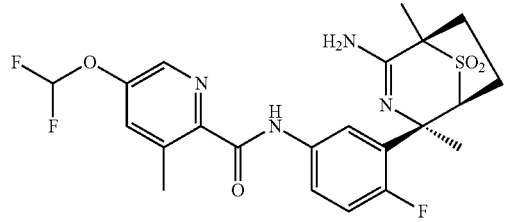 [SMILES: Cc1cc(OC(F)F)cnc1C(=O)Nc1ccc(F)c([C@@]2(C)N=C(N)[C@@]3(C)CC[C@@H]2S3(=O)=O)c1]

Synthesis of N-(3-((1S,2R,5R)-4-Amino-2,5-dimethyl-8,8-dioxido-8-thia-3-azabicyclo[3.2.1]oct-3-en-2-yl)-4-fluorophenyl)-5-(difluoromethoxy)-3-methylpicolinamide In a sequence of reactions analogous to those described in Example 22, Intermediate 12 (53 mg, 0.104 mmol) and 5-(difluoromethoxy)-methylpyridine-2-carboxylic acid (27 mg, 0.135 mmol) were combined to provide the title compound (16 mg, 31.1% yield). $^1$H NMR (400 MHz, DMSO-d$_6$) δ ppm 1.28-1.37 (m, 1 H) 1.46 (s, 3 H) 1.66-1.72 (m, 1 H) 1.74 (s, 3H) 1.85-2.11 (m, 2 H) 2.60 (s, 3 H) 3.68 (d, J=5.67 Hz, 1 H) 6.04 (br. s., 2 H) 7.16 (dd, J=11.79, 8.75 Hz, 1 H) 7.25-7.62 (m, 1H) 7.72 (d, J=2.25 Hz, 1 H) 7.79 (dd, J=7.09, 2.69 Hz, 1 H) 7.85 (dt, J=8.85, 3.50 Hz, 1 H) 8.43 (d, J=2.54 Hz, 1 H) 10.50 (s, 1 H). LC/MS (ESI$^+$) m/z=497.1 (M+H).

Example 24

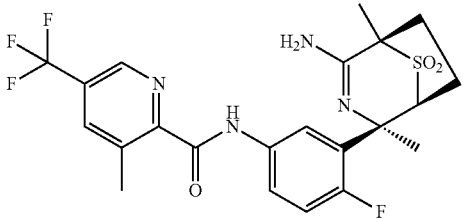 [SMILES: Cc1cc(C(F)(F)F)cnc1C(=O)Nc1ccc(F)c([C@@]2(C)N=C(N)[C@@]3(C)CC[C@@H]2S3(=O)=O)c1]

Synthesis of N-(3-((1S,2R,5R)-4-Amino-2,5-dimethyl-8,8-dioxido-8-thia-3-azabicyclo[3.2.1]oct-3-en-2-yl)-4-fluorophenyl)-3-methyl-5-(trifluoromethyl)picolinamide In a sequence of reactions analogous to those described in Example 22, Intermediate 12 (68 mg, 0.133 mmol) and 3-methyl-5-(trifluoromethyl)picolinic acid (35 mg, 0.173 mmol) were combined to provide the title compound (58 mg, 88% yield). $^1$H NMR (400 MHz, DMSO-d$_6$) δ ppm 1.28-1.37 (m, 1 H) 1.46 (s, 3 H) 1.68-1.74 (m, 1 H) 1.75 (s, 3H) 1.88-2.09 (m, 2 H) 2.60 (s, 3 H) 3.69 (d, J=5.48 Hz, 1 H) 6.04 (br. s., 2 H) 7.19 (dd, J=11.69, 8.75 Hz, 1 H) 7.75-7.81 (m, 1 H) 7.83-7.87 (m, 1H) 8.26-8.34 (m, 1 H) 8.86-8.94 (m, 1 H) 10.66 (s, 1 H). LC/MS (ESI$^+$) m/z=499.1 (M+H).

Example 25

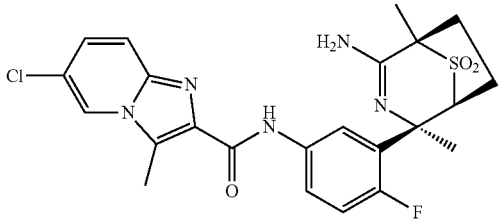 [SMILES: Cc1c(C(=O)Nc2ccc(F)c([C@@]3(C)N=C(N)[C@@]4(C)CC[C@@H]3S4(=O)=O)c2)nc2ccc(Cl)cn12]

Synthesis of N-(3-((1S,2R,5R)-4-Amino-2,5-dimethyl-8,8-dioxido-8-thia-3-azabicyclo[3.2.1]oct-3-en-2-yl)-4-fluorophenyl)-6-chloro-3-methylimidazo[1,2-a]pyridine-2-carboxamide In a sequence of reactions analogous to those described in Example 22, Intermediate 12 (60 mg, 0.117 mmol) and 6-chloro-3-methylimidazo[1,2-a]pyridine-2-carboxylic acid (32 mg, 0.152 mmol) were combined to provide the title compound (52 mg, 88% yield). $^1$H NMR (400 MHz, DMSO-d$_6$) δ ppm 1.30-1.36 (m, 1 H) 1.48 (s, 3 H) 1.68-1.74 (m, 1 H) 1.76 (s, 3H) 1.87-2.01 (m, 1 H) 2.05-2.19 (m, 1 H) 2.81 (s, 3H) 3.67 (d, J=6.06 Hz, 1 H) 6.10 (br. s, 2 H) 7.15 (dd, J=11.74, 8.80 Hz, 1 H) 7.43 (dd, J=9.63, 2.01 Hz, 1 H) 7.69 (dd, J=9.63, 0.83 Hz, 1 H) 7.84 (dd, J=7.14, 2.64 Hz, 1 H) 7.87-7.94 (m, 1 H) 8.69 (dd, J=1.96, 0.78 Hz, 1 H) 10.19 (s, 1 H). LC/MS (ESI$^+$) m/z=504.1 (M+H).

Example 26

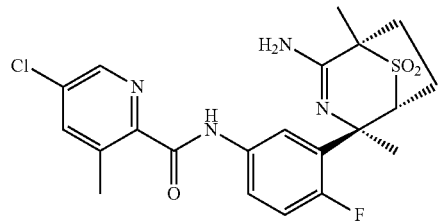 [SMILES: Cc1cc(Cl)cnc1C(=O)Nc1ccc(F)c([C@@]2(C)N=C(N)[C@]3(C)CC[C@H]2S3(=O)=O)c1]

Synthesis of N-(3-((1R,2R,5S)-4-Amino-2,5-dimethyl-8,8-dioxido-8-thia-3-azabicyclo[3.2.1]oct-3-en-2-yl)-4-fluorophenyl)-5-chloro-3-methylpicolinamide In a sequence of reactions analogous to those described in Example 22, Intermediate 13 (80 mg, 0.156 mmol) and 5-chloro-3-methylpicolinic acid (35 mg, 0.203 mmol) were combined to provide the title compound (15 mg, 21% yield). $^1$H NMR (400 MHz, DMSO-d$_6$) δ ppm 1.24 (s, 1 H) 1.42 (s, 3 H) 1.50 (s, 3 H) 1.82-1.94 (m, 1 H) 2.14-2.28 (m, 2 H) 2.36-2.45 (m, 1 H) 2.56 (s, 3 H) 3.76 (d, J=3.72 Hz, 1 H) 6.04 (br. s., 1 H) 7.12 (dd, J=12.18, 8.85 Hz, 1 H) 7.63 (dd, J=7.38, 2.69 Hz, 1 H) 7.77-7.89 (m, 1 H) 8.02 (dd, J=2.30, 0.64 Hz, 1 H) 8.50-8.62 (m, 1 H) 10.42 (s, 1 H). LC/MS (ESI$^+$) m/z=465.1 (M+H).

Example 27

N-(3-((1R,2R,5S)-4-Amino-2,5-dimethyl-8,8-dioxido-8-thia-3-azabicyclo[3.2.1]oct-3-en-2-yl)-4-fluorophenyl)-3-methyl-5-(trifluoromethyl)picolinamide

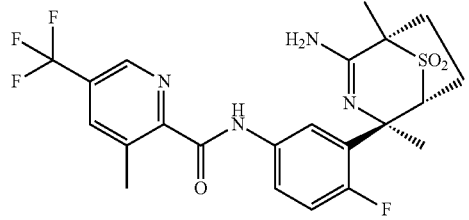 [SMILES: Cc1cc(C(F)(F)F)cnc1C(=O)Nc1ccc(F)c([C@@]2(C)N=C(N)[C@]3(C)CC[C@H]2S3(=O)=O)c1]

Synthesis of N-(3-((1R,2R,5S)-4-Amino-2,5-dimethyl-8,8-dioxido-8-thia-3-azabicyclo[3.2.1]oct-3-en-2-yl)-4-fluorophenyl)-3-methyl-5-(trifluoromethyl)picolinamide In a sequence of reactions analogous to those described in Example 22, Intermediate 13 (53 mg, 0.104 mmol) and 3-methyl-5-(trifluoromethyl)picolinic acid (27 mg, 0.135 mmol)

were combined to provide the title compound (36 mg, 70% yield). ¹H NMR (400 MHz, DMSO-d₆) δ ppm 1.24 (s, 1 H) 1.42 (s, 3 H) 1.51 (s, 3 H) 1.90 (d, J=12.42 Hz, 1 H) 2.12-2.30 (m, 1 H) 2.30-2.45 (m, 1 H) 2.58 (s, 3 H) 3.76 (d, J=5.87 Hz, 1 H) 6.08 (s, 2 H) 7.13 (dd, J=12.08, 8.85 Hz, 1 H) 7.63 (dd, J=7.43, 2.74 Hz, 1 H) 7.79-7.92 (m, 1 H) 8.29 (s, 1 H) 8.89 (s, 1 H) 10.58 (s, 1 H). LC/MS (ESI⁺) m/z=499.1 (M+H).

Example 28

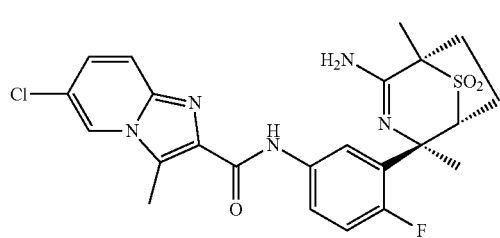 [SMILES: Cc1c(C(=O)Nc2ccc(F)c([C@@]3(C)N=C(N)[C@]4(C)CC[C@H]3S4(=O)=O)c2)nc2ccc(Cl)cn12]

N-(3-((1R,2R,5S)-4-Amino-2,5-dimethyl-8,8-dioxido-8-thia-3-azabicyclo[3.2.1]oct-3-en-2-yl)-4-fluorophenyl)-6-chloro-3-methylimidazo[1,2-a]pyridine-2-carboxamide In a sequence of reactions analogous to those described in Example 22, Intermediate 13 (35 mg, 0.068 mmol) and 6-chloro-3-methylimidazo[1,2-a]pyridine-2-carboxylic acid (18 mg, 0.088 mmol) were combined to provide the title compound (18 mg, 52% yield). ¹H NMR (400 MHz, CDCl₃) δ ppm 1.60 (s, 3 H) 1.67 (s, 3 H) 2.10 (ddd, J=12.57, 10.17, 4.35 Hz, 1 H) 2.28-2.53 (m, 3 H) 2.83 (s, 3 H) 3.98 (d, J=5.58 Hz, 1 H) 5.56 (br. s., 2 H) 7.05 (dd, J=11.93, 8.80 Hz, 1 H) 7.21 (dd, J=9.68, 1.96 Hz, 1 H) 7.46-7.57 (m, 2 H) 7.92 (ddd, J=8.80, 4.21, 2.84 Hz, 1 H) 7.96 (dd, J=1.86, 0.78 Hz, 1 H) 9.38 (s, 1 H). LC/MS (ESI⁺) m/z=504.1 (M+H).

Example 29

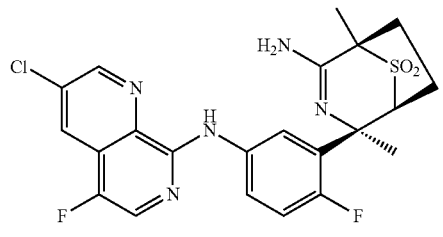 [SMILES: C[C@]1(c2cc(Nc3ncc(F)c4cc(Cl)cnc34)ccc2F)N=C(N)[C@@]2(C)CC[C@@H]1S2(=O)=O]

Synthesis of (1R,4R,5S)-2-Amino-4-(5-((3-chloro-5-fluoro-1,7-naphthyridin-8-yl)amino)-2-fluorophenyl)-1,4-dimethyl-8-thia-3-azabicyclo[3.2.1]oct-2-ene 8,8-dioxide To a solution of Intermediate 12 (60 mg, 0.117 mmol), and 3,8-dichloro-5-fluoro-1,7-naphthyridine (28.0 mg, 0.129 mmol) in 2-propanol (0.78 mL) was added p-toluenesulfonic acid (66.9 mg, 0.352 mmol), and the mixture was stirred at 85° C. for 5 hours. Saturated aqueous sodium bicarbonate and ethyl acetate were added to the reaction and the layers were separated. The organic portion was dried over anhydrous sodium sulfate, filtered and concentrated. The crude product was purified by silica-gel column chromatography, eluting with 0-80% (9:1 DCM/methanol) in DCM, to provide the title compound (35 mg, 60.7% yield). ¹H NMR (400 MHz, DMSO-d₆) δ ppm 1.22-1.24 (m, 1H) 1.38-1.52 (m, 1 H) 1.62 (br. s., 3 H) 1.99 (br. s., 3 H) 2.07 (br. s., 2 H) 4.33 (d, J=3.72 Hz, 1 H) 7.20-7.38 (m, 1 H) 8.04 (dd, J=7.24, 2.64 Hz, 1 H) 8.19 (d, J=1.27 Hz, 1 H) 8.33 (br. s., 1 H) 8.63 (d, J=2.35 Hz, 1 H) 9.02 (d, J=2.35 Hz, 1 H) 9.85 (br. s., 1 H) LC/MS (ESI⁺) m/z=492.2 (M+H).

Example 30

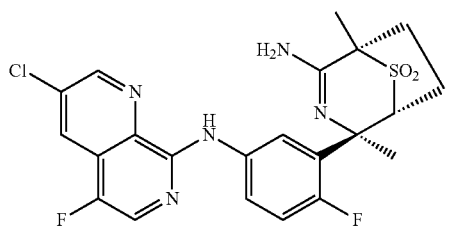 [SMILES: C[C@]12CC[C@H]([C@@](C)(c3cc(Nc4ncc(F)c5cc(Cl)cnc45)ccc3F)N=C1N)S2(=O)=O]

Synthesis of (1S,4R,5S)-2-Amino-4-(5-((3-chloro-5-fluoro-1,7-naphthyridin-8-yl)amino)-2-fluorophenyl)-1,4-dimethyl-8-thia-3-azabicyclo[3.2.1]oct-2-ene 8,8-dioxide In a sequence of reactions analogous to those described in Example 29, Intermediate 13 (45 mg, 0.088 mmol) and 3,8-dichloro-5-fluoro-1,7-naphthyridine (21 mg, 0.097 mmol) were combined to provide the title compound (7 mg, 16% yield). ¹H NMR (400 MHz, CDCl₃) δ ppm 1.58-1.66 (m, 2 H) 1.72 (s, 2 H) 2.08-2.21 (m, 2 H) 2.34-2.54 (m, 3 H) 4.04 (d, J=5.67 Hz, 1 H) 5.31 (s, 1 H) 5.38 (br. s., 3 H) 7.08 (dd, J=11.98, 8.85 Hz, 1 H) 7.63 (dd, J=7.24, 2.64 Hz, 1 H) 8.02 (d, J=1.47 Hz, 1 H) 8.16 (dt, J=7.24, 4.35 Hz, 1 H) 8.25 (d, J=2.25 Hz, 1 H) 8.73 (d, J=2.25 Hz, 1 H). LC/MS (ESI⁺) m/z=492.2 (M+H).

Example 31

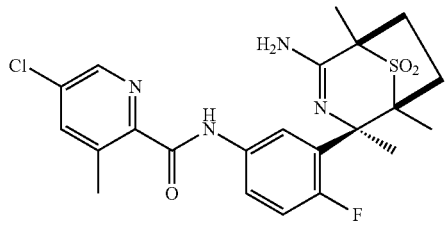 [SMILES: Cc1cc(Cl)cnc1C(=O)Nc1ccc(F)c([C@@]2(C)N=C(N)[C@@]3(C)CC[C@]2(C)S3(=O)=O)c1]

Synthesis of N-(3-((1S,2R,5R)-4-amino-1,2,5-trimethyl-8,8-dioxido-8-thia-3-azabicyclo[3.2.1]oct-3-en-2-yl)-4-fluorophenyl)-5-chloro-3-methylpicolinamide To a solution of Intermediates 14A and 14B (0.218 g, 0.415 mmol) in dicholomethane (4 mL) were added 5-chloro-3-methylpicolinic acid (0.075 g, 0.435 mmol), triethylamine (0.115 mL, 0.829 mmol) and (O-(7-azabenzotriazol-1-yl)-N,N,N',N'-tetramethyluronium hexafluorophosphate) (0.173 g, 0.456 mmol). The mixture was stirred at room temperature for 90 minutes and then concentrated. The crude product was purified by silica-gel column chromatography, eluting with 5% to 40% ethyl acetate in heptanes, to provide two diastereomeric intermediates. The major diastereomer was redissolved in DCM (1.0 mL), and trifluoroacetic acid (0.39 mL, 5.3 mmol) was added. The reaction was stirred at ambient temperature for 30 minutes, concentrated, and partitioned between saturated aqueous sodium bicarbonate and DCM. The organic layer was washed with brine, dried over anhydrous sodium sulfate, filtered, and concentrated to provide the title compound (48 mg, 24% yield). $^1$H NMR (400 MHz, DMSO-$d_6$) δ 10.67 (s, 1H), 8.60 (d, J=1.86 Hz, 1H), 8.03 (d, J=1.66 Hz, 1H), 7.90 (d, J=8.41 Hz, 1H), 7.64 (br. s., 1H), 7.06-7.25 (m, 1H), 6.01 (br. s., 2H), 2.56 (s, 3H), 2.25-2.42 (m, 1H), 1.83 (br. s., 3H), 1.71 (t, J=7.19 Hz, 2H), 1.56 (d, J=10.37 Hz, 1H), 1.50 (s, 3H), 1.41 (br. s., 3H). LC/MS (ESI$^+$) m/z=479.0 (M+H).

Example 32

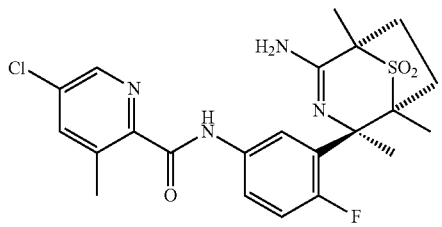 [SMILES: Cc1cc(Cl)cnc1C(=O)Nc1ccc(F)c([C@@]2(C)N=C(N)[C@]3(C)CC[C@@]2(C)S3(=O)=O)c1]

Synthesis of N-(3-((1R,2R,5S)-4-amino-1,2,5-trimethyl-8,8-dioxido-8-thia-3-azabicyclo[3.2.1]oct-3-en-2-yl)-4-fluorophenyl)-5-chloro-3-methylpicolinamide The minor diastereomer isolated from the reaction described in Example 31 was redissolved in DCM (1.0 mL), and TFA (0.39 mL, 5.3 mmol) was added. The reaction was stirred at RT for 30 minutes, concentrated, and partitioned between saturated aqueous sodium bicarbonate and DCM. The organic layer was washed with brine, dried over anhydrous sodium sulfate, filtered, and concentrated to provide the title compound (42 mg, 21% yield). $^1$H NMR (400 MHz, DMSO-$d_6$) δ 10.67 (s, 1H), 9.33 (br. s., 1H), 9.18 (br. s., 1H), 8.59 (d, J=1.76 Hz, 1H), 7.92-8.13 (m, 2H), 7.70 (d, J=5.58 Hz, 1H), 7.19 (dd, J=8.90, 12.72 Hz, 1H), 2.73-2.89 (m, 1H), 2.67 (d, J=9.10 Hz, 1H), 2.54 (s, 3H), 2.01-2.19 (m, 2H), 1.97 (s, 3H), 1.64 (s, 3H), 1.45 (br. s., 3H). LC/MS (ESI$^+$) m/z=479.0 (M+H).

The following compounds in Table 1 are examples of compounds of Formulas I, II and III, and sub-formulas thereof, provided by the present invention in Table 1 hereinabove. The methods used to prepare the exemplary compounds are included in Table 1. Table I further provides the mass and biological data (average nM IC$_{50}$'s for the enzyme and cell assays) for each compound, where available.

TABLE 1

| Example No | Compound Name | BACE1 FRET assay IC$_{50}$ (uM) | HEK cell assay IC$_{50}$ (uM) | CatD IC50 (μM) |
|---|---|---|---|---|
| 1 | N-(3-((1S,2R,5R)-4-amino-2,5-dimethyl-9,9-dioxido-9-thia-3-azabicyclo[3.3.1]non-3-en-2-yl)-4-fluorophenyl)-2-methoxypyrido[3,4-b]pyrazin-5-amine | 0.037 | 0.057 | 45.8 |
| 2 | N-(3-((1R,2R,5S)-4-amino-2,5-dimethyl-9,9-dioxido-9-thia-3-azabicyclo[3.3.1]non-3-en-2-yl)-4-fluorophenyl)-2-methoxypyrido[3,4-b]pyrazin-5-amine | 0.13 | 0.055 | 166 |
| 3 | N-(3-((1S,2R,5R)-4-amino-2,5-dimethyl-9,9-dioxido-9-thia-3-azabicyclo[3.3.1]non-3-en-2-yl)-4-fluorophenyl)-5-chloro-3-methyl-2-pyridinecarboxamide | 0.002 | 0.007 | 119 |
| 4 | N-(3-((1R,2R,5S)-4-amino-2,5-dimethyl-9,9-dioxido-9-thia-3-azabicyclo[3.3.1]non-3-en-2-yl)-4-fluorophenyl)-5-chloro-3-methyl-2-pyridinecarboxamide | 0.007 | 0.020 | 270 |
| 5 | N-(3-((1S,2R,5R)-4-amino-2,5-dimethyl-9,9-dioxido-9-thia-3-azabicyclo[3.3.1]non-3-en-2-yl)-4-fluorophenyl)-5-(difluoromethoxy)-3-methyl-2-pyridinecarboxamide | 0.003 | 0.004 | 105 |
| 6 | N-(3-((1R,2R,5S)-4-amino-2,5-dimethyl-9,9-dioxido-9-thia-3-azabicyclo[3.3.1]non-3-en-2-yl)-4-fluorophenyl)-5-(difluoromethoxy)-3-methyl-2-pyridinecarboxamide | 0.010 | 0.004 | 215 |
| 7 | N-(3-((1S,2R,5R)-4-amino-1-fluoro-2,5-dimethyl-9, 9-dioxido-9-thia-3-azabicyclo[3.3.1]non-3-en-2-yl)-4-fluorophenyl)-5-chloro-3-methyl-2-pyridinecarboxamide | 0.007 | 0.22 | 22.6 |
| 9 | N-(3-((1S,2R,5R)-4-amino-1-fluoro-2,5-dimethyl-9, 9-dioxido-9-thia-3-azabicyclo[3.3.1]non-3-en-2-yl)-4-fluorophenyl)-5-(difluoromethoxy)-3-methyl-2-pyridinecarboxamide | 0.007 | 0.149 | 19 |

TABLE 1-continued

| Example No | Compound Name | BACE1 FRET assay IC$_{50}$ (uM) | HEK cell assay IC$_{50}$ (uM) | CatD IC50 (μM) |
|---|---|---|---|---|
| 8 | N-(3-((1R,2R,5S)-4-amino-1-fluoro-2,5-dimethyl-9, 9-dioxido-9-thia-3-azabicyclo[3.3.1]non-3-en-2-yl)-4-fluorophenyl)-5-chloro-3-methyl-2-pyridinecarboxamide | 0.004 | 0.113 | 22.7 |
| 10 | N-(3-((1R,2R,5S)-4-amino-1-fluoro-2,5-dimethyl-9,9-dioxido-9-thia-3-azabicyclo[3.3.1]non-3-en-2-yl)-4-fluorophenyl)-5-(difluoromethoxy)-3-methyl-2-pyridinecarboxamide | 0.009 | 0.035 | 8.75 |
| 11 | N-(3-((1S,2R,5R)-4-amino-1,2,5-trimethyl-9,9-dioxido-9-thia-3-azabicyclo[3.3.1]non-3-en-2-yl)-4-fluorophenyl)-5-chloro-3-methyl-2-pyridinecarboxamide | 0.006 | 0.031 | 51.5 |
| 12 | N-(3-((1R,2R,5S)-4-amino-1,2,5-trimethyl-9,9-dioxido-9-thia-3-azabicyclo[3.3.1]non-3-en-2-yl)-4-fluorophenyl)-5-chloro-3-methyl-2-pyridinecarboxamide | 0.005 | 0.033 | 29.7 |
| 13 | N-(3-((1S,2R,5R)-4-amino-1,2,5-trimethyl-9,9-dioxido-9-thia-3-azabicyclo[3.3.1]non-3-en-2-yl)-4-fluorophenyl)-5-(difluoromethoxy)-3-methyl-2-pyridinecarboxamide | 0.013 | 0.006 | 8.64 |
| 14 | N-(3-((1R,2R,5S)-4-amino-1,2,5-trimethyl-9,9-dioxido-9-thia-3-azabicyclo[3.3.1]non-3-en-2-yl)-4-fluorophenyl)-5-(difluoromethoxy)-3-methyl-2-pyridinecarboxamide | 0.009 | 0.002 | 17.7 |
| 15 | N-(3-((1S,2R,5R)-4-amino-1,2,5-trimethyl-9,9-dioxido-9-thia-3-azabicyclo[3.3.1]non-3-en-2-yl)-4-fluorophenyl)-5-methoxy-2-pyrazinecarboxamide | 0.049 | 0.027 | 138 |
| 16 | N-(3-((1R,2R,5S)-4-amino-1,2,5-trimethyl-9,9-dioxido-9-thia-3-azabicyclo[3.3.1]non-3-en-2-yl)-4-fluorophenyl)-5-methoxy-2-pyrazinecarboxamide | 0.020 | 0.016 | 85.2 |
| 17 | N-(3-((1R,2R,5R)-4-amino-2-methyl-9,9-dioxido-9-thia-3-azabicyclo[3.3.1]non-3-en-2-yl)-4-fluorophenyl)-5-chloro-3-methyl-2-pyridinecarboxamide | 0.015 | 0.064 | 2780 |
| 18 | N-(3-((1R,2R,5R)-4-amino-2-methyl-9,9-dioxido-9-thia-3-azabicyclo[3.3.1]non-3-en-2-yl)-4-fluorophenyl)-5-(difluoromethoxy)-3-methyl-2-pyridinecarboxamide | 0.043 | 0.018 | 690 |
| 20 | N-(3-((1S,2R,5S)-4-amino-2-methyl-9,9-dioxido-9-thia-3-azabicyclo[3.3.1]non-3-en-2-yl)-4-fluorophenyl)-5-chloro-3-methyl-2-pyridinecarboxamide | 0.003 | 0.006 | 717 |
| 19 | N-(3-((1R,2R,5R)-4-amino-2-methyl-9,9-dioxido-9-thia-3-azabicyclo[3.3.1]non-3-en-2-yl)-4-fluorophenyl)-2-methoxypyrido[3,4-b]pyrazin-5-amine | 0.323 | 0.179 | 1210 |
| 21 | N-(3-((1R,2R,5S)-4-amino-2-methyl-8,8-dioxido-8-thia-3-azabicyclo[3.2.1]oct-3-en-2-yl)-4-fluorophenyl)-5-chloro-3-methyl-2-pyridinecarboxamide | 0.016 | 0.081 | 1640 |
| 33 | N-(3-((1S,2R,5R)-4-amino-2-methyl-8,8-dioxido-8-thia-3-azabicyclo[3.2.1]oct-3-en-2-yl)-4-fluorophenyl)-5-chloro-3-methyl-2-pyridinecarboxamide | 8.46 | >15.6 | 1540 |
| 22 | N-(3-((1S,2R,5R)-4-amino-2,5-dimethyl-8,8-dioxido-8-thia-3-azabicyclo[3.2.1]oct-3-en-2-yl)-4-fluorophenyl)-5-chloro-3-methyl-2-pyridinecarboxamide | 0.002 | 0.002 | 1740 |
| 34 | N-(3-((1R,2S,5S)-4-amino-2,5-dimethyl-8,8-dioxido-8-thia-3-azabicyclo[3.2.1]oct-3-en-2-yl)-4-fluorophenyl)-5-chloro-3-methyl-2-pyridinecarboxamide N-(3-((1S,2R,5R)-4-amino-2,5-dimethyl-8,8- | 4.54 | 2.03 | 4310 |

TABLE 1-continued

| Example No | Compound Name | BACE1 FRET assay IC$_{50}$ (uM) | HEK cell assay IC$_{50}$ (uM) | CatD IC50 (μM) |
|---|---|---|---|---|
| 23 | dioxido-8-thia-3-azabicyclo[3.2.1]oct-3-en-2-yl)-4-fluorophenyl)-5-(difluoromethoxy)-3-methyl-2-pyridinecarboxamide | 0.002 | 0.001 | 117 |
| 35 | (1R,4R,5S)-4-(5-amino-2-fluorophenyl)-1,4-dimethyl-8-thia-3-azabicyclo[3.2.1]oct-2-en-2-amine 8,8-dioxide | 10.1 | 5.81 | 287 |
| 26 | N-(3-((1 R,2R,5S)-4-amino-2,5-dimethyl-8,8-dioxido-8-thia-3-azabicyclo[3.2.1]oct-3-en-2-yl)-4-fluorophenyl)-5-chloro-3-methyl-2-pyridinecarboxamide | 0.008 | 0.017 | 577 |
| 24 | N-(3-((1S,2R,5R)-4-amino-2,5-dimethyl-8,8-dioxido-8-thia-3-azabicyclo[3.2.1]oct-3-en-2-yl)-4-fluorophenyl)-3-methyl-5-(trifluoromethyl)-2-pyridinecarboxamide | 0.005 | 0.001 | 591 |
| 25 | N-(3-((1S,2R,5R)-4-amino-2,5-dimethyl-8,8-dioxido-8-thia-3-azabicyclo[3.2.1]oct-3-en-2-yl)-4-fluorophenyl)-6-chloro-3-methylimidazo[1,2-a]pyridine-2-carboxamide | 0.021 | 0.004 | 318 |
| 29 | N-(3-((1S,2R,5R)-4-amino-2,5-dimethyl-8,8-dioxido-8-thia-3-azabicyclo[3.2.1]oct-3-en-2-yl)-4-fluorophenyl)-3-chloro-5-fluoro-1,7-naphthyridin-8-amine | 0.001 | 0.052 | 733 |
| 28 | N-(3-((1R,2R,5S)-4-amino-2,5-dimethyl-8,8-dioxido-8-thia-3-azabicyclo[3.2.1]oct-3-en-2-yl)-4-fluorophenyl)-6-chloro-3-methylimidazo[1,2-a]pyridine-2-carboxamide | 0.070 | 0.010 | >400.0 |
| 27 | N-(3-((1R,2R,5S)-4-amino-2,5-dimethyl-8,8-dioxido-8-thia-3-azabicyclo[3.2.1]oct-3-en-2-yl)-4-fluorophenyl)-3-methyl-5-(trifluoromethyl)-2-pyridinecarboxamide | 0.014 | 0.002 | 2040 |
| 31 | N-(3-((1S,2R,5R)-4-amino-1,2,5-trimethyl-8,8-dioxido-8-thia-3-azabicyclo[3.2.1]oct-3-en-2-yl)-4-fluorophenyl)-5-chloro-3-methyl-2-pyridinecarboxamide | 0.004 | 0.012 | 56.9 |
| 32 | N-(3-((1R,2R,5S)-4-amino-1,2,5-trimethyl-8, 8-dioxido-8-thia-3-azabicyclo[3.2.1]oct-3-en-2-yl)-4-fluorophenyl)-5-chloro-3-methyl-2-pyridinecarboxamide | 0.007 | 0.017 | 131 |
| 30 | N-(3-((1R,2R,5S)-4-amino-2,5-dimethyl-8,8-dioxido-8-thia-3-azabicyclo[3.2.1]oct-3-en-2-yl)-4-fluorophenyl)-3-chloro-5-fluoro-1,7-naphthyridin-8-amine | 0.033 | 0.163 | 4500 |
| 36 | N-(3-((1S,2R,5R)-4-amino-2,5-dimethyl-8,8-dioxido-8-thia-3-azabicyclo[3.2.1]oct-3-en-2-yl)-4-fluorophenyl)-5-fluoro-3-methoxy-1,7-naphthyridin-8-amine | 0.002 | 0.006 | 5490 |
| 37 | N-(3-((1S,2R,5R)-4-amino-2,5-dimethyl-8,8-dioxido-8-thia-3-azabicyclo[3.2.1]oct-3-en-2-yl)-4-fluorophenyl)-5-methoxy-2-pyrazinecarboxamide | 0.004 | 0.001 | 1170 |

Intermediate 28

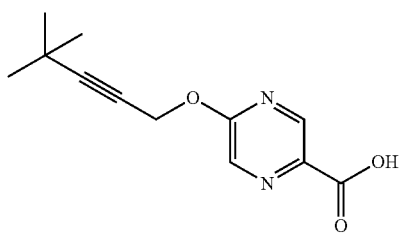 [SMILES: CC(C)(C)C#CCOc1cnc(C(=O)O)cn1]

Synthesis of 5-((4,4-Dimethylpent-2-yn-1-yl)oxy)pyrazine-2-carboxylic acid 3,3-Dimethyl-1-butyne (1.0 mL, 8.12 mmol) was dissolved in dry tetrahydrofuran (5 mL) under nitrogen and cooled in a dry ice bath. Butyllithium (2.5 M in hexanes, 3.25 mL, 8.12 mmol) was added slowly and the reaction stirred for 20 minutes. The clear solution was removed from the dry ice bath and placed in an acetone/ice bath and stirred for another 5 minutes. Paraformaldehyde (0.200 g, 8.12 mmol) was added in one portion. The mixture was stirred for 3 hours then quenched by addition of saturated ammonium chloride (20 mL). Dichloromethane (100 mL) and water (100 mL) were added and the phases mixed and separated. The organic was dried with magnesium sulfate and evaporated to ~2 mL. The crude solution of 4,4-dimethylpent-2-yn-1-ol was treated with lithium bis(trimethylsilyl)amide (1.0 M solution in tetrahydrofuran, 2.5 ml, 2.500 mmol) under nitrogen. Dry dimethylformamide (1 mL) was added and the mixture heated in a 60° C. bath. A solution of methyl 5-chloro-2-pyrazinecarboxylate (0.250 g, 1.449 mmol) in dry dimethylformamide (2 mL) was added dropwise over 30 minutes. Once the addition was complete the reaction was cooled and water (50 mL) and hexanes (100 mL) were added. The phases were mixed and separated. The aqueous washed with DCM (50 mL) then concentrated to ~10 mL under reduced pressure. The pH was adjusted to 5 using 2 N HCl and the product extracted with ethyl acetate (3×50 mL). The combined ethyl acetate fractions were dried with magnesium sulfate and evaporated to dryness under reduced pressure. The crude 5-((4,4-dimethyl-pent-2-yn-1-yl)oxy)pyrazine-2-carboxylic acid (0.112 g, 0.478 mmol, 33.0% yield) was used without further purification. $^1$H NMR (300 MHz, CHLOROFORM-d) δ ppm 1.23 (s, 9 H) 5.05 (s, 2 H) 8.30 (s, 1 H) 8.90 (s, 1 H). LC/MS (ESI$^+$) m/z=235.1 (M+H).

Intermediate 29

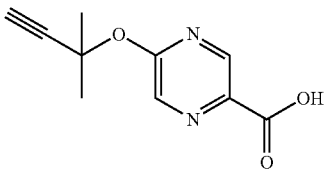

Synthesis of 5-((2-Methylbut-3-yn-2-yl)oxy)pyrazine-2-carboxylic acid

Step 1. methyl 5-((2-methylbut-3-yn-2-yl)oxy)pyrazine-2-carboxylate

5-Chloro-2-methoxycarbonyl pyrazine (0.250 g, 1.449 mmol), 2-methyl-3-butyn-2-ol (Fluka, 1.5 ml, 15.48 mmol), 1,8-diazabicyclo-[5.4.0]undec-7-ene (0.75 ml, 5.02 mmol), and 4-dimethylaminopyridine (0.102 g, 0.835 mmol) were combined in a vial and heated in the microwave to 100° C. for 10 minutes. The vial was opened and the crude partitioned between water (75 mL) and hexane (100 mL). The organic was dried with magnesium sulfate and evaporated to dryness under reduced pressure to give methyl 5-((2-methylbut-3-yn-2-yl)oxy)pyrazine-2-carboxylate (0.210 g, 0.954 mmol, 65.8% yield) as an off white solid. $^1$H NMR (300 MHz, CHLOROFORM-d) δ ppm 1.86 (s, 6 H) 2.55 (s, 1 H) 3.98 (s, 3 H) 8.23 (d, J=1.32 Hz, 1 H) 8.91 (d, J=1.32 Hz, 1 H).

Step 2. 5-((2-Methylbut-3-yn-2-yl)oxy)pyrazine-2-carboxylic acid

Methyl 5-((2-methylbut-3-yn-2-yl)oxy)pyrazine-2-carboxylate (0.210 g, 0.954 mmol) was dissolved in methanol (20 mL). A solution of lithium hydroxide monohydrate (0.078 ml, 2.81 mmol) in water (5 mL) was added and the reaction stirred for 35 minutes then quenched by addition of 1 N hydrochloric acid (2.8 mL). The solution was evaporated to dryness under reduced pressure and the crude further dried by azeotroping with toluene (3×30 mL). The crude solids were used without further purification. LC/MS (ESI$^+$) m/z=207.1 (M+H).

Intermediate 30

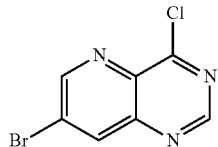

Synthesis of 7-Bromo-4-chloropyrido[3,2-d]pyrimidine

Step 1. 3-amino-5-bromopicolinamide

5-Bromo-2-cyano-3-nitropyridine (2.00 g, 8.77 mmol) was dissolved in dioxane (10 mL). Water (5 mL) and ammonium hydroxide (28% NH$_3$ in water, 5.0 ml, 36.0 mmol) were added and the mixture stirred for 10 minutes. Sodium hydrosulfite (5.0 g, 28.7 mmol) was added in 1 g portions every 5 minutes. After the addition was complete, the mixture was stirred at RT for 2 hours. Additional water (100 mL) and ethyl acetate (100 mL) were added and the phases mixed and separated. The organic was dried with magnesium sulfate and evaporated to dryness under reduced pressure. Purification using silica chromatography (1-15% methanol in DCM gradient, dry load on silica gel) gave 3-amino-5-bromopicolinamide (1.00 g, 4.63 mmol, 52.8% yield) as a light yellow solid.

Step 2. 3-amino-5-bromopicolinamide

3-Amino-5-bromopicolinamide (1.00 g, 4.63 mmol) was suspended in triethyl orthoformate (10 ml, 60.1 mmol) and heated in a 145° C. bath under nitrogen. The reaction was heated for 2½ hours then the mixture was evaporated to dryness under reduced pressure. The dark crude was azeotroped with toluene (3×50 mL) then further dried under high vacuum. The crude 7-bromopyrido[3,2-d]pyrimidin-4-ol (1.02 g, 4.51 mmol) was used without purification.

Step 3. 7-bromopyrido[3,2-d]pyrimidin-4-ol

7-Bromopyrido[3,2-d]pyrimidin-4-ol (1.02 g, 4.51 mmol) was suspended in dry toluene (80 mL) under nitrogen. Phosphorus oxychloride (5.0 mL, 54.6 mmol) was added and the mixture heated to reflux under nitrogen. After 5 hours the reaction was cooled to RT. The solution was placed in a water bath and saturated sodium bicarbonate (50 mL) was added slowly with strong stirring. After 45 minutes the phases were separated and the organic evaporated to dryness under reduced pressure. The crude 7-bromo-4-chloropyrido[3,2-d]pyrimidine (0.46 g, 1.89 mmol, 42% yield) was used without further purification. $^1$H NMR (400 MHz, CHLOROFORM-d) δ ppm 8.59 (d, J=1.96 Hz, 1 H) 9.11-9.15 (m, 2 H). LC/MS (ESI$^+$) m/z=243.8 (M+H).

Intermediate 31

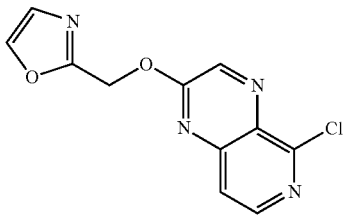 [SMILES: Clc1nccc2nc(OCc3ncco3)cnc12]

Synthesis of 2-(((5-chloropyrido[3,4-b]pyrazin-2-yl)oxy)methyl)oxazole

Step 1. 2,5-dichloropyrido[3,4-b]pyrazine

A mixture of 5-chloro-2-methoxypyrido[3,4-b]pyrazine (2.76 g, 14.11 mmol), phosphorus oxychloride (17.10 mL, 183 mmol) and DMF (1.09 mL, 14.12 mmol) was heated at 100° C. overnight. The mixture was concentrated in vacuo. The residue was diluted with EtOAc (150 mL) and cooled to 0° C. It was treated with ice water followed by solid NaHCO$_3$ in small portions. The layers were separated. The basic aqueous layer was extracted with EtOAc. The combined organic solution was washed with brine, dried over Na$_2$SO$_4$ and concentrated in vacuo to afford 2,5-dichloropyrido[3,4-b]pyrazine (2.57 g, 12.85 mmol, 91% yield) as a brown solid. LC/MS (ESI$^-$) m/z=200, 202 (M+H)$^+$.

Step 2. 2-(((5-chloropyrido[3,4-b]pyrazin-2-yl)oxy)methyl)oxazole

At 0° C., to a mixture of 2,5-dichloropyrido[3,4-b]pyrazine (1.64 g, 8.20 mmol), oxazol-2-ylmethanol (1.19 g, 8.85 mmol) in THF (50 mL) under N$_2$ was added sodium hydride (60% wt. dispersion in mineral oil) (0.35 g, 8.85 mmol) in batches. After 40 min, the reaction was quenched with saturated NH$_4$Cl (20 mL) and water (20 mL). The mixture was diluted with EtOAc (150 mL) and the organic layer was washed with brine (50 mL), dried over Na$_2$SO$_4$, filtered, and concentrated in vacuo. The solid was suspended in heptane-EtOAc and filtered to afford 2-(((5-chloropyrido[3,4-b]pyrazin-2-yl)oxy)methyl)oxazole (1.89 g, 7.20 mmol, 88% yield) as a brown powder. LC/MS (ESI$^-$) m/z=263, 265 (M+H)$^+$. $^1$H NMR (400 MHz, CHLOROFORM-d) δ=8.70 (s, 1H), 8.51 (d, J=5.7 Hz, 1H), 7.74 (d, J=0.8 Hz, 1H), 7.69-7.64 (m, 1H), 7.21 (s, 1H), 5.68 (s, 2H).

Intermediate 32

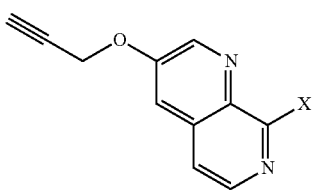

(X = Cl & Br)

Synthesis of 8-Chloro-3-(prop-2-yn-1-yloxy)-1,7-naphthyridine and 8-bromo-3-(prop-2-yn-1-yloxy)-1,7-naphthyridine To a stirring solution of 8-chloro-3-methoxy-1,7-naphthyridine (0.75 g, 3.85 mmol) in 1,2-dichloroethane (40 mL) at 20° C. under nitrogen was added boron tribromide (3.71 mL, 38.5 mmol) dropwise. The reaction mixture was then heated to 70° C. for 2 h. The solvents were removed under reduced pressure. The resulting solid was suspended in CH$_2$Cl$_2$ (10 mL) and collected by filtration. The solid was further washed with CH$_2$Cl$_2$ (10 mL). The solid was air dried for 30 min to afford crude a tan solid which was used without further purification. To a stirring suspension of the above crude and cesium carbonate (6.31 g, 19.38 mmol) in DMF (5 mL) at 20° C. under nitrogen was added propargyl bromide (691 µL, 7.75 mmol) in one portion and stirred for 18 h. The reaction mixture was partitioned between EtOAc (25 mL) and 5% NaHCO$_3$ (50 mL). The organic layer was separated, washed with 5% NaHCO$_3$ (50 mL) and sat. NaCl (20 mL). The organic solution was dried over MgSO$_4$, concentrated under reduced pressure, then purified by silica gel chromatography eluting with a gradient of 0-30% EtOAc/heptane to afford 540 mg of off-white solid, as a mixture of 8-chloro-3-(prop-2-yn-1-yloxy)-1,7-naphthyridine (MS m/z=219.1 [M+H]) and 8-bromo-3-(prop-2-yn-1-yloxy)-1,7-naphthyridine (MS m/z=263/265 [M+H]$^+$) in a ratio of about 3:2.

Intermediate 33

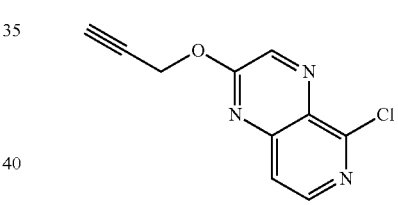

Synthesis of 5-Chloro-2-(prop-2-yn-1-yloxy)pyrido[3,4-b]pyrazine

A solution of 3-propynol (0.62 mL, 10.72 mmol) in THF (1 mL) was added under N$_2$ to a slurry of sodium hydride (60% wt. dispersion in mineral oil) (0.43 g, 10.72 mmol) in THF (30 mL) at 0° C. The slurry was stirred for 15 min then added to a mixture of 2,5-dichloropyrido[3,4-b]pyrazine (1.95 g, 9.75 mmol) in THF (20 mL) at 0° C. After 20 min, the reaction was quenched with saturated NH$_4$Cl (20 mL) and water (20 mL). The mixture was diluted with EtOAc (200 mL) and the organic layer was washed with brine (50 mL), dried over Na$_2$SO$_4$, filtered, and concentrated in vacuo. The solid (2.26 g) was suspended in heptane-DCM and filtered to afford the first batch of 5-chloro-2-(prop-2-yn-1-yloxy)pyrido[3,4-b]pyrazine as a brown powder (1.81 g). The filtrate was concentrated in vacuo and was purified by silica gel chromatography (40 g, 0-50% EtOAC in DCM) to afford the second batch of 5-chloro-2-(prop-2-yn-1-yloxy)pyrido[3,4-b]pyrazine as a white solid (0.32 g). LC/MS (ESI$^-$) m/z=220, 222 (M+H)$^+$. $^1$H NMR (400 MHz, CHLOROFORM-d) δ=8.66 (s, 1H), 8.50 (d, J=5.7 Hz, 1H), 7.67 (d, J=5.7 Hz, 1H), 5.18 (d, J=2.3 Hz, 2H), 2.58 (t, J=2.4 Hz, 1H).

Intermediate 34

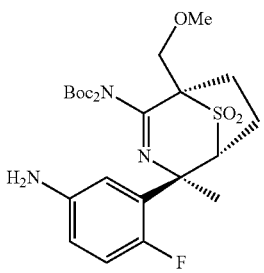

Synthesis of tert-butyl N-[(1R,2R,5S)-2-(5-amino-2-fluoro-phenyl)-5-(methoxymethyl)-2-methyl-8,8-dioxido-8-thia-3-azabicyclo[3.2.1]oct-3-en-4-yl]-N-tert-butoxycarbonyl-carbamate Step 1: 2-(methylsulfonyl)pent-4-enenitrile To a solution of (methanesulfonyl)acetonitrile (43 g, 361 mmol) in dry acetonitrile (350 mL) at 0° C. was added cesium carbonate (141 g, 433 mmol), followed by a solution of allyl bromide (26.5 ml, 307 mmol) in acetonitrile (50 mL) dropwise. The reaction was stirred at ambient temperature overnight, and then concentrated. The residue was partitioned between ethyl acetate and water, and 2N aqueous HCl was added slowly with stirring. When gas evolution ceased, the layers were separated, and the aqueous layer was extracted with ethyl acetate. The combined organic phases were washed water and brine, and concentrated. The crude product was dissolved in toluene and passed through a pad of silica-gel, eluting first with 15% ethyl acetate in heptane to remove a higher running impurity followed by 30% ethyl acetate in heptane to provide the title compound (20.5 g, 129 mmol, 35.7% yield).

Step 2: 2-(methoxymethyl)-2-(methylsulfonyl)pent-4-enenitrile

To a solution of 2-(methylsulfonyl)pent-4-enenitrile (5 g, 31.4 mmol) in acetonitrile (50 mL) was added cesium carbonate (10.23 g, 31.4 mmol) and methoxymethyl chloride (2.86 mL, 37.7 mmol). The reaction was stirred at RT. After 16 hours, the reaction mixture was partitioned between water and ethyl acetate; the organic layer was concentrated. The crude product was purified by column chromatography, eluting with 5-50% ethyl acetate in heptane, to the title compound (3.9 g, 19.19 mmol, 61.1% yield) as a colorless oil.

Step 3: (R)—N—((R)-1-(((S)-2-cyano-1-methoxy-pent-4-en-2-yl)sulfonyl)-2-(2-fluoro-5-nitrophenyl)propan-2-yl)-2-methylpropane-2-sulfinamide To a solution of 2-(methoxymethyl)-2-(methylsulfonyl)pent-4-enenitrile (3.91 g, 19.24 mmol) in MeTHF (20 mL) at −78° C. was added a 2.8 N solution of n-butyllithium in heptane (7.00 mL, 19.75 mmol), and the mixture was stirred for 30 minutes at −78° C. Separately, to a −40° C. solution of (R,E)-N-(1-(2-fluoro-5-nitrophenyl)ethylidene)-2-methylpropane-2-sulfinamide (2.9 g, 10.13 mmol) in toluene (20 mL) was added a 2 M solution of trimethylaluminum in toluene (5.06 mL, 10.13 mmol), and the mixture was stirred for 15 minutes at −40° C. The ketimine mixture was transferred to the sulfone anion solution via syringe at −78° C., and the reaction was stirred at −78° C. After 3 hours, the reaction was quenched with the addition of saturated aqueous ammonium chloride and allowed to warm to RT. The reaction mixture was partitioned between water and ethyl acetate; the organic layer was filtered through Celite to remove the aluminum salts. The organic layer was concentrated, adsorbed onto a silica-gel loading column, and purified by column chromatography, eluting with 30-70% ethyl acetate in heptane, to provide the title compound (1.25 g, 2.55 mmol, 25.2% yield). LC/MS (ESI⁺) m/z=490.0 (M+H).

Step 4: tert-butyl N-[(1R,2R,5S)-2-(5-amino-2-fluoro-phenyl)-5-(methoxymethyl)-2-methyl-8,8-dioxido-8-thia-3-azabicyclo[3.2.1]oct-3-en-4-yl]-N-tert-butoxycarbonyl-carbamate In a series of reactions analogous to those described in Intermediate 11, steps 3-4 and Intermediate 12, steps 1-5, (R)—N—((R)-1-(((S)-2-cyano-1-methoxypent-4-en-2-yl)sulfonyl)-2-(2-fluoro-5-nitrophenyl)propan-2-yl)-2-methyl-propane-2-sulfinamide was converted to the title compound. LC/MS (ESI⁺) m/z=565.1 (M+Na).

Intermediate 35

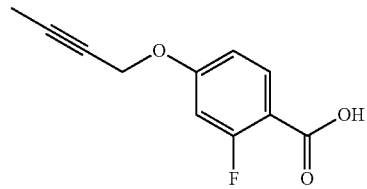

Synthesis of 4-(But-2-yn-1-yloxy)-2-fluorobenzoic acid

To a 0° C. solution of methyl 2-fluoro-4-hydroxybenzoate (1.0 g, 5.88 mmol) and 2-butyn-1-ol (0.824 mL, 11.76 mmol) in THF (25 mL) was added triphenylphosphine (2.312 g, 8.82 mmol) and diisopropyl azodicarboxylate (1.732 mL, 8.82 mmol). The reaction was stirred at RT for 2 hours. After 2 hours, the reaction mixture was diluted with DCM and washed with saturated aqueous sodium bicarbonate. The organic layer was concentrated, and the crude product was purified by column chromatography, eluting with 10-50% ethyl acetate in heptane. LC/MS (ESI⁺) m/z=223.1 (M+H).

To a solution of methyl 4-(but-2-yn-1-yloxy)-2-fluorobenzoate (0.82 g, 3.69 mmol) in THF (10 mL) and methanol (5 mL) was added lithium hydroxide monohydrate (0.170 g, 4.06 mmol). The reaction was stirred at ambient temperature. After 16 hours, another portion of LiOH (85 mg, 0.5 eq) was added, and the reaction was continued. After another 24 hours, the reaction mixture was concentrated and partitioned between water and ethyl acetate. The aqueous layer was acidified to pH<3 with 6 N aqueous HCl and extracted with ethyl acetate. The combined organic layers were concentrated to provide the title compound (0.78 g, 3.75 mmol, quantitative yield) as an off-white solid. LC/MS (ESI⁺) m/z=209.1 (M+H).

Intermediate 36

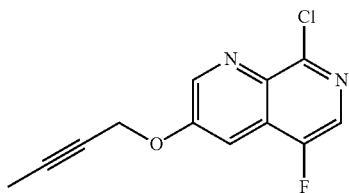 [SMILES: CC#CCOc1cnc2c(Cl)ncc(F)c2c1]

Synthesis of 3-(but-2-yn-1-yloxy)-8-chloro-5-fluoro-1,7-naphthyridine

Step 1: 8-chloro-5-fluoro-1,7-naphthyridin-3-ol

A 75 mL pressure-resistant vessel was charged with 8-chloro-5-fluoro-3-methoxy-1,7-naphthyridine (0.922 g, 4.34 mmol) and DCE (10.84 ml). To this was added boron tribromide (2.460 ml, 26.0 mmol) dropwise via syringe. The resulting heterogeneous mixture was placed in a 70° C. preheated oil bath and stirred for 6 hours. The reaction mixture was concentrated to dryness, and the residue was washed with DCM. The solids were purified by column chromatography, eluting with 2-10% MeOH in DCM/1% ammonium hydroxide to give 8-chloro-5-fluoro-1,7-naphthyridin-3-ol (0.70 g, 3.52 mmol, 81% yield). LC/MS (ESI⁺) m/z=199.1 (M+H).

Step 2: 3-(but-2-yn-1-yloxy)-8-chloro-5-fluoro-1,7-naphthyridine

To a 0° C. solution of 8-chloro-5-fluoro-1,7-naphthyridin-3-ol (0.2 g, 1.007 mmol) and 2-butyn-1-ol (0.28 mL, 4.0 mmol) in THF (8 mL) was added triphenylphosphine (0.53 g, 2.01 mmol) and diisopropyl azodicarboxylate (0.40 mL, 2.01 mmol). The reaction was stirred at ambient temperature. After 16 hours, the reaction mixture was concentrated and purified by column chromatography, eluting with 10-50% ethyl acetate in heptane. The isolated product was triturated with ether to provide the title compound (0.13 g, 0.519 mmol, 51.5% yield). LC/MS (ESI⁺) m/z=251.0 (M+H).

Intermediate 37

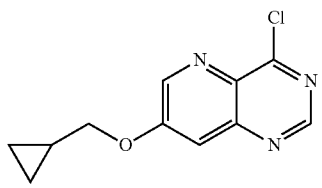 [SMILES: Clc1ncnc2cc(OCC3CC3)cnc12]

Synthesis of 4-chloro-7-(cyclopropylmethoxy)pyrido[3,2-d]pyrimidine

Step 1: 7-(cyclopropylmethoxy)pyrido[3,2-d]pyrimidin-4(3H)-one

A microwave vial was charged with cyclopropylmethanol (2231 µl, 27.5 mmol), and 60% sodium hydride in mineral oil (413 mg, 10.33 mmol) was added slowly. The mixture was stirred at RT for 5 minutes, and then 7-chloropyrido[3,2-d]pyrimidin-4(3H)-one (250 mg, 1.377 mmol) was added. The vial was capped and irradiated in the microwave for 30 minutes at 140° C. After 30 minutes, the reaction mixture was diluted with dichloromethane and purified by column chromatography, eluting with 15-100% (90:10:1 DCM/methanol/ammonium hydroxide) in DCM, to provide the title compound (66 mg, 0.304 mmol, 22.07% yield). LC/MS (ESI⁺) m/z=218.1 (M+H).

Step 2: 4-chloro-7-(cyclopropylmethoxy)pyrido[3,2-d]pyrimidine

To a solution of 7-(cyclopropylmethoxy)pyrido[3,2-d]pyrimidin-4(3H)-one (66 mg, 0.304 mmol) in toluene (2.2 mL) were added phosphorus oxychloride (0.5 mL, 5.46 mmol) and Hunig's base (53 µL, 0.304 mmol). A reflux condenser was installed, and the mixture was stirred at 130° C. for 40 minutes. The brown solution was concentrated, diluted with dichloromethane, and the pH was adjusted to 6-7 with saturated sodium bicarbonate. The reaction mixture was extracted with DCM, and the organic layer was washed with water and brine, dried over anhydrous sodium sulfate, filtered, and concentrated to yield the title compound as a dark brown solid, which was used without further purification. LC/MS (ESI⁺) m/z=236.1 (M+H).

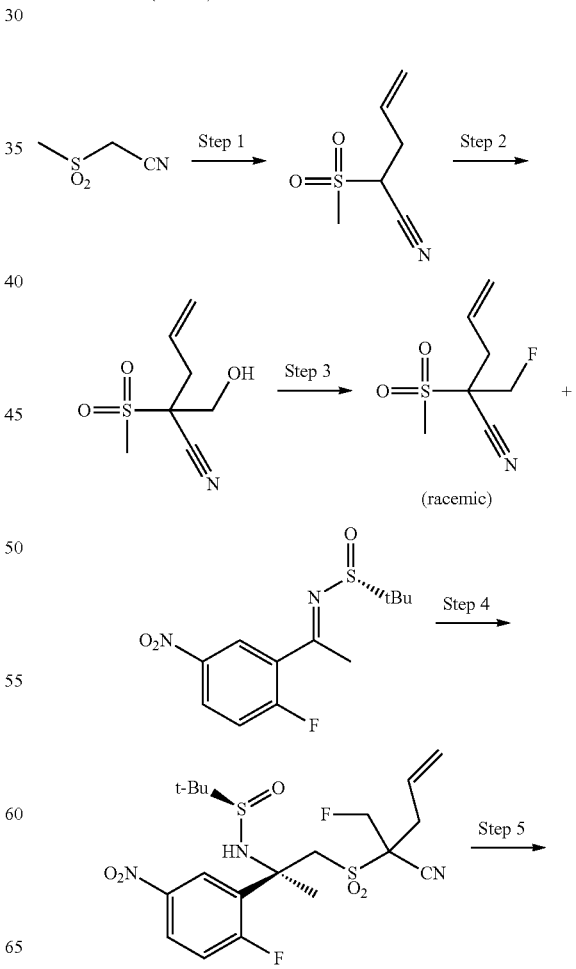

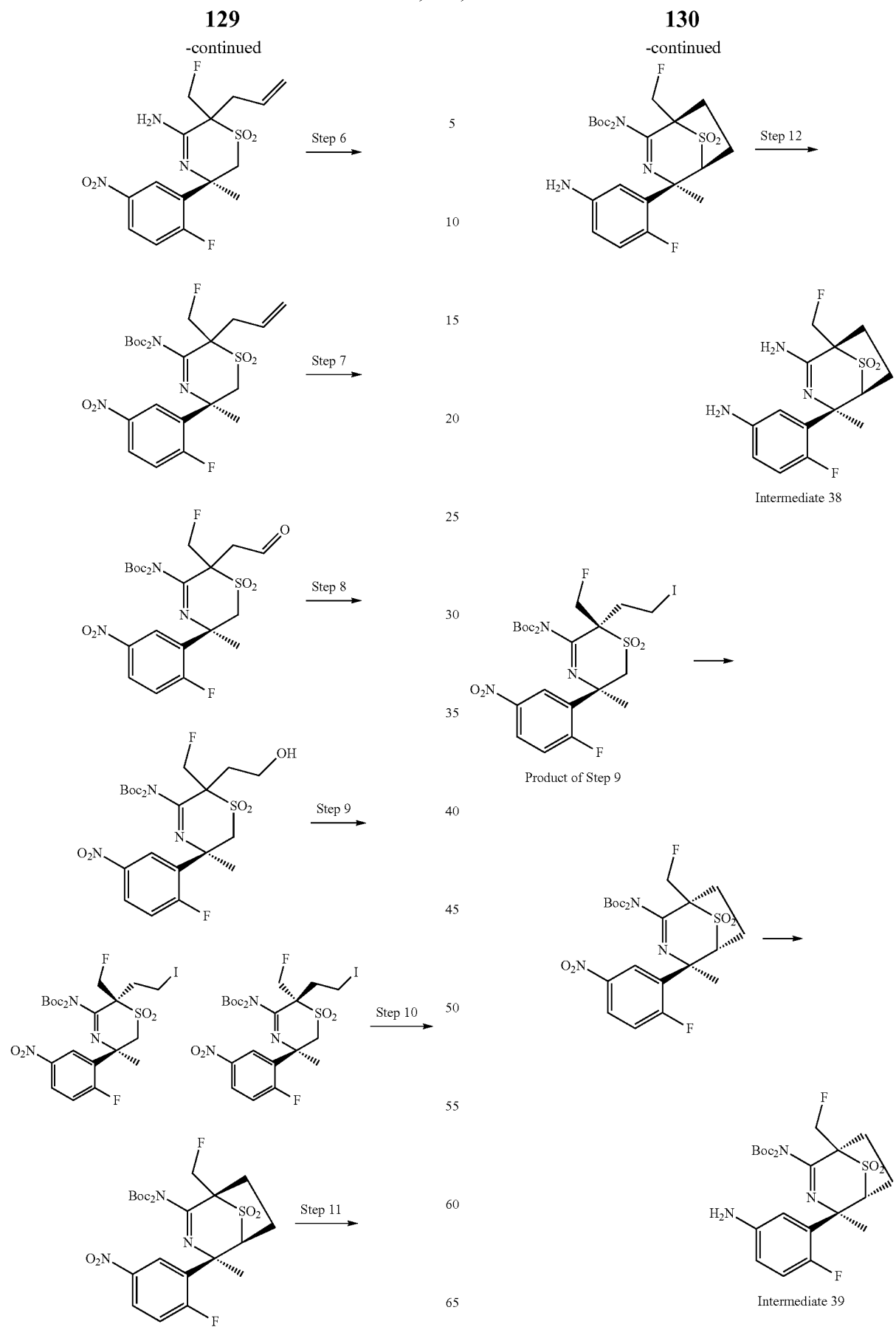

Synthetic Scheme for Intermediates 38 and 39

Intermediate 38

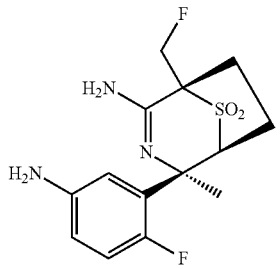 [SMILES: C[C@]1(c2cc(N)ccc2F)N=C(N)[C@@]2(CF)CC[C@@H]1S2(=O)=O]

Synthesis of (1S,2R,5R)-2-(5-amino-2-fluoro-phenyl)-5-(fluoromethyl)-2-methyl-8,8-dioxo-8-thia-3-azabicyclo[3.2.1]oct-3-en-4-amine

Step 1: 2-(methylsulfonyl)pent-4-enenitrile.

To a suspension of (methanesulphonyl)acetonitrile (5 g, 42.0 mmol) in acetonitrile (210 mL) was added potassium carbonate (325 mesh; 7.54 g, 54.6 mmol). The reaction mixture was stirred for 5 minutes and to this was added a solution of allyl bromide (3.63 mL, 42.0 mmol) in 5 mL of acetonitrile. The reaction mixture was stirred at RT for 24 hours. The reaction mixture was partitioned between aqueous ammonium chloride and ethyl acetate. The organic portion was dried over sodium sulfate and concentrated. The crude product was purified by silica gel chromatography, eluting with 5-30% ethyl acetate in heptane to afford the title compound (3.78 g, 23.7 mmol, 56.6% yield) as a clear oil.

Step 2: 2-(hydroxymethyl)-2-(methylsulfonyl)pent-4-enenitrile

To a suspension of 2-(methylsulfonyl)pent-4-enenitrile (3.324 g, 20.9 mmol) in 1,4-dioxane (20.9 mL) was added formaldehyde (37% wt in water; 3.9 ml, 52.2 mmol) followed by a 1M solution of TEA in THF (1.0 mL, 1.0 mmol). The reaction mixture was stirred at 38° C. for 4 hours. The reaction mixture was partitioned between water and ethyl acetate. The organic portion was dried over sodium sulfate and concentrated. The crude product was purified by silica gel chromatography, eluting with 10-40% ethyl acetate in heptane to afford the title compound (3.8 g, 20.1 mmol, 96% yield) as a tan oil.

Step 3: 2-(fluoromethyl)-2-(methylsulfonyl)pent-4-enenitrile

A solution of 2-(hydroxymethyl)-2-(methylsulfonyl)pent-4-enenitrile (3.32 g, 17.54 mmol) in DCM (88 mL) was placed in a water bath and stirred for 5 minutes. To this was added a solution of deoxofluor (9.70 ml, 52.6 mmol) in 10 mL of dichloromethane followed by ethanol (0.205 mL, 3.51 mmol). The water bath was removed and the reaction was stirred at RT for 24 hours. The reaction mixture was partitioned between aqueous sodium bicarbonate solution and DCM. The organic portion was dried over sodium sulfate and concentrated. The crude product was purified by silica gel chromatography, eluting with 5-30% ethyl acetate in heptane to afford the title compound (2.55 g, 13.34 mmol, 76% yield) as a light yellow oil.

Step 4: (R)—N-((2R)-1-((2-cyano-1-fluoropent-4-en-2-yl)sulfonyl)-2-(2-fluoro-5-nitrophenyl)propan-2-yl)-2-methylpropane-2-sulfinamide A solution of n-butyllithium (2.61 M in THF; 8.75 mL, 22.84 mmol) was added dropwise to a solution of 2-(fluoromethyl)-2-(methylsulfonyl)pent-4-enenitrile (3.66 g, 19.16 mmol) in THF (46.1 mL) at −78° C. The reaction mixture was stirred at −78° C. for 40 minutes. In a separate flask, a solution of (R,E)-N-(1-(2-fluoro-5-nitrophenyl)ethylidene)-2-methylpropane-2-sulfinamide (4.22 g, 14.74 mmol) in toluene (46.1 ml) was cooled to −40° C. and charged with a solution of trimethylaluminum (2M in toluene; 7.37 mL, 14.74 mmol) dropwise. The reaction mixture was stirred at −40° C. for 15 minutes and then transferred via cannula to the alkyl-lithium solution. Upon complete addition, the reaction was stirred at −40° C. for 2 hours. The reaction was quenched with aqueous saturated ammonium chloride solution and diluted with water and ethyl acetate. The organic portion was dried over sodium sulfate and concentrated. The crude product was purified by silica gel chromatography, eluting with 10-50% ethyl acetate in Heptane to provide the title compound (5.422 g, 11.35 mmol, 77% yield) as a yellow solid. LC/MS (ESI$^+$) m/z=478.1 (M+H).

Step 5: (3R)-6-allyl-6-(fluoromethyl)-3-(2-fluoro-5-nitro-phenyl)-3-methyl-1,1-dioxo-2H-1,4-thiazin-5-amine To a solution of (R)—N-((2R)-1-((2-cyano-1-fluoropent-4-en-2-yl)sulfonyl)-2-(2-fluoro-5-nitrophenyl)propan-2-yl)-2-methylpropane-2-sulfinamide (5.422 g, 11.35 mmol) in DCM (56.8 mL) was added HCl (4N in Dioxane) (8.52 mL, 34.1 mmol). The resulting mixture was stirred at RT for 2 hours. The reaction mixture was concentrated and dried under high vacuum for 16 hours. The crude solid was dissolved in ethanol (56.8 mL) and treated with copper (I) chloride (1.461 g, 14.76 mmol). The reaction was stirred at 85° C. for 4 hours. The mixture was concentrated and partitioned between ethyl acetate (80 mL) and 10% aq. ammonium hydroxide (15 mL). The organic portion was concentrated to afford the title compound (4.2 g), which was taken onto the next step without further purification. LC/MS (ESI$^+$) m/z=374.0 (M+H).

Step 6: tert-butyl N-[(3R)-6-allyl-6-(fluoromethyl)-3-(2-fluoro-5-nitro-phenyl)-3-methyl-1,1-dioxo-2H-1,4-thiazin-5-yl]-N-tert-butoxycarbonyl-carbamate To a solution of (3R)-6-allyl-5-amino-3-(2-fluoro-5-nitrophenyl)-6-(fluoromethyl)-3-methyl-3,6-dihydro-2H-1,4-thiazine 1,1-dioxide (4.2 g, 11.25 mmol) in dichloromethane (45.0 mL) was added DMAP (0.825 g, 6.75 mmol) and boc anhydride (6.14 g, 28.1 mmol). The reaction mixture was stirred vigorously at RT for 18 hours. The mixture was partitioned between DCM and water. The organic portion was concentrated and the crude was purified by silica gel chromatography, eluting with 0-40% ethyl acetate in heptane to provide the title compound (3.73 g, 6.499 mmol, 58% yield) as an off-white foam. LC/MS (ESI$^+$) m/z=596.2 (M+Na).

Step 7: tert-butyl N-tert-butoxycarbonyl-N-[(3R)-6-(fluoromethyl)-3-(2-fluoro-5-nitro-phenyl)-3-methyl-1,1-dioxo-6-(2-oxoethyl)-2H-1,4-thiazin-5-yl] carbamate A suspension of tert-butyl N-[(3R)-6-allyl-6-(fluoromethyl)-3-(2-fluoro-5-nitro-phenyl)-3-methyl-1,1-dioxo-2H-

1,4-thiazin-5-yl]-N-tert-butoxycarbonyl-carbamate (3.08 g, 5.36 mmol) in DCM (30.05 mL) and methanol (6.01 mL) was cooled to −78° C. and stirred at this temperature for 5 minutes. A stream of ozone in oxygen was then bubbled through the solution for 30 min until the solution turned light blue. Nitrogen was then passed through the reaction for 15 minutes until the solution turned colorless. Triphenylphosphine (1.69 g, 6.44 mmol) was added and the mixture was stirred for 5 minutes at −78° C. and then brought to RT. The reaction was stirred at RT for 30 minutes and then concentrated under reduced pressure. The crude residue was purified by silica gel chromatography, eluting with 0-40% ethyl acetate in heptane to provide the title compound (2.94 g, 5.11 mmol, 95% yield) as a white foam. LC/MS (ESI$^+$) m/z=598.1 (M+Na).

Step 8: tert-butyl N-tert-butoxycarbonyl-N-[(3R)-6-(fluoromethyl)-3-(2-fluoro-5-nitro-phenyl)-6-(2-hydroxyethyl)-3-methyl-1,1-dioxo-2H-1,4-thiazin-5-yl]carbamate A solution of borane tetrahydrofuran complex (1M in THF; 7.66 ml, 7.66 mmol) was added dropwise to a solution of tert-butyl N-tert-butoxycarbonyl-N-[(3R)-6-(fluoromethyl)-3-(2-fluoro-5-nitro-phenyl)-3-methyl-1,1-dioxo-6-(2-oxoethyl)-2H-1,4-thiazin-5-yl]carbamate (2.94 g, 5.11 mmol) in THF (25.5 ml) at 0° C. The mixture was stirred at 0° C. for 35 minutes. The reaction was quenched with saturated ammonium chloride solution and then diluted with water and ethyl acetate. The organic portion was washed with brine and concentrated to afford the crude product. This was purified by silica gel chromatography, eluting with 10-80% ethyl acetate in heptane to provide the title compound (2.36 g, 4.09 mmol, 80% yield) as an off-white foam. LC/MS (ESI$^+$) m/z=600.2 (M+Na).

Step 9: tert-butyl N-tert-butoxycarbonyl-N-[(3R,6S)-6-(fluoromethyl)-3-(2-fluoro-5-nitro-phenyl)-6-(2-iodoethyl)-3-methyl-1,1-dioxo-2H-1,4-thiazin-5-yl]carbamate and tert-butyl N-tert-butoxycarbonyl-N-[(3R,6R)-6-(fluoromethyl)-3-(2-fluoro-5-nitro-phenyl)-6-(2-iodoethyl)-3-methyl-1,1-dioxo-2H-1,4-thiazin-5-yl]carbamate To a suspension of imidazole (1.089 g, 16.00 mmol) and triphenylphosphine (2.098 g, 8.00 mmol) in DCM (20.00 mL) was added iodine (2.030 g, 8.00 mmol) at 0° C. The reaction was stirred at 0° C. for 5 minutes and then a solution of tert-butyl N-tert-butoxycarbonyl-N-[(3R)-6-(fluoromethyl)-3-(2-fluoro-5-nitro-phenyl)-6-(2-hydroxyethyl)-3-methyl-1,1-dioxo-2H-1,4-thiazin-5-yl]carbamate (2.31 g, 4.00 mmol) in DCM (20.00 mL) was added dropwise via an addition funnel. The ice bath was removed, and the reaction was brought to RT. The resulting mixture was stirred at ambient temperature for 16 hours and then concentrated to afford a crude residue. This was purified by silica gel chromatography, eluting with 10-40% ethyl acetate in heptane to provide the title compounds. The first eluted peak (retention time at 3.00 minutes) provided tert-butyl N-tert-butoxycarbonyl-N-[(3R,6S)-6-(fluoromethyl)-3-(2-fluoro-5-nitro-phenyl)-6-(2-iodoethyl)-3-methyl-1,1-dioxo-2H-1,4-thiazin-5-yl]carbamate (1.1 g, 1.60 mmol, 40.0% yield). The second eluted peak (retention time at 2.95 minutes) provided tert-butyl N-tert-butoxycarbonyl-N-[(3R,6R)-6-(fluoromethyl)-3-(2-fluoro-5-nitro-phenyl)-6-(2-iodoethyl)-3-methyl-1,1-dioxo-2H-1,4-thiazin-5-yl]carbamate (1.41 g, 2.05 mmol, 51.3% yield). LC/MS (ESI$^+$) m/z=710.0 (M+Na).

Step 10: tert-butyl N-tert-butoxycarbonyl-N-[(1S,2R,5R)-5-(fluoromethyl)-2-(2-fluoro-5-nitro-phenyl)-2-methyl-8,8-dioxo-8-thia-3-azabicyclo[3.2.1]oct-3-en-4-yl]carbamate To a solution of tert-butyl N-tert-butoxycarbonyl-N-[(3R,6R)-6-(fluoromethyl)-3-(2-fluoro-5-nitro-phenyl)-6-(2-iodoethyl)-3-methyl-1,1-dioxo-2H-1,4-thiazin-5-yl]carbamate (1.41 g, 2.05 mmol) in THF (17.04 mL) was added a solution of lithium bis(trimethylsilyl)amide (1M in THF; 3.07 mL, 3.07 mmol) at −78° C. The reaction was stirred at −78° C. for 1 hour and then quenched with aqueous ammonium chloride solution and slowly warmed up to ambient temperature. The reaction mixture was then diluted with water and ethyl acetate. The organic portion was dried over sodium sulfate and concentrated to give a crude residue. This was purified by silica gel chromatography, eluting with 10-60% ethyl acetate in heptane to provide the title compound (1.14 g, 2.05 mmol, 100% yield) as a light yellow solid. LC/MS (ESI$^+$) m/z=582.2 (M+Na).

Step 11: tert-butyl N-[(1S,2R,5R)-2-(5-amino-2-fluoro-phenyl)-5-(fluoromethyl)-2-methyl-8,8-dioxo-8-thia-3-azabicyclo[3.2.1]oct-3-en-4-yl]-N-tert-butoxycarbonyl-carbamate A sealable vessel was charged with tert-butyl N-tert-butoxycarbonyl-N-[(1S,2R,5R)-5-(fluoromethyl)-2-(2-fluoro-5-nitro-phenyl)-2-methyl-8,8-dioxo-8-thia-3-azabicyclo[3.2.1]oct-3-en-4-yl]carbamate (1.14 g, 2.037 mmol) and purged with Nitrogen (g). 10% Pd/C (0.434 g, 0.407 mmol) was added portion-wise followed by ethyl acetate (5.28 mL) and ethanol (15.09 mL). The reaction mixture was purged with Nitrogen (g) once more, then evacuated and backfilled with Hydrogen (g). The reaction was stirred at RT for 5 hours. The reaction mixture was filtered through a pad of celite and rinsed with ethyl acetate and ethanol. The filtrate was concentrated to provide the title compound (1.05 g, 1.99 mmol, 97% yield) as a light yellow solid. LC/MS (ESI$^+$) m/z=552.2 (M+Na).

Step 12: (1S,2R,5R)-2-(5-amino-2-fluoro-phenyl)-5-(fluoromethyl)-2-methyl-8,8-dioxo-8-thia-3-azabicyclo[3.2.1]oct-3-en-4-amine To a suspension of tert-butyl N-[(1S,2R,5R)-2-(5-amino-2-fluoro-phenyl)-5-(fluoromethyl)-2-methyl-8,8-dioxo-8-thia-3-azabicyclo[3.2.1]oct-3-en-4-yl]-N-tert-butoxycarbonyl-carbamate (0.17 g, 0.321 mmol) in dichloromethane (3 mL) was added trifluoroacetic acid (0.247 ml, 3.21 mmol). The reaction mixture was stirred at RT for 1 hour. The mixture was diluted with aqueous sodium bicarbonate solution and stirred vigorously for 30 minutes. The product was then extracted with DCM. The organic portion was concentrated to dryness and the residue was dried under high vac. for 2 hours.

The residue was triturated with ethanol and the solids were dried to afford the title compound (0.077 g, 0.234 mmol, 77% yield) as a white solid. LC/MS (ESI$^+$) m/z=330.0 (M+H).

Intermediate 39

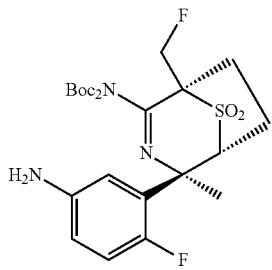

Synthesis of tert-butyl N-[(1R,2R,5S)-2-(5-amino-2-fluoro-phenyl)-5-(fluoromethyl)-2-methyl-8,8-dioxo-8-thia-3-azabicyclo[3.2.1]oct-3-en-4-yl]-N-tert-butoxycarbonyl-carbamate Step 1: tert-butyl N-tert-butoxycarbonyl-N-[(1R,2R,5S)-5-(fluoromethyl)-2-(2-fluoro-5-nitro-phenyl)-2-methyl-8,8-dioxo-8-thia-3-azabicyclo[3.2.1]oct-3-en-4-yl]carbamate To a solution of tert-butyl N-tert-butoxycarbonyl-N-[(3R,6S)-6-(fluoromethyl)-3-(2-fluoro-5-nitro-phenyl)-6-(2-iodoethyl)-3-methyl-1,1-dioxo-2H-1,4-thiazin-5-yl]carbamate (1.1 g, 1.60 mmol) in THF (13.33 mL) was added a solution of lithium bis(trimethylsilyl)amide (1M in THF; 2.240 ml, 2.240 mmol) at −78° C. The reaction was stirred at −78° C. for 1 hour and then quenched with aqueous ammonium chloride solution and slowly warmed up to RT. The reaction mixture was then diluted with water and ethyl acetate. The organic portion was dried over sodium sulfate and concentrated to give a crude residue. This was purified by silica gel chromatography, eluting with 10-60% ethyl acetate in heptane to provide the title compound (0.895 g, 1.60 mmol, 100% yield) as a light yellow solid. LC/MS (ESI$^+$) m/z=582.2 (M+Na).

Step 2: tert-butyl N-[(1R,2R,5S)-2-(5-amino-2-fluoro-phenyl)-5-(fluoromethyl)-2-methyl-8,8-dioxo-8-thia-3-azabicyclo[3.2.1]oct-3-en-4-yl]-N-tert-butoxycarbonyl-carbamate A sealable vessel was charged with tert-butyl N-tert-butoxycarbonyl-N-[(1R,2R,5S)-5-(fluoromethyl)-2-(2-fluoro-5-nitro-phenyl)-2-methyl-8,8-dioxo-8-thia-3-azabicyclo[3.2.1]oct-3-en-4-yl]carbamate (0.77 g, 1.376 mmol) and purged with Nitrogen (g). 10% Pd/C (0.293 g, 0.275 mmol) was added portion-wise followed by ethyl acetate (3.44 mL) and ethanol (10.32 mL). The reaction mixture was purged with Nitrogen (g) once more, then evacuated and backfilled with H$_2$ (g). The reaction was stirred at RT for 5 hours. The reaction mixture was filtered through a pad of celite and rinsed with ethyl acetate and ethanol. The filtrate was concentrated to provide the title compound (0.70 g, 1.322 mmol, 96% yield) as a light yellow solid. LC/MS (ESI$^+$) m/z=552.2 (M+Na).

Intermediate 40

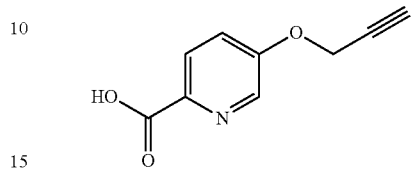

5-(Prop-2-yn-1-yloxy)picolinic acid was purchased from a commercially available source, such as from Aurora Fine Chemicals LLC.

Intermediate 41

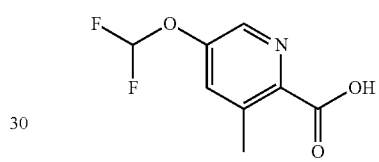

Synthesis of 5-(difluoromethoxy)-3-methylpicolinic acid

Step 1: Synthesis of 5-(difluoromethoxy)-3-methylpicolinonitrile

A mixture of 2-chloro-5-(difluoromethoxy)-3-methylpyridine (12.4 g, 64.1 mmol), zinc cyanide (4.07 mL, 64.1 mmol), 1,1'-bis(diphenylphosphino)ferrocene (2.5 g, 4.51 mmol) and 1,1'-bis(diphenylphosphino)ferrocene (2.5 g, 4.51 mmol) in DMA (50 mL) was heated to 110° C. under N$_2$ for 18 h. The reaction mixture was diluted with water and extracted with ethyl acetate. The organic phase obtained was concentrated under reduced pressure and the residue was purified by silica gel chromatography eluting with 0-70% EtOAc/hex to give 5-(difluoromethoxy)-3-methylpicolinonitrile (5.88 g, 31.9 mmol, 49.8% yield). MS m/z: 185.0 [M+H].

Step 2: Synthesis of 5-(difluoromethoxy)-3-methylpicolinic acid

A solution of 5-(difluoromethoxy)-3-methylpicolinonitrile (5.8 g, 31.5 mmol) and sodium hydroxide 1.0 normal (100 ml, 100 mmol) in EtOH (50 ml) was heated to 80° C. for 18 h. The reaction mixture was concentrated and diluted with water and extracted with ether (2×). The aqueous layer was acidified to pH 3 with 1N HCl solution and extracted with TBME (2×). The combined organic layers were dried over sodium sulfate, filtered, and concentrated to give desired product 5-(difluoromethoxy)-3-methylpicolinic acid (4.6 g, 22.64 mmol, 71.9% yield) as a tan solid. MS m/z: 204.1 [M+H].

Intermediate 42

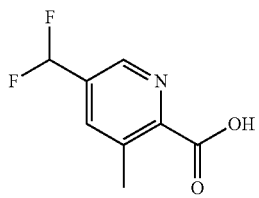

Synthesis of
5-Difluoromethyl-3-methyl-pyridine-2-carboxylic acid

Step 1:
2-Chloro-5-difluoromethyl-3-methyl-pyridine

To a precooled solution of 6-chloro-5-methyl-pyridine-3-carbaldehyde (500 mg, 3.21 mmol) in DCM (15 ml) was added at −78° C. DAST (0.632 ml, 0.777 g, 4.82 mmol).

The reaction mixture was stirred for 18 h at −78° C. to rt, then quenched at 0° C. with saturated aq. NaHCO$_3$ solution, diluted with water and extracted with DCM. The organic layer was washed with water and dried over sodium sulfate, filtered, and concentrated. 2-Chloro-5-difluoromethyl-3-methyl-pyridine was obtained as a yellow oil after flash chromatography on silica gel (cyclohexane/EtOAc gradient 0-5 min 100:0, 5-40 min 100:0 to 80:20). ESI MS: 178 [M+H]; $^1$H NMR (400 MHz, CDCl$_3$): δ=8.38 (d, 1H) 7.72 (d, 1H), 6.69 (t, 1H), 2.46 (s, 3H).

Step 2:
5-Difluoromethyl-3-methyl-pyridine-2-carbonitrile

A solution of 2-chloro-5-difluoromethyl-3-methyl-pyridine (337 mg, 1.898 mmol), Zn(CN)$_2$ (159 mg, 1.328 mmol) and Pd (PPh$_3$)$_4$ (132 mg, 0.114 mmol) in DMF (10 ml) was stirred for 10 min at 120° C. in a microwave, filtered over hyflo and washed with water and brine. The combined aqueous layers were extracted with TBME, the combined organic layers were dried over sodium sulfate, filtered and concentrated. 5-Difluoromethyl-3-methyl-pyridine-2-carbonitrile was obtained as a yellow oil after flash chromatography on silica gel (cyclohexane/EtOAc gradient 0-3 min 100:0, 3-35 min 100:0 to 80:20). ESI MS: 169 [M+H]; $^1$H NMR (400 MHz, CDCl$_3$): δ=8.68 (s, 1H), 7.84 (s, 1H), 6.75 (t, 1H), 2.65 (s, 3H).

Step 3:
5-Difluoromethyl-3-methyl-pyridine-2-carboxylic acid

A solution of 5-difluoromethyl-3-methyl-pyridine-2-carbonitrile (209 mg, 0.787 mmol) in concentrated aqueous HCl solution (2 ml) was stirred for 2 h at 120° C. in a sealed tube. The reaction mixture was cooled to rt, diluted with TBME and extracted twice with water. The combined aqueous layers were washed with TBME and lyophilized. The residue was dissolved in water, 1M aqueous NaOH solution was added to adjust the pH to 2 and the solution was extracted three times with DCM. The combined organic layers were dried over sodium sulfate, filtered and concentrated to afford 5-Difluoromethyl-3-methyl-pyridine-2-carboxylic acid. ESI MS: 188 [M+H]; $^1$H NMR (400 MHz, CD$_3$OD): δ=8.62 (s, 1H), 7.98 (s, 1H), 6.95 (t, 1H), 2.65 (s, 3H).

Intermediate 43

Synthesis of 5-(methoxymethyl)picolinic acid

Step 1: 2-Chloro-5-(methoxymethyl)pyridine

To a solution of 2-chloro-5-hydroxymethylpyridine (1 g, 6.97 mmol) in THF (34.8 ml) was added sodium hydride (60% wt) (0.418 g, 10.45 mmol). The reaction was stirred for 10 minutes and treated with methyl iodide (0.653 ml, 10.45 mmol). The reaction was stirred at RT for 4 hrs. The reaction mixture was quenched with saturated NH$_4$Cl and extracted with EtOAc. The organic portion was concentrated and purified in 10-40% EtOAc/Heptanes to give the title compound (880 mg, 5.58 mmol, 80% yield) as a tan solid. MS m/z=157.9 (M+H).

Step 2: 5-(Methoxymethyl)picolinonitrile

A mixture of 2-chloro-5-(methoxymethyl)pyridine (0.831 g, 5.27 mmol), tetrakis (1.219 g, 1.055 mmol), dicyanozinc (0.929 g, 7.91 mmol) and DMF (17.58 ml) was stirred at 100° C. for 3 hrs. The reaction was treated with water and extracted with ethyl acetate. The organic portion was dried over Na$_2$SO$_4$, filtered, and concentrated in vacuo. The crude material was purified by column chromatography, eluting with 10-40% EtOAc/Heptanes to give the title compound (550 mg, 3.71 mmol, 70.4%). MS m/z=149.1 (M+H).

Step 3: 5-(Methoxymethyl)picolinic acid

A mixture of 5-(methoxymethyl)picolinonitrile (207 mg, 1.397 mmol) in NaOH (aq. 5N) (2794 μl, 13.97 mmol) and EtOH (5588 μl) was stirred at 80° C. for 16 hrs. The reaction was concentrated to half its volume and treated with 2N HCl until the pH reached ~5. The product was extracted with ethyl acetate. The organic portion was dried over Na$_2$SO$_4$, filtered and concentrated in vacuo to give the title compound (210 mg, 1.26 mmol, 90%) as an off-white solid. MS m/z=167.9 (M+H).

Intermediate 44

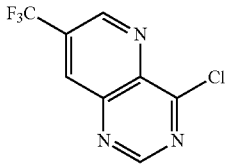 [SMILES: FC(F)(F)c1cnc2c(Cl)ncnc2c1]

Synthesis of 4-chloro-7-(trifluoromethyl)pyrido[3,2-d]pyrimidine

Step 1: 3-Nitro-5-(trifluoromethyl)picolinonitrile

A microwave reaction vial was charged with 2-chloro-3-nitro-5-(trifluoromethyl)pyridine (2 g, 8.83 mmol), NMP (4.41 ml) and CuCN (0.830 g, 9.27 mmol). The vial was sealed and the mixture was irradiated in the MW at 175° C. for 15 min. Upon cooling to RT, the reaction mixture was poured onto ice and EtOAc was added. The mixture was filtered through Celite, washing with EtOAc and a small amount of MeOH. The layers of the filtrate were separated, and the aqueous portion was extracted again with EtOAc. The combined organic portions were dried with sodium sulfate, filtered and concentrated. The crude material was purified by silica gel chromatography, using a gradient of 0-30% EtOAc in heptane to provide 3-nitro-5-(trifluoromethyl)picolinonitrile (645 mg, 2.97 mmol, 33.7% yield) as a yellow oil that solidified upon standing. LC/MS (ESI$^+$) m/z=218.1 (M+H).

Step 2: 3-Nitro-5-(trifluoromethyl)picolinamide

A round bottom flask was charged with 3-nitro-5-(trifluoromethyl)picolinonitrile (910 mg, 4.19 mmol) and sulfuric acid (4192 µl, 4.19 mmol), and the mixture was stirred at 60° C. for 16 h. Upon cooling to RT the crude mixture was poured onto ice, and the resulting solids were filtered, washed with water and dried. 3-nitro-5-(trifluoromethyl)picolinamide (850 mg, 3.62 mmol, 86% yield) was isolated as a light yellow solid. LC/MS (ESI$^+$) m/z=236.1 (M+H).

Step 3: 3-Amino-5-(trifluoromethyl)picolinamide

A round bottom flask was charged with 3-nitro-5-(trifluoromethyl)picolinamide (850 mg, 3.62 mmol) and wet 5 wt. % Pd/C (769 mg, 0.362 mmol) and was purged with nitrogen. EtOAc (7230 µl) and then MeOH (7230 µl) were added, and the flask was evacuated and filled with hydrogen. The reaction was stirred at RT under hydrogen atmosphere for 17 h. The mixture was filtered through Celite and washed with EtOAc and MeOH. The filtrate was concentrated to provide 3-amino-5-(trifluoromethyl)picolinamide (720 mg, 3.51 mmol, 97% yield) as a white solid. LC/MS (ESI$^+$) m/z=206.1 (M+H).

Step 4: 7-(Trifluoromethyl)pyrido[3,2-d]pyrimidin-4(3H)-one

A vial was charged with 3-amino-5-(trifluoromethyl)picolinamide (615 mg, 3.00 mmol) and triethyl orthoformate (2496 µl, 14.99 mmol). The vial was sealed and the mixture was heated at 120° C. for 17 h. Upon cooling, the heterogeneous mixture was filtered and the solids were washed with heptane. 7-(trifluoromethyl)pyrido[3,2-d]pyrimidin-4(3H)-one (540 mg, 2.51 mmol, 84% yield) was isolated as a tan solid. LC/MS (ESI$^+$) m/z=216.0 (M+H).

Step 5: 4-Chloro-7-(trifluoromethyl)pyrido[3,2-d]pyrimidine

A pressure bottle was charged with 7-(trifluoromethyl)pyrido[3,2-d]pyrimidin-4(3H)-one (540 mg, 2.51 mmol), toluene (10.000 mL) and Hunig's base (1.315 mL, 7.53 mmol). POCl$_3$ (0.702 mL, 7.53 mmol) was added, and the bottle was sealed. The mixture was heated to 115° C. for 4 h. After cooling to RT, the mixture was diluted with EtOAc and water, and the layers were separated. The aqueous portion was extracted with additional EtOAc, and the combined organic portions were washed with saturated sodium bicarbonate, dried over sodium sulfate, filtered and concentrated. 4-chloro-7-(trifluoromethyl)pyrido[3,2-d]pyrimidine (560 mg, 2.397 mmol, 96% yield) was isolated as a brown solid. LC/MS (ESI$^+$) m/z=234.0 (M+H).

Intermediate 45

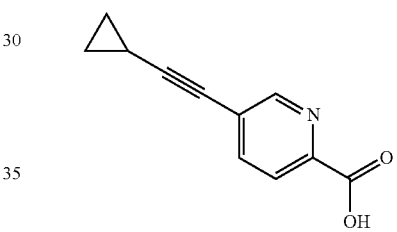

Synthesis of 5-(cyclopropylethynyl)picolinic acid

Step 1: Methyl 5-(cyclopropylethynyl)picolinate

To a microwave vial were added methyl 5-bromopyridine-2-carboxylate (0.285 mL, 2.083 mmol), THF (4 mL), tetrakis(triphenylphosphine)palladium (193 mg, 0.167 mmol), copper(i) iodide (3.53 µl, 0.104 mmol), and triethylamine (2.318 mL, 16.66 mmol) under nitrogen. Cyclopropylacetylene (0.353 mL, 4.17 mmol) was added and the resulting yellow mixture was stirred at 40° C. overnight. The reaction mixture was diluted with water and extracted with EtOAc. The organic extract was washed with saturated NaCl and dried over MgSO4. The solution was filtered and concentrated in vacuo to give the crude material as an orange oil. The crude material was absorbed onto a plug of silica gel and purified by chromatography through a silica gel column, eluting with a gradient of 15% to 30% to 45% EtOAc in Heptane, to provide methyl 5-(cyclopropylethynyl)picolinate (390 mg, 1.938 mmol, 93% yield) as an orange solid. m/z (ESI$^+$) 202.2 (M+H)$^+$.

Step 2: 5-(Cyclopropylethynyl)picolinic acid

To a sealed tube were added methyl 5-(cyclopropylethynyl)picolinate (240 mg, 1.193 mmol), potassium hydroxide (0.072 mL, 2.62 mmol), and MeOH (3.98 mL). The mixture was stirred at 50° C. for 20 minutes. The reaction was cooled to RT and concentrated. The white solid salt was dissolved in a minimum amount of water (~1.5 mL), and acidified by 6N HCl to pH=2 (~0.6 mL). A light brown precipitate formed and the resulting mixture was cooled to 0° C. The precipitate was collected by Buchner funnel to yield 5-(cyclopropylethynyl) picolinic acid (163 mg, 0.871 mmol, 73.0% yield) as a light yellow solid. m/z (ESI⁺) 188.1 (M+H)⁺.

Intermediate 46

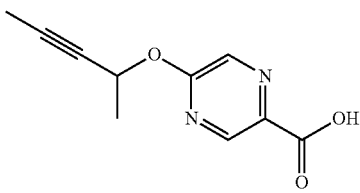

Synthesis of
5-(pent-3-yn-2-yloxy)pyrazine-2-carboxylic acid

A RBF was charged with 3-pentyn-2-ol (2.06 mL, 22.08 mmol) and DMF (10 mL). Potassium t-butoxide, sublimed, 99.99% trace metals basis (1.24 g, 11.04 mmol) was added portionwise (cooling with water). The mixture was stirred at room temperature for 10 min until all t-BuOK went into solution, then 5-chloropyrazine-2-carboxylic acid (0.500 g, 3.15 mmol) was added in portions and the resulting brown suspension was heated at 75° C. for 45 minutes. The mixture was cooled to RT and diluted with water (~20 ml) until all solids dissolved, then acidified with 2M HCl (~5.5 ml) to pH 2. The resulting solution was extracted with EtOAc and the organic layer was washed with water and brine, filtered through a pad of celite and concentrated in vacuo. The resulting suspension was diluted with 3 mL heptane/EtOAc (20:1) mixture then filtered. The solid was washed with heptane and dried in vacuo to afford 5-(pent-3-yn-2-yloxy)pyrazine-2-carboxylic acid (424 mg, 2.056 mmol, 65.2% yield) as a tan solid. m/z (ESI) 207.1 (M+H)⁺.

Intermediate 47

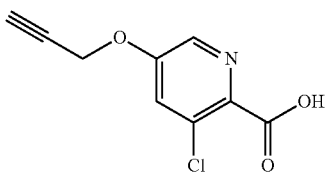

Synthesis of 3-chloro-5-(prop-2-yn-1-yloxy)picolinic acid

Step 1: Prop-2-yn-1-yl 3-chloro-5-(prop-2-yn-1-yloxy)picolinate

To a suspension of 3-chloro-5-hydroxypicolinic acid (0.400 g, 2.305 mmol, Afferchem) and potassium carbonate (1.115 g, 8.070 mmol) in DMF (10 mL) was added propargyl bromide, 80% solution in toluene (0.565 mL, 5.070 mmol) dropwise at RT. The mixture was heated to 45° C. for 1 h, then diluted with EtOAc and washed with water and brine. The organic solution was dried over Na₂SO₄ and concentrated in vacuo. The crude was purified by silica gel chromatography: 0-50% EtOAc-Hexane. The product prop-2-yn-1-yl 3-chloro-5-(prop-2-yn-1-yloxy)picolinate was obtained as yellow solid (0.449 g, 78% yield). LC/MS (ESI⁻) m/z=250 (M+H)⁺. ¹H NMR (400 MHz, CHLOROFORM-d) δ ppm 2.53 (t, J=2.35 Hz, 1 H) 2.63 (t, J=2.25 Hz, 1 H) 4.81 (d, J=2.15 Hz, 2 H) 4.98 (d, J=2.35 Hz, 2 H) 7.41 (d, J=2.54 Hz, 1 H) 8.37 (d, J=2.54 Hz, 1 H).

Step 2: 3-chloro-5-(prop-2-yn-1-yloxy)picolinic acid

A mixture of prop-2-yn-1-yl 3-chloro-5-(prop-2-yn-1-yloxy)picolinate (0.448 g, 1.795 mmol), lithium hydroxide monohydrate (0.079 g, 1.884 mmol), THF (6 mL), and water (2 mL) was stirred at RT for 1 h. LCMS showed the reaction was complete. 1.9 mL of 1N HCl was added to neutralize the base. The mixture was concentrated in vacuo and dried on vacuum. The product was obtained as off-white solid (0.456 g, 1.795 mmol, 100% yield). LC/MS (ESI⁻) m/z=212 (M+H)⁺. ¹H NMR (400 MHz, MeOH-d4) δ ppm 3.06 (t, J=2.35 Hz, 1 H) 4.85 (m, 2 H) 7.52 (d, J=2.54 Hz, 1 H) 8.01-8.30 (m, 1 H).

Intermediate 48

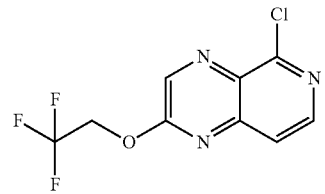 [SMILES: FC(F)(F)COc1cnc2c(Cl)nccc2n1]

Synthesis of 5-chloro-2-(2,2,2-trifluoroethoxy)pyrido[3,4-b]pyrazine

To a RBF was added 2,2,2-trifluoroethanol (4.85 ml, 66.6 mmol, Sigma-Aldrich Chemical Company, Inc.) and sodium hydride (0.200 g, 4.99 mmol, Sigma-Aldrich Chemical Company, Inc.) to stir for 10 minutes. 2,5-Dichloropyrido[3,4-b]pyrazine (0.3329 g, 1.664 mmol) was added in batches to stir at rt. The reaction was allowed to stir for 1 hour. The reaction was quenched with satd. ammonium chloride. The reaction mixture was extracted with EtOAc. The organic extract was washed with satd NaCl, dried over MgSO4, filtered and concentrated in vacuo to give 5-chloro-2-(2,2,2-trifluoroethoxy) pyrido[3,4-b]pyrazine (0.5104 g, 1.936 mmol, 116% yield). LCMS showed product peak at 2.13 min (m+11=263.9). ¹H NMR (300 MHz, CHLOROFORM-d) δ ppm 4.98 (q, J=8.18 Hz, 2 H) 7.67 (d, J=5.70 Hz, 1 H) 8.55 (d, J=5.70 Hz, 1 H) 8.75 (s, 1 H).

Intermediate 48A and 48B

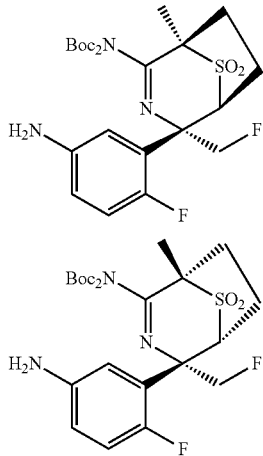

Synthesis of tert-butyl N-[(1S,2S,5R)-2-(5-amino-2-fluoro-phenyl)-2-(fluoromethyl)-5-methyl-8,8-dioxo-8-thia-3-azabicyclo[3.2.1]oct-3-en-4-yl]-N-tert-butoxycarbonyl-carbamate and tert-butyl N-[(1R,2R,5S)-2-(5-amino-2-fluoro-phenyl)-2-(fluoromethyl)-5-methyl-8,8-dioxo-8-thia-3-azabicyclo[3.2.1]oct-3-en-4-yl]-N-tert-butoxycarbonyl-carbamate Step 1: (R)—N—((S)-2-(5-bromo-2-fluorophenyl)-1-(((R)-2-cyanopent-4-en-2-yl)sulfonyl)-3-fluoropropan-2-yl)-2-methylpropane-2-sulfinamide and (R)—N—((R)-2-(5-bromo-2-fluorophenyl)-1-(((S)-2-cyanopent-4-en-2-yl)sulfonyl)-3-fluoropropan-2-yl)-2-methylpropane-2-sulfinamide A RBF was charged with 2-methyl-2-(methylsulfonyl)pent-4-enenitrile (2.77 g, 15.97 mmol) and THF (17.74 ml), and the solution was cooled to −78° C. under nitrogen. N-Butyl lithium (2.7 M, 5.91 ml, 15.97 mmol) was added dropwise, and the mixture was stirred at −78° C. for 30 min. A separate RBF was charged with (R,E)-N-(1-(5-bromo-2-fluorophenyl)-2-fluoroethylidene)-2-methylpropane-2-sulfinamide (3 g, 8.87 mmol) and THF (17.74 ml) and the solution was cooled to 0° C. under nitrogen. BF$_3$—OEt$_2$ (1.124 ml, 8.87 mmol) was added and the mixture was stirred at 0° C. for 15 min before being added dropwise via cannula to the lithiate. After addition was complete, the reaction was stirred at −78° C. for 1.5 h. The reaction was quenched with saturated aqueous NH$_4$Cl and allowed to warm to RT. Water and EtOAc were added, and the layers were separated. The aqueous portion was washed with EtOAc, and the combined organics were washed with brine, dried over sodium sulfate, filtered and concentrated. The crude material was carried forward without additional purification as part of a mixture of 4 diastereomers. LC/MS (ESI$^+$) m/z=511.0 (M+H).

Step 2: (3S,6R)-6-allyl-5-amino-3-(5-bromo-2-fluorophenyl)-3-(fluoromethyl)-6-methyl-3,6-dihydro-2H-1,4-thiazine 1,1-dioxide and (3R,6S)-6-allyl-5-amino-3-(5-bromo-2-fluorophenyl)-3-(fluoromethyl)-6-methyl-3,6-dihydro-2H-1,4-thiazine 1,1-dioxide Step 2 was carried out in analogy to Intermediate 11, Step 3 to provide the racemic title compound as part of a mixture of 4 diastereomers (1.5 g, 42% yield over 2 steps). LC/MS (ESI$^+$) m/z=408.0 (M+H).

Step 3: tert-butyl N-[(3S,6R)-6-allyl-3-(5-bromo-2-fluoro-phenyl)-3-(fluoromethyl)-6-methyl-1,1-dioxo-2H-1,4-thiazin-5-yl]-N-tert-butoxycarbonyl-carbamate and tert-butyl N-[(3R,6S)-6-allyl-3-(5-bromo-2-fluoro-phenyl)-3-(fluoromethyl)-6-methyl-1,1-dioxo-2H-1,4-thiazin-5-yl]-N-tert-butoxycarbonyl-carbamate Step 3 was carried out in analogy to Intermediate 11, Step 4 to provide the racemic title compound as part of a mixture of 4 diastereomers (1.25 g, 56% yield). LC/MS (ESI$^+$) m/z=629.0 (M+Na).

Step 4: tert-butyl N-[(3S,6R)-3-(5-bromo-2-fluoro-phenyl)-3-(fluoromethyl)-6-methyl-1,1-dioxo-6-(2-oxoethyl)-2H-1,4-thiazin-5-yl]-N-tert-butoxycarbonyl-carbamate and tert-butyl N-[(3R,6S)-3-(5-bromo-2-fluoro-phenyl)-3-(fluoromethyl)-6-methyl-1,1-dioxo-6-(2-oxoethyl)-2H-1,4-thiazin-5-yl]-N-tert-butoxycarbonyl-carbamate Step 4 was carried out in analogy to Intermediate 12, Step 1 to provide the racemic title compound as part of a mixture of 4 diastereomers. (1.1 g, 88% yield). LC/MS (ESI$^+$) m/z=631.0 (M+Na).

Step 5: tert-butyl N-[(3S,6R)-3-(5-bromo-2-fluoro-phenyl)-3-(fluoromethyl)-6-(2-hydroxyethyl)-6-methyl-1,1-dioxo-2H-1,4-thiazin-5-yl]-N-tert-butoxycarbonyl-carbamate and tert-butyl N-[(3R,6S)-3-(5-bromo-2-fluoro-phenyl)-3-(fluoromethyl)-6-(2-hydroxyethyl)-6-methyl-1,1-dioxo-2H-1,4-thiazin-5-yl]-N-tert-butoxycarbonyl-carbamate Step 5 was carried out in analogy to Intermediate 12, Step 2 to provide the racemic title compound as part of a mixture of 4 diastereomers (1.05 g, 95% yield). LC/MS (ESI$^+$) m/z=633.0 (M+Na).

Step 6: tert-butyl N-[(3S,6R)-3-(5-bromo-2-fluoro-phenyl)-3-(fluoromethyl)-6-(2-iodoethyl)-6-methyl-1,1-dioxo-2H-1,4-thiazin-5-yl]-N-tert-butoxycarbonyl-carbamate and tert-butyl N-[(3R,6S)-3-(5-bromo-2-fluoro-phenyl)-3-(fluoromethyl)-6-(2-iodoethyl)-6-methyl-1,1-dioxo-2H-1,4-thiazin-5-yl]-N-tert-butoxycarbonyl-carbamate A RBF was charged with triphenylphosphine (0.901 g, 3.43 mmol), imidazole (0.468 g, 6.87 mmol) and 4.5 mL DCM, and the mixture was cooled to 0° C. Iodine (0.872 g, 3.43 mmol) was added. The mixture became yellow and then brown. After stirring for 5 min, a solution of tert-butyl N-[(3S,6R)-3-(5-bromo-2-fluoro-phenyl)-3-(fluoromethyl)-6-(2-hydroxyethyl)-6-methyl-1,1-dioxo-2H-1,4-thiazin-5-yl]-N-tert-butoxycarbonyl-carbamate and tert-butyl N-[(3R,6S)-3-

(5-bromo-2-fluoro-phenyl)-3-(fluoromethyl)-6-(2-hydroxyethyl)-6-methyl-1,1-dioxo-2H-1,4-thiazin-5-yl]-N-tert-butoxycarbonyl-carbamate (1.05 g, 1.717 mmol) in 4.5 mL DCM was added. The reaction was allowed to warm to RT and was stirred overnight. The mixture was concentrated and was purified by silica gel chromatography, using a gradient of 0-50% EtOAc/heptane. tert-butyl N-[(3S,6R)-3-(5-bromo-2-fluoro-phenyl)-3-(fluoromethyl)-6-(2-iodoethyl)-6-methyl-1,1-dioxo-2H-1,4-thiazin-5-yl]-N-tert-butoxycarbonyl-carbamate and tert-butyl N-[(3R,6S)-3-(5-bromo-2-fluoro-phenyl)-3-(fluoromethyl)-6-(2-iodoethyl)-6-methyl-1,1-dioxo-2H-1,4-thiazin-5-yl]-N-tert-butoxycarbonyl-carbamate (520 mg, 0.721 mmol, 42.0% yield) eluted second, and was isolated as a racemic mixture. LC/MS (ESI⁺) m/z=742.9 (M+Na).

Step 7: tert-butyl N-[(1S,2S,5R)-2-(5-bromo-2-fluoro-phenyl)-2-(fluoromethyl)-5-methyl-8,8-dioxo-8-thia-3-azabicyclo[3.2.1]oct-3-en-4-yl]-N-tert-butoxycarbonyl-carbamate and tert-butyl N-[(1R,2R,5S)-2-(5-bromo-2-fluoro-phenyl)-2-(fluoromethyl)-5-methyl-8,8-dioxo-8-thia-3-azabicyclo[3.2.1]oct-3-en-4-yl]-N-tert-butoxycarbonyl-carbamate A RBF was charged with tert-butyl N-[(3S,6R)-3-(5-bromo-2-fluoro-phenyl)-3-(fluoromethyl)-6-(2-iodoethyl)-6-methyl-1,1-dioxo-2H-1,4-thiazin-5-yl]-N-tert-butoxycarbonyl-carbamate and tert-butyl N-[(3R,6S)-3-(5-bromo-2-fluoro-phenyl)-3-(fluoromethyl)-6-(2-iodoethyl)-6-methyl-1,1-dioxo-2H-1,4-thiazin-5-yl]-N-tert-butoxycarbonyl-carbamate (520 mg, 0.721 mmol) and THF (3604 µl) and the solution was cooled to −78° C. under nitrogen. LHMDS (1 M, 1081 µl, 1.081 mmol) was added dropwise and the mixture was stirred at −78° C. for 20 min. The reaction was quenched with saturated aqueous NH₄Cl and allowed to warm to RT. Water and EtOAc were added and the layers were separated. The aqueous portion was extracted with additional EtOAc and the combined organics were dried over sodium sulfate, filtered and concentrated to provide the title compound as a mixture of enantiomers (428 mg, 100% yield). LC/MS (ESI⁺) m/z=615.0 (M+Na).

Step 8: tert-butyl N-[(1S,2S,5R)-2-(5-azido-2-fluoro-phenyl)-2-(fluoromethyl)-5-methyl-8,8-dioxo-8-thia-3-azabicyclo[3.2.1]oct-3-en-4-yl]-N-tert-butoxycarbonyl-carbamate and tert-butyl N-[(1R,2R,5S)-2-(5-azido-2-fluoro-phenyl)-2-(fluoromethyl)-5-methyl-8,8-dioxo-8-thia-3-azabicyclo[3.2.1]oct-3-en-4-yl]-N-tert-butoxycarbonyl-carbamate A vial was charged with tert-butyl N-[(1S,2S,5R)-2-(5-bromo-2-fluoro-phenyl)-2-(fluoromethyl)-5-methyl-8,8-dioxo-8-thia-3-azabicyclo[3.2.1]oct-3-en-4-yl]-N-tert-butoxycarbonyl-carbamate and tert-butyl N-[(1R,2R,5S)-2-(5-bromo-2-fluoro-phenyl)-2-(fluoromethyl)-5-methyl-8,8-dioxo-8-thia-3-azabicyclo[3.2.1]oct-3-en-4-yl]-N-tert-butoxycarbonyl-carbamate (387 mg, 0.652 mmol), CuI (8.84 µl, 0.261 mmol), sodium azide (183 µl, 5.22 mmol), (+)-sodium 1-ascorbate (51.7 mg, 0.261 mmol), trans-n,n'-dimethyl-1,2-cyclohexanediamine (82 µl, 0.522 mmol), EtOH (4658 µl), and water (1863 µl). The vial was purged with argon and capped, and the reaction was heated to 60° C. for 4.5 h. The mixture was poured into 10:1 saturated aqueous NH₄Cl:30% NH₄OH and was extracted twice with EtOAc. The combined organic extracts were dried over sodium sulfate, filtered and concentrated. The crude material was dissolved in THF (1629 µl) and water (1629 µl) in a RBF.

Trimethylphosphine (717 µl, 0.717 mmol) was added, and the reaction was stirred at RT for 15 min. Water and EtOAc were added, and the layers were separated. The organic portion was dried over sodium sulfate, filtered and concentrated to provide the title compound as a mixture of enantiomers (345 mg, 100% yield). LC/MS (ESI⁺) m/z=552.2 (M+Na).

Intermediate 49A and 49B

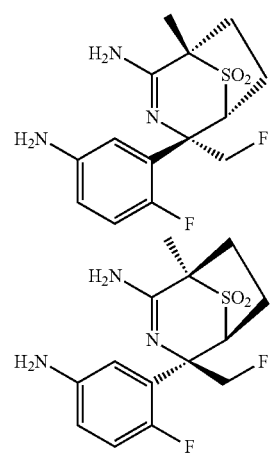

Synthesis of (1S,4S,5R)-2-amino-4-(5-amino-2-fluorophenyl)-4-(fluoromethyl)-1-methyl-8-thia-3-azabicyclo[3.2.1]oct-2-ene 8,8-dioxide and (1R,4R,5S)-2-amino-4-(5-amino-2-fluorophenyl)-4-(fluoromethyl)-1-methyl-8-thia-3-azabicyclo[3.2.1]oct-2-ene 8,8-dioxide Steps 1-6: tert-butyl N-[(3S,6S)-3-(5-bromo-2-fluoro-phenyl)-3-(fluoromethyl)-6-(2-iodoethyl)-6-methyl-1,1-dioxo-2H-1,4-thiazin-5-yl]-N-tert-butoxycarbonyl-carbamate and tert-butyl N-[(3R,6R)-3-(5-bromo-2-fluoro-phenyl)-3-(fluoromethyl)-6-(2-iodoethyl)-6-methyl-1,1-dioxo-2H-1,4-thiazin-5-yl]-N-tert-butoxycarbonyl-carbamate Steps 1-6 were carried out as detailed for Intermediate 48, steps 1-6. In the purification of Step 6, tert-butyl N-[(3S,6S)-3-(5-bromo-2-fluoro-phenyl)-3-(fluoromethyl)-6-(2-iodoethyl)-6-methyl-1,1-dioxo-2H-1,4-thiazin-5-yl]-N-tert-butoxycarbonyl-carbamate and tert-butyl N-[(3R,6R)-3-(5-bromo-2-fluoro-phenyl)-3-(fluoromethyl)-6-(2-iodoethyl)-6-methyl-1,1-dioxo-2H-1,4-thiazin-5-yl]-N-tert-butoxycarbonyl-carbamate (598 mg, 0.829 mmol, 48.3% yield) eluted first, and was isolated as a racemic mixture. LC/MS (ESI⁺) m/z=742.9 (M+Na).

Step 7: tert-butyl N-[(1R,2S,5S)-2-(5-bromo-2-fluoro-phenyl)-2-(fluoromethyl)-5-methyl-8,8-dioxo-8-thia-3-azabicyclo[3.2.1]oct-3-en-4-yl]-N-tert-butoxycarbonyl-carbamate and tert-butyl N-[(1S,2R,5R)-2-(5-bromo-2-fluoro-phenyl)-2-(fluoromethyl)-5-methyl-8,8-dioxo-8-thia-3-azabicyclo[3.2.1]oct-3-en-4-yl]-N-tert-butoxycarbonyl-carbamate Step 7 was carried out in analogy to Intermediate 48, Step 7 to provide the title compound as a racemic mixture (468 mg, 99% yield). LC/MS (ESI⁺) m/z=615.0 (M+Na).

Step 8: tert-butyl N-tert-butoxycarbonyl-N-[(1R,2S, 5S)-2-(fluoromethyl)-2-(2-fluorophenyl)-5-methyl-8, 8-dioxo-8-thia-3-azabicyclo[3.2.1]oct-3-en-4-yl] carbamate And tert-butyl N-tert-butoxycarbonyl-N-[(1S,2R,5R)-2-(fluoromethyl)-2-(2-fluorophenyl)-5-methyl-8,8-dioxo-8-thia-3-azabicyclo[3.2.1]oct-3-en-4-yl]carbamate A RBF was flushed with nitrogen and charged with wet Pd/C (166 mg, 0.078 mmol), tert-butyl N-[(1R,2S,5S)-2-(5-bromo-2-fluoro-phenyl)-2-(fluoromethyl)-5-methyl-8,8-dioxo-8-thia-3-azabicyclo[3.2.1]oct-3-en-4-yl]-N-tert-butoxycarbonyl-carbamate and tert-butyl N-[(1S,2R,5R)-2-(5-bromo-2-fluoro-phenyl)-2-(fluoromethyl)-5-methyl-8,8-dioxo-8-thia-3-azabicyclo[3.2.1]oct-3-en-4-yl]-N-tert-butoxycarbonyl-carbamate (462 mg, 0.778 mmol), EtOAc (3892 µl) and MeOH (3892 µl). The mixture was flushed with nitrogen, evacuated, and filled with hydrogen. The reaction was stirred at RT under hydrogen atmosphere overnight. The mixture was filtered through Celite and washed with EtOAc. The filtrate was concentrated to provide the title compound as a racemic mixture (400 mg, 99% yield). LC/MS (ESI$^+$) m/z=537.1 (M+Na).

Step 9: (1S,4S,5R)-2-amino-4-(2-fluoro-5-nitrophenyl)-4-(fluoromethyl)-1-methyl-8-thia-3-azabicyclo [3.2.1]oct-2-ene 8,8-dioxide and (1R,4R,5S)-2-amino-4-(2-fluoro-5-nitrophenyl)-4-(fluoromethyl)-1-methyl-8-thia-3-azabicyclo[3.2.1]oct-2-ene 8,8-dioxide A RBF was charged with tert-butyl N-tert-butoxycarbonyl-N-[(1R,2S,5S)-2-(fluoromethyl)-2-(2-fluorophenyl)-5-methyl-8,8-dioxo-8-thia-3-azabicyclo[3.2.1]oct-3-en-4-yl]carbamate and tert-butyl N-tert-butoxycarbonyl-N-[(1S,2R,5R)-2-(fluoromethyl)-2-(2-fluorophenyl)-5-methyl-8,8-dioxo-8-thia-3-azabicyclo[3.2.1]oct-3-en-4-yl]carbamate (400 mg, 0.777 mmol) and potassium nitrate (39.1 µl, 0.816 mmol). Sulfuric acid (1243 µl, 23.32 mmol) was cooled to 0° C. and was added, and the reaction was stirred at 0° C. for 10 min. The reaction was allowed to warm to RT and was stirred for 3 h. The mixture was cooled to 0° C. and was brought to pH 8 with saturated aqueous NaHCO$_3$. Water and EtOAc were added and the layers were separated. The aqueous portion was extracted with EtOAc and the combined organic portions were dried over sodium sulfate, filtered and concentrated to provide the title compound as a mixture of enantiomers (275 mg, 98% yield). LC/MS (ESI$^+$) m/z=360.0 (M+H).

Step 10: (1S,4S,5R)-2-amino-4-(5-amino-2-fluorophenyl)-4-(fluoromethyl)-1-methyl-8-thia-3-azabicyclo[3.2.1]oct-2-ene 8,8-dioxide and (1R,4R,5S)-2-amino-4-(5-amino-2-fluorophenyl)-4-(fluoromethyl)-1-methyl-8-thia-3-azabicyclo[3.2.1] oct-2-ene 8,8-dioxide A RBF was purged with nitrogen and charged with Pd/C (wet) (118 mg, 0.056 mmol), (1S,4S,5R)-2-amino-4-(2-fluoro-5-nitrophenyl)-4-(fluoromethyl)-1-methyl-8-thia-3-azabicyclo[3.2.1]oct-2-ene 8,8-dioxide and (1R,4R,5S)-2-amino-4-(5-amino-2-fluorophenyl)-4-(fluoromethyl)-1-methyl-8-thia-3-azabicyclo[3.2.1]oct-2-ene 8,8-dioxide (100 mg, 0.278 mmol), EtOAc (696 µl) and MeOH (696 µl). The flask was evacuated and filled with hydrogen and the reaction was stirred at RT under hydrogen atmosphere for 2 h. The mixture was filtered through Celite and washed with EtOAc. The filtrate was concentrated and purified by silica gel chromatography, using a gradient of 0-70% 75/25/2 EtOAc/EtOH/NH$_4$OH in heptane to provide the title compound as a mixture of enantiomers (90 mg, 99% yield). LC/MS (ESI$^+$) m/z=330.0 (M+H).

Intermediate 50

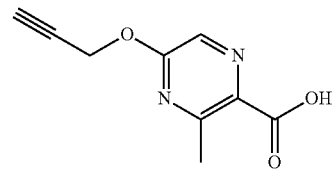

Synthesis of 3-Methyl-5-(prop-2-yn-1-yloxy)pyrazine-2-carboxylic acid

Step 1. Methyl 5-chloro-3-methylpyrazine-2-carboxylate

A solution of methyl 3-methylpyrazine-2-carboxylate (9.1 g, 59.8 mmol) in DCM (100 mL) was cooled to 0° C. was added urea hydrogen peroxide adduct (7.8 g, 83.0 mmol), followed by dropwise addition of trifluoroacetic acid anhydride (10.8 mL, 78.0 mmol). The resulting mixture was stirred at 0° C. for 1 h, and at RT for 18 h, during which LCMS indicated a mixture of two peaks corresponding to MS m/z=169.0 [M+H]$^+$. The reaction was diluted with DCM and quenched with saturated Na$_2$SO$_3$ solution; the aqueous layer was back-extracted with DCM (2×). The combined organic extracts were dried (MgSO$_4$), filtered and concentrated in vacuo. ISCO purification (20-80% EtOAc/hexanes) afforded a mixture of two regioisomers, containing 3-(methoxycarbonyl)-2-methylpyrazine 1-oxide and 2-(methoxycarbonyl)-3-methylpyrazine 1-oxide (5.2 g, 30.9 mmol, 51.7% yield). The mixture of regioisomers was taken to next step without further purification. MS m/z=169.0 [M+H]$^+$. A solution of the mixture of 3-(methoxycarbonyl)-2-methylpyrazine 1-oxide and 2-(methoxycarbonyl)-3-methylpyrazine 1-oxide (5.1 g, 15.2 mmol) in toluene (50 mL) was cooled to 0° C. and phosphorus oxychloride (2.8 mL, 30.3 mmol) was added under nitrogen followed by DMF (0.12 mL, 1.52 mmol). The reaction mixture was stirred at RT for 4 h, and heated to 65° C. for 18 h, cooled to RT, diluted with EtOAc and washed with saturated NaHCO$_3$ solution. The aqueous layer was back-extracted with EtOAc (2×). The combined organic extracts were dried (MgSO$_4$), filtered and concentrated in vacuo. ISCO purification (0-50% EtOAc/hexanes) with care afforded both isomers: methyl 5-chloro-3-methylpyrazine-2-carboxylate (0.68 g) (minor product) denoted by peak 1 and methyl 6-chloro-3-methylpyrazine-2-carboxylate (1.50 g) (major product) denoted by peak 2. MS m/z=187.0 [M+H]$^+$. Peak 1: $^1$H NMR (300 MHz, DMSO-d$_6$) δ 8.73 (s, 1H), 3.91 (s, 3H), 2.71 (s, 3H). Peak 2: $^1$H NMR (300 MHz, DMSO-d$_6$) δ 8.89 (s, 1H), 3.91 (s, 3H), 2.71 (s, 3H).

Step 2. Methyl 3-methyl-5-(prop-2-yn-1-yloxy)pyrazine-2-carboxylate

To a solution of methyl 5-chloro-3-methylpyrazine-2-carboxylate (750 mg, 4.02 mmol) and propargyl alcohol (356 µL, 6.03 mmol) in 3 mL of DMF was added potassium carbonate (833 mg, 6.03 mmol). After 1 h, about 70% desired conversion was detected by LCMS. Additional propargyl alcohol (356 µL, 6.03 mmol) was added and the reaction was stirred overnight. The reaction was directly loaded to flash column (hexanes/EtOAc=10:1 to 5:1 to 4:1) to give methyl 3-methyl-5-(prop-2-yn-1-yloxy)pyrazine-2-carboxylate (800 mg, 3.88 mmol, 97% yield) as a white gum. MS m/z=207.0 [M+H]+. $^1$H NMR (300 MHz, CHLOROFORM-d) δ 8.18 (s, 1H), 5.06 (d, J=2.48 Hz, 2H), 3.97 (s, 3H), 2.80 (s, 3H), 2.52 (t, J=2.41 Hz, 1H).

Step 3 3-Methyl-5-(prop-2-yn-1-yloxy)pyrazine-2-carboxylic acid

A solution of methyl 3-methyl-5-(prop-2-yn-1-yloxy)pyrazine-2-carboxylate (800 mg, 3.88 mmol) in THF (10 mL) was treated with lithium hydroxide hydrate (488 mg, 11.64 mmol) in 10 mL of water and the mixture was stirred at RT for 3 h. The mixture was treated with 5 M aqueous HCl (2.4 mL), and extracted with DCM (3×50 mL). The combined organic extracts were dried ($Na_2SO_4$) and concentrated to give 3-methyl-5-(prop-2-yn-1-yloxy)pyrazine-2-carboxylic acid (380 mg, 1.98 mmol, 51% yield) as a white solid. MS m/z=193.0 [M+H]+. $^1$H NMR (300 MHz, CHLOROFORM-d) δ 8.05 (s, 1H), 5.09 (d, J=2.48 Hz, 2H), 2.92 (s, 3H), 2.54 (t, J=2.41 Hz, 1H).

Scheme for Intermediate 51

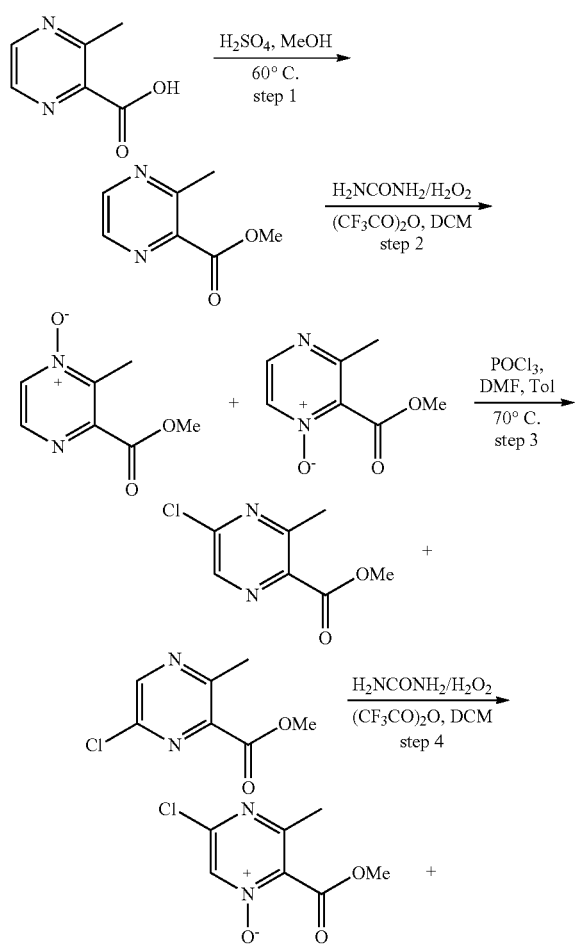

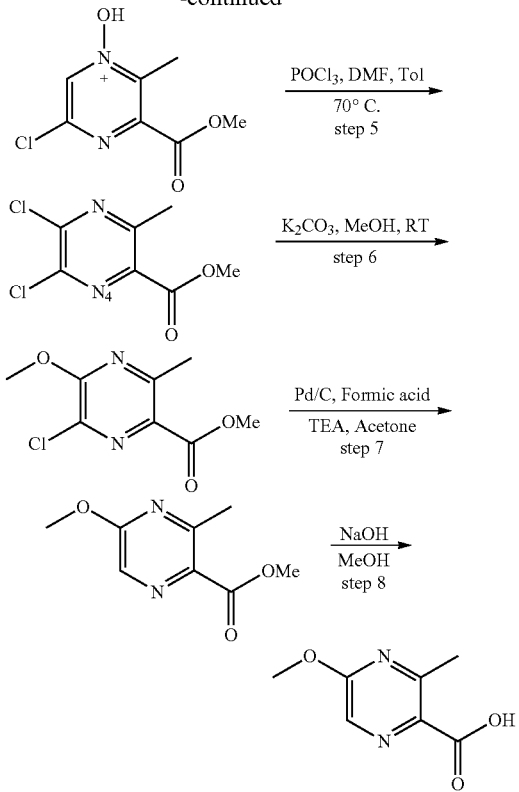

Intermediate 51

Synthesis of 5-methoxy-3-methylpyrazine-2-carboxylic acid

Step 1 3-Methylpyrazine-2-carboxylate

A solution of 3-methylpyrazine-2-carboxylic acid (10 g, 72.4 mmol) in MeOH (80 mL) and sulfuric acid, 95% (5 mL, 90 mmol) was heated to 60° C. for 4 hours. The solution was concentrated to remove MeOH, the residue dissolved in 50 mL of water and neutralized with 10% aq $Na_2CO_3$ solution to pH 12. The resulting solution was extracted with ethyl acetate (2×). The combine organic was dried and concentrated to give crude product methyl 3-methylpyrazine-2-carboxylate (9.1 g, 59.8 mmol, 83% yield). It was used for next step without further purification. $^1$H NMR (300 MHz, CHLOROFORM-d) δ ppm 8.63 (1 H, s), 8.53 (1 H, s), 4.02 (3 H, s), 2.87 (3 H, s). MS m/z=153 [M+H]+. Calculated for $C_7H_8N_2O_2$: 152.0.

Step 2 3-(Methoxycarbonyl)-2-methylpyrazine 1-oxide and 2-(methoxycarbonyl)-3-methylpyrazine 1-oxide A solution of methyl 3-methylpyrazine-2-carboxylate (9.1 g, 59.8 mmol) in $CH_2Cl_2$ (100 mL) was cooled to 0° C. was added urea hydrogen peroxide adduct, 97% (7.81 g, 83 mmol), followed by dropwise addition of trifluoroacetic acid anhydride (10.81 ml, 78 mmol). The resulting mixture was stirred at 0° C. for 1 h, and at RT for 18 h, during which LCMS indicated a mixture of the desired product and the side product, 2-(methoxycarbonyl)-3-methylpyrazine 1,4-dioxide. The reaction was diluted with $CH_2Cl_2$ and quenched with saturated $Na_2SO_3$ solution; the aqueous layer was back-extracted with CH$_2$Cl$_2$ (2×). The combined organic extracts were dried (MgSO$_4$), filtered and concentrated in vacuo. ISCO purification (20% to 80% EtOAc/Hexanes) afforded mixture of two regioisomers 3-(methoxycarbonyl)-2-methylpyrazine 1-oxide and 2-(methoxycarbonyl)-3-methylpyrazine 1-oxide (5.2 g, 30.9 mmol, 51.7% yield). The mixture of regioisomers was taken to next step without further purification. MS m/z=169.0 [M+H]$^+$. Calculated for C$_7$H$_8$N$_2$O$_3$: 168.0.

Step 3: Methyl 5-chloro-3-methylpyrazine-2-carboxylate (and methyl 6-chloro-3-methylpyrazine-2-carboxylate A solution of mixture of 3-(methoxycarbonyl)-2-methylpyrazine 1-oxide and 2-(methoxycarbonyl)-3-methylpyrazine 1-oxide (5.1 g, 15.17 mmol) in toluene (50 mL) was cooled to 0° C. and phosphorus oxychloride (2.78 ml, 30.3 mmol) was added under nitrogen followed by DMF (0.117 ml, 1.517 mmol). The reaction mixture was stirred at RT for 4 h, and heated to 65° C. for 18 h, cooled to RT, diluted with EtOAc and washed with saturated NaHCO$_3$ solution. The aqueous layer was back-extracted with EtOAc (2×). The combined organic extracts were dried (MgSO$_4$), filtered and concentrated in vacuo. ISCO purification (0% to 50% EtOAc/Hexanes) with care afforded both isomers methyl 5-chloro-3-methylpyrazine-2-carboxylate (0.68 g) as the desired and minor product denoted by peak 1 and methyl 6-chloro-3-methylpyrazine-2-carboxylate (1.5 g), as the undesired and denoted by peak 2. MS m/z=187.0 [M+H]. Calculated for C$_7$H$_7$ClN$_2$O$_2$: 186.0. Peak 1: $^1$H NMR (300 MHz, DMSO-d$_6$) δ 8.73 (s, 1H), 3.91 (s, 3H), 2.71 (s, 3H). Peak 2: $^1$H NMR (300 MHz, DMSO-d$_6$) δ 8.89 (s, 1H), 3.91 (s, 3H), 2.71 (s, 3H)

Step 4: 5-Chloro-2-(methoxycarbonyl)-3-methylpyrazine 1-oxide and 5-chloro-3-(methoxycarbonyl)-2-methylpyrazine 1-oxide To a solution of mixture of methyl 5-chloro-3-methylpyrazine-2-carboxylate and methyl 6-chloro-3-methylpyrazine-2-carboxylate (8.6 g, 46.1 mmol) and hydrogen peroxide urea adduct (8.1 g, 86 mmol) in DCM (100 mL) was added 2,2,2-trifluoroacetic anhydride (10.89 ml, 78 mmol) dropwise. The resulting mixture was stirred at RT for 2 h, during which LCMS indicated complete transformation to the desired products. The reaction was diluted with CH$_2$Cl$_2$ and quenched with water. The aqueous layer was back-extracted with CH$_2$Cl$_2$ (2×). The combined organic extracts were dried (MgSO$_4$), filtered, and concentrated in vacuo to give crude products 5-chloro-2-(methoxycarbonyl)-3-methylpyrazine 1-oxide and 5-chloro-3-(methoxycarbonyl)-2-methylpyrazine 1-oxide (8.83 g, 43.6 mmol, 95% yield). MS m/z=203.0 [M+H]. Calculated for C$_7$H$_7$ClN$_2$O$_3$: 202.0. The mixture of the crude products were used without further purification.

Step 5 methyl 5,6-dichloro-3-methylpyrazine-2-carboxylate

A solution of mixture of 5-chloro-2-(methoxycarbonyl)-3-methylpyrazine 1-oxide and 5-chloro-3-(methoxycarbonyl)-2-methylpyrazine 1-oxide (8.83 g, 43.6 mmol) in toluene (100 mL) was cooled to 0° C. and phosphorus oxychloride (10 ml, 109 mmol) was added under nitrogen followed by DMF (1.0 mL, 12.91 mmol). The reaction mixture was stirred at RT for 1 h, and at 85° C. for 18 h, cooled to RT and concentrated. The residue was diluted with EtOAc and washed with saturated NaHCO$_3$ solution (CAUTION—generation of CO$_2$ gas, work up reaction batches as a precaution). The combined organic extracts were dried (MgSO$_4$), filtered and concentrated in vacuo. The residue was purified by ISCO using silica eluting with 0% to 10% EtOAc/Hexanes to give methyl 5,6-dichloro-3-methylpyrazine-2-carboxylate (6.51 g, 29.5 mmol, 67.6% yield). $^1$H NMR (300 MHz, CHLOROFORM-d) δ ppm 4.00 (3 H, s), 2.83 (3 H, s). MS m/z=221.0 [M+H]$^+$. Calculated for C$_7$H$_6$Cl$_2$N$_2$O$_2$: 219.9.

Step 6. Methyl 6-chloro-5-methoxy-3-methylpyrazine-2-carboxylate

To a solution of methyl 5,6-dichloro-3-methylpyrazine-2-carboxylate (6.17 g, 27.9 mmol) in anhydrous MeOH (100 ml, 2469 mmol) at 0° C. was added slowly potassium carbonate (4.30 g, 31.1 mmol). The suspension was stirred at 0° C. for 30 min and warmed to RT for 1 h. The reaction was filtered and filtrate concentrated to give crude product methyl 6-chloro-5-methoxy-3-methylpyrazine-2-carboxylate (6.2 g, 28.6 mmol, 103% yield). It was used in the next step without further purification. $^1$H NMR (300 MHz, CHLOROFORM-d) δ ppm 4.11 (3 H, s), 3.96 (3 H, s), 2.78 (3 H, s). MS m/z=217.0 [M+H]$^+$. Calculated for C$_8$H$_9$ClN$_2$O$_3$: 216.0

Step 7. Methyl 5-methoxy-3-methylpyrazine-2-carboxylate

Acetone (200 mL) was added slowly and carefully to a mixture of methyl 6-chloro-5-methoxy-3-methylpyrazine-2-carboxylate (6.5 g, 30.0 mmol) and 10% Pd/C (3.19 g, 3.00 mmol) in a 500 mL flask under nitrogen. The flask was cooled to 0° C. and triethylamine (30 mL, 216 mmol) was added followed by formic acid, 96% (5.66 mL, 150 mmol) dropwise. The suspension was warmed to RT with stirring and then heated at 40° C. for 1 h. LCMS showed complete conversion. The reaction mixture was concentrated, diluted with saturated sodium hydrogenocarbonate solution and extracted with dichloromethane (2×). The organic layer was dried and concentrated. The crude product was purified by ISCO column chromatography using 0-20% EtOAc in DCM to give methyl 5-methoxy-3-methylpyrazine-2-carboxylate (5.2 g, 28.5 mmol, 95% yield). $^1$H NMR (300 MHz, CHLOROFORM-d) δ ppm 8.11 (1 H, s), 4.03 (3 H, s), 3.97 (3 H, s), 2.80 (3 H, s). MS m/z=183.0 [M+H]$^+$. Calculated for C$_8$H$_{10}$N$_2$O$_3$: 182.0

Step 8. 5-Methoxy-3-methylpyrazine-2-carboxylic acid

To a solution of methyl 5-methoxy-3-methylpyrazine-2-carboxylate (5.1 g, 28.0 mmol) in MeOH (50 mL) was added sodium hydroxide 1N solution (30.8 mL, 30.8 mmol). The reaction was heated to 40° C. for 2 h. LCMS showed complete conversion to product. The reaction mixture was concentrated, diluted with water and the pH was adjusted to between 3-4 with 1N HCl solution. The solid that precipitated was filtered and dried. The acidic filtrate was extracted with EtOAc (3×) and later DCM (2×) while maintaining the pH between 3-4 by addition of 1N HCl solution as necessary. The combined organic was dried with Na$_2$SO$_4$, and concentrated in vacuo to give another batch of solid. The solids were combined and dried to give product 5-methoxy-3-methylpyrazine-2-carboxylic acid (4.5 g, 26.8 mmol, 96% yield). $^1$H NMR (300 MHz, DMSO-d$_6$) δ 13.00 (br. s., 1H), 8.19 (s, 1H), 3.96 (s, 3H), 2.68 (s, 3H). MS m/z=169.0 [M+H]⁺. Calculated for $C_7H_8N_2O_3$: 168.0.

Intermediate 52

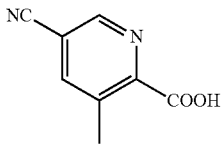

Synthesis of 5-Cyano-3-methylpicolinic acid

To a solution of tert-butyl 5-cyano-3-methylpicolinate (synthesized according to procedure described in WO2012095521; 4.18 g, 19.15 mmol) in DCM (96 mL) was added TFA (Aldrich, 148 mL, 1915 mmol). The reaction mixture was stirred at RT for 2 h. The reaction mixture was concentrated under reduced pressure and the residue was triturated with EtOAc. The yellow slurry was concentrated under reduced pressure. The residue was triturated with 30 mL of methyl tert-butyl ether (30 mL) and of hexanes (50 mL) to yield 5-cyano-3-methylpicolinic acid (2.91 g, 17.95 mmol, 94% yield) as yellow solid. MS m/z=163.2 [M+H]⁺.

Intermediate 53

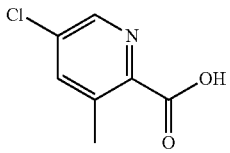

Synthesis of 5-Chloro-3-methylpicolinic acid

Step 1. 5-Chloro-3-methylpicolinonitrile

A mixture of 2-bromo-5-chloro-3-methylpyridine (45 g, 218 mmol), zinc cyanide (8.30 mL, 131 mmol), tris(dibenzylideneacetone)dipalladium (0) (4.99 g, 5.45 mmol), and 1,1'-bis(diphenylphosphino)ferrocene (6.04 g, 10.90 mmol) in dimethylacetamide (40 mL) was heated to 110° C. for 4 h. The reaction mixture was cooled to RT, diluted with water and extracted with ethyl acetate. The organic phase obtained was concentrated under reduced pressure and residue purified by chromatography on silica gel using ISCO eluting with 0-60% EtOAc/hexanes to afford 5-chloro-3-methylpicolinonitrile (25.4 g, 166 mmol, 76% yield). LC/MS (ESI⁺) m/z=153.1 (M+H).

Step 2. 5-Chloro-3-methylpicolinic acid

To a solution of 5-chloro-3-methylpicolinonitrile (24.0 g, 157 mmol) in EtOH (100 mL) was added NaOH (110 mL of 5 N solution, 550 mmol). The resulting mixture was refluxed at 90° C. for 18 h. After cooling to RT, the reaction mixture was concentrated. The residue was diluted with water and the pH of the solution was adjusted to 4 by addition of 5 N HCl. The solid that precipitated was filtered and set aside. The filtrate was extracted with EtOAc (2×). The aqueous layer was again acidified with 5 N HCl to pH 4 and extracted with EtOAc (2×). The EtOAc extracts were combined, dried, and concentrated. The solid obtained from all the workup steps were combined and dried in a high vac oven at 40° C. for 12 h to give 5-chloro-3-methylpicolinic acid (268) (24.1 g, 140 mmol, 89% yield). LC/MS (ESI⁺) m/z=172.0 (M+H)⁺. ¹H NMR (400 MHz, CHLOROFORM-d) δ ppm 11.29 (br. s., 1 H), 8.41 (d, J=1.76 Hz, 1 H), 7.73 (d, J=1.76 Hz, 1 H), 2.75 (s, 3 H).

Intermediate 54

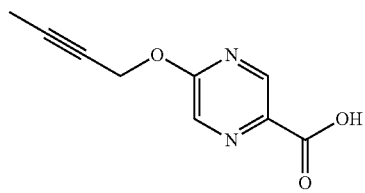

The titled compound, 5-(but-2-yn-1-yloxy)pyrazine-2-carboxylic acid, was synthesized as described in J. Med. Chem. 2013, 56, 3980.

General Methods

In addition to the general amidation procedures (Method A and Method B) described above to couple the aniline core intermediates R to carboxylic acid intermediates L, described below are 2 general N-arylation procedures (Method C and Method D) that may be used to couple the aniline core intermediates R to heterocyclic intermediates L.

Method C: Sulfuric Acid and Deprotection Procedure

To a solution of intermediates L and R (1 equivalent each) in 2-propanol is added concentrated sulfuric acid (1 equivalent). The reaction is stirred for 20 minutes at 100° C. After 30 minutes, the reaction mixture is diluted with DCM, washed with saturated aqueous sodium bicarbonate, and concentrated.

The residue is redissolved in DCM, and TFA (up to 10 equivalents) is added. The reaction is stirred at RT for 1 hour, diluted with DCM, and washed with saturated aqueous sodium bicarbonate and brine, and concentrated. The crude product is purified by silica-gel chromatography to provide the title compound.

Method D: p-Toluenesulfonic Acid Procedure

To a solution of Intermediates L and R (1 equivalent each) in 2-propanol was added p-toluenesulfonic acid (3 equivalents), and the mixture was stirred at 85° C. for 5 hours. Saturated aqueous sodium bicarbonate and ethyl acetate were added to the reaction and the layers were separated. The organic portion was dried over anhydrous sodium sulfate, filtered and concentrated. The crude product was purified by silica-gel column chromatography to provide the title compound.

155

Additional methods used to exemplary prepare compounds of the invention.

Example 38

Method E

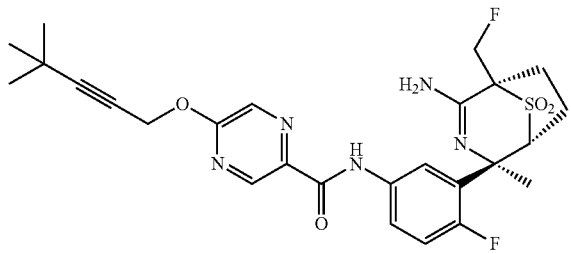 [SMILES: CC(C)(C)C#CCOc1cnc(C(=O)Nc2ccc(F)c([C@@]3(C)N=C(N)[C@]4(CF)CC[C@H]3S4(=O)=O)c2)cn1]

Synthesis of N-(3-((1S,2R,5R)-4-Amino-5-(fluoromethyl)-2-methyl-8,8-dioxido-8-thia-3-azabicyclo[3.2.1]oct-3-en-2-yl)-4-fluorophenyl)-5-((4,4-dimethylpent-2-yn-1-yl)oxy)pyrazine-2-carboxamide (1R,4R,5S)-2-Amino-4-(5-amino-2-fluorophenyl)-1-(fluoromethyl)-4-methyl-8-thia-3-azabicyclo[3.2.1]oct-2-ene 8,8-dioxide (0.100 g, 0.304 mmol) and 5-((4,4-dimethylpent-2-yn-1-yl)oxy)pyrazine-2-carboxylic acid (0.078 g, 0.334 mmol) were dissolved in dry dimethylformamide (1 mL) under nitrogen and cooled in an ice bath. 1-Propanephosphonic acid cyclic anhydride (Aldrich, 0.75 ml, 1.260 mmol) was added and the reaction allowed to stir at RT. After 30 minutes water (50 mL), saturated sodium bicarbonate (50 mL) and ethyl acetate (100 mL) were added. The phases were mixed and separated. The organic was dried with magnesium sulfate and evaporated to dryness under reduced pressure. Purification using silica chromatography (0-5% methanol in DCM gradient) gave N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-((4,4-dimethylpent-2-yn-1-yl)oxy)pyrazine-2-carboxamide (0.035 g, 0.064 mmol, 21.13% yield) as an off white solid. 1H NMR (400 MHz, CHLOROFORM-d) δ ppm 1.21-1.30 (m, 9 H) 1.59-1.70 (m, 1 H) 1.92 (s, 3 H) 1.97-2.07 (m, 3 H) 2.08-2.28 (m, 2 H) 3.86 (d, J=5.28 Hz, 1 H) 4.87-5.09 (m, 4 H) 5.21 (dd, J=46.95, 10.37 Hz, 2 H) 7.09 (dd, J=11.44, 8.90 Hz, 1 H) 7.76 (dd, J=6.75, 2.64 Hz, 1 H) 7.90 (dt, J=8.46, 3.59 Hz, 1 H) 8.97 (s, 1 H) 9.52 (s, 1 H). LC/MS (ESI+) m/z=546.0 (M+H).

Example 39

Method F

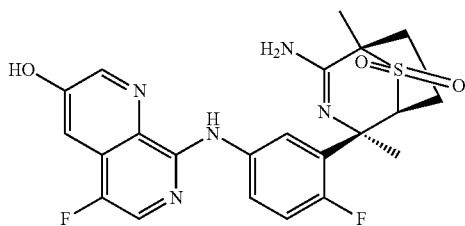 [SMILES: C[C@]1(c2cc(Nc3ncc(F)c4cc(O)cnc34)ccc2F)N=C(N)[C@@]2(C)CC[C@@H]1S2(=O)=O]

156

Synthesis of (1R,4R,5S)-2-amino-4-(2-fluoro-5-((5-fluoro-3-hydroxy-1,7-naphthyridin-8-yl)amino)phenyl)-1,4-dimethyl-8-thia-3-azabicyclo[3.2.1]oct-2-ene 8,8-dioxide A pressure-resistant vessel was charged with (1R,4R,5S)-2-amino-4-(2-fluoro-5-((5-fluoro-3-methoxy-1,7-naphthyridin-8-yl)amino)phenyl)-1,4-dimethyl-8-thia-3-azabicyclo[3.2.1]oct-2-ene 8,8-dioxide (0.2 g, 0.410 mmol) and DCE (1.03 mL). To this solution was added boron tribromide (0.40 mL, 4.10 mmol) dropwise via syringe. The resulting heterogeneous mixture was placed in an 85° C. preheated oil bath and stirred overnight. The reaction was cooled to RT and slowly added to ice cold methanol. The resulting yellow solution was concentrated down and the crude material was eluted through a reverse phase column using 10-75% 1% TFA in MeCN/1% TFA in water, extracted into ethyl acetate, washed once with sodium carbonate, once with water, dried with sodium sulfate, filtered through a fritted funnel, and concentrated to yield (1R,4R,5S)-2-amino-4-(2-fluoro-5-((5-fluoro-3-hydroxy-1,7-naphthyridin-8-yl)amino)phenyl)-1,4-dimethyl-8-thia-3-azabicyclo[3.2.1]oct-2-ene 8,8-dioxide as a light yellow solid. m/z (ESI) 474.0 (M+H)+.

Examples 114, 118 and 120

Racemic intermediates 48A/48B were carried forward to final compounds by the methods referred to in Table 2, and the final compounds were purified by chiral SFC chromatography using a Chiralpak AD-H column, 25% methanol with 0.2% diethylamine, to provide single enantiomeric exemplary compounds:

Example 113—Peak 1—(ee>99%), Example 114—Peak 2—(ee>99%);

Example 117—Peak 1—(ee>99%), Example 118—Peak 2—(ee>99%); and

Example 119—Peak 1—(ee>99%), Example 120—Peak 2—(ee>99%).

Examples 115 and 116

Similarly, racemic intermediates 49A/49B were carried forward to final compounds, and the final compounds were separated by chiral SFC chromatography using a Chiralpak AD-H column, 25% methanol with 0.2% diethylamine, to provide: Example 116—Peak 1—(ee>99%) and, Example 115—Peak 2—(ee>99%).

The following compounds in Table 2 are examples 38-148 of compounds of Formulas I, II and III, and sub-formulas thereof, provided by the present invention. The methods used to prepare the exemplary compounds, including intermediates L and R that were used to prepare the compound example, are included in Table 2. Table 2 further includes the mass spec and NMR for each compound example where available.

TABLE 2

| Example No | Synthetic Method | Intermediate L | Intermediate R | Mass - Observed [M + H]+ | NMR |
|---|---|---|---|---|---|
| 40 | D | synthesized analogous to 18 | 39 | 484 | 1H MNR (400 MHz, CHLOROFORM-d) δ ppm 1.60 (m, 1 H) 1.92 (s, 3 H) 2.04-2.22 (m, 3H) 3.82 (m, 1 H) 4.88 (dd, J = 46.37, 10.76 Hz, 1 H) 5.10 (dd, J = 47.4, 10.76 Hz, 1 H) 7.10 (dd, J = 11.34, 8.80 Hz, 1 H) 7.68 (dd, J = 6.75, 2.84 Hz, 1 H) 8.11 (m, 1 H) 8.46 (d, J = 1.76 Hz, 1 H) 8.72 (s, 1 H) 8.94 (d, J = 1.76 Hz, 1 H). |
| 41 | D | 17 | 39 | 488.9 | 1H NMR (400 MHz, CHLOROFORM-d) δ ppm 1.65-1.83 (m, 1 H) 1.95 (s, 3 H) 2.02-2.27 (m, 3 H) 3.88 (m, 1 H) 4.13 (s, 3 H) 4.93 (dd, J = 46.55, 10.37 Hz, 1 H) 5.17 (dd, J = 47.54, 10.37 Hz, 1 H) 7.05 (d, J = 5.87 Hz 2 H) 7.10 (dd, J = 11.54, 9.00 Hz, 1 H) 7.70 (dd, J = 6.85, 2.74 Hz, 1 H) 8.18-8.25 (m, 1 H) 8.22 (d, J = 5.87 Hz, 1 H) 8.29 (s, 1 H) 8.61 (s, 1 H). |
| 42 | A | commercial | 39 | 479 | 1H NMR (400 MHz, CHLOROFORM-d) a ppm 1.65 (m, 1 H) 1.92 (s, 3 H) 1.96-2.25 (m, 3 H) 2.76 (s, 3 H) 3.86 (m, 1 H) 3.90 (s, 3 H) 4.91 (dd, J = 46.56, 10.37 Hz, 1 H) 5.14 (dd, J = 47.15, 10.56 Hz, 1 H) 7.02-7.10 (m, 2 H) 7.60 (dd, J = 6.85, 2.54 Hz, 1 H) 7.94-8.01 (m, 1 H) 8.04 (d, J = 2.54 Hz, 1 H) 10.08 (s, 1H). |
| 43 | A | commercial | 39 | 482.9 | $^1$H NMR (400 MHz, CHLOROFORM-d) δ ppm 1.60-1.70 (m, 1 H) 1.92 (s, 3 H) 1.96-2.06 (m, 1 H) 2.09-2.26 (m, 2 H) 3.85 (d, J = 4.69 Hz, 1 H) 3.93 (s, 3 H) 4.96 (dd, J = 46.75, 10.56 Hz, 1 H) 5.19 (dd, J = 47.14, 10.56 Hz, 1 H) 6.92-7.14 (m, 2 H) 7.72-7.91 (m, 2 H) 8.05 (d, J = 1.96 Hz, 1 H) 9.68 (s, 1 H). |
| 38 | E | 28 | 39 | 546 | $^1$H NMR (400 MHz, CHLOROFORM-d) δ ppm 1.21-1.30 (m, 9 H) 1.59-1.70 (m, 1 H) 1.92 (s, 3 H) 1.97-2.07 (m, 3 H) 2.08-2.28 (m, 2 H) 3.86 (d, J = 5.28 Hz, 1 H) 4.87-5.09 (m, 4 H) 5.21 (dd, J = 46.95, 10.37 Hz, 2 H) 7.09 (dd, J = 11.44, 8.90 Hz, 1 H) 7.76 (dd, J = 6.75, 2.64 Hz, 1 H) 7.90 (dt, J = 8.46, 3.59 Hz, 1 H) 8.97 (s, 1 H) 9.52 (s, 1 H). |
| 44 | E | 29 | 39 | 518 | $^1$H NMR (400 MHz, CHLOROFORM-d) δ ppm 1.59-1.71 (m, 1 H) 1.83-1.95 (m, 9 H) 1.99-2.28 (m, 3 H) 2.57 (s, 1 H) 3.86 (d, J = 4.89 Hz, 1 H) 4.97 (dd, J = 46.56, 10.37 Hz, 2 H) 5.21 (dd, J = 47.14, 10.56 Hz, 1 H) 7.08 (dd, J = 11.44, 8.90 Hz, 1 H) 7.68 (dd, J = 6.65, 2.54 Hz, 1 H) 7.89-7.96 (m, 1 H) 8.09 (s, 1 H) 9.03 (s, 1 H) 9.50 (s, 1 H). |
| 45 | E | synthesized analgous to 29 | 39 | 504 | $^1$H NMR (400 MHz, CHLOROFORM-d) δ ppm 1.60-1.73 (m, 4 H) 1.93 (s, 3 H) 1.99-2.32 (m, 3 H) 2.49 (d, J = 1.96 Hz, 1 H) 3.87 (d, J = 4.89 Hz, 1 H) 4.99 (dd, J = 46.56, 10.56 Hz, 1 H) 5.21 (dd, J = 47.14, 10.56 Hz, 1 H) 5.83 (qd, J = 6.65, 1.96 Hz, 1 H) 7.09 (dd, J = 11.54, 8.80 Hz, 1 H) 7.73 (dd, J = 6.85, 2.74 Hz, 1 H) 7.90 (dt, J = 8.41, 3.62 Hz, 1 H) 8.14 (d, J = 0.98 Hz, 1 H) 9.01 (d, J = 1.17 Hz, 1 H) 9.54 (s, 1 H). |
| 46 | D | 33 | 39 | 513 | $^1$H NMR (400 MHz, CHLOROFORM-d) δ ppm 1.63-1.78 (m, 1 H) 1.95 (s, 3 H) 2.00-2.28 (m, 3 H) 2.57 (t, J = 2.35 Hz, 1 H) 3.87 (d, J = 4.69 Hz, 1 H) 4.98 (dd, J = 46.56, 10.37 Hz, 1 H) 5.21 (dd, J = 47.34, 10.56 Hz, 1 H) 7.03-7.13 (m, 2 H) 7.70 (dd, J = 6.85, 2.74 Hz, 1 H) 8.18 (dt, J = 8.61, 3.62 Hz, 1 H) 8.22 (d, J = 5.87 Hz, 1 H) 8.32 (s, 1 H) 8.60 (s, 1 H) |
| 47 | D | 30 | 39 | 536.9 | $^1$H NMR (400 MHz, CHLOROFORM-d) δ ppm 1.62-1.74 (m, 1 H) 1.96 (s, 3 H) 2.05-2.31 (m, 3 H) 3.89 (d, J = 4.93 Hz, 1 H) 5.00 (dd, J = 46.56, 10.37 Hz, 1 H) 5.23 (dd, J = 47.14, 10.37 Hz, 1 H) 7.09-7.20 (m, 1 H) 7.79-7.86 (m, 1 H) 8.13-8.21 (m, 1 H) 8.35 (s, 1 H) 8.74 (s, 1 H) 8.80 (s, 1 H) 9.06 (br. s., 1 H). |
| 48 | A | commercial (Anichem, NJ) | 14A | 513.1 | 1H NMR (400 MHz, DMSO-d6) 10.93 (br. s., 1H), 9.44 (br. s., 1H), 9.32 (br. s., 1H), 8.93 (s, 1H), 8.35 (s, 1H), 8.25-8.27 (m, 1H), 8.12 (d, J = 14.77 Hz, 1H), 7.88 (br. s., 1H), 7.39 (d, J = 7.24 Hz, 1H), 2.70-2.62 (m, 2H), 2.65 (s, 3H), 2.08 (br. s., 3H), 1.96-2.05 (m, 1H), 1.86 (br. s., 1H), 1.68 (s, 3H), 1.52 (s, 3H) |
| 49 | A | commercial (Anichem, NJ) | 14B | 513.1 | 1H NMR (400 MHz, DMSO-d6) d 10.88 (br. s., 1H), 10.79 (s, 1H), 9.46 (br. s., 1H), 9.19 (br. s., 1H), 8.91 (s, 1H), 8.31 (s, 1H), 7.94-8.16 (m, 1H), 7.68 (dd, J = 2.15, 7.34 Hz, 1H), 7.22 (dd, J = 9.00, 12.81 Hz, 1H), 2.74-2.87 (m, 1H), 2.61-2.74 (m, 1H), 2.57 (s, 3H), 2.01-2.17 (m, 2H), 1.98-2.01 (m, 3H), 1.97 (s, 3H), 1.64 (s, 3H), 1.45 (s, 3H) |

TABLE 2-continued

| Example No | Synthetic Method | Intermediate L | Intermediate R | Mass - Observed [M + H]+ | NMR |
|---|---|---|---|---|---|
| 50 | D | 19 | 14A | 506 | 1H NMR (400 MHz, DMSO-d6) δ 9.83 (br. s., 1H), 9.01 (s, J = 5.35, 5.35 Hz, 1H), 8.59 (s, J = 5.22 Hz, 1H), 8.12 (s, J = 5.36, 5.36 Hz, 1H), 8.07 (br. s., 1H), 7.93 (s, 1H), 7.09-7.16 (m, 1H), 5.97 (br.s., 2H), 2.48-2.61 (m, 2H), 1.84 (br. s., 3H), 1.68-1.79 (m, 1H), 1.52-1.61 (m, 1H), 1.52 (s, 3H), 1.44 (br. s., 3H) |
| 51 | D | 19 | 14B | 506 | 1H NMR (400 MHz, DMSO-d6) d 9.08 (br. s., 1H), 9.04 (d, J = 1.96 Hz, 1H), 8.60 (d, J = 1.96 Hz, 1H), 8.17 (s, 1H), 8.06-8.16 (m, 1H), 7.59 (br. s., 1H), 7.05 (dd, J = 9.10, 12.32 Hz, 1H), 6.04 (br. s., 2H), 2.55-2.65 (m, 1H), 2.14-2.27 (m, 1H), 1.83 (d, J = 8.51 Hz, 2H), 1.70 (d, J = 3.91 Hz, 3H), 1.50 (s, 3H), 1.35 (d, J = 3.91 Hz, 3H) |
| 52 | A | commercial | 39 | 489 | 1H NMR (400 MHz, MeOH-d4) δ ppm 1.58 (m, 1 H) 1.92 (s, 3 H) 1.70-2.26 (m, 3 H) 3.09 (t, J = 2.15 Hz, 1 H) 3.83 (m, 1 H) 4.94 (d, J = 2.15 Hz, 2 H) 4.98-5.07 (m, 1 H) 5.08-5.23 (m, 1 H) 7.14 (dd, J = 11.74, 8.80 Hz, 1 H) 7.62 (dd, J = 8.61, 2.74 Hz, 1 H) 7.77-7.86 (m, 1 H) 7.90 (d, J = 5.09 Hz, 1 H) 8.17 (d, J = 8.80 Hz, 1 H) 8.40 (d, J = 2.74 Hz, 1 H). |
| 53 | D | synthesized analogous to 18 | 39 | 501 | 1H NMR (400 MHz, MeOH-d4) δ ppm 1.52-1.72 (m, 1 H) 1.95 (s, 3 H) 1.75-2.29 (m, 3 H) 3.83 (m, 1 H) 5.03-5.11 (m, 1 H) 5.14-5.22 (m, 1 H) 7.12 (dd, J = 11.64, 8.90 Hz, 1 H) 7.93-8.02 (m, 1 H) 8.11 (m, 1 H) 8.14 (s, 1 H) 8.90 (s, 1 H) 9.15 (s, 1 H) |
| 54 | D | 19 | 39 | 510 | 1H NMR (400 MHz, MeOH-d4) δ ppm 1.53-1.72 (m, 1 H) 1.95 (s, 3 H) 1.75-2.28 (m, 3 H) 3.83 (m, 1 H) 4.98-5.09 (m, 1 H) 5.10-5.21 (m, 1 H) 7.11 (dd, J = 11.74, 8.80 Hz, 1 H) 7.96-8.01 (m, 1 H) 8.02 (s, 1H) 7.99-8.14 (m, 2 H) 8.44 (d, J = 2.35 Hz, 1 H) 8.90 (d, J = 2.35 Hz, 1 H). |
| 55 | D | commercial | 39 | 527.2 | 1H NMR (400 MHz, CHLOROFORM-d) δ ppm 1.75 (m, 1 H) 2.00 (s, 3 H) 2.06-2.45 (m, 3 H) 3.93 (m, 1 H) 4.96 (dd, J = 47.14, 10.56 Hz, 1 H) 5.20 (dd, J = 46.55, 10.37 Hz, 1 H) 7.15 (dd, J = 11.64, 8.90 Hz, 1 H) 7.36 (d, J = 6.06 Hz, 1 H) 7.83 (dd, J = 6.85, 2.74 Hz, 1 H) 8.21-8.33 (m, 1 H) 8.42 (d, J = 6.06 Hz, 1 H) 8.93 (s, 1 H) 9.05 (s, 1 H). |
| 56 | D | 16 | 39 | 488.1 | 1H NMR (400 MHz, CHLOROFORM-d) δ ppm 1.63-1.80 (m, 1 H) 1.95 (s, 3 H) 1.98-2.35 (m, 3 H) 3.87 (m, 1 H) 3.97 (s, 3 H) 4.92 (dd, J = 46.56, 10.56 Hz, 1 H) 5.16 (dd, J = 47.15, 10.56 Hz, 1 H) 6.93 (d, J = 5.87 Hz, 1 H) 7.08 (dd, J = 11.64, 8.90 Hz, 1 H) 7.23 (d, J = 2.74 Hz, 1 H) 7.31-7.32 (m, 1 H) 7.70 (dd, J = 6.85, 2.74 Hz, 1 H) 8.05 (d, J = 5.67 Hz, 1 H) 8.26 (dt, J = 8.51, 3.67 Hz, 1 H) 8.49 (d, J = 2.54 Hz, 1 H) 8.91 (s, 1 H). |
| 57 | A | synthesized analogous to 50 | 39 | 548 | 1H NMR (400 MHz, CHLOROFORM-d) δ ppm 1.59-1.71 (m, 1 H) 1.92 (s, 3 H) 2.00-2.32 (m, 3 H) 2.96 (s, 3 H) 3.88 (m, 1 H) 4.85 (d, J = 8.41 Hz, 1 H) 4.89 (d, J = 8.41 Hz, 1 H) 4.93 (dd, J = 46.75, 10.56 Hz, 1 H) 5.15 (dd, J = 47.15, 10.37 Hz, 1 H) 7.08 (dd, J = 11.54, 8.80 Hz, 1 H) 7.58 (dd, J = 6.85, 2.74 Hz, 1 H) 7.97 (dt, J = 8.71, 3.57 Hz, 1 H) 7.92-8.02 (m, 1 H) 8.15 (s, 1 H) 9.75 (s, 1 H). |
| 58 | D | 15 | 39 | 492 | 1H NMR (400 MHz, CHLOROFORM-d) δ ppm 1.69-1.85 (m, 1 H) 1.99 (s, 3 H) 2.03-2.37 (m, 3 H) 3.91 (m, 1 H) 4.91 (dd, J = 46.56, 10.37 Hz, 1 H) 5.16 (dd, J = 47.34, 10.56 Hz, 1 H) 6.95 (d, J = 5.87 Hz, 1 H) 7.12 (dd, J = 11.54, 9.00 Hz, 1 H) 7.77 (dd, J = 6.85, 2.74 Hz, 1 H) 8.03 (d, J = 2.35 Hz, 1 H) 8.14 (d, J = 5.87 Hz, 1 H) 8.22-8.33 (m, 1 H) 8.72 (d, J = 2.15 Hz, 1 H) 8.99 (s, 1 H). |
| 59 | A | 50 | 39 | 504 | 1H NMR (400 MHz, CHLOROFORM-d) δ = 9.77 (s, 1H), 8.07-8.00 (m, 1H), 7.93 (ddd, J = 2.9, 4.1, 8.8 Hz, 1H), 7.61 (dd, J = 2.7, 6.8 Hz, 1H), 7.07 (dd, J = 8.9, 11.4 Hz, 1H), 5.38-4.85 (m, 4H), 3.87 (d, J = 4.7 Hz, 1H), 2.93 (s, 3H), 2.54 (t, J = 2.3 Hz, 1H), 2.28-1.98 (m, 4H), 1.92 (d, J = 0.8 Hz, 3H), 1.72-1.58 (m, 1H). |
| 60 | A | 47 | 39 | 523 | 1H NMR (400 MHz, CHLOROFORM-d) δ ppm 1.58-1.72 (m, 1 H) 1.92 (s, 3 H) 1.97-2.04 (m, 1 H) 2.07-2.28 (m, 2 H) 2.65 (t, J = 2.35 Hz, 1 H) 3.86 (d, J = 4.50 Hz, 1 H) 4.82 (d, J = 2.35 Hz, 2 H) 4.87-5.31 (m, 2 H) 7.07 (dd, J = 11.54, 8.80 Hz, 1 H) 7.43 (d, J = 2.54 Hz, 1 H) 7.64 (dd, J = 6.85, 2.74 Hz, 1 H) 7.91-8.04 (m, 1 H) 8.21 (d, J = 2.54 Hz, 1 H) 9.81 (s, 1 H). |
| 61 | A | commercial | 12 | 448.1 | 1H NMR (400 MHz, DMSO-d6) a ppm 1.32 (t, J = 11.20 Hz, 1 H) 1.49 (s, 3 H) 1.78 (br. s., 4 H) 1.98 (d, J = 8.80 Hz, 1 H) 2.11 (br. s., 1 H) 2.67-2.71 (m, 1 H) 3.63-3.84 (m, |

TABLE 2-continued

| Example No | Synthetic Method | Intermediate L | Intermediate R | Mass - Observed [M + H]⁺ | NMR |
|---|---|---|---|---|---|
| | | | | | 1 H) 3.98-4.07 (m, 3 H) 5.83-6.33 (m, 1 H) 7.20 (t, J = 10.07 Hz, 1 H) 7.81-7.96 (m, 2 H) 8.42 (d, J = 1.37 Hz, 1 H) 8.85-8.96 (m, 1 H) 10.51 (br. s., 1 H) |
| 62 | D | synthesized analogous to 33 | 12 | 509.1 | $^1$H NMR (400 MHz, DMSO-d$_6$) δ ppm 1.23 (s, 3 H) 1.47 (s, 3 H) 1.77 (s, 1 H) 1.87 (t, J = 2.35 Hz, 3 H) 1.90-2.01 (m, 2H) 3.66 (d, J = 6.36 Hz, 1 H) 5.15 (q, J = 2.35 Hz, 2 H) 5.93-6.23 (m, 1 H) 7.06 (d, J = 5.77 Hz, 1 H) 7.11-7.19 (m, 1 H) 7.96-8.02 (m, 1 H) 8.06-8.14 (m, 1 H) 8.21-8.26 (m, 1 H) 8.55-8.61 (m, 1 H) 9.47 (s, 1 H) |
| 63 | D | synthesized analogous to 33 | 13 | 509.1 | $^1$H NMR (400 MHz, CHLOROFORM-d) δ ppm 1.21-1.35 (m, 1 H) 1.44 (d, J = 6.26 Hz, 1 H) 1.59 (s, 3 H) 1.69 (d, J = 0.78 Hz, 3 H) 1.92 (t, J = 2.35 Hz, 3 H) 2.11 (ddd, J = 12.67, 10.22, 4.40 Hz, 1 H) 2.30-2.51 (m, 3 H) 4.01 (d, J = 5.67 Hz, 1 H) 5.10 (q, J = 2.31 Hz, 2 H) 6.95-7.02 (m, 1 H) 7.07 (dd, J = 11.93, 8.90 Hz, 1 H) 7.60 (dd, J = 7.14, 2.74 Hz, 1 H) 8.12 (ddd, J = 8.78, 4.18, 2.89 Hz, 1 H) 8.21 (d, J = 5.87 Hz, 1 H) 8.29 (s, 1 H) 8.62 (s, 1 H) |
| 64 | A | 45 | 12 | 481.1 | $^1$H NMR (400 MHz, DMSO-d$_6$) δ ppm 0.78-0.87 (m, 2 H) 0.92-1.01 (m, 2 H) 1.19-1.37 (m, 2 H) 1.47 (s, 3 H) 1.65 (tt, J = 8.25, 5.05 Hz, 1 H) 1.71-1.79 (m, 4 H) 1.87-2.01 (m, 1 H) 2.08 (td, J = 11.98, 4.99 Hz, 1 H) 3.67 (d, J = 5.67 Hz, 1 H) 6.06 (br. s., 1 H) 7.10-7.24 (m, 1 H) 7.88 (dd, J = 6.06, 3.42 Hz, 2 H) 7.99-8.05 (m, 1 H) 8.06-8.12 (m, 1 H) 8.69 (dd, J = 2.00, 0.83 Hz, 1 H) 10.62 (s, 1 H) |
| 65 | A | 45 | 13 | 481.1 | $^1$H NMR (400 MHz, DMSO-d$_6$) δ ppm 0.79-0.86 (m, 2 H) 0.93-1.00 (m, 2 H) 1.42 (s, 3 H) 1.50 (s, 3 H) 1.65 (tt, J = 8.25, 5.00 Hz, 1 H) 1.89 (d, J = 13.20 Hz, 1 H) 2.15-2.29 (m, 3 H) 2.39 (d, J = 12.62 Hz, 1 H) 3.75 (br. s., 1 H) 6.04 (br. s., 1 H) 7.12 (dd, J = 12.03, 8.71 Hz, 1 H) 7.70-7.88 (m, 2 H) 7.98-8.04 (m, 1 H) 8.05-8.12 (m, 1 H) 8.69 (dd, J = 2.05, 0.88 Hz, 1 H) 10.29-10.45 (m, 1 H) |
| 66 | A | commercial | 13 | 448.1 | 1H NMR (400 MHz, DMSO-d6) a ppm 1.42 (s, 3 H) 1.49 (s, 3 H) 1.75 (s, 1 H) 1.82-1.92 (m, 1 H) 2.12-2.28 (m, 2 H) 2.35-2.46 (m, 1 H) 3.75 (d, J = 3.62 Hz, 1 H) 3.99-4.05 (m, 3 H) 6.03 (br. s., 1 H) 7.11 (dd, J = 12.08, 8.66 Hz, 1 H) 7.73-7.86 (m, 2 H) 8.41 (d, J = 1.37 Hz, 1 H) 8.88 (d, J = 1.27 Hz, 1 H) 10.24 (br. s., 1 H) |
| 67 | D | synthesized analogous to 31 | 13 | 511.1 | $^1$H NMR (400 MHz, CHLOROFORM-d) δ ppm 0.38-0.47 (m, 2 H) 0.63-0.73 (m, 2 H) 1.32-1.42 (m, 1 H) 1.62-1.67 (m, 3 H) 1.75 (s, 3 H) 2.02 (s, 3 H) 2.39-2.55 (m, 3 H) 4.06 (d, J = 5.18 Hz, 1 H) 5.39-5.69 (m, 2 H) 6.80-6.88 (m, 1 H) 6.94-6.99 (m, 1 H) 7.01-7.13 (m, 1 H) 7.54-7.67 (m, 1 H) 8.13-8.22 (m, 2 H) 8.58 (s, 1 H) |
| 68 | D | synthesized analogous to 31 | 12 | 511.1 | $^1$H NMR (400 MHz, CHLOROFORM-d) δ ppm 0.38-0.48 (m, 2 H) 0.63-0.75 (m, 2 H) 1.19-1.31 (m, 2 H) 1.31-1.42 (m, 1 H) 1.55-1.58 (m, 3 H) 1.65 (s, 3 H) 1.67-1.77 (m, 2 H) 1.93-2.00 (m, 4 H) 2.11-2.25 (m, 2 H) 3.88 (d, J = 5.58 Hz, 1 H) 7.00 (d, J = 5.87 Hz, 1 H) 7.05-7.14 (m, 1 H) 7.71 (dd, J = 6.85, 2.74 Hz, 1 H) 8.16-8.25 (m, 2 H) 8.62 (s, 1 H) |
| 69 | A | synthesized analogous to 45 | 12 | 455.1 | $^1$H NMR (400 MHz, DMSO-d$_6$) δ ppm 1.31 (t, J = 11.84 Hz, 1 H) 1.47 (s, 3 H) 1.68-1.80 (m, 4 H) 1.89-2.01 (m, 2 H) 2.04-2.12 (m, 1 H) 2.14 (s, 3 H) 3.68 (d, J = 5.87 Hz, 1 H) 6.06 (br. s., 2 H) 7.10-7.23 (m, 1 H) 7.85-7.94 (m, 2 H) 8.02-8.07 (m, 1 H) 8.08-8.14 (m, 1 H) 8.73 (d, J = 1.27 Hz, 1 H) 10.63 (s, 1 H) |
| 70 | A | 46 | 12 | 500.1 | $^1$H NMR (400 MHz, DMSO-d$_6$) δ ppm 0.81-0.91 (m, 1 H) 1.22-1.26 (s, 3 H) 1.28-1.37 (m, 1 H) 1.47 (s, 3 H) 1.59 (d, J = 6.65 Hz, 3 H) 1.75 (s, 3 H) 1.79-1.85 (m, 1 H) 1.88-2.01 (m, 1 H) 2.01-2.13 (m, 1 H) 3.67 (d, J = 6.06 Hz, 1 H) 5.75-5.83 (m, 1 H) 6.07 (br. s., 1 H) 7.17 (dd, J = 11.84, 8.71 Hz, 1 H) 7.85 (dd, J = 8.31, 4.01 Hz, 1 H) 7.91 (dd, J = 7.09, 2.69 Hz, 1 H) 8.41 (d, J = 1.37 Hz, 1 H) 8.90 (d, J = 1.37 Hz, 1 H) 10.49 (s, 1 H) |
| 71 | A | 46 | 12 | 500.1 | $^1$H NMR (400 MHz, DMSO-d$_6$) δ ppm 1.09-1.19 (m, 1 H) 1.23 (s, 3 H) 1.27-1.37 (m, 1 H) 1.47 (s, 3 H) 1.59 (d, J = 6.55 Hz, 3 H) 1.75 (s, 3 H) 1.79-1.83 (m, 1 H) 1.88-2.01 (m, 1 H) 2.02-2.15 (m, 1 H) 3.67 (d, J = 6.36 Hz, 1 H) 5.73-5.85 (m, 1 H) 6.10 (s, 1 H) 7.17 (dd, J = 11.84, 8.71 Hz, 1 H) 7.81-7.95 (m, 2 H) 8.42 (d, J = 1.27 Hz, 1 H) 8.90 (d, J = 1.27 Hz, 1 H) 10.49 (s, 1 H) |
| 72 | A | 53 | 49A | 482.9 | $^1$H NMR (400 MHz, DMSO-d6) δ ppm 1.45 (s, 3 H) 1.84-1.98 (m, 1 H) 1.85-1.97 (m, 1 H) 2.14-2.32 (m, 2 H) 2.37-2.47 (m, 1 H) 2.54-2.59 (m, 3 H) 3.99 (dd, J = 5.99, 2.57 Hz, 1 H) 4.44-4.54 (m, 1 H) 4.56-4.66 (m, 1 H) 7.12 (d, J = 8.86 Hz, 1 H) 7.15 (d, J = 8.91 Hz, 1 H) |

TABLE 2-continued

| Example No | Synthetic Method | Intermediate L | Intermediate R | Mass - Observed [M + H]+ | NMR |
|---|---|---|---|---|---|
| | | | | | 7.77 (dd, J = 7.15, 2.70 Hz, 1 H) 7.85 (ddd, J = 8.86, 4.17, 2.98 Hz, 1 H) 8.02 (dd, J = 2.33, 0.78 Hz, 1 H) 8.56-8.66 (m, 1 H) 10.46 (s, 1 H) |
| 73 | A | 53 | 49B | 482.9 | $^1$H NMR (400 MHz, DMSO-d6) δ ppm 1.45 (s, 3 H) 1.82-2.00 (m, 1 H) 2.12-2.32 (m, 2 H) 2.40 (br. s., 1 H) 2.54-2.59 (m, 3 H) 3.98-4.05 (m, 1 H) 4.44-4.54 (m, 1 H) 4.56-4.66 (m, 1 H) 6.28 (br. s., 1 H) 7.12 (d, J = 8.81 Hz, 1 H) 7.15 (d, J = 8.97 Hz, 1 H) 7.77 (dd, J = 7.36, 2.75 Hz, 1 H) 7.81-7.93 (m, 1 H) 8.00-8.12 (m, 1 H) 8.56-8.68 (m, 1 H) 10.46 (s, 1 H) |
| 74 | A | commercial | 49B | 466 | 1H NMR (400 MHz, DMSO-d6) δ ppm 1.37-1.51 (m, 3 H) 1.85-1.95 (m, 1H) 2.13-2.32 (m, 1 H) 2.18-2.30 (m, 1 H) 2.39-2.47 (m, 1 H) 3.40-3.44 (m, 1 H) 3.46-3.53 (m, 1 H) 4.01 (dd, J = 6.40, 2.36 Hz, 1 H) 4.03 (s, 3 H) 4.50-4.60 (m, 1 H) 4.63 (s, 1 H) 7.14 (dd, J = 12.15, 8.84 Hz, 1 H) 7.79-7.86 (m, 1 H) 7.95 (dd, J = 7.31, 2.85 Hz, 1 H) 8.42 (d, J = 1.35 Hz, 1 H) 8.89 (d, J = 1.35 Hz, 1 H) 10.31 (s, 1 H) |
| 75 | A | commercial | 49A | 466 | 1H NMR (400 MHz, DMSO-d6) δ ppm 1.41-1.50 (m, 3 H) 1.84-1.93 (m, 1 H) 2.18-2.31 (m, 2 H) 2.39-2.48 (m, 1 H) 3.40-3.44 (m, 1 H) 3.46-3.53 (m, 2 H) 4.01 (d, J = 5.23 Hz, 1 H) 4.03 (s, 3 H) 4.50-4.60 (m, 1 H) 7.14 (dd, J = 12.13, 8.86 Hz, 1 H) 7.79-7.86 (m, 1 H) 7.95 (dd, J = 7.15, 2.85 Hz, 1 H) 8.42 (d, J = 1.35 Hz, 1 H) 8.89 (d, J = 1.35 Hz, 1 H) 10.31 (s, 1 H) |
| 39 | F | synthesized analogous to 20 | 12 | 474 | 1H NMR (400 MHz, DMSO-d6) δ 9.27 (s, 1H), 8.60 (d, J = 2.70 Hz, 1H), 8.07-8.17 (m, 1H), 7.94-8.01 (m, 2H), 7.44 (d, J = 2.70 Hz, 1H), 7.12 (dd, J = 8.81, 11.71 Hz, 1H), 4.28-4.40 (m, 1H), 3.66 (d, J = 6.84 Hz, 1H), 3.44 (q, J = 6.84 Hz, 2H), 2.05-2.17 (m, 1H), 1.88-2.01 (m, 1H), 1.76 (s, 3H), 1.68-1.75 (m, 1H), 1.47 (s, 3H), 1.37 (t, J = 13.58 Hz, 1H) |
| 76 | A | 51 | 38 | 480 | 1H NMR (400 MHz, DMSO-d6) δ ppm 10.43 (br. s, 1 H) 8.26 (s, 1 H) 7.80-7.88 (m, 1 H) 7.78 (d, J = 6.70 Hz, 1 H) 7.12-7.28 (m, 1 H) δ 6.22 (br. s., 2 H) 4.91-5.25 (m, 2 H) 4.00 (s, 3 H) 3.71-3.79 (m, 1 H) 2.78 (s, 3 H) 1.97-2.03 (m, 2 H) 1.76 (s, 3 H) 1.35-1.42 (m, 2 H) |
| 77 | A | commercial | 38 | 469 | 1H NMR (400 MHz, DMSO-d6) δ ppm 10.66 (br. s, 1 H) 8.79 (dd, J = 2.31, 0.65 Hz, 1 H) 8.14-8.22 (m, 2 H) 7.78-7.87 (m, 2 H) 7.15-7.26 (m, 1 H) 6.23 (br. s., 2 H) 4.89-5.23 (m, 2 H) 3.71-3.80 (m, 1 H) 1.86-2.05 (m, 2 H) 1.78 (s, 3 H) 1.21-1.38 (m, 2 H) |
| 78 | D | 20 | 12 | 488 | 1H NMR (400 MHz, DMSO-d6) δ ppm 9.34 (s, 1 H) 8.72 (d, J = 2.74 Hz, 1 H) 8.07-8.14 (m, 2 H) 8.00 (dd, J = 7.24, 2.84 Hz, 1 H) 7.72 (d, J = 2.84 Hz, 1 H) 7.14-7.22 (m, 1 H) 6.06 (br. s., 2 H) 4.05 (s, 3 H) 3.62-3.73 (m, 1 H) 1.92-2.13 (m, 2 H) 1.77 (s, 3 H) 1.48 (s, 3 H) 1.19-1.41 (m, 2 H) |
| 79 | A | 51 | 12 | 462 | 1H NMR (500 MHz, DMSO-d6) δ ppm 10.38 (br. s., 1 H) 8.23 (s, 1 H) 7.81-7.87 (m, 1 H) 7.78 (d, J = 4.98 Hz, 1 H) 7.11-7.28 (m, 1 H) 6.01 (br. s., 2 H) 3.99 (s, 3 H) 3.63-3.78 (m, 1 H) 2.76 (s, 3 H) 1.88-2.08 (m, 2 H) 1.74 (s, 3 H) 1.46 (s, 3 H) 1.22-1.39 (m, 2 H) |
| 80 | C | 17 | 12 | 471.2 | 1H NMR (400 MHz, DMSO-d6) δ ppm 9.51 (br. s., 1 H) 8.62 (s, 1 H) 8.28 (d, J = 5.77 Hz, 1 H) 8.10-8.20 (m, 1 H) 8.02-8.10 (m, 1 H) 7.10-7.26 (m, 2 H) 6.12 (br. s., 2 H) 4.16 (s, 3 H) 3.68-3.75 (m, 1 H) 1.94-2.24 (m, 2 H) 1.69-1.73 (m, 1 H) 1.80 (s, 3 H) 1.53 (s, 3 H) 1.34-1.39 (m, 1 H) |
| 81 | A | 17 | 13 | 471.2 | 1H NMR (400 MHz, DMSO-d6) δ ppm 9.12 (br. s., 1 H) 8.56 (s, 1 H) 8.25 (d, J = 6.03 Hz, 1 H) 8.11-8.18 (m, 1 H) 7.77-7.93 (m, 1 H) 7.03-7.16 (m, 2 H) 6.10 (br. s, 2 H) 4.08 (s, 3 H) 3.69-3.89 (m, 1 H) 2.38-2.42 (m, 1 H) 2.19-2.31 (m, 1 H) 1.86-1.74 (m, 1 H) 1.53 (s, 3 H) 1.42 (s, 3 H) |
| 82 | A | 54 | 12 | 486.2 | 1H NMR (400 MHz, CHLOROFORM-d) δ ppm 9.45 (s, 1 H) 8.94 (s, 1 H) 8.11 (s, 1 H) 7.72-7.84 (m, 1 H) 7.64 (dd, J = 6.85, 2.74 Hz, 1 H) 7.02 (dd, J = 11.49, 8.85 Hz, 1 H) 4.94-5.01 (m, 2 H) 3.74-3.79 (m, 1 H) 2.04-2.16 (m, 3 H) 1.87 (s, 3 H) 1.82 (s, 3 H) 1.56 (s, 3 H) 1.47-1.52 (m, 1 H) |
| 83 | A | 54 | 13 | 486.2 | 1H NMR (400 MHz, DMSO-d6) δ ppm 10.32 (br. s., 1 H) 8.94 (s, 1 H) 8.51 (s, 1 H) 7.80-7.94 (m, 2 H) 7.12-7.22 (m, 1 H) 6.07 (br. s, 2 H) 5.08-5.16 (m, 2 H) |

TABLE 2-continued

| Example No | Synthetic Method | Intermediate L | Intermediate R | Mass - Observed [M + H]+ | NMR |
|---|---|---|---|---|---|
| | | | | | 3.77-3.86 (m, 1 H) 2.40-2.51 (m, 1 H) 2.18-2.35 (m, 2 H) 1.95-1.99 (m, 1 H) 1.88-1.93 (m, 3 H) 1.56 (s, 3 H) 1.48 (s, 3 H) |
| 84 | D | 18 | 12 | 465 | 1H NMR (400 MHz, DMSO-d6) δ ppm 9.72 (br. s, 1 H) 9.23 (d, J = 1.96 Hz, 1 H) 8.99 (d, J = 1.96 Hz, 1 H) 8.21 (d, J = 5.67 Hz, 1 H) 8.11-8.17 (m, 1 H) 8.02-8.05 (m, 1 H) 7.14-7.24 (m, 2 H) 6.07 (br. s., 2 H) 3.66-3.69 (m, 1 H) 2.07-2.13 (m, 1 H) 1.92-1.98 (m, 1 H) 1.78 (s, 3 H) 1.69-1.75 (m, 1 H) 1.48 (s, 3 H) 1.35-1.42 (m, 1 H) |
| 85 | D | 18 | 13 | 465 | 1H NMR (400 MHz, DMSO-d6) δ ppm 9.39 (br. s., 1 H) 9.23 (d, J = 1.96 Hz, 1 H) 8.99 (d, J = 1.96 Hz, 1 H) 8.24 (d, J = 5.77 Hz, 1 H) 8.14-8.20 (m, 1 H) 7.83-7.90 (m, 1 H) 7.23 (d, J = 5.77 Hz, 1 H) 7.09-7.16 (m, 1 H) 6.09 (br. s., 2 H) 3.71-3.81 (m, 1 H) 2.38-2.46 (m, 1 H) 2.16-2.30 (m, 2 H) 1.84-1.93 (m, 1 H) 1.54 (s, 3 H) 1.42 (s, 3 H) |
| 86 | C | commercial | 12 | 509.1 | 1H NMR (400 MHz, DMSO-d6) δ ppm 10.05 (br. s, 1 H) 9.37 (s, 1 H) 8.41 (d, J = 5.97 Hz, 1 H) 8.06-8.15 (m, 2 H) 7.37 (d, J = 5.87 Hz, 1 H) 7.18-7.26 (m, 1 H) 6.06 (br. s., 2 H) 3.65-3.71 (m, 1 H) 2.08-2.16 (m, 1 H) 1.91-2.01 (m, 1 H) 1.79 (s, 3 H) 1.69-1.76 (m, 1 H) 1.48 (s, 3 H) 1.30-1.44 (m, 1 H) |
| 87 | C | commercial | 13 | 509.1 | 1H NMR (400 MHz, DMSO-d6) δ ppm 9.71 (br. s., 1 H) 9.37 (s, 1 H) 8.44 (d, J = 5.97 Hz, 1 H) 8.03-8.12 (m, 2 H) 7.36 (d, J = 5.87 Hz, 1 H) 7.11-7.19 (m, 1 H) 6.06 (br. s., 2 H) 3.73-3.82 (m, 1 H) 2.38-2.41 (m, 1 H) 2.15-2.28 (m, 2 H) 1.86-1.92 (m, 1 H) 1.53 (s, 3 H) 1.42 (s, 3 H) |
| 88 | A | 53 | 38 | 483 | 1H NMR (400 MHz, DMSO-d6) δ ppm 10.56 (br. s, 1 H) 8.58-8.61 (m, 1 H) 8.02-8.06 (m, 1 H) 7.81-7.89 (m, 1 H) 7.78 (d, J = 6.10 Hz, 1 H) 7.19 (dd, J = 11.64, 8.71 Hz, 1 H) 6.22 (br. s., 2 H) 4.89-5.23 (m, 2 H) 3.71-3.77 (m, 1 H) 2.58 (s, 3 H) 1.82-1.99 (m, 2 H) 1.78 (s, 3 H) 1.69-1.76 (m, 1 H) 1.29-1.41 (m, 1 H) |
| 89 | A | 53 | 39 | 483 | 1H NMR (400 MHz, DMSO-d6) δ ppm 10.46 (br. s, 1 H) 8.57 (d, J = 1.76 Hz, 1 H) 8.02 (d, J = 1.76 Hz, 1 H) 7.83-7.91 (m, 1 H) 7.61-7.67 (m, 1 H) 7.09-7.17 (m, 1 H) 6.22 (br. s., 2 H) 4.86-5.27 (m, 2 H) 3.73-3.80 (m, 1 H) 2.56 (s, 3 H) 2.41-2.48 (m, 1 H) 2.17-2.28 (m, 1 H) 2.05-2.17 (m, 1 H) 1.86-1.94 (m, 1 H) 1.52 (s, 3 H) |
| 90 | A | 43 | 12 | 461.1 | 1H NMR (400 MHz, DMSO-d6) δ ppm 10.64 (br. s, 1 H) 8.68-8.71 (m, 1 H) 8.12-8.18 (m, 1 H) 7.98-8.02 (m, 1 H) 7.92 (d, J = 5.00 Hz, 2 H) 7.16-7.23 (m, 1 H) 6.07 (br. s., 2 H) 4.60 (s, 2 H) 3.65-3.75 (m, 1 H) 3.38 (s, 3 H) 2.06-2.14 (m, 1 H) 1.91-2.02 (m, 1 H) 1.77 (s, 3 H) 1.72-1.76 (m, 1 H) 1.48 (s, 3 H) 1.32-1.39 (m, 1 H) |
| 91 | A | 43 | 13 | 461.1 | 1H NMR (400 MHz, DMSO-d6) δ ppm 10.40 (br. s., 1 H) 8.67-8.71 (m, 1 H) 8.11-8.15 (m, 1 H) 7.98-8.02 (m, 1 H) 7.78-7.90 (m, 2 H) 7.14 (dd, J = 12.08, 8.75 Hz, 1 H) 6.06 (br. s., 2 H) 4.59 (s, 2 H) 3.73-3.85 (m, 1 H) 3.37 (s, 3 H) 2.38-2.42 (m, 1 H) 2.16-2.30 (m, 2 H) 1.84-1.94 (m, 1 H) 1.52 (s, 3 H) 1.44 (s, 3 H) |
| 92 | A | commercial | 38 | 517.1 | 1H NMR (400 MHz, DMSO-d6) δ ppm 10.69 (br. s, 1 H) 8.91-8.93 (m, 1 H) 8.30-8.32 (m, 1 H) 7.84-7.92 (m, 1 H) 7.77-7.81 (m, 1 H) 7.18-7.23 (m, 1 H) 6.21 (br. s., 2 H) 4.91-5.24 (m, 2 H) 3.74-3.78 (m, 1 H) 2.62 (s, 3 H) 1.94-2.05 (m, 1 H) 1.81-1.91 (m, 2 H) 1.78 (s, 3 H) 1.32-1.38 (m, 1 H) |
| 93 | A | commercial | 39 | 517.1 | 1H NMR (400 MHz, DMSO-d6) δ ppm 10.62 (s, 1 H) 8.88-8.91 (m, 1 H) 8.27-8.31 (m, 1 H) 7.86-7.91 (m, 1 H) 7.65 (dd, J = 7.43, 2.74 Hz, 1 H) 7.11-7.15 (m, 1 H) 6.22 (br. s., 2 H) 4.84-5.27 (m, 2 H) 3.74-3.79 (m, 1 H) 2.59 (s, 3 H) 2.40-2.48 (m, 1 H) 2.21-2.25 (m, 1 H) 2.05-2.18 (m, 1 H) 1.86-1.95 (m, 1 H) 1.52 (s, 3 H) |
| 94 | A | 54 | 38 | 504 | 1H NMR (400 MHz, DMSO-d6) δ ppm 10.52 (br. s, 1 H) 8.91 (s, 1 H) 8.47 (s, 1 H) 7.84-7.92 (m, 2 H) 7.16-7.21 (m, 1 H) 6.23 (br. s, 2 H) 4.93-5.23 (m, 4 H) 3.73-3.78 (m, 1 H) 1.90-2.03 (m, 2 H) 1.87 (s, 3 H) 1.80-1.82 (m, 1 H) 1.79 (s, 3 H) 1.30-1.38 (m, 1 H) |
| 95 | A | 54 | 39 | 504 | 1H NMR (500 MHz, DMSO-d6) δ ppm 10.30 (br. s., 1 H) 8.88 (s, 1 H) 8.44 (s, 1 H) 7.71-7.88 (m, 2 H) 7.08-7.16 (m, 1 H) 6.24 (br. s., 2 H) 4.89-5.20 (m, 4 H) 3.69-3.85 (m, 1 H) 2.41-2.48 (m, 1 H) 2.17-2.29 (m, 1 H) 2.00-2.15 (m, 1 H) 1.89-1.99 (m, 1 H) 1.86 (s, 3 H) 1.51 (s, 3 H) |
| 96 | A | 52 | 38 | 474.2 | 1H NMR (400 MHz, DMSO-d6) δ ppm 10.71 (br. s, 1 H) 9.00 (s, 1 H) 8.41 (s, 1 H) 7.83-7.89 (m, 1 H) 7.76-7.81 (m, 1 H) 7.18-7.22 (m, 1 H) 6.21 (br. s., 2 H) |

TABLE 2-continued

| Example No | Synthetic Method | Intermediate L | Intermediate R | Mass - Observed [M + H]+ | NMR |
|---|---|---|---|---|---|
| | | | | | 4.84-5.24 (m, 2 H) 3.74-3.78 (m, 1 H) 2.57 (s, 3 H) 1.91-2.04 (m, 1 H) 1.72-1.86 (m, 5 H) 1.29-1.34 (m, 1 H) |
| 97 | D | 22 | 38 | 489 | 1H NMR (400 MHz, DMSO-d6) δ ppm 10.15 (br. s, 1 H) 8.65 (d, J = 2.84 Hz, 1 H) 8.61 (s, 1 H) 7.99-8.09 (m, 2 H) 7.63 (d, J = 2.84 Hz, 1 H) 7.18-7.22 (m, 1 H) 6.24 (br. s., 2 H) 4.92-5.27 (m, 2 H) 4.01 (s, 3 H) 3.71-3.75 (m, 1 H) 1.94-2.05 (m, 2 H) 1.82 (s, 3 H) 1.73-1.79 (m, 1 H) 1.32-1.43 (m, 1 H) |
| 98 | Ex 29 | 21 | 38 | 493 | 1H NMR (400 MHz, DMSO-d6) δ ppm 10.46 (br. s, 1 H) 8.95 (d, J = 2.35 Hz, 1 H) 8.67 (s, 1 H) 8.42 (d, J = 2.25 Hz, 1 H) 8.09 (dd, J = 7.24, 2.74 Hz, 1 H) 7.96-8.02 (m, 1 H) 7.21-7.25 (m, 1 H) 6.24 (br. s., 2 H) 4.91-5.26 (m, 2 H) 3.72-3.77 (m, 1 H) 1.94-2.04 (m, 2 H) 1.81 (s, 3 H) 1.74-1.79 (m, 1 H) 1.30-1.40 (m, 1 H) |
| 99 | D | 20 | 38 | 506.1 | 1H NMR (400 MHz, DMSO-d6) δ ppm 9.39 (br. s, 1 H) 8.73 (d, J = 2.84 Hz, 1 H) 8.07-8.14 (m, 2 H) 8.02 (dd, J = 7.19, 2.79 Hz, 1 H) 7.73 (d, J = 2.84 Hz, 1 H) 7.12-7.16 (m, 1 H) 6.24 (br. s., 2 H) 4.91-5.26 (m, 2 H) 4.05 (s, 3 H) 3.71-3.75 (m, 1 H) 1.92-2.03 (m, 2 H) 1.80 (s, 3 H) 1.72-1.78 (m, 1 H) 1.35-1.44 (m, 1 H) |
| 100 | D | 18 | 38 | 483 | 1H NMR (400 MHz, DMSO-d6) δ ppm 9.75 (s, 1 H) 9.23 (d, J = 2.07 Hz, 1 H) 8.99 (d, J = 2.07 Hz, 1 H) 8.12-8.23 (m, 2 H) 8.03 (dd, J = 7.26, 2.80 Hz, 1 H) 7.15-7.25 (m, 2 H) 6.25 (br. s., 2 H) 4.91-5.25 (m, 2 H) 3.72-3.76 (m, 1 H) 1.89-2.04 (m, 2 H) 1.80 (s, 3 H) 1.73-1.79 (m, 1 H) 1.35-1.45 (m, 1 H) |
| 101 | A | commercial (American Advanced Scientific, Inc) | 38 | 463.1 | 1H NMR (400 MHz, DMSO-d6) δ ppm 10.59 (br. s, 1 H) 8.60-8.63 (m, 1 H) 8.09 (d, J = 8.11 Hz, 1 H) 7.86-7.95 (m, 3 H) 7.17-7.22 (m, 1 H) 6.25 (br. s., 2 H) 4.92-5.24 (m, 2 H) 3.73-3.78 (m, 1 H) 2.76 (q, J = 7.53 Hz, 2 H) 1.89-2.05 (m, 2H) 1.79 (s, 3 H) 1.71-1.76 (m, 1 H) 1.32-1.40 (m, 1 H) 1.26 (t, J = 7.63 Hz, 3 H) |
| 102 | A | 41 | 38 | 515 | $^1$H NMR (400 MHz, DMSO-d$_6$) δ ppm 10.52 (br. s., 1 H) 8.44 (s, 1 H) 7.73 (m, 3 H) 7.45 (t, J = 73.06 Hz, 1 H) 7.15-7.22 (m, 1 H) 6.22 (br. s., 2 H) 4.90-5.24 (m, 2 H) 3.73-3.78 (m, 1 H) 2.62 (s, 3 H) 1.89-2.05 (m, 2 H) 1.83-1.89 (m, 1 H) 1.78 (s, 3 H) 1.32-1.38 (m, 1 H) |
| 103 | A | 42 | 38 | 499.1 | $^1$H NMR (400 MHz, DMSO-d$_6$) δ ppm 10.63 (s, 1 H) 8.73 (s, 1 H) 8.06 (s, 1 H) 7.84-7.90 (m, 1 H) 7.78-7.82 (m, 1 H) 7.09-7.37 (m, 2 H) 6.21 (br. s., 2 H) 4.91-5.24 (m, 2 H) 3.74-3.78 (m, 1 H) 2.61 (s, 3 H) 1.93-2.05 (m, 1 H) 1.81-1.92 (m, 2 H) 1.79 (s, 3 H) 1.33-1.38 (m, 1 H) |
| 104 | D | 31 | 38 | 556 | $^1$H NMR (400 MHz, DMSO-d$_6$) δ ppm 9.53 (s, 1 H) 8.66 (s, 1 H) 8.20-8.25 (m, 2 H) 8.05-8.12 (m, 1 H) 8.00 (dd, J = 7.20, 2.64 Hz, 1 H) 7.28-7.33 (m, 1 H) 7.12-7.16 (m, 1 H) 7.06 (d, J = 5.80 Hz, 1 H) 6.22 (br. s, 2 H) 5.66 (s, 2 H) 4.87-5.26 (m, 2 H) 3.71-3.76 (m, 1 H) 1.92-2.11 (m, 2 H) 1.80 (s, 3 H) 1.71-1.77 (m, 1 H) 1.33-1.47 (m, 1 H) |
| 105 | A | commercial (matrix) | 38 | 503.9 | $^1$H NMR (400 MHz, DMSO-d$_6$) δ ppm 10.76 (s, 1 H) 8.74 (d, J = 2.07 Hz, 1 H) 8.45 (d, J = 2.07 Hz, 1 H) 7.80-7.86 (m, 1 H) 7.72-7.76 (m, 1 H) 7.18-7.22 (m, 1 H) 6.21 (br. s., 2 H) 4.90-5.24 (m, 2 H) 3.75-3.79 (m, 1 H) 1.92-2.07 (m, 2 H) 1.80-1.84 (m, 1 H) 1.74 (s, 3 H) 1.30-1.34 (m, 1 H) |
| 106 | D | 44 | 38 | 509 | $^1$H NMR (400 MHz, DMSO-d$_6$) δ ppm 10.59 (br. s, 1 H) 9.22 (d, J = 2.28 Hz, 1 H) 8.75 (s, 1 H) 8.66 (s, 1 H) 8.12-8.18 (m, 1 H) 7.96-8.02 (m, 1 H) 7.24-7.28 (m, 1 H) 6.05 (br. s., 2 H) 3.66-3.72 (m, 1 H) 1.78 (s, 3H) 1.72-1.75 (m, 2 H) 1.48 (s, 3 H) 1.34-1.22 (m, 2 H) |
| 107 | D | 44 | 38 | 527 | $^1$H NMR (400 MHz, DMSO-d$_6$) δ ppm 10.61 (br. s, 1 H) 9.21 (d, J = 2.18 Hz, 1 H) 8.74 (s, 1 H) 8.66 (s, 1 H) 8.10 (d, J = 6.98 Hz, 1 H) 7.95-8.01 (m, 1 H) 7.23-7.29 (m, 1 H) 6.23 (br. s, 2 H) 5.01-5.13 (m, 2 H) 3.65-3.74 (m, 1 H) 1.92-2.02 (m, 2 H) 1.80 (s, 3 H) 1.71-1.76 (m, 2 H) |
| 108 | A | commercial (Matrix) | 38 | 536.9 | $^1$H NMR (400 MHz, DMSO-d$_6$) δ ppm 10.81 (s, 1 H) 9.01 (s, 1 H) 8.65 (s, 1 H) 7.72-7.81 (m, 1 H) 7.65-7.72 (m, 1 H) 7.13-7.20 (m, 1 H) 6.16 (br. s, 2 H) 4.80-5.18 (m, 2 H) 3.72 (m, 1 H) 1.84-2.05 (m, 1 H) 1.75-1.81 (m, 2 H) 1.72 (s, 3 H) 1.30-1.34 (m, 1 H) |
| 109 | A | 26 | 38 | 485.9 | $^1$H NMR (400 MHz, DMSO-d$_6$) δ ppm 10.91 (s, 1 H) 9.40 (s, 1 H) 9.10 (s, 1 H) 7.84-7.98 (m, 2 H) 7.19-7.38 (m, 2 H) 6.23 (br. s., 2 H) 4.92-5.25 (m, 2 H) 3.74-3.78 (m, 1 H) 1.87-2.04 (m, 2 H) 1.80-1.83 (m, 1 H) 1.79 (s, 3 H) 1.30-1.36 (m, 1 H) |

TABLE 2-continued

| Example No | Synthetic Method | Intermediate L | Intermediate R | Mass - Observed [M + H]+ | NMR |
|---|---|---|---|---|---|
| 110 | A | commercial | 38 | 503 | ¹H NMR (400 MHz, DMSO-d₆) δ ppm 10.87 (s, 1 H) 9.17 (s, 1 H) 8.55 (dd, J = 8.19, 1.87 Hz, 1 H) 8.39 (d, J = 8.24 Hz, 1 H) 7.92-7.96 (m, 2 H) 7.22-7.29 (m, 1 H) 6.28 (br. s., 2 H) 4.94-5.29 (m, 2 H) 3.77-3.80 (m, 1 H) 1.89-2.07 (m, 2 H) 1.84 (s, 3 H) 1.76-1.80 (m, 1 H) 1.33-1.41 (m, 1 H) |
| 111 | A | commercial | 38 | 460 | ¹H NMR (400 MHz, DMSO-d₆) δ ppm 10.82 (s, 1 H) 9.20 (s, 1 H) 8.58 (dd, J = 8.19, 2.02 Hz, 1 H) 8.28 (d, J = 8.66 Hz, 1 H) 7.86-7.91 (m, 2 H) 7.17-7.25 (m, 1 H) 6.22 (br. s., 2 H) 4.88-5.24 (m, 2 H) 3.72-3.76 (m, 1 H) 1.83-2.08 (m, 3 H) 1.74 (s, 3 H) 1.30-1.34 (m, 1 H) |
| 112 | D | 48 | 39 | 557.0 | 1H NMR (300 MHz, DMSO-d6) δ ppm 1.31-1.47 (m, 1 H) 1.80 (s, 4 H) 1.88-2.05 (m, 2 H) 2.08 (s, 2 H) 3.73 (br. s., 1 H) 4.92 (d, J = 11.11 Hz, 1 H) 5.08 (d, J = 11.40 Hz, 1 H) 5.21 (q, J = 8.92 Hz, 3 H) 6.21 (br. s., 2 H) 7.09 (d, J = 5.85 Hz, 1 H) 7.16 (dd, J = 11.62, 8.84 Hz, 1 H) 7.95-8.05 (m, 1 H) 8.08 (br. s., 1 H) 8.26 (d, J = 5.85 Hz, 1 H) 8.73 (s, 1 H) 9.58 (s, 1 H) |
| 113 | B | commercial | 48B | 517.1 | ¹H NMR (400 MHz, DMSO-d₆) δ ppm 1.37-1.45 (m, 1 H) 1.48 (s, 3 H) 1.72-1.84 (m, 1 H) 1.98-2.13 (m, 2 H) 2.61 (s, 3 H) 3.85-3.93 (m, 1 H) 4.58-4.77 (m, 1 H) 4.91-5.09 (m, 1 H) 6.24-6.37 (m, 2 H) 7.14-7.23 (m, 1 H) 7.84-7.91 (m, 2 H) 8.26-8.32 (m, 1 H) 8.87-8.92 (m, 1 H) 10.39-10.91 (m, 1 H) |
| 114 | B | commercial | 48A | 517.1 | ¹H NMR (400 MHz, DMSO-d₆) δ ppm 1.37-1.45 (m, 1 H) 1.48 (s, 3 H) 1.72-1.84 (m, 1 H) 1.98-2.13 (m, 2 H) 2.61 (s, 3 H) 3.85-3.93 (m, 1 H) 4.58-4.77 (m, 1 H) 4.91-5.09 (m, 1 H) 6.24-6.37 (m, 2 H) 7.14-7.23 (m, 1 H) 7.84-7.91 (m, 2 H) 8.26-8.32 (m, 1 H) 8.87-8.92 (m, 1 H) 10.39-10.91 (m, 1 H) |
| 115 | B, no TFA | commercial | 49B | 517.1 | ¹H NMR (400 MHz, CHLOROFORM-d) δ ppm 1.68 (s, 3 H) 2.11-2.20 (m, 1 H) 2.43-2.56 (m, 2 H) 2.65-2.74 (m, 1 H) 2.86 (s, 3 H) 4.12-4.18 (m, 1 H) 4.46-4.63 (m, 1 H) 4.82-4.99 (m, 1 H) 7.06-7.15 (m, 1 H) 7.54-7.59 (m, 1 H) 7.85-7.88 (m, 1 H) 8.10-8.17 (m, 1 H) 8.67-8.72 (m, 1 H) 10.13-10.18 (m, 1 H) |
| 116 | B, no TFA | commercial | 49A | 517.1 | ¹H NMR (400 MHz, CHLOROFORM-d) δ ppm 1.68 (s, 3 H) 2.11-2.20 (m, 1 H) 2.43-2.56 (m, 2 H) 2.65-2.74 (m, 1 H) 2.86 (s, 3 H) 4.12-4.18 (m, 1 H) 4.46-4.63 (m, 1 H) 4.82-4.99 (m, 1 H) 7.06-7.15 (m, 1 H) 7.54-7.59 (m, 1 H) 7.85-7.88 (m, 1 H) 8.10-8.17 (m, 1 H) 8.67-8.72 (m, 1 H) 10.13-10.18 (m, 1 H) |
| 117 | B | 53 | 48B | 483 | ¹H NMR (400 MHz, DMSO-d₆) δ ppm 1.37-1.45 (m, 1 H) 1.46-1.50 (m, 3 H) 1.73-1.84 (m, 1 H) 1.98-2.14 (m, 2 H) 2.56-2.59 (m, 3 H) 3.83-3.93 (m, 1 H) 4.56-4.76 (m, 1 H) 4.89-5.09 (m, 1 H) 6.26-6.38 (m, 2 H) 7.11-7.21 (m, 1 H) 7.81-7.90 (m, 2 H) 8.00-8.05 (m, 1 H) 8.53-8.61 (m, 1 H) 10.49-10.58 (m, 1 H) |
| 118 | B | 53 | 48A | 483 | ¹H NMR (400 MHz, DMSO-d₆) δ ppm 1.37-1.45 (m, 1 H) 1.46-1.50 (m, 3 H) 1.73-1.84 (m, 1 H) 1.98-2.14 (m, 2 H) 2.56-2.59 (m, 3 H) 3.83-3.93 (m, 1 H) 4.56-4.76 (m, 1 H) 4.89-5.09 (m, 1 H) 6.26-6.38 (m, 2 H) 7.11-7.21 (m, 1 H) 7.81-7.90 (m, 2 H) 8.00-8.05 (m, 1 H) 8.53-8.61 (m, 1 H) 10.49-10.58 (m, 1 H) |
| 119 | B | commercial | 48B | 466.1 | ¹H NMR (400 MHz, DMSO-d₆) δ ppm 1.35-1.46 (m, 1 H) 1.46-1.51 (m, 3 H) 1.72-1.83 (m, 1 H) 1.93-2.06 (m, 1 H) 2.07-2.18 (m, 1 H) 3.85-3.91 (m, 1 H) 4.02 (s, 3 H) 4.58-4.76 (m, 1 H) 4.91-5.10 (m, 1 H) 6.26-6.40 (m, 2 H) 7.09-7.22 (m, 1 H) 7.80-7.89 (m, 1 H) 7.95-8.02 (m, 1 H) 8.39-8.44 (m, 1 H) 8.87-8.92 (m, 1 H) 10.33-10.85 (m, 1 H) |
| 120 | B | commercial | 48A | 466.1 | ¹H NMR (400 MHz, DMSO-d₆) δ ppm 1.35-1.46 (m, 1 H) 1.46-1.51 (m, 3 H) 1.72-1.83 (m, 1 H) 1.93-2.06 (m, 1 H) 2.07-2.18 (m, 1 H) 3.85-3.91 (m, 1 H) 4.02 (s, 3 H) 4.58-4.76 (m, 1 H) 4.91-5.10 (m, 1 H) 6.26-6.40 (m, 2 H) 7.09-7.22 (m, 1 H) 7.80-7.89 (m, 1 H) 7.95-8.02 (m, 1 H) 8.39-8.44 (m, 1 H) 8.87-8.92 (m, 1 H) 10.33-10.85 (m, 1 H) |
| 121 | B | commercial (Aldrich) | 12 | 502.1 | ¹H NMR (400 MHz, DMSO-d₆) δ = 10.71 (s, 1H), 7.92-7.83 (m, 2H), 7.81-7.71 (m, 3H), 7.24-7.16 (m, 1H), 6.3 (br.s., 2H), 3.74 (d, J = 4.5 Hz, 1H), 2.04-1.89 (m, 2H), 1.81-1.72 (m, 4H), 1.47 (s, 3H), 1.43-1.22 (m, 1H) |
| 122 | B | commercial (Aldrich) | 13 | 502.1 | ¹H NMR (400 MHz, DMSO-d₆) δ = 10.69 (s, 1H), 7.91-7.77 (m, 3H), 7.70 (d, J = 7.7 Hz, 1H), 7.60 (dd, J = 2.7, 7.4 Hz, |

TABLE 2-continued

| Example No | Synthetic Method | Intermediate L | Intermediate R | Mass - Observed [M + H]+ | NMR |
|---|---|---|---|---|---|
| | | | | | 1H), 7.14 (dd, J = 8.8, 12.1 Hz, 1H), 3.83-3.75 (m, 1H), 2.52-2.42 (m, 1H), 2.33-2.15 (m, 2H), 1.96-1.85 (m, 1H), 1.52 (s, 3H), 1.43 (s, 3H) |
| 123 | B | commercial (Matrix) | 12 | 464.1 | $^1$H NMR (400 MHz, DMSO-d$_6$) δ = 10.27 (s, 1H), 7.89-7.69 (m, 2H), 7.64 (t, J = 8.6 Hz, 1H), 7.22 (m, 1H), 6.98 (dd, J = 2.0, 12.5 Hz, 1H), 6.91 (dd, J = 2.3, 8.7 Hz, 1H), 6.28-5.80 (m, 2H), 3.88-3.81 (m, 4H), 2.19-1.94 (m, 2H), 1.94-1.68 (m, 4H), 1.63-1.43 (m, 3H), 1.36 (m, 1H) |
| 124 | B | commercial (Matrix) | 13 | 464.0 | $^1$H NMR (400 MHz, DMSO-d$_6$) δ = 10.22 (s, 1H), 7.75-7.68 (m, 1H), 7.66-7.56 (m, 2H), 7.08 (dd, J = 8.8, 12.1 Hz, 1H), 6.95-6.86 (m, 2H), 6.32-5.86 (m, 2H), 3.75 (d, J = 6.2 Hz, 1H), 2.50-2.30 (m, 1H), 2.28-2.13 (m, 2H), 1.92-1.82 (m, 1H), 1.49 (s, 3H), 1.41 (s, 3H) |
| 125 | B | commercial (Matrix) | 12 | 530.0, 532.0 (2 Br isotopes) | $^1$H NMR (400 MHz, DMSO-d$_6$) δ = 10.92 (s, 1H), 7.80-7.65 (m, 4H), 7.21 (dd, J = 8.9, 11.6 Hz, 1H), 6.30 (br.s., 1H), 3.90-3.64 (m, 1H), 2.03-1.90 (m, 2H), 1.85-1.68 (m, 4H), 1.47 (s, 3H), 1.39-1.22 (m, 1H) |
| 126 | B | commercial (Matrix) | 13 | 530.0, 532.0 (2 Br isotopes) | $^1$H NMR (400 MHz, DMSO-d$_6$) δ = 10.86 (s, 1H), 7.84-7.78 (m, 1H), 7.67-7.62 (m, 2H), 7.50 (dd, J = 2.7, 7.3 Hz, 1H), 7.12 (dd, J = 8.9, 12.1 Hz, 1H), 6.30 (br.s., 2H), 3.73 (d, J = 6.3 Hz, 1H), 2.45-2.32 (m, 1H), 2.28-2.13 (m, 2H), 1.92-1.82 (m, 1H), 1.49 (s, 3H), 1.41 (s, 3H) |
| 127 | B | commercial (Matrix) | 12 | 459.0 | $^1$H NMR (400 MHz, DMSO-d$_6$) δ = 10.77 (s, 1H), 8.06 (d, J = 10.0 Hz, 1H), 7.87-7.76 (m, 4H), 7.25 (br. s., 1H), 2.10-1.95 (m, 2H), 1.92-1.79 (m, 4H), 1.51 (br. s., 3H), 1.42-1.30 (m, 1H) |
| 128 | B | commercial (Matrix) | 13 | 459.1 | $^1$H NMR (400 MHz, DMSO-d$_6$) δ = 10.73 (s, 1H), 8.03 (d, J = 9.9 Hz, 1H), 7.86-7.78 (m, 3H), 7.59 (dd, J = 2.7, 7.4 Hz, 1H), 7.13 (dd, J = 8.8, 12.1 Hz, 1H), 6.20 (br.s., 2H), 3.77 (d, J = 6.2 Hz, 1H), 2.47-2.35 (m, 1H), 2.30-2.15 (m, 2H), 1.96-1.75 (m, 1H), 1.51 (s, 3H), 1.42 (s, 3H) |
| 129 | B | 35 | 13 | 502.1 | $^1$H NMR (400 MHz, DMSO-d$_6$) δ = 10.26 (s, 1H), 7.75-7.67 (m, 1H), 7.67-7.57 (m, 2H), 7.08 (dd, J = 8.8, 12.1 Hz, 1H), 6.98-6.88 (m, 2H), 6.10 (br. s., 2H), 4.87-4.82 (m, 2H), 3.75 (d, J = 6.7 Hz, 1H), 2.45-2.32 (m, 1H), 2.27-2.13 (m, 2H), 1.92-1.79 (m, 4H), 1.49 (s, 3H), 1.41 (s, 3H) |
| 130 | C | 21 | 12 | 475.1 | $^1$H NMR (400 MHz, DMSO-d$_6$) δ = 10.41 (br. s., 1H), 8.92 (d, J = 2.5 Hz, 1H), 8.65 (s, 1H), 8.39 (d, J = 2.3 Hz, 1H), 8.08 (dd, J = 2.8, 7.2 Hz, 1H), 7.97 (td, J = 3.7, 8.2 Hz, 1H), 7.21 (dd, J = 8.8, 11.7 Hz, 1H), 6.14 (br.s., 1H), 3.67 (d, J = 6.0 Hz, 1H), 2.32-2.07 (m, 1H), 2.03-1.87 (m, 1H), 1.81-1.72 (m, 4H), 1.51-1.45 (m, 3H), 1.45-1.28 (m, 1H) |
| 131 | C | 21 | 13 | 475.1 | $^1$H NMR (400 MHz, DMSO-d$_6$) δ = 10.15 (br. s., 1H), 8.94 (d, J = 2.2 Hz, 1H), 8.70 (s, 1H), 8.40 (d, J = 2.2 Hz, 1H), 8.07 (d, J = 4.7 Hz, 1H), 7.92 (br. s., 1H), 7.16 (dd, J = 8.8, 12.1 Hz, 1H), 6.04 (br. s., 2H), 3.77 (br. s., 1H), 2.48-2.37 (m, 1H), 2.29-2.13 (m, 2H), 1.97-1.81 (m, 1H), 1.53 (s, 3H), 1.47-1.37 (m, 3H) |
| 132 | C | 20 | 12 | 471.0 | $^1$H NMR (400 MHz, DMSO-d$_6$) δ = 10.31 (br. s., 1H), 8.68-8.62 (m, 2H), 8.41-8.19 (m, 1H), 8.04 (dd, J = 2.7, 7.3 Hz, 1H), 7.65 (d, J = 2.7 Hz, 1H), 7.34 (br. s., 1H), 4.01 (s, 3H), 2.22-1.88 (m, 3H), 1.61 (br. s., 4H), 1.48-1.35 (m, 1H), 1.32-1.19 (m, 3H) |
| 133 | C | 20 | 13 | 471.2 | $^1$H NMR (400 MHz, DMSO-d$_6$) δ = 10.03 (br. s., 1H), 8.64 (s, 2H), 8.22-7.98 (m, 2H), 7.62 (d, J = 2.7 Hz, 1H), 7.21 (t, J = 10.2 Hz, 1H), 4.02-3.98 (m, 4H), 2.64-2.53 (m, 1H), 2.38-2.21 (m, 1H), 2.12-1.94 (m, 1H), 1.77-1.60 (m, 4H), 1.51 (br. s., 3H) |
| 134 | D | 36 | 12 | 526.1 | $^1$H NMR (400 MHz, DMSO-d$_6$) δ = 9.35 (s, 1H), 8.72 (d, J = 2.8 Hz, 1H), 8.11 (dd, J = 3.6, 8.2 Hz, 1H), 8.08 (d, J = 1.7 Hz, 1H), 8.00 (dd, J = 2.8, 7.2 Hz, 1H), 7.77 (d, J = 2.8 Hz, 1H), 7.13 (dd, J = 8.9, 11.7 Hz, 1H), 6.06 (br. s., 2H), 5.10-5.06 (m, 2H), 3.66 (d, J = 6.0 Hz, 1H), 2.16-2.04 (m, 1H), 2.01-1.89 (m, 1H), 1.87 (t, J = 2.3 Hz, 3H), 1.79-1.71 (m, 4H), 1.47 (s, 3H), 1.43-1.32 (m, 1H) |
| 135 | D | 36 | 12 | 526.1 | $^1$H NMR (400 MHz, DMSO-d$_6$) δ = 9.06 (br. s., 1H), 8.73 (d, J = 2.8 Hz, 1H), 8.18-8.12 (m, 1H), 8.11 (d, J = 1.8 Hz, 1H), 7.84-7.75 (m, 2H), 7.13-7.05 (m, J = 8.9, 12.1 Hz, 1H), 6.13 (br. s., 2H), 5.08 (d, J = 2.3 Hz, 2H), 3.76 (d, J = 4.1 Hz, 1H), 2.46-2.36 (m, 1H), 2.29-2.13 (m, 2H), 1.87 (t, J = 2.3 Hz, 4H), 1.52 (s, 3H), 1.42 (s, 3H) |

TABLE 2-continued

| Example No | Synthetic Method | Intermediate L | Intermediate R | Mass - Observed [M + H]+ | NMR |
|---|---|---|---|---|---|
| 136 | D | synthesized analogous to 36 | 13 | 528.2 | ¹H NMR (400 MHz, DMSO-d₆) δ = 9.03 (s, 1H), 8.73 (d, J = 2.8 Hz, 1H), 8.19-8.13 (m, 1H), 8.08 (d, J = 1.8 Hz, 1H), 7.79 (dd, J = 2.7, 7.2 Hz, 1H), 7.64 (d, J = 2.8 Hz, 1H), 7.09 (dd, J = 8.9, 12.1 Hz, 1H), 6.21 (br.s., 2H), 4.10 (d, J = 7.1 Hz, 2H), 3.77 (d, J = 5.5 Hz, 1H), 2.47-2.36 (m, 1H), 2.30-2.13 (m, 2H), 1.95-1.82 (m, 1H), 1.52 (s, 3H), 1.42 (s, 3H), 1.38-1.28 (m, 2H), 0.68-0.59 (m, 2H), 0.45-0.37 (m, 2H) |
| 137 | D | synthesized analogous to 36 | 12 | 528.2 | ¹H NMR (400 MHz, DMSO-d₆) δ = 9.33 (s, 1H), 8.72 (d, J = 2.8 Hz, 1H), 8.16-8.08 (m, 1H), 8.08-8.03 (m, 1H), 7.99 (dd, J = 2.8, 7.2 Hz, 1H), 7.65 (d, J = 2.8 Hz, 1H), 7.13 (dd, J = 8.9, 11.7 Hz, 1H), 6.06 (br. s., 2H), 4.11 (d, J = 7.1 Hz, 2H), 3.66 (d, J = 5.8 Hz, 1H), 2.17-2.03 (m, 1H), 2.01-1.88 (m, 1H), 1.82-1.67 (m, 4H), 1.47 (s, 3H), 1.42-1.26 (m, 2H), 0.69-0.60 (m, 2H), 0.46-0.38 (m, 2H) |
| 138 | B | 35 | 12 | 502.2 | ¹H NMR (500 MHz, DMSO-d₆) δ = 10.25 (br. s., 1H), 7.78 (d, J = 4.8 Hz, 1H), 7.72 (br. s., 1H), 7.63 (t, J = 8.5 Hz, 1H), 7.15 (dd, J = 9.0, 11.4 Hz, 1H), 7.02-6.87 (m, 2H), 5.99 (br. s., 2H), 4.85 (d, J = 2.0 Hz, 2H), 3.74-3.62 (m, 1H), 1.97 (br. s., 2H), 1.85 (s, 3H), 1.81-1.68 (m, 4H), 1.46 (s, 3H), 1.32 (br. s., 1H) |
| 139 | C | 37 | 12 | 511.1 | ¹H NMR (400 MHz, DMSO-d₆) δ = 10.09 (s, 1H), 8.64 (d, J = 2.7 Hz, 1H), 8.57 (s, 1H), 8.09-7.97 (m, 2H), 7.54 (d, J = 2.7 Hz, 1H), 7.18 (dd, J = 8.8, 11.5 Hz, 1H), 6.06 (br.s., 2H), 4.07 (d, J = 7.1 Hz, 2H), 3.68 (br. s., 1H), 2.20-2.06 (m, 1H), 2.00-1.87 (m, 1H), 1.81-1.69 (m, 4H), 1.47 (m, 3H), 1.40-1.26 (m, 2H), 0.69-0.57 (m, 2H), 0.43-0.37 (m, 2H) |
| 140 | D | 31 | 12 | 538.0 | ¹H NMR (400 MHz, DMSO-d₆) δ = 9.50 (s, 1H), 8.65 (s, 1H), 8.26-8.19 (m, 2H), 8.13-8.05 (m, 1H), 8.00 (dd, J = 2.9, 7.3 Hz, 1H), 7.31 (d, J = 0.8 Hz, 1H), 7.15 (dd, J = 8.9, 11.8 Hz, 1H), 7.05 (d, J = 5.8 Hz, 1H), 6.11 (br.s., 2H), 5.66 (s, 2H), 3.67 (d, J = 6.0 Hz, 1H), 2.20-2.03 (m, 1H), 2.01-1.89 (m, 1H), 1.82-1.70 (m, 4H), 1.47 (s, 3H), 1.44-1.30 (m, 1H) |
| 141 | D | 21 | 34 | 505.1 | ¹H NMR (400 MHz, DMSO-d₆) δ = 10.13 (br. s., 1H), 8.92 (d, J = 2.3 Hz, 1H), 8.69 (s, 1H), 8.39 (d, J = 2.3 Hz, 1H), 8.04 (dd, J = 2.8, 7.5 Hz, 1H), 7.96-7.91 (m, 1H), 7.15 (dd, J = 8.9, 12.1 Hz, 1H), 5.99 (br. s., 2H), 3.86 (q, J = 12.9 Hz, 2H), 3.74 (d, J = 6.1 Hz, 1H), 3.32 (s, 3H), 2.47-2.37 (m, 1H), 2.27-2.13 (m, 2H), 1.98-1.90 (m, 1H), 1.53 (s, 3H) |
| 142 | A | 53 | 34 | 495.0 | ¹H NMR (400 MHz, DMSO-d₆) δ = 10.62 (br. s., 1H), 8.56 (d, J = 2.3 Hz, 1H), 8.02 (dd, J = 0.6, 2.3 Hz, 1H), 7.94 (d, J = 8.8 Hz, 1H), 7.69 (dd, J = 2.4, 7.4 Hz, 1H), 7.20 (dd, J = 9.2, 11.5 Hz, 1H), 4.21-3.95 (m, 2H), 3.88 (d, J = 11.5 Hz, 1H), 3.32 (s, 3H), 2.60-2.52 (m, 4H), 2.49-2.30 (m, 2H), 2.14-2.02 (m, 1H), 1.71 (s, 3H) |
| 143 | D | synthesized analogous to 31 | 12 | 513.2 | ¹H NMR (400 MHz, DMSO-d₆) δ = 9.44 (br. s., 1H), 8.55 (s, 1H), 8.20 (d, J = 5.8 Hz, 1H), 8.18-8.06 (m, 1H), 7.98 (dd, J = 2.8, 7.3 Hz, 1H), 7.14 (dd, J = 8.9, 11.7 Hz, 1H), 7.04 (d, J = 5.8 Hz, 1H), 6.05 (br. s., 2H), 4.25 (d, J = 6.6 Hz, 2H), 3.66 (d, J = 5.9 Hz, 1H), 2.19-2.06 (m, 2H), 2.01-1.88 (m, 1H), 1.82-1.70 (m, 4H), 1.47 (s, 3H), 1.43-1.32 (m, 1H), 1.04 (d, J = 6.7 Hz, 6H) |
| 144 | D | synthesized analogous to 31 | 12 | 499.0 | ¹H NMR (400 MHz, DMSO-d₆) δ = 9.43 (br. s., 1H), 8.53 (s, 1H), 8.20 (d, J = 5.9 Hz, 1H), 8.14-8.07 (m, 1H), 7.98 (dd, J = 2.9, 7.3 Hz, 1H), 7.14 (dd, J = 8.8, 11.7 Hz, 1H), 7.03 (d, J = 5.8 Hz, 1H), 6.05 (br. s., 2H), 4.42 (t, J = 6.7 Hz, 2H), 3.66 (d, J = 6.2 Hz, 1H), 2.17-2.05 (m, 1H), 1.99-1.89 (m, 1H), 1.88-1.68 (m, 4H), 1.77 (s, 3H), 1.47 (s, 3H), 1.44-1.31 (m, 2H), 1.03 (t, J = 7.4 Hz, 3H) |
| 145 | D | synthesized analogous to 31 | 12 | 515.0 | ¹H NMR (400 MHz, DMSO-d₆) δ = 9.44 (br. s., 1H), 8.58 (s, 1H), 8.21 (d, J = 5.8 Hz, 1H), 8.14-8.07 (m, 1H), 7.98 (dd, J = 2.9, 7.3 Hz, 1H), 7.14 (dd, J = 8.9, 11.7 Hz, 1H), 7.04 (d, J = 5.8 Hz, 1H), 6.04 (br. s., 2H), 4.61-4.57 (m, 2H), 3.78-3.73 (m, 2H), 3.66 (d, J = 5.7 Hz, 1H), 3.32 (s, 3H), 2.17-2.06 (m, 1H), 2.00-1.89 (m, 1H), 1.81-1.68 (m, 4H), 1.47 (s, 3H), 1.42-1.31 (m, 1H) |
| 146 | D | synthesized analogous to 31 | 12 | 551.9 | ¹H NMR (400 MHz, DMSO-d₆) δ = 9.48 (s, 1H), 8.64 (s, 1H), 8.23 (d, J = 5.9 Hz, 1H), 8.14-8.05 (m, 1H), 8.00 (dd, J = 2.8, 7.3 Hz, 1H), 7.14 (dd, J = 8.9, 11.7 Hz, 1H), 7.06 (d, J = 5.9 Hz, 1H), 6.92 (q, J = 1.1 Hz, 1H), 6.04 (br. s., 2H), 5.57 (s, 2H), 3.66 (d, J = 5.9 Hz, 1H), 2.33 (d, J = 1.2 Hz, 3H), 2.19-2.05 (m, 1H), 2.03-1.87 (m, 1H), 1.81-1.70 (m, 1H), 1.77 (s, 3H), 1.47 (s, 3H), 1.37 (br. s., 1H) |

TABLE 2-continued

| Example No | Synthetic Method | Intermediate L | Intermediate R | Mass - Observed [M + H]+ | NMR |
|---|---|---|---|---|---|
| 147 | D | synthesized analogous to 31 | 12 | 551.0 | $^1$H NMR (400 MHz, DMSO-$d_6$) δ = 9.46 (br. s., 1H), 8.55 (s, 1H), 8.23 (d, J = 5.8 Hz, 1H), 8.10 (d, J = 6.6 Hz, 1H), 7.99 (dd, J = 2.9, 7.3 Hz, 1H), 7.70 (d, J = 2.2 Hz, 1H), 7.15 (dd, J = 9.0, 11.7 Hz, 1H), 7.10 (d, J = 5.9 Hz, 1H), 6.41 (d, J = 2.2 Hz, 1H), 6.07 (br. s., 1H), 5.45 (s, 2H), 3.85 (s, 3H), 3.76-3.63 (m, 1H), 2.13 (br. s., 1H), 2.03-1.89 (m, 1H), 1.83-1.70 (m, 4H), 1.48 (s, 3H), 1.43-1.33 (m, 1H) |
| 148 | D | synthesized analogous to 17 | 38 | 475.0 | $^1$H NMR (400 MHz, DMSO-$d_6$) δ = 9.20 (s, 1H), 8.10 (s, 1H), 8.06 (d, J = 5.7 Hz, 1H), 8.02-7.96 (m, 1H), 7.87 (dd, J = 2.8, 7.3 Hz, 1H), 7.13 (dd, J = 8.8, 11.7 Hz, 1H), 6.61 (d, J = 5.7 Hz, 1H), 5.25-4.89 (m, 2H), 3.73 (d, J = 4.9 Hz, 1H), 2.06-1.88 (m, 2H), 1.85-1.74 (m, 5H), 1.48-1.32 (m, 1H) |

Table 3 hereinbelow includes the biological data (average μM IC$_{50}$'s for the BACE 1 enzyme and cell assays, BACE 2 enzyme assay and CatD enzyme assay) for each compound example, where available.

TABLE 3

| Example No | Compound Name | BACE1 Enzyme assay IC$_{50}$ (uM) | BACE1 cell assay IC$_{50}$ (uM) | BACE2 Enzyme assay IC$_{50}$ (uM) | CatD IC50 (μM) |
|---|---|---|---|---|---|
| 40 | 4-((3-((1S,2R,5R)-4-amino-5-(fluoromethyl)-2-methyl-8,8-dioxido-8-thia-3-azabicyclo[3.2.1]oct-3-en-2-yl)-4-fluorophenyl)amino)pyrido[3,2-d]pyrimidine-7-carbonitrile | 0.008 | 0.035 | 0.022 | 650.44 |
| 41 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-2-methoxypyrido[3,4-b]pyrazin-5-amine | 0.009 | 0.015 | 0.010 | 867.43 |
| 42 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-methoxy-3-methyl-2-pyridinecarboxamide | 0.013 | 0.030 | 0.003 | 757.35 |
| 43 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-3-fluoro-5-methoxy-2-pyridinecarboxamide | 0.009 | 0.007 | 0.014 | >400.0 |
| 38 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-((4,4-dimethyl-2-pentyn-1-yl)oxy)-2-pyrazinecarboxamide | 0.004 | 0.031 | 0.011 | 436.69 |
| 44 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-((1,1-dimethyl-2-propyn-1-yl)oxy)-2-pyrazinecarboxamide | 0.034 | 0.153 | 0.283 | >400.0 |
| 45 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-(((1S)-1-methyl-2-propyn-1-yl)oxy)-2-pyrazinecarboxamide | 0.003 | 0.003 | 0.019 | 595.77 |
| 46 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-2-(2-propyn-1-yloxy)pyrido[3,4-b]pyrazin-5-amine | 0.001 | 0.005 | 0.009 | 1003.7 |
| 47 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-7-bromopyrido[3,2-d]pyrimidin-4-amine | 0.007 | 0.036 | 0.002 | 174 |

TABLE 3-continued

| Example No | Compound Name | BACE1 Enzyme assay IC$_{50}$ (uM) | BACE1 cell assay IC$_{50}$ (uM) | BACE2 Enzyme assay IC$_{50}$ (uM) | CatD IC50 (μM) |
|---|---|---|---|---|---|
| 48 | N-(3-((1S,2R,5R)-4-amino-1,2,5-trimethyl-8,8-dioxido-8-thia-3-azabicyclo[3.2.1]oct-3-en-2-yl)-4-fluorophenyl)-3-methyl-5-(trifluoromethyl)-2-pyridinecarboxamide | 0.011 | 0.004 | | 54.1 |
| 49 | N-(3-((1R,2R,5S)-4-amino-1,2,5-trimethyl-8,8-dioxido-8-thia-3-azabicyclo[3.2.1]oct-3-en-2-yl)-4-fluorophenyl)-3-methyl-5-(trifluoromethyl)-2-pyridinecarboxamide | 0.011 | 0.004 | | 66.6 |
| 50 | N-(3-((1S,2R,5R)-4-amino-1,2,5-trimethyl-8,8-dioxido-8-thia-3-azabicyclo[3.2.1]oct-3-en-2-yl)-4-fluorophenyl)-3-chloro-5-fluoro-1,7-naphthyridin-8-amine | 0.004 | 0.28 | | 12.05 |
| 51 | N-(3-((1R,2R,5S)-4-amino-1,2,5-trimethyl-8,8-dioxido-8-thia-3-azabicyclo[3.2.1]oct-3-en-2-yl)-4-fluorophenyl)-3-chloro-5-fluoro-1,7-naphthyridin-8-amine | 0.011 | 0.381 | | 21.5 |
| 52 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-(2-propyn-1-yloxy)-2-pyridinecarboxamide | 0.001 | 0.004 | 0.018 | 810.63 |
| 53 | 8-((3-((1S,2R,5R)-4-amino-5-(fluoromethyl)-2-methyl-8,8-dioxido-8-thia-3-azabicyclo[3.2.1]oct-3-en-2-yl)-4-fluorophenyl)amino)-5-fluoro-1,7-naphthyridine-3-carbonitrile | 0.003 | 0.038 | 0.002 | >14.8 |
| 54 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-3-chloro-5-fluoro-1,7-naphthyridin-8-amine | 0.002 | 0.090 | 0.002 | 755.35 |
| 55 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-2-(trifluoromethyl)pyrido[3,4-b]pyrazin-5-amine | 0.018 | 0.351 | 0.024 | >133.0 |
| 56 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-3-methoxy-1,7-naphthyridin-8-amine | 0.0188 | 0.0167 | 0.0185 | >400.0 |
| 57 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-3-methyl-5-(2,2,2-trifluoroethoxy)-2-pyrazinecarboxamide | 0.003 | 0.048 | 0.076 | >400.0 |
| 58 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-3-chloro-1,7-naphthyridin-8-amine | 0.001 | 0.046 | 0.002 | 341.92 |
| 59 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-3-methyl-5-(2-propyn-1-yloxy)-2-pyrazinecarboxamide | 0.001 | 0.001 | 0.003 | 836.73 |
| 60 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-3-chloro-5-(2-propyn-1-yloxy)-2-pyridinecarboxamide | 0.001 | 0.008 | 0.010 | 952.92 |
| 61 | N-(3-((1S,2R,5R)-4-amino-2,5-dimethyl-8,8-dioxido-8-thia-3-azabicyclo[3.2.1]oct-3-en-2-yl)-4-fluorophenyl)-5-methoxy-2-pyrazinecarboxamide | 0.005 | 0.002 | 0.007 | 2498.7 |
| 62 | N-(3-((1S,2R,5R)-4-amino-2,5-dimethyl-8,8-dioxido-8-thia-3-azabicyclo[3.2.1]oct-3-en-2-yl)-4-fluorophenyl)-2-(2-butyn-1-yloxy)pyrido[3,4-b]pyrazin-5-amine | 0.001 | 0.001 | 0.007 | 123.65 |
| 63 | N-(3-((1R,2R,5S)-4-amino-2,5-dimethyl-8,8-dioxido-8-thia-3-azabicyclo[3.2.1]oct-3-en-2-yl)-4-fluorophenyl)-2-(2-butyn-1-yloxy)pyrido[3,4-b]pyrazin-5-amine | 0.003 | 0.002 | 0.321 | 1175.4 |

TABLE 3-continued

| Example No | Compound Name | BACE1 Enzyme assay IC$_{50}$ (uM) | BACE1 cell assay IC$_{50}$ (uM) | BACE2 Enzyme assay IC$_{50}$ (uM) | CatD IC50 (μM) |
|---|---|---|---|---|---|
| 64 | N-(3-((1S,2R,5R)-4-amino-2,5-dimethyl-8,8-dioxido-8-thia-3-azabicyclo[3.2.1]oct-3-en-2-yl)-4-fluorophenyl)-5-(cyclopropylethynyl)-2-pyridinecarboxamide | 0.001 | 0.005 | | 469.88 |
| 65 | N-(3-((1R,2R,5S)-4-amino-2,5-dimethyl-8,8-dioxido-8-thia-3-azabicyclo[3.2.1]oct-3-en-2-yl)-4-fluorophenyl)-5-(cyclopropylethynyl)-2-pyridinecarboxamide | 0.007 | 0.016 | | >400.0 |
| 66 | N-(3-((1R,2R,5S)-4-amino-2,5-dimethyl-8,8-dioxido-8-thia-3-azabicyclo[3.2.1]oct-3-en-2-yl)-4-fluorophenyl)-5-methoxy-2-pyrazinecarboxamide | 0.070 | 0.018 | | >400.0 |
| 67 | N-(3-((1R,2R,5S)-4-amino-2,5-dimethyl-8,8-dioxido-8-thia-3-azabicyclo[3.2.1]oct-3-en-2-yl)-4-fluorophenyl)-2-(cyclopropylmethoxy)pyrido[3,4-b]pyrazin-5-amine | 0.156 | 0.522 | | 99.3 |
| 68 | N-(3-((1S,2R,5R)-4-amino-2,5-dimethyl-8,8-dioxido-8-thia-3-azabicyclo[3.2.1]oct-3-en-2-yl)-4-fluorophenyl)-2-(cyclopropylmethoxy)pyrido[3,4-b]pyrazin-5-amine | 0.005 | 0.033 | | >400.0 |
| 69 | N-(3-((1S,2R,5R)-4-amino-2,5-dimethyl-8,8-dioxido-8-thia-3-azabicyclo[3.2.1]oct-3-en-2-yl)-4-fluorophenyl)-5-(1-propyn-1-yl)-2-pyridinecarboxamide | 0.002 | 0.003 | | >133.0, >400.0 |
| 70 | N-(3-((1S,2R,5R)-4-amino-2,5-dimethyl-8,8-dioxido-8-thia-3-azabicyclo[3.2.1]oct-3-en-2-yl)-4-fluorophenyl)-5-(((1R)-1-methyl-2-butyn-1-yl)oxy)-2-pyrazinecarboxamide | 0.014 | 0.007 | 0.050 | >400.0 |
| 71 | N-(3-((1S,2R,5R)-4-amino-2,5-dimethyl-8,8-dioxido-8-thia-3-azabicyclo[3.2.1]oct-3-en-2-yl)-4-fluorophenyl)-5-(((1S)-1-methyl-2-butyn-1-yl)oxy)-2-pyrazinecarboxamide | 0.003 | 0.0001 | 0.008 | >400.0 |
| 72 | N-(3-((1R,2S,5S)-4-amino-2-(fluoromethyl)-5-methyl-8,8-dioxido-8-thia-3-azabicyclo[3.2.1]oct-3-en-2-yl)-4-fluorophenyl)-5-chloro-3-methyl-2-pyridinecarboxamide | 0.024 | 0.111 | | >400.0 |
| 75 | N-(3-((1R,2S,5S)-4-amino-2-(fluoromethyl)-5-methyl-8,8-dioxido-8-thia-3-azabicyclo[3.2.1]oct-3-en-2-yl)-4-fluorophenyl)-5-methoxy-2-pyrazinecarboxamide | 0.097 | 0.095 | | >400.0 |
| 39 | 8-((3-((1S,2R,5R)-4-amino-2,5-dimethyl-8,8-dioxido-8-thia-3-azabicyclo[3.2.1]oct-3-en-2-yl)-4-fluorophenyl)amino)-5-fluoro-1,7-naphthyridin-3-ol | 0.001 | 0.009 | | 191 |
| 76 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-methoxy-3-methyl-2-pyrazinecarboxamide | 0.010 | 0.008 | 0.004 | 1061.2 |
| 77 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-chloro-2-pyridinecarboxamide | 0.003 | 0.003 | 0.001 | 569.72 |
| 78 | N-(3-((1S,2R,5R)-4-amino-2,5-dimethyl-8,8-dioxido-8-thia-3-azabicyclo[3.2.1]oct-3-en-2-yl)-4-fluorophenyl)-5-fluoro-3-methoxy-1,7-naphthyridin-8-amine | 0.003 | 0.012 | 0.005 | 3235.3 |
| 79 | N-(3-((1S,2R,5R)-4-amino-2,5-dimethyl-8,8-dioxido-8-thia-3-azabicyclo[3.2.1]oct-3-en-2-yl)-4-fluorophenyl)-5-methoxy-3-methyl-2-pyrazinecarboxamide | 0.009 | 0.003 | | 1828.1 |
| 80 | N-(3-((1S,2R,5R)-4-amino-2,5-dimethyl-8,8-dioxido-8-thia-3-azabicyclo[3.2.1]oct-3-en-2-yl)-4-fluorophenyl)-2-methoxypyrido[3,4-b]pyrazin-5-amine | 0.008 | 0.006 | 0.015 | >400.0 |
| 81 | N-(3-((1R,2R,5S)-4-amino-2,5-dimethyl-8,8-dioxido-8-thia-3-azabicyclo[3.2.1]oct-3-en-2-yl)-4-fluorophenyl)-2-methoxypyrido[3,4-b]pyrazin-5-amine | 0.225 | 0.062 | | >348.0 |

TABLE 3-continued

| Example No | Compound Name | BACE1 Enzyme assay IC$_{50}$ (uM) | BACE1 cell assay IC$_{50}$ (uM) | BACE2 Enzyme assay IC$_{50}$ (uM) | CatD IC50 (μM) |
|---|---|---|---|---|---|
| 82 | N-(3-((1S,2R,5R)-4-amino-2,5-dimethyl-8,8-dioxido-8-thia-3-azabicyclo[3.2.1]oct-3-en-2-yl)-4-fluorophenyl)-5-(2-butyn-1-yloxy)-2-pyrazinecarboxamide | 0.0005 | 0.00007 | 0.003 | 717.19 |
| 83 | N-(3-((1R,2R,5S)-4-amino-2,5-dimethyl-8,8-dioxido-8-thia-3-azabicyclo[3.2.1]oct-3-en-2-yl)-4-fluorophenyl)-5-(2-butyn-1-yloxy)-2-pyrazinecarboxamide | 0.001 | 0.0005 | 0.082 | 1103.2 |
| 84 | 8-((3-((1S,2R,5R)-4-amino-2,5-dimethyl-8,8-dioxido-8-thia-3-azabicyclo[3.2.1]oct-3-en-2-yl)-4-fluorophenyl)amino)-1,7-naphthyridine-3-carbonitrile | 0.002 | 0.003 | 0.002 | >118.0 |
| 85 | 8-((3-((1R,2R,5S)-4-amino-2,5-dimethyl-8,8-dioxido-8-thia-3-azabicyclo[3.2.1]oct-3-en-2-yl)-4-fluorophenyl)amino)-1,7-naphthyridine-3-carbonitrile | 0.013 | 0.011 | 0.024 | 1453.5 |
| 86 | N-(3-((1S,2R,5R)-4-amino-2,5-dimethyl-8,8-dioxido-8-thia-3-azabicyclo[3.2.1]oct-3-en-2-yl)-4-fluorophenyl)-2-(trifluoromethyl)pyrido[3,4-b]pyrazin-5-amine | 0.023 | 0.067 | | >44.4 |
| 87 | N-(3-((1R,2R,5S)-4-amino-2,5-dimethyl-8,8-dioxido-8-thia-3-azabicyclo[3.2.1]oct-3-en-2-yl)-4-fluorophenyl)-2-(trifluoromethyl)pyrido[3,4-b]pyrazin-5-amine | 0.084 | 0.313 | | >44.4 |
| 88 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-chloro-3-methyl-2-pyridinecarboxamide | 0.003 | 0.005 | 0.0008 | 684.74 |
| 89 | N-(3-((1R,2R,5S)-4-amino-5-(fluoromethyl)-2-methyl-8,8-dioxido-8-thia-3-azabicyclo[3.2.1]oct-3-en-2-yl)-4-fluorophenyl)-5-chloro-3-methyl-2-pyridinecarboxamide | 0.016 | 0.053 | 0.006 | 1552 |
| 90 | N-(3-((1S,2R,5R)-4-amino-2,5-dimethyl-8,8-dioxido-8-thia-3-azabicyclo[3.2.1]oct-3-en-2-yl)-4-fluorophenyl)-5-(methoxymethyl)-2-pyridinecarboxamide | 0.057 | 0.020 | | 3416.5 |
| 91 | N-(3-((1R,2R,5S)-4-amino-2,5-dimethyl-8,8-dioxido-8-thia-3-azabicyclo[3.2.1]oct-3-en-2-yl)-4-fluorophenyl)-5-(methoxymethyl)-2-pyridinecarboxamide | 0.255 | 0.046 | | 3256.7 |
| 92 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-3-methyl-5-(trifluoromethyl)-2-pyridinecarboxamide | 0.004 | 0.005 0175 | | 789.47 |
| 93 | N-(3-((1R,2R,5S)-4-amino-5-(fluoromethyl)-2-methyl-8,8-dioxido-8-thia-3-azabicyclo[3.2.1]oct-3-en-2-yl)-4-fluorophenyl)-3-methyl-5-(trifluoromethyl)-2-pyridinecarboxamide | 0.040 | 0.035 | | 1589.4 |
| 94 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-(2-butyn-1-yloxy)-2-pyrazinecarboxamide | 0.0005 | 0.0002 | | 256.77 |
| 95 | N-(3-((1R,2R,5S)-4-amino-5-(fluoromethyl)-2-methyl-8,8-dioxido-8-thia-3-azabicyclo[3.2.1]oct-3-en-2-yl)-4-fluorophenyl)-5-(2-butyn-1-yloxy)-2-pyrazinecarboxamide | 0.007 | 0.003 | | 603.01 |
| 96 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-cyano-3-methyl-2-pyridinecarboxamide | 0.002 | 0.002 | 0.001 | 732.83 |
| 97 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-7-methoxypyrido[3,2-d]pyrimidin-4-amine | 0.007 | 0.007 | 0.02 | 359.18 |

TABLE 3-continued

| Example No | Compound Name | BACE1 Enzyme assay IC$_{50}$ (uM) | BACE1 cell assay IC$_{50}$ (uM) | BACE2 Enzyme assay IC$_{50}$ (uM) | CatD IC50 (μM) |
|---|---|---|---|---|---|
| 98 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-7-chloropyrido[3,2-d]pyrimidin-4-amine | 0.005 | 0.015 | | 286.13 |
| 99 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-fluoro-3-methoxy-1,7-naphthyridin-8-amine | 0.006 | 0.028 | | 317.37 |
| 100 | 8-((3-((1S,2R,5R)-4-amino-5-(fluoromethyl)-2-methyl-8,8-dioxido-8-thia-3-azabicyclo[3.2.1]oct-3-en-2-yl)-4-fluorophenyl)amino)-1,7-naphthyridine-3-carbonitrile | 0.001 | 0.004 | 0.0006 | 337.29 |
| 101 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-ethyl-2-pyridinecarboxamide | 0.026 | 0.012 | | 1851.3 |
| 102 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-(difluoromethoxy)-3-methyl-2-pyridinecarboxamide | 0.004 | 0.002 | 0.008 | 451.06 |
| 103 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-(difluoromethyl)-3-methyl-2-pyridinecarboxamide | 0.009 | 0.007 | | 890.76 |
| 104 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-2-(1,3-oxazol-2-ylmethoxy)pyrido[3,4-b]pyrazin-5-amine | 0.002 | 0.0009 | 0.003 | 799.04 |
| 105 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-3,5-dichloro-2-pyridinecarboxamide | 0.002 | 0.004 | | 926.18 |
| 106 | N-(3-((1S,2R,5R)-4-amino-2,5-dimethyl-8,8-dioxido-8-thia-3-azabicyclo[3.2.1]oct-3-en-2-yl)-4-fluorophenyl)-7-(trifluoromethyl)pyrido[3,2-d]pyrimidin-4-amine | 0.011 | 0.006 | 0.067 | 317 |
| 107 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-7-(trifluoromethyl)pyrido[3,2-d]pyrimidin-4-amine | 0.010 | 0.018 | | 185 |
| 108 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-3-chloro-5-(trifluoromethyl)-2-pyridinecarboxamide | 0.008 | 0.007 | | >400.0 |
| 109 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-(difluoromethyl)-2-pyrazinecarboxamide | 0.017 | 0.007 | | 1036 |
| 110 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-(trifluoromethyl)-2-pyridinecarboxamide | 0.006 | 0.005 | | 536.4 |
| 111 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-5-cyano-2-pyridinecarboxamide | 0.002 | 0.004 | | 956.79 |
| 112 | N-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-2-(2,2,2-trifluoroethoxy)pyrido[3,4-b]pyrazin-5-amine | 0.008 | 0.188 | 0.058 | 1305.9 |

TABLE 3-continued

| Example No | Compound Name | BACE1 Enzyme assay IC$_{50}$ (uM) | BACE1 cell assay IC$_{50}$ (uM) | BACE2 Enzyme assay IC$_{50}$ (uM) | CatD IC50 (μM) |
|---|---|---|---|---|---|
| 114 | N-(3-((1S,2S,5R)-4-amino-2-(fluoromethyl)-5-methyl-8,8-dioxido-8-thia-3-azabicyclo[3.2.1]oct-3-en-2-yl)-4-fluorophenyl)-3-methyl-5-(trifluoromethyl)-2-pyridinecarboxamide | 0.061 | 0.082 | | 3455.6 |
| 116 | N-(3-((1R,2S,5S)-4-amino-2-(fluoromethyl)-5-methyl-8,8-dioxido-8-thia-3-azabicyclo[3.2.1]oct-3-en-2-yl)-4-fluorophenyl)-3-methyl-5-(trifluoromethyl)-2-pyridinecarboxamide | 0.044 | 0.047 | | 254.74 |
| 118 | N-(3-((1S,2S,5R)-4-amino-2-(fluoromethyl)-5-methyl-8,8-dioxido-8-thia-3-azabicyclo[3.2.1]oct-3-en-2-yl)-4-fluorophenyl)-5-chloro-3-methyl-2-pyridinecarboxamide | 0.017 | 0.062 | 0.002 | >400.0 |
| 120 | N-(3-((1S,2S,5R)-4-amino-2-(fluoromethyl)-5-methyl-8,8-dioxido-8-thia-3-azabicyclo[3.2.1]oct-3-en-2-yl)-4-fluorophenyl)-5-methoxy-2-pyrazinecarboxamide | 0.049 | 0.088 | | >400.0 |
| 121 | N-(3-((1S,2R,5R)-4-amino-2,5-dimethyl-8,8-dioxido-8-thia-3-azabicyclo[3.2.1]oct-3-en-2-yl)-4-fluorophenyl)-2-fluoro-4-(trifluoromethyl)benzamide | 0.41 | 0.15 | | >400.0 |
| 122 | N-(3-((1R,2S,5S)-4-amino-2,5-dimethyl-8,8-dioxido-8-thia-3-azabicyclo[3.2.1]oct-3-en-2-yl)-4-fluorophenyl)-2-fluoro-4-(trifluoromethyl)benzamide | 0.905 | 0.255 | | >400.0 |
| 123 | N-(3-((1S,2R,5R)-4-amino-2,5-dimethyl-8,8-dioxido-8-thia-3-azabicyclo[3.2.1]oct-3-en-2-yl)-4-fluorophenyl)-2-fluoro-4-methoxybenzamide | 0.13 | 0.083 | | 1621.7 |
| 124 | N-(3-((1R,2R,5S)-4-amino-2,5-dimethyl-8,8-dioxido-8-thia-3-azabicyclo[3.2.1]oct-3-en-2-yl)-4-fluorophenyl)-2-fluoro-4-methoxybenzamide | 0.588 | 0.103 | | 4440.9 |
| 125 | N-(3-((1S,2R,5R)-4-amino-2,5-dimethyl-8,8-dioxido-8-thia-3-azabicyclo[3.2.1]oct-3-en-2-yl)-4-fluorophenyl)-4-bromo-2,6-difluorobenzamide | 0.103 | 0.065 | | >400.0 |
| 126 | N-(3-((1R,2R,5S)-4-amino-2,5-dimethyl-8,8-dioxido-8-thia-3-azabicyclo[3.2.1]oct-3-en-2-yl)-4-fluorophenyl)-4-bromo-2,6-difluorobenzamide | 0.315 | 0.073 | | 2199.2 |
| 127 | N-(3-((1S,2R,5R)-4-amino-2,5-dimethyl-8,8-dioxido-8-thia-3-azabicyclo[3.2.1]oct-3-en-2-yl)-4-fluorophenyl)-4-cyano-2-fluorobenzamide | 0.056 | 0.025 | | >400.0 |
| 128 | N-(3-((1R,2R,5S)-4-amino-2,5-dimethyl-8,8-dioxido-8-thia-3-azabicyclo[3.2.1]oct-3-en-2-yl)-4-fluorophenyl)-4-cyano-2-fluorobenzamide | 0.123 | 0.037 | | >400.0 |
| 129 | N-(3-((1R,2R,5S)-4-amino-2,5-dimethyl-8,8-dioxido-8-thia-3-azabicyclo[3.2.1]oct-3-en-2-yl)-4-fluorophenyl)-4-(2-butyn-1-yloxy)-2-fluorobenzamide | 0.061 | 0.044 | 7.0002 | 348.46 |
| 130 | N-(3-((1S,2R,5R)-4-amino-2,5-dimethyl-8,8-dioxido-8-thia-3-azabicyclo[3.2.1]oct-3-en-2-yl)-4-fluorophenyl)-7-chloropyrido[3,2-d]pyrimidin-4-amine | 0.005 | 0.004 | | 363.3 |
| 131 | N-(3-((1R,2R,5S)-4-amino-2,5-dimethyl-8,8-dioxido-8-thia-3-azabicyclo[3.2.1]oct-3-en-2-yl)-4-fluorophenyl)-7-chloropyrido[3,2-d]pyrimidin-4-amine | 0.029 | 0.018 | | 481.94 |
| 132 | N-(3-((1S,2R,5R)-4-amino-2,5-dimethyl-8,8-dioxido-8-thia-3-azabicyclo[3.2.1]oct-3-en-2-yl)-4-fluorophenyl)-7-methoxypyrido[3,2-d]pyrimidin-4-amine | 0.006 | 0.003 | 0.051 | 964.56 |
| 133 | N-(3-((1R,2R,5S)-4-amino-2,5-dimethyl-8,8-dioxido-8-thia-3-azabicyclo[3.2.1]oct-3-en-2-yl)-4-fluorophenyl)-7-methoxypyrido[3,2-d]pyrimidin-4-amine | 0.096 | 0.026 | | 1164.9 |

TABLE 3-continued

| Example No | Compound Name | BACE1 Enzyme assay IC$_{50}$ (uM) | BACE1 cell assay IC$_{50}$ (uM) | BACE2 Enzyme assay IC$_{50}$ (uM) | CatD IC50 (μM) |
|---|---|---|---|---|---|
| 134 | N-(3-((1S,2R,5R)-4-amino-2,5-dimethyl-8,8-dioxido-8-thia-3-azabicyclo[3.2.1]oct-3-en-2-yl)-4-fluorophenyl)-3-(2-butyn-1-yloxy)-5-fluoro-1,7-naphthyridin-8-amine | 0.001 | 0.004 | | 1605.4 |
| 135 | N-(3-((1R,2R,5S)-4-amino-2,5-dimethyl-8,8-dioxido-8-thia-3-azabicyclo[3.2.1]oct-3-en-2-yl)-4-fluorophenyl)-3-(2-butyn-1-yloxy)-5-fluoro-1,7-naphthyridin-8-amine | 0.003 | 0.021 | | 613.76 |
| 136 | N-(3-((1R,2R,5S)-4-amino-2,5-dimethyl-8,8-dioxido-8-thia-3-azabicyclo[3.2.1]oct-3-en-2-yl)-4-fluorophenyl)-3-(cyclopropylmethoxy)-5-fluoro-1,7-naphthyridin-8-amine | 0.061 | 0.253 | | 5341.8 |
| 137 | N-(3-((1S,2R,5R)-4-amino-2,5-dimethyl-8,8-dioxido-8-thia-3-azabicyclo[3.2.1]oct-3-en-2-yl)-4-fluorophenyl)-3-(cyclopropylmethoxy)-5-fluoro-1,7-naphthyridin-8-amine | 0.003 | 0.0654 | | >400.0 |
| 138 | N-(3-((1S,2R,5R)-4-amino-2,5-dimethyl-8,8-dioxido-8-thia-3-azabicyclo[3.2.1]oct-3-en-2-yl)-4-fluorophenyl)-4-(2-butyn-1-yloxy)-2-fluorobenzamide | 0.061 | 0.122 | | >400.0 |
| 139 | N-(3-((1S,2R,5R)-4-amino-2,5-dimethyl-8,8-dioxido-8-thia-3-azabicyclo[3.2.1]oct-3-en-2-yl)-4-fluorophenyl)-7-(cyclopropylmethoxy)pyrido[3,2-d]pyrimidin-4-amine | 0.005 | 0.005 | 0.067 | 1281.1 |
| 140 | N-(3-((1S,2R,5R)-4-amino-2,5-dimethyl-8,8-dioxido-8-thia-3-azabicyclo[3.2.1]oct-3-en-2-yl)-4-fluorophenyl)-2-(1,3-oxazol-2-ylmethoxy)pyrido[3,4-b]pyrazin-5-amine | 0.001 | 0.0004 | 0.020 | 855 |
| 141 | N-(3-((1R,2R,5S)-4-amino-5-(methoxymethyl)-2-methyl-8,8-dioxido-8-thia-3-azabicyclo[3.2.1]oct-3-en-2-yl)-4-fluorophenyl)-7-chloropyrido[3,2-d]pyrimidin-4-amine | 0.408 | 0.327 | | 1185 |
| 142 | N-(3-((1R,2R,5S)-4-amino-5-(methoxymethyl)-2-methyl-8,8-dioxido-8-thia-3-azabicyclo[3.2.1]oct-3-en-2-yl)-4-fluorophenyl)-5-chloro-3-methyl-2-pyridinecarboxamide | 0.093 | 0.482 | | >400.0 |
| 143 | N-(3-((1S,2R,5R)-4-amino-2,5-dimethyl-8,8-dioxido-8-thia-3-azabicyclo[3.2.1]oct-3-en-2-yl)-4-fluorophenyl)-2-(2-methylpropoxy)pyrido[3,4-b]pyrazin-5-amine | 0.009 | 0.164 | | 149.83 |
| 144 | N-(3-((1S,2R,5R)-4-amino-2,5-dimethyl-8,8-dioxido-8-thia-3-azabicyclo[3.2.1]oct-3-en-2-yl)-4-fluorophenyl)-2-propoxypyrido[3,4-b]pyrazin-5-amine | 0.004 | 0.071 | | >400.0 |
| 145 | N-(3-((1S,2R,5R)-4-amino-2,5-dimethyl-8,8-dioxido-8-thia-3-azabicyclo[3.2.1]oct-3-en-2-yl)-4-fluorophenyl)-2-(2-methoxyethoxy)pyrido[3,4-b]pyrazin-5-amine | 0.003 | 0.002 | 0.065 | 1984.9 |
| 146 | N-(3-((1S,2R,5R)-4-amino-2,5-dimethyl-8,8-dioxido-8-thia-3-azabicyclo[3.2.1]oct-3-en-2-yl)-4-fluorophenyl)-2-((5-methyl-1,3-oxazol-2-yl)methoxy)pyrido[3,4-b]pyrazin-5-amine | 0.001 | 0.001 | | 416.78 |
| 147 | N-(3-((1S,2R,5R)-4-amino-2,5-dimethyl-8,8-dioxido-8-thia-3-azabicyclo[3.2.1]oct-3-en-2-yl)-4-fluorophenyl)-2-((1-methyl-1H-pyrazol-3-yl)methoxy)pyrido[3,4-b]pyrazin-5-amine | 0.002 | 0.001 | | >400.0 |
| 148 | 5-((3-((1S,2R,5R)-4-amino-5-(fluoromethyl)-2-methyl-8,8-dioxido-8-thia-3-azabicyclo[3.2.1]oct-3-en-2-yl)-4-fluorophenyl)amino)pyrido[3,4-b]pyrazin-2(1H)-one | 0.016 | 0.019 | | 216.5 |

The present invention also provides methods for making compounds of Formulas I-III, and sub-formulas therein. For example, the compounds of the present invention and additional examples may be made by the following methods, as similarly described in the literature references mentioned below.

In one embodiment of the invention, there is provided a process for preparing a compound according to any of Formula I, II or III, of a sub-formula thereof, the process comprising the step of reacting a compound 20

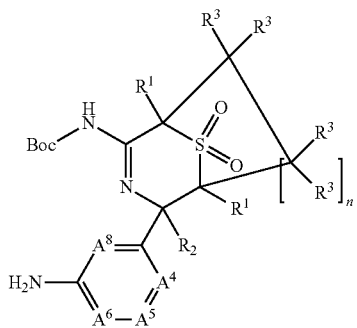

wherein $A^4, A^5, A^6, A^8, R^1, R^2, R^3$ and o of compound 20 are as defined herein with respect to Formulas I, II or III, with a compound having the structure or $R^9$—C(=O)OH or $R^9$—Cl, wherein $R^9$ is as defined herein with respect to Formulas I, II or III, to prepare the compound according to any of Formulas I, II or III, or a subformula thereof.

In one embodiment of the invention, there is provided a method of making a compound of Formula II-C-1 having a general structure of

II-C-1

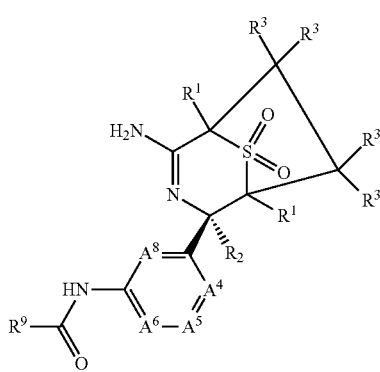

the method comprising the step of reacting a compound 20

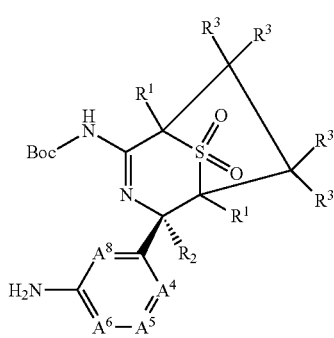

wherein $A^4, A^5, A^6, A^8$, each $R^1$, $R^2$ and $R^3$ of Formula II-C-1 are as defined herein, with a compound having the structure $R^9$—COOH, wherein $R^9$ is as defined herein, to make a compound of Formula II-C-1.

In one embodiment of the invention, there is provided a method of making a compound of Formula II-C-3 having a general structure of

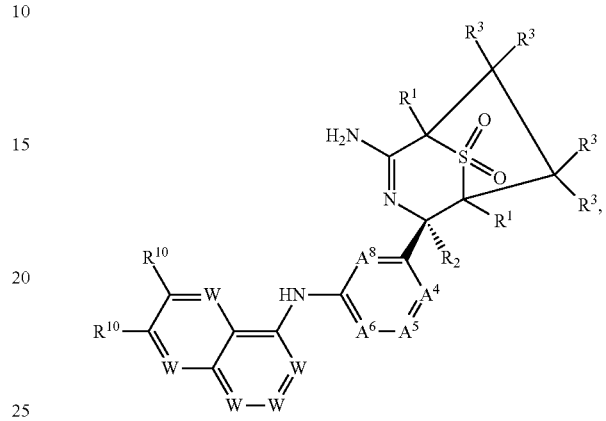

the method comprising the step of reacting a compound 20

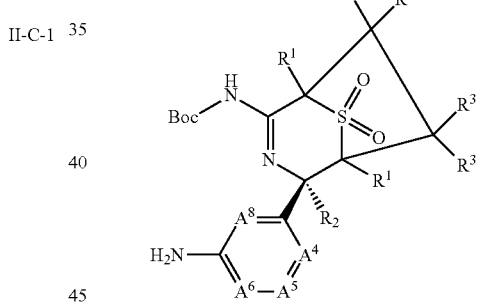

wherein $A^4$, $A^5$, $A^6$, $A^8$, each $R^1$, $R^2$, each $R^3$, Y and o of Formula II-B are as defined herein, with a compound having the structure

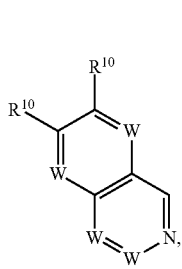

wherein each W and each $R^{10}$ are, independently, as defined herein, in the presence of acid to make a compound of Formula II-B.

In one embodiment of the invention, there is provided a method of making a compound of Formula II-C-2

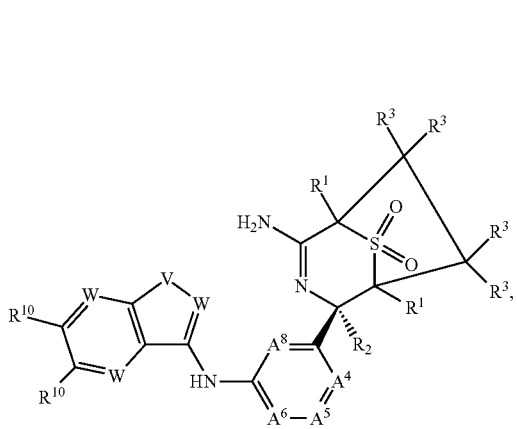

the method comprising the step of reacting a compound 20

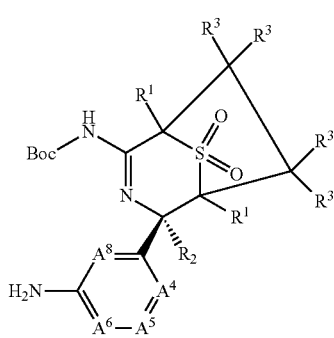

wherein $A^4$, $A^5$, $A^6$, $A^8$, each $R^1$, $R^2$ and each $R^3$ of Formula II-E are as defined herein, with a compound having the structure

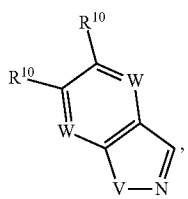

wherein V, each W and each $R^{10}$ are, independently, as defined herein, to make a compound of Formula II-C-2.

In another embodiment of the invention, there is provided a method of making a compound of Formula III-A-1 having a general formula of

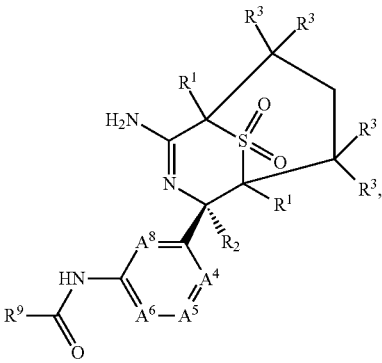

the method comprising the step of reacting a compound 20

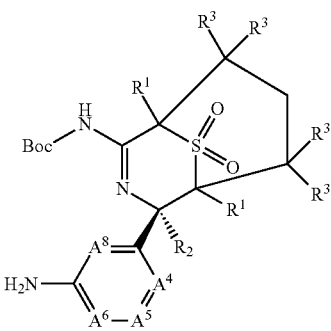

wherein $A^4$, $A^5$, $A^6$, $A^8$, each $R^1$, $R^2$ and each $R^3$ of Formula III are as defined herein, with a compound having either structure of $R^7$—COOH in the presence of a base or $R^7$ in the presence of an acid, wherein R is as defined herein, to make a compound of Formula III-A-1.

In another embodiment of the invention, there is provided a method of making a compound of Formula II-C having a general formula of

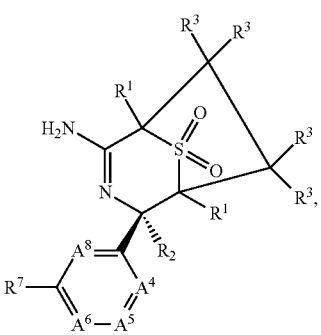

the method comprising the step of reacting a compound 20

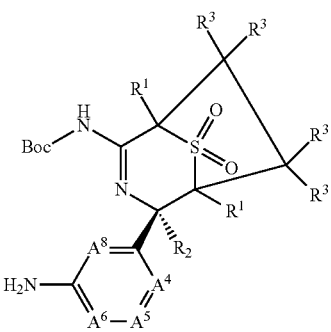

wherein $A^4$, $A^5$, $A^6$, $A^8$, each $R^1$, $R^2$ and each $R^3$ of Formula II are as defined herein, with a compound having either structure of $R^9$—COOH in the presence of a base or $R^9$ in the presence of an acid, wherein $R^9$ is as defined herein, to make a compound of Formula II-C.

In another embodiment of the invention, there is provided a method of making a compound of Formula III-C having a general formula of

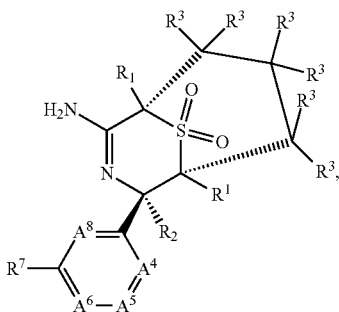

the method comprising the step of reacting a compound 20

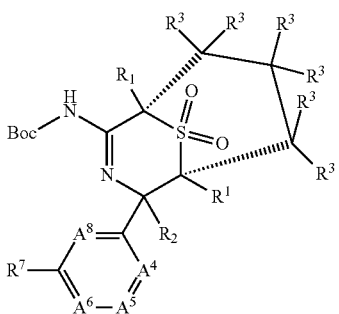

wherein $A^4$, $A^5$, $A^6$, $A^8$, each $R^1$, $R^2$ and each $R^3$ of Formula III-C are as defined herein, with a compound having either structure of $R^9$—COOH in the presence of a base or $R^9$ in the presence of an acid, wherein $R^9$ is as defined herein, to make a compound of Formula III-C.

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

Salts, including pharmaceutically acceptable salts, of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary and suitable salts, and their preparation, are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the $H^+$ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., $Et_2O$ and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including $CH_3CN$; halogenated hydrocarbons, including $CH_2Cl_2$, $CHCl_3$ and $CCl_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, $H_2SO_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

The invention further encompasses "intermediate" compounds, including structures produced from the synthetic procedures described, whether isolated or generated in-situ and not isolated, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

The invention also provides new starting materials and/or intermediates, as well as processes for the preparation thereof. In select embodiments, such starting materials are used and reaction conditions so selected as to obtain the desired compound(s). Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. While shown without respect to stereochemistry in Formulas I-III, the present invention includes such optical isomers and diastereomers, as well as the racemic and resolved, enantiomerically pure R and S stereoisomers, as well as other mixtures of R and S stereoisomers and pharmaceutically acceptable salts thereof.

The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. All such isomeric forms of such compounds are expressly included in the present invention.

The compounds of the invention may also be represented in multiple tautomeric forms. Tautomers often exist in equilibrium with each other, and interconvert under environmental and physiological conditions. The compounds of the invention may also occur in cis- or trans- or E- or Z-double bond isomeric forms. The invention expressly includes all tautomeric forms of the compounds described herein.

All crystal forms of the compounds described herein are expressly included in the present invention.

The present invention also includes isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$ (deuterium), $^3H$ (tritium), $^{13}C$, $^{14}C$, $^{15}N$, $^{16}O$, $^{17}O$, $^{31}P$, $^{32}P$, $^{35}S$, $^{18}F$, and $^{36}Cl$.

Compounds of the present invention that contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Deuterated ($^2H$), Tritiated ($^3H$) and carbon-14, i.e., $^{14}C$, isotopes are particularly preferred for their ease of preparation and detection. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of this invention can generally be prepared by substituting a readily available isotopically labeled reagent for a non-isotopically labeled reagent.

BIOLOGICAL EVALUATION

The compounds of the invention may be modified by appending appropriate functionalities to enhance selective biological properties. The pharmacokinetic and pharmacodynamic properties of a compound relate, directly and indirectly, to the ability of the compound to be effective for its intended use.

Although the pharmacological properties of the compounds of the invention (Formulas I-III) vary with structural change, in general, activity possessed by compounds of Formulas I-III may be demonstrated both in vitro as well as in vivo. The following exemplified pharmacological assays have been carried out with the compounds according to the invention, to assess and characterize the compound's ability to modulate BACE activity and to regulate the cleavage of amyloid beta precursor protein, thereby reducing or inhibiting the production of amyloid beta.

In Vitro Enzymatic BACE FRET (Fluorescence Resonance Energy Transfer) Assay

Enzyme Assay Data in the Example Table I

The assay buffer used in this screen is 0.05 M acetate, pH 4.2, 10% DMSO final, 100 uM genapol (which is a nonionic detergent, below its Critical Micelle Concentration). The Beta Secretase enzyme (0.2 nM) is pre-incubated for one hour with inhibitors, typically in about 1 uL of DMSO according to a serial dilution, are added thereto. This assay is effectively started by the addition of FRET substrate (50 nM) and the combination is incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. Proteolytic cleavage of the FRET substrate releases quenching of fluorescence (excitation 488 nm and emission 425 nm).

Where available, the in-vitro BACE FRET enzyme data for each of the Examples is provided in Tables 1 and 3.

In Vitro BACE Cell-Based Assay

The cell-based assay measures inhibition or reduction of Aβ40 in conditioned medium of test compound treated cells expressing amyloid precursor protein.

Cells stably expressing Amyloid Precursor Protein (APP) were plated at a density of 40K cells/well in 96 well plates (Costar). The cells were cultivated for 24 hours at 37° C. and 5% $CO_2$ in DMEM supplemented with 10% FBS. The test compounds were then added to cells in 10-point dose response concentrations with the starting concentration being either 100 μM or 10 μM. The compounds were diluted from stock solutions in DMSO and the final DMSO concentration of the test compounds on cells was 0.1%. After 24 h of incubation with the test compounds the supernatant conditioned media was collected and the Aβ 40 levels were determined using a sandwich ELISA. The $IC_{50}$ of the compound was calculated from the percent of control or percent inhibition of Aβ 40 as a function of the concentration of the test compound.

The sandwich ELISA to detect Aβ 40 was performed in 96 well microtiter plates, which were pre-treated with goat anti-rabbit IgG (Pierce). The capture and detecting antibody pair that were used to detect Aβ 40 from cell supernatants were affinity purified pAb40 (Biosource) and biotinylated 6E10 (Signet Labs Inc.), respectively. The optimal concentration for the pAb40 antibody was 3 μg/ml in Superblock/TBS (Pierce) that was supplemented with 0.05% Tween 20 (Sigma). Optimal concentration for the detection antibody 6E10-biotinylated was 0.5 μg/ml in Superblock/TBS (Pierce) that had been supplemented with 2% normal goat serum and 2% normal mouse serum.

Cellular supernatants were incubated with the capture antibody for 3 h at 4° C., followed by 3 wash steps in TBS-tween (0.05%). The detecting antibody incubation was for 2 h at 4° C., again followed by the wash steps as described previously. The final readout of the ELISA is Time-Resolved Fluorescence (counts per minute) using Delfia reagents Streptavidin-Europium and Enhancement solutions (Perkin Elmer) and the Victor 2 multilabel counter (Perkin Elmer).

Where available, the in-vitro BACE cell based data for each of the Examples is provided in Tables 1 and 3.

In Vitro Enzymatic BACE2 FRET (Fluorescence Resonance Energy Transfer) Assay

Enzyme Assay Data in the Table 3

The assay buffer used in this screen is 0.05 M acetate, pH 4.2, 10% DMSO final, 100 uM genapol (which is a nonionic detergent, below its Critical Micelle Concentration). The Beta Secretase2 enzyme (human Bace2 protein with C-terminal V5 and 6-His tag; 0.2 nM) is pre-incubated for one hour with inhibitors, typically in about 1 uL of DMSO according to a serial dilution, are added thereto. This assay is effectively started by the addition of FRET substrate (50 nM) and the combination is incubated for one hour. Final assay concentration of about 0.64 nM. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. Proteolytic cleavage of the FRET substrate releases quenching of fluorescence (excitation 488 nm and emission 425 nm).

Where available, the in-vitro BACE2 FRET enzyme data for each of the Examples is provided in Table 3.

In Vitro Enzymatic Cathepsin D (Cat D) FRET (Fluorescence Resonance Energy Transfer) Assay Recombinant Cat D was expressed in CHO cells. The assay buffer for CathepsinD is 0.05 M citrate pH 3.5, 10% DMSO final, 5 mM CHAPS. The Cat D enzyme (9 nM) is pre-incubated for one hour with inhibitors, typically in about 1 uL of DMSO according to a serial dilution, is added thereto. The assays are effectively started by the addition of different FRET substrates (20 nM for Cat D) and the combination is incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. The Cat D substrate peptide sequence is based on sequence #1 of Table 1 from Gulnik et al. FEBS Letters v413 p 379-384 1997. Proteolytic cleavage of the FRET substrate releases quenching of fluorescence (Cat D excitation 500 nm and emission 580 nm).

Alternatively, a Cat D assay may also be run according to the procedure described in the article, Characterization of new fluorgenic substrates for the rapid and sensitive assay of cathepsin E and cathepsin D, *J. Biochem.*, 125:1137, 1999. In addition, the cathepsin D and cathepsin E assays are described in PCT publication WO2011069934. This WIPO publication describes BACE inhibitor compounds having an amide linker connecting two aromatic groups with extremely poor cathepsin D and/or cathepsin E inhibitory activity (see Table 2).

Where available, the in-vitro Cat D FRET assay data for each of the Examples, conducted by the first procedure, is provided in Tables 1 and 3. For example, the compound of example 28 has a Cat D $IC_{50}$ value of >400 uM. As shown by the high micromolar Cat D data (very poorly active or inactive against Cat D), the compounds of the present invention possess the unexpected property of little to no ability to inhibit the activity of Cat D. The compounds of the present invention are believed to minimize, reduce or eliminate any risk of retinal atrophy and abnormal development of the eye and of the retinal pigmented epithelium as it relates to the normal function and activity of Cat D.

In Vivo Inhibition of Beta-Secretase

Several animal models, including mouse, rat, dog, and monkey, may be used to screen for inhibition of beta-secretase activity in vivo following administration of a test compound sample. Animals used in this invention can be wild type, transgenic, or gene knockout animals. For example, the Tg2576 mouse model, prepared and conducted as described in Hsiao et al., 1996, *Science* 274, 99-102, and other non-transgenic or gene knockout animals are useful to analyze in vivo inhibition of Amyloid beta peptide (Abeta) production in the presence of inhibitory test compounds. Generally, 2 to 18 month old Tg2576 mice, gene knockout mice or non-transgenic animals are administered test compounds formulated in vehicles, such as cyclodextran, phosphate buffers, hydroxypropyl methylcellulose or other suitable vehicles. One to twenty-four hours following the administration of compound, animals are sacrificed, and brains as well as cerebrospinal fluid (CSF) and plasma are removed for analysis of A-beta levels and drug or test compound concentrations (Dovey et al., 2001, *Journal of Neurochemistry*, 76, 173-181) Beginning at time 0, animals are administered by oral gavage, or other means of delivery such as intravenous injection, an inhibitory test compound of up to 100 mg/kg in a standard, conventional formulation, such as 2% hydroxypropyl methylcellulose, 1% Tween80. A separate group of animals receive 2% hydroxypropyl methylcellulose, 1% Tween80 alone, containing no test compound, and serve as a vehicle-control group. At the end of the test period, animals are sacrificed and brain tissues, plasma or cerebrospinal fluid are collected. Brains are either homogenized in 10 volumes (w/v) of 0.2% diethylamine (DEA) in 50 mM NaCl (Best et al., 2005, *Journal of Pharmacology and Experimental Therapeutics*, 313, 902-908), or in 10 volumes of 0.5% TritonX-100 in Tris-buffered saline (pH at about 7.6). Homogenates are centrifuged at 355,000 g, 4° C. for 30 minutes. CSF or brain supernatants are then analyzed for the presence of A-beta peptide by specific sandwich ELISA assays based on ECL (Electrochemiluminescence) technology. For example, rat Abeta40 is measured using biotinylated-4G8 (Signet) as a capture antibody and Fab40 (an in-house antibody specific to the C-terminal of Abeta40) as a detection antibody. For example, 4 hours after administration of 30 mg/kg oral dose of the test compound in 2% hydroxypropyl methylcellulose, 1% Tween80 (pH2.2) to 200 g male Sprague Dawley rats, amyloid beta peptide levels are measured for reduction by X % and Y % in cerebrospinal fluid and brain, respectively, when compared to the levels measured in the vehicle-treated or control mice.

Actual vehicles used: Oral: 2% HPMC, 1% Tween80, pH 2.2
IV: 5% EtOH, 45% Propylene glycol in 5% Dextrose The compounds of the invention may be shown to reduce the formation and/or deposition of amyloid beta peptide in the cerebrospinal fluid (CSF) as well as in the brain of a mouse or rat at either 3 mpk, 10 mpk or 30 mpk (mpk=mg compound per kg weight of the animal) dosing concentrations after 4 hrs. The following examples exhibited the following percent Abeta 40 reductions at 10 mpk (unless otherwise noted) in the CSF and brain of the rat, respectively.

| Ex. No. | % reduction of rat CSF levels at 10 pmk | % reduction of rat brain levels at 10 mpk |
|---|---|---|
| 22 | 76 | 66 |
| 24 | 72 | 62 |
| 35 | 52 | 46 |
| 37 | 80 | 79 |
| 40 | 59 | 24 |
| 41 | 76 | 62 |
| 42 | 21 (3 mpk) | 0 (3 mpk) |
| 52 | 67 | 62 |
| 56 | 69 | 6- |
| 59 | 80 | 76 |
| 61 | 80 | 79 |
| 69 | 42 | 9 |
| 76 | 76 | 66 |
| 77 | 77 | 67 |
| 78 | 52 | 46 |
| 79 | 71 | 62 |
| 80 | 72 | 63 |
| 82 | 71 | 56 |
| 88 | 77 | 70 |
| 92 | 73 | 67 |
| 96 | 60 (3 mpk) | 39 (3 mpk) |
| 97 | 75 | 76 |
| 98 | 70 | 74 |
| 100 | 67 | 59 |
| 102 | 67 | 68 |
| 103 | 62 | 58 |
| 104 | 74 | 71 |
| 105 | 74 | 71 |
| 106 | 59 | 29 |
| 107 | 53 | 43 |
| 109 | 70 | 57 |
| 110 | 65 | 54 |
| 132 | 70 | 50 |
| 140 | 41 | 39 |
| 146 | 35 | 13 |

INDICATIONS

According to the amyloid cascade hypothesis, cerebral deposition of amyloid-beta peptide (Aβ) is critical for Alzheimer's disease (AD) pathogenesis. Aβ generation is initiated when β-secretase (BACE1) cleaves the amyloid precursor protein. De Meyer et al re-affirm the believed role which the accumulation of beta-amyloid protein (A-beta) in cerebral spinal fluid (CSF) in a subject plays in the progression of symptoms, initially revealed as mild cognitive impairment, which ultimately leads to AD. *Arch Neuro.* 67(8):949-956, 2010. Amyloid-b (Ab) peptides generated from amyloid precursor protein (APP) by proteolytic cleavage, such as by aspartyl protease enzymes including beta-secreatase (BACE) and gamma-secretase, likely play a causal role in AD pathogenesis (Tanzi and Bertram, *Cell*, (120): 545-555, 2005; Walsh and Selkoe, *Neuron*, (44): 181-193, 2004). Although the precise mechanisms of Ab toxicity are unclear, oligomeric forms of Ab may contribute to cognitive decline by altering synaptic structure and function (Palop and Mucke, *Nat. Neuroscience*, (13): 812-818, 2010; Selkoe, *Behavioral Brain Res.*, (192): 106-113, 2008; Shankar et al., *Nat. Medicine*

(14): 837-842, 2008). Transgenic mouse models that overexpress mutant APP and produce high levels of Ab show amyloid plaque deposition, synaptic deficits, learning and memory impairments, and other behavioral abnormalities (Games et al., *Nature*, (373): 523-527, 1995; Gotz et al., *Molecular Psychiatry* (9): 664-683, 2004; Hsia et al., *Proc. Natl. Academy of Science USA* (96): 3228-3233, 1999; Hsiao et al., *Science* (274): 99-102, 1996, citing Harris et al, *Neuron* (68): 428-441, 2010).

For more than a decade, BACE1 has been a prime target for designing drugs to prevent or treat AD. However, development of such agents has turned out to be extremely challenging, with major hurdles in cell penetration, oral bioavailability/metabolic clearance, and brain access.

Bapineuzamab, a monoclonal amino-terminus specific anti-amyloid antibody is presently in Phase III clinical trials for the treatment of AD. *Alzheimer's Research & Therapy*, 1:2, 2009. Each of the known genetic causes of AD is linked to A-beta.

Dementia, Down's Syndrome to APP over-production, are all believed to be linked to the deposition of A-beta on the brain. With methods for identifying brain amyloid deposition, positron emission scanning (PET) and CSF measurements of Ab42, identification of AD suffering individuals needing treatment is becoming easier amd more common. It is firmly believed that by reducing the formation of A-beta, one can begin to pre-treat AD. Vassar et al, *Journal of Neuroscience*, 29 (41):12787-12794, 2009. One published pathway for treatment of AD is inhibition of beta-secretase. Tirrell, *Bloomberg News, The Boston Globe*, Jan. 7, 2010.

The US biotech company CoMentis is developing an orally bioavailable small molecule CTS-21166, a highly potent, highly selective and efficacious brain-penetrating beta-secretase inhibitor. CoMentis successfully completed a Phase I study of CTS-21166 in healthy volunteers in 2008. Results indicated that CTS-21166 was safe, well-tolerated and pharmacodynamically active at all dose levels. All clinical subjects administered CTS-21166 showed area-under-curve (AUC) reduction in plasma A-Beta40 reductions ranging from 40-75%. Because of the urgent need for AD treatment, Phase II studies for CTS-2166 are planned, or ongoing, for AD patients. In preclinical studies, CTS-21166 exhibits excellent efficacy, selectivity, brain penetration and pharmacologic activity.

Using a fragment-based chemistry strategy, Eli Lilly and company generated LY2811376 [(S)-4-(2,4-difluoro-5-pyrimidin-5-yl-phenyl)-4-methyl-5,6-dihydro-4H-[1,3]thiazin-2-ylamine], an orally available non-peptidic BACE1 inhibitor that produces profound Aβ-lowering effects in animals. The biomarker changes obtained in preclinical animal models translate into man at doses of LY2811376 that were safe and well tolerated in healthy volunteers (US Ph I Clinical trial—www.clinicaltrials.gov). Prominent and long-lasting Aβ reductions in lumbar CSF were measured after oral dosing of 30 or 90 mg of LY2811376. This represents the first translation of BACE1-driven biomarker changes in CNS from preclinical animal models to man. Because of toxicology findings identified in longer-term preclinical studies, this compound is no longer progressing in clinical development. However, BACE1 remains a viable target because the potential adverse effects discussed herein were recapitulated in LY2811376-treated BACE1 KO mice and thus are unrelated to BACE1 inhibition. The magnitude and duration of central Aβ reduction obtainable with BACE1 inhibition positions this protease as a tractable small-molecule target through which to test the amyloid hypothesis in man. *Neuroscience*, 31(46):16507-16515, 2011

The compounds of the invention have been shown to modulate, and specifically inhibit the activity of the beta-secretase enzyme, thereby reducing the A-beta peptide fragments. Accordingly, compounds of the invention are useful for, but not limited to, the prevention or treatment of beta-secretase related diseases, including Alzheimer's disease. The compounds of the invention have the ability to modulate the activity of beta secretase enzyme, thereby regulating the production of amyloid beta (Abeta peptide) and reducing the formation and deposition of Abeta peptide in both the cerebral spinal fluid as well as in the brain, resulting in a decrease of amyloid plaque on the brain. In one embodiment of the invention, there is provided a method of treating a disorder related to a beta-secretase enzyme in a subject, the method comprising administering to the subject an effective dosage amount of a compound of Formulas I, II, III, and sub-formulae thereof. In another embodiment, there is provided a method of reducing production of amyloid beta, and of reducing plaque formation on the brain. In another embodiment, there is provided a method for the treatment, prevention or amelioration of a disease or disorder characterized by the elevated beta-amyloid deposits or beta-amyloid levels in a subject, the method comprising administering to the subject a therapeutically effective amount of a compound according to any of Formulas I-III. In yet another embodiment, the invention provides a method of treating Alzheimer's disease, cognitive impairment including mild, moderate and/or severe, Down's Syndrome, cognitive decline, senile dementia, cerebral amyloid angiopathy or a neurodegenerative disorder.

Accordingly, the compounds of the invention would be useful in therapy as CNS agents in treating neurological disorders and related conditions in subjects.

In one embodiment, the compounds of the invention are provided for the manufacture of a medicament, or a pharmaceutical composition, for the therapeutic and/or prophylactic treatment of diseases and disorders characterized by elevated levels of f3-amyloid and/or β-amyloid oligomers and/or b-amyloid plaques and further deposits, including Alzheimer's Disease. In another embodiment, the invention provides compounds, in effective dosage amounts, for the therapeutic and/or prophylactic treatment of AD. Thus, the compounds of the invention may be used to treat prodromol patients, i.e., subjects exhibiting the biomarkers and/or hallmarks of developing AD.

Besides being useful for human treatment, the compounds of the invention may be useful for veterinary treatment of companion animals, exotic animals and farm animals, including mammals, rodents, and the like. For example, animals including horses, dogs, and cats may be treated with compounds provided herein.

FORMULATIONS AND METHOD OF USE

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in need of preventative treatment, such as, for example, for pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating neurological disorders and beta-secretase mediated diseases with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, and even more advantageously between about 0.1 and about 10 mg/kg body weight may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable excipient, which includes diluents, carriers, adjuvants and the like (collectively referred to herein as "excipient" materials) as described herein, and, if desired, other active ingredients. A pharmaceutical composition of the invention may comprise an "effective amount" of a compound of the invention or an "effective dosage amount" of a compound of the invention. An "effective dosage amount" of a compound of the invention includes an amount less than, equal to or greater than an effective amount of the compound. For example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, advantageously from about 1 to 500 mg, and typically from about 5 to 150 mg. A suitable daily dose for a human or other mammal may vary widely depending on the condition of the patient and other factors, but, once again, can be determined using routine methods and practices.

For therapeutic purposes, the active compounds of this invention are ordinarily combined with one or more adjuvants or other "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, and preferably from about 0.1 to about 10 mg/kg.

For pulmonary administration, the pharmaceutical composition may be administered in the form of an aerosol or with an inhaler including dry powder aerosol.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents. Accordingly, in yet another embodiment of the present invention, there is provided a method of manufacturing a medicament, the method comprising combining an amount of a compound according to Formulas I-III with a pharmaceutically acceptable carrier to manufacture the medicament.

In yet another embodiment, the invention provides a method of manufacturing a medicament for the treatment of Alzheimer's disease, the method comprising combining an amount of a compound according to Formulas I-III with a pharmaceutically acceptable carrier to manufacture the medicament.

COMBINATIONS

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of beta-secretase, gamma-secretase and/or other reagents known in influence the formation and/or deposition of amyloid beta, otherwise responsible for the formation of plaque on the brain.

If formulated as a fixed dose, such combination products employ the compounds of this invention within the accepted dosage ranges. Compounds of Formulas I, II and III may also be administered sequentially with other known medicinal agents. The invention is not limited in the sequence of administration; compounds of the invention may be administered either prior to, simultaneous with or after administration of the known anti-inflammatory agent.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:
1. A compound of Formula I

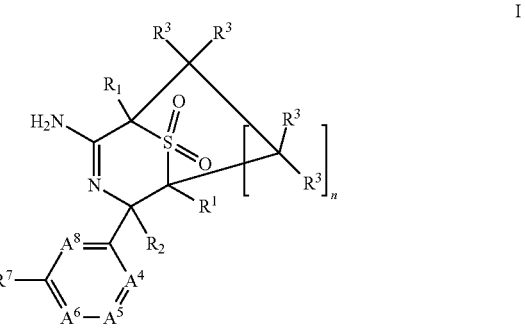

or a stereoisomer, tautomer, hydrate, solvate or pharmaceutically acceptable salt thereof, wherein
$A^4$ is $CR^4$ or N;
$A^5$ is $CR^5$ or N;
$A^6$ is $CR^6$ or N;
$A^8$ is $CR^8$ or N, provided that no more than one of $A^4$, $A^5$, $A^6$ and $A^8$ is N;
each $R^1$, independently, is H, F, Cl, $C_{1-4}$alkyl, $CH_2OC_{1-4}$alkyl, cyclopropyl or CN, wherein the $C_{1-4}$alkyl and $CH_2OC_{1-4}$alkyl are optionally substituted with 1-3 substituents of F;
$R^2$ is $C_{1-4}$alkyl, $CH_2OC_{1-4}$alkyl, $CH_2OH$, $CH_2CN$, $C_{3-6}$cycloalkyl or CN, wherein each of the $C_{1-4}$alkyl, $CH_2OC_{1-4}$alkyl and $C_{3-6}$cycloalkyl is optionally substituted with 1-4 substituents of F;
each $R^3$, independently, is H, halo, $C_{1-4}$alkyl, $OC_{1-4}$alkyl, $CH_2OC_{1-4}$alkyl, $CH_2OH$, $C_{1-4}$haloalkyl, cyclopropyl or CN, wherein each of the $OC_{1-4}$alkyl, $CH_2OC_{1-4}$alkyl and cyclopropyl is optionally substituted with 1-4 substituents of F;
each of $R^4$, $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;
$R^7$ is —NH—$R^9$, —NHC(=O)—$R^9$, —C(=O)NH—$R^9$, —O—$R^9$ or —S—$R^9$;
$R^9$ is acetyl, $C_{1-6}$-alkyl, $C_{2-4}$alkenyl, $C_{2-4}$alkynyl or a fully or partially unsaturated 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$;
each $R^{10}$, independently, is H, halo, haloalkyl, CN, OH, $NO_2$, $NH_2$, $SF_5$, acetyl, —C(O)NHCH$_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl, dioxolyl, —NHC(O)R$^{11}$— or —C(O)NHR$^{11}$, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, isobutyl, sec-butyl, tert-butyl, $C_{1-3}$alkylamino-, $C_{1-3}$dialkylamino, $C_{1-3}$thioalkoxyl, oxetan-3yl or a ring selected from oxazolyl, isoxazolyl, pyrazolyl, thiazolyl, isothiazolyl or oxadiazolyl wherein the ring is optionally substituted independently with 1-5 substituents of F, Cl, CN or $CH_3$;

$R^{11}$ is $C_{1-6}$alkyl, $C_{1-6}$alkoxyl or $C_{3-6}$cycloalkyl; and n is 0, 1 or 2.

2. The compound according to claim 1, or a stereoisomer, tautomer or pharmaceutically acceptable salt thereof, wherein n is 1 or 2.

3. The compound according to claim 2, or a stereoisomer, tautomer or pharmaceutically acceptable salt thereof, wherein $A^4$ is $CR^4$;

$A^5$ is $CR^5$;

$A^6$ is $CR^6$; and $A^8$ is $CR^8$.

4. The compound according to claim 2, or a stereoisomer, tautomer or pharmaceutically acceptable salt thereof, wherein each $R^1$, independently, is H, F, Cl, $CH_3$, $CH_2CH_3$, cyclopropyl or CN, wherein the $CH_3$ and $CH_2CH_3$ are optionally substituted with 1-3 substituents of F.

5. The compound according to claim 2, or a stereoisomer, tautomer or pharmaceutically acceptable salt thereof, wherein $R^2$ is $CH_3$, $CH_2F$ or $CHF_2$.

6. The compound according to claim 2, or a stereoisomer, tautomer or pharmaceutically acceptable salt thereof, wherein $A^4$ is $CR^4$;

$A^5$ is $CR^5$ or N;

$A^6$ is $CR^6$;

$A^8$ is $CR^8$;

each $R^1$, independently, is H, F, Cl, $CF_3$, $CH_3$, $CH_2CH_3$, $CH_2OCH_3$, CN, $CH_2F$ or $CHF_2$;

R is $CH_3$, $CH_2F$ or $CHF_2$;

each $R^3$, independently, is H, F, Cl, $CF_3$, $OCF_3$, $CH_3$, $CH_2CH_3$, CN, OH, $OCH_3$, $CH_2OCH_2F$ or $CH_2OCHF_2$; and each of $R^4$, $R^5$, $R^6$ and $R^8$, independently, is H, F, Cl, $CF_3$, $OCF_3$, $CH_3$, $CH_2CH_3$, CN, OH, $OCH_3$, $SCH_3$, $NHCH_3$ or $C(O)CH_3$.

7. The compound according to claim 2, or a stereoisomer, tautomer or pharmaceutically acceptable salt thereof, wherein $R^7$ is —NH—C(=O)—$R^9$.

8. The compound according to claim 2, or a stereoisomer, tautomer or pharmaceutically acceptable salt thereof, wherein $R^7$ is

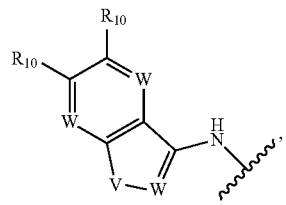

-continued

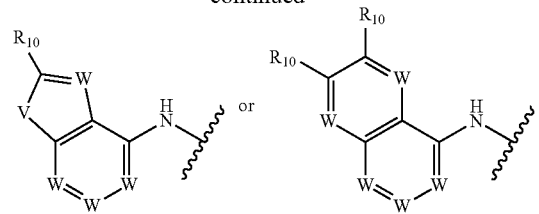

wherein V is $NR^{10}$, O or S; and each W, independently, is CH, CF, CCl or N.

9. The compound according to claim 2, or a stereoisomer, tautomer or pharmaceutically acceptable salt thereof, wherein $A^4$ is $CR^4$ wherein $R^4$ is F, Cl or $CH_3$;

$A^5$ is $CR^5$ wherein $R^5$ is H, F, Cl or $CH_3$;

$A^6$ is CH; and $A^8$ is CH.

10. A compound according to claim 1, or a stereoisomer, tautomer, hydrate, solvate or pharmaceutically acceptable salt thereof, having a Formula II-C:

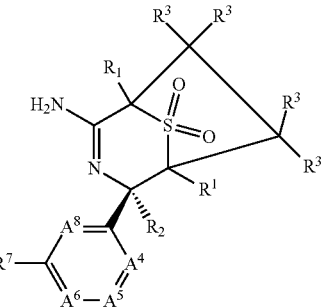

II-C or a stereoisomer, tautomer, hydrate, solvate or pharmaceutically acceptable salt thereof, wherein $A^4$ is $CR^4$;

$A^5$ is $CR^5$ or N;

$A^6$ is $CR^6$;

$A^8$ is $CR^8$;

each $R^1$, independently, is H, F, Cl, $CF_3$, $CH_3$, $CH_2CH_3$, $CH_2OCH_3$, CN, $CH_2F$ or $CHF_2$;

$R^2$ is $CH_3$, $CH_2F$ or $CHF_2$;

each $R^3$, independently, is H, F, Cl, $CF_3$, $OCF_3$, $CH_3$, $CH_2CH_3$, CN, OH, $OCH_3$, $CH_2OCH_2F$ or $CH_2OCHF_2$;

each of $R^4$, $R^5$, $R^6$ and $R^8$, independently, is H, F, Cl, $CF_3$, $OCF_3$, $CH_3$, $CH_2CH_3$, CN, OH, $OCH_3$, $SCH_3$, $NHCH_3$ or $C(O)CH_3$;

$R^7$ is —NH—C(=O)—$R^9$ or

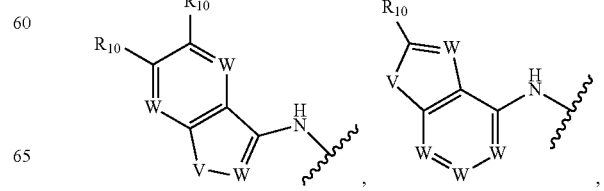

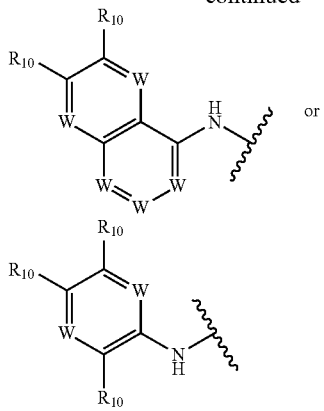

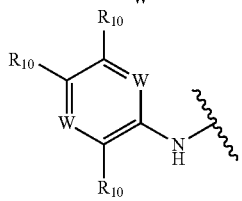

wherein V is NR[10], O or S; and
each W, independently, is CH, CF, CCl or N;
R[9] is acetyl, $C_{1-6}$-alkyl, $C_{2-4}$alkenyl, $C_{2-4}$alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, imidazo-pyridyl, cyclopropyl, cyclobutyl, cyclopentyl and cyclohexyl, wherein the $C_{1-6}$-alkyl, $C_{2-4}$alkenyl, $C_{2-4}$alkynyl and ring are optionally substituted, independently, with 1-5 substituents of R[10]; and
each R[10], independently, is H, halo, haloalkyl, CN, OH, $NO_2$, $NH_2$, $SF_5$, acetyl, —C(O)NHCH$_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl, dioxolyl, —NHC(O)R[11]— or —C(O)NHR[11]—, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, isobutyl, sec-butyl, tert-butyl, $C_{1-3}$alkylamino-, $C_{1-3}$dialkylamino, $C_{1-3}$thioalkoxyl, oxetan-3yl or a ring selected from oxazolyl, isoxazolyl, pyrazolyl, thiazolyl, isothiazolyl or oxadiazolyl wherein the ring is optionally substituted independently with 1-5 substituents of F, Cl, CN or CH$_3$; and
R[11] is $C_{1-6}$alkyl, $C_{1-6}$alkoxyl or $C_{3-6}$cycloalkyl.

11. The compound according to claim 10, or a stereoisomer, tautomer or pharmaceutically acceptable salt thereof, wherein
A[4] is CR[4];
A[5] is CR[5];
A[6] is CR[6]; and
A[8] is CR[8];

each R[1], independently, is H, F, CH$_2$F or CH$_3$;
R[2] is CH$_3$, CH$_2$F or CHF$_2$;
each R[3], independently, is H, F, CH$_2$F or CH$_3$;
R[7] is —NH—C(=O)—R[9]; or R[7] is

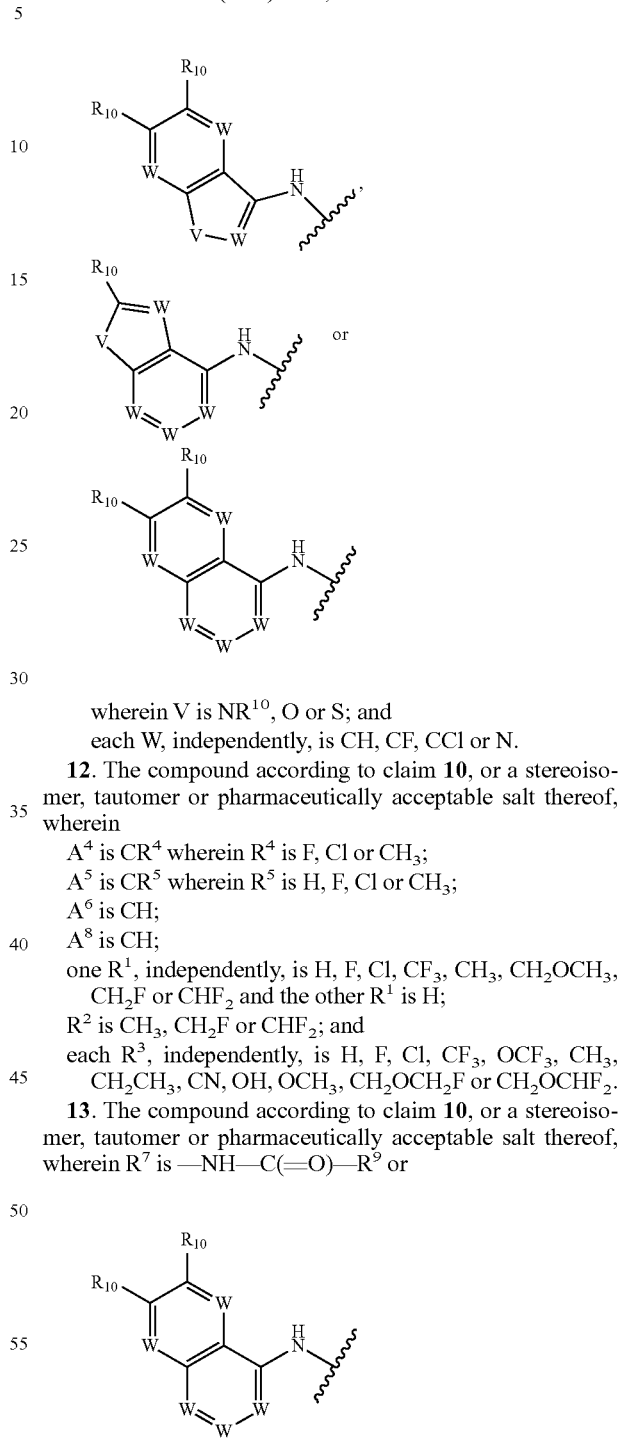

wherein V is NR[10], O or S; and
each W, independently, is CH, CF, CCl or N.

12. The compound according to claim 10, or a stereoisomer, tautomer or pharmaceutically acceptable salt thereof, wherein
A[4] is CR[4] wherein R[4] is F, Cl or CH$_3$;
A[5] is CR[5] wherein R[5] is H, F, Cl or CH$_3$;
A[6] is CH;
A[8] is CH;
one R[1], independently, is H, F, Cl, CF$_3$, CH$_3$, CH$_2$OCH$_3$, CH$_2$F or CHF$_2$ and the other R[1] is H;
R[2] is CH$_3$, CH$_2$F or CHF$_2$; and
each R[3], independently, is H, F, Cl, CF$_3$, OCF$_3$, CH$_3$, CH$_2$CH$_3$, CN, OH, OCH$_3$, CH$_2$OCH$_2$F or CH$_2$OCHF$_2$.

13. The compound according to claim 10, or a stereoisomer, tautomer or pharmaceutically acceptable salt thereof, wherein R[7] is —NH—C(=O)—R[9] or

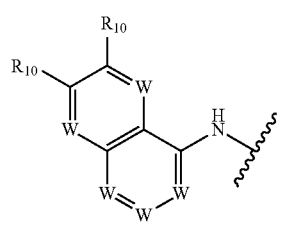

wherein each W, independently, is CH, CF, CCl or N.

14. The compound according to claim 10, or a stereoisomer, tautomer or pharmaceutically acceptable salt thereof, wherein R[7] is —NH—C(=O)—R[9].

15. The compound according to claim 1, or a stereoisomer, tautomer or pharmaceutically acceptable salt thereof, having a Formula II-C-1-A or Formula II-C-1-B

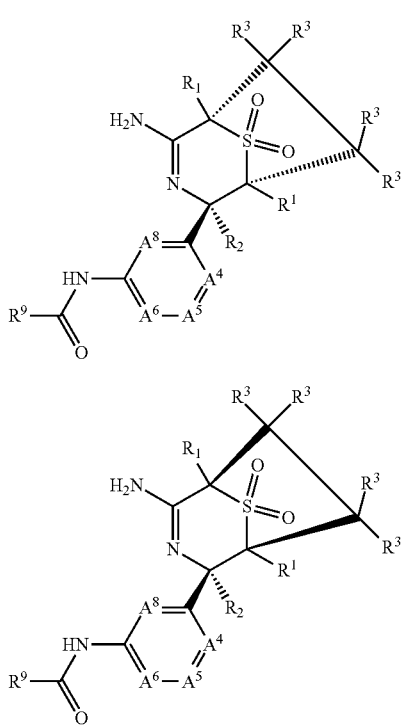

II-C-1-A

II-C-1-B wherein
A⁴ is CR⁴;
A⁵ is CR⁵ or N;
A⁶ is CR⁶;
A⁸ is CR⁸;
each R¹, independently, is H, F, Cl, CF₃, CH₃, CH₂CH₃, CH₂OCH₃, CN, CH₂F or CHF₂;
R² is CH₃, CH₂F or CHF₂;
each R³, independently, is H, F, Cl, CF₃, OCF₃, CH₃, CH₂CH₃, CN, OH, OCH₃, CH₂OCH₂F or CH₂OCHF₂;
each of R⁴, R⁵, R⁶ and R⁸, independently, is H, F, Cl, CF₃, OCF₃, CH₃, CH₂CH₃, CN, OH, OCH₃, SCH₃, NHCH₃ or C(O)CH₃;
R⁹ is acetyl, C₁₋₆-alkyl, C₂₋₄alkenyl, C₂₋₄alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, imidazo-pyridyl, cyclopropyl, cyclobutyl, cyclopentyl and cyclohexyl, wherein the C₁₋₆-alkyl, C₂₋₄alkenyl, C₂₋₄alkynyl and ring are optionally substituted, independently, with 1-5 substituents of R¹⁰; and
each R¹⁰, independently, is H, halo, haloalkyl, CN, OH, NO₂, NH₂, SF₅, acetyl, —C(O)NHCH₃, oxo, C₁₋₆alkyl, C₂₋₆alkenyl, C₂₋₆alkynyl, C₃₋₆cycloalkyl, C₁₋₆alkylamino-, C₁₋₆dialkylamino-, C₁₋₆alkoxyl, C₁₋₆thioalkoxyl, 2-propynyloxy, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the C₁₋₆alkyl, C₂₋₆alkenyl, C₂₋₆alkynyl, C₃₋₆cycloalkyl, C₁₋₆alkylamino-, C₁₋₆dialkylamino-, C₁₋₆alkoxyl, C₁₋₆thioalkoxyl, 2-propynyloxy, 2-butynyloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO₂, NH₂, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-propynyloxy, 2-butynyloxy, isobutyl, sec-butyl, tert-butyl, C₁₋₃alkylamino-, C₁₋₃dialkylamino, C₁₋₃thioalkoxyl oxetan-3yl or a ring selected from oxazolyl, isoxazolyl, pyrazolyl, thiazolyl, isothiazolyl or oxadiazolyl wherein the ring is optionally substituted independently with 1-5 substituents of F, Cl, CN or CH₃.

16. The compound according to claim 15, or a tautomer, tautomer or pharmaceutically acceptable salt thereof, wherein
A⁴ is CR⁴ wherein R⁴ is F, Cl or CH₃;
A⁵ is CR⁵ wherein R⁵ is H, F, Cl or CH₃;
A⁶ is CH;
A⁸ is CH;
each R¹, independently, is H, F, CH₃, CF₃, CF₂H, CH₂F or CH₂OCH₃;
R² is CH₃, CH₂F or CHF₂;
each R³, independently, is H or F;
R⁹ is a ring selected from phenyl, pyridyl, pyrimidyl, pyrazinyl, pyridazinyl, pyrazolyl, isoxazolyl, thiazolyl, furanyl, thienyl, pyrrolyl, wherein the ring is optionally substituted, independently, with 1-5 substituents of R¹⁰; and
each R¹⁰, independently, is H, F, Cl, Br, CN, OH, NO₂, NH₂, acetyl, C₁₋₆alkyl, C₂₋₆alkenyl, C₂₋₆alkynyl, C₃₋₆cycloalkyl, C₁₋₆alkylamino-, C₁₋₆dialkylamino-, C₁₋₆alkoxyl, C₁₋₆thioalkoxyl, 2-propynyloxy or 2-butynyloxy, wherein each of the C₁₋₆alkyl, C₂₋₆alkenyl, C₂₋₆alkynyl, C₃₋₆cycloalkyl, C₁₋₆alkylamino-, C₁₋₆dialkylamino-, C₁₋₆alkoxyl, C₁₋₆thioalkoxyl, 2-propynyloxy and 2-butynyloxy is optionally substituted independently with 1-5 substituents of F, Cl, CN, NO₂, NH₂, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-propynyloxy, 2-butynyloxy, isobutyl, sec-butyl, tert-butyl, C₁₋₃alkylamino-, C₁₋₃dialkylamino, C₁₋₃thioalkoxyl oxetan-3yl or a ring selected from oxazolyl, isoxazolyl, pyrazolyl, thiazolyl, isothiazolyl or oxadiazolyl wherein the ring is optionally substituted independently with 1-5 substituents of F, Cl, CN or CH₃.

17. The compound according to claim 10, or a stereoisomer, tautomer or pharmaceutically acceptable salt thereof, having a Formula II-C-3

II-C-3

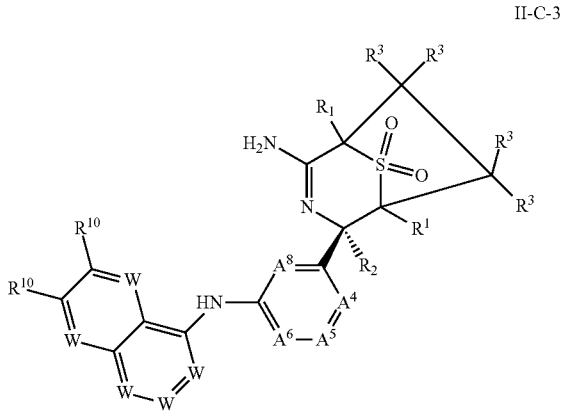

wherein
A⁴ is CR⁴;
A⁵ is CR⁵ or N;
A⁶ is CR⁶;
A⁸ is CR⁸;
each $R^1$, independently, is H, F, Cl, CF$_3$, CH$_3$, CH$_2$CH$_3$, CH$_2$OCH$_3$, CN, CH$_2$F or CHF$_2$;
$R^2$ is CH$_3$, CH$_2$F or CHF$_2$;
each $R^3$, independently, is H, F, Cl, CF$_3$, OCF$_3$, CH$_3$, CH$_2$CH$_3$, CN, OH, OCH$_3$, CH$_2$OCH$_2$F or CH$_2$OCHF$_2$;
each of $R^4$, $R^5$, $R^6$ and $R^8$, independently, is H, F, Cl, CF$_3$, OCF$_3$, CH$_3$, CH$_2$CH$_3$, CN, OH, OCH$_3$, SCH$_3$, NHCH$_3$ or C(O)CH$_3$;
each W, independently, is CH, CF, CCl or N; and
each $R^{10}$, independently, is H, halo, haloalkyl, CN, OH, NO$_2$, NH$_2$, SF$_5$, acetyl, —C(O)NHCH$_3$, oxo, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, 2-propynyloxy, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, 2-propynyloxy, 2-butynyloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO$_2$, NH$_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-propynyloxy, 2-butynyloxy, isobutyl, sec-butyl, tert-butyl, C$_{1-3}$alkylamino-, C$_{1-3}$dialkylamino, C$_{1-3}$thioalkoxyl oxetan-3yl or a ring selected from oxazolyl, isoxazolyl, pyrazolyl, thiazolyl, isothiazolyl or oxadiazolyl wherein the ring is optionally substituted independently with 1-5 substituents of F, Cl, CN or CH$_3$.

18. The compound according to claim 17, or a stereoisomer, tautomer or pharmaceutically acceptable salt thereof, wherein
A⁴ is CR⁴ wherein $R^4$ is F, Cl or CH$_3$;
A⁵ is CR⁵ wherein $R^5$ is H, F, Cl or CH$_3$;
A⁶ is CH;
A⁸ is CH;
each $R^1$, independently, is H, F, CH$_3$, CF$_3$, CF$_2$H, CH$_2$F or CH$_2$OCH$_3$;
$R^2$ is CH$_3$, CH$_2$F or CHF$_2$;
each $R^3$, independently, is H or F;

each W, independently, is CH, CF or N, provided no more than 3 W's are N; and
each $R^{10}$, independently, is H, F, Cl, Br, CN, OH, NO$_2$, NH$_2$, acetyl, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, 2-propynyloxy or 2-butynyloxy, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, 2-propynyloxy and 2-butynyloxy is optionally substituted independently with 1-5 substituents of F, Cl, CN, NO$_2$, NH$_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-propynyloxy, 2-butynyloxy, isobutyl, sec-butyl, tert-butyl, C$_{1-3}$alkylamino-, C$_{1-3}$dialkylamino, C$_{1-3}$thioalkoxyl oxetan-3yl or a ring selected from oxazolyl, isoxazolyl, pyrazolyl, thiazolyl, isothiazolyl or oxadiazolyl wherein the ring is optionally substituted independently with 1-5 substituents of F, Cl, CN or CH$_3$.

19. A compound according to claim 1, or a stereoisomer, tautomer, hydrate, solvate or pharmaceutically acceptable salt thereof, having a Formula III:

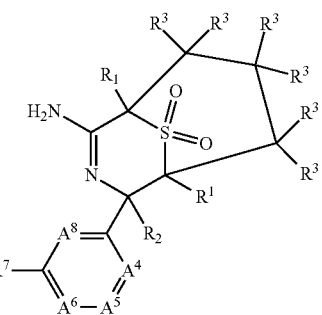

III or a stereoisomer, tautomer, hydrate, solvate or pharmaceutically acceptable salt thereof, wherein
A⁴ is CR⁴ or N;
A⁵ is CR⁵ or N;
A⁶ is CR⁶ or N;
A⁸ is CR⁸ or N, provided that no more than one of A⁴, A⁵, A⁶ and A⁸ is N;
each $R^1$, independently, is H, F, Cl, C$_{1-4}$alkyl, CH$_2$OC$_{1-4}$alkyl, cyclopropyl or CN, wherein the C$_{1-4}$alkyl and CH$_2$OC$_{1-4}$alkyl are optionally substituted with 1-3 substituents of F;
$R^2$ is C$_{1-4}$alkyl, CH$_2$OC$_{1-4}$alkyl, CH$_2$OH, CH$_2$CN, C$_{3-6}$cycloalkyl or CN, wherein each of the C$_{1-4}$alkyl, CH$_2$OC$_{1-4}$alkyl and C$_{3-6}$cycloalkyl is optionally substituted with 1-4 substituents of F;
each $R^3$, independently, is H, halo, C$_{1-4}$alkyl, OC$_{1-4}$alkyl, CH$_2$OC$_{1-4}$alkyl, CH$_2$OH, C$_{1-4}$haloalkyl, cyclopropyl or CN, wherein each of the OC$_{1-4}$alkyl, CH$_2$OC$_{1-4}$alkyl and cyclopropyl is optionally substituted with 1-4 substituents of F;
each of $R^4$, $R^5$, $R^6$ and $R^8$, independently, is H, halo, haloalkyl, haloalkoxyl, C$_{1-4}$-alkyl, CN, OH, OC$_{1-4}$-alkyl, S(O)$_o$C$_{1-4}$-alkyl, NHC$_{1-4}$-alkyl or C(O)C$_{1-4}$-alkyl;
$R^7$ is —NH—$R^9$, —NHC(=O)—$R^9$, —C(=O)NH—$R^9$, —O—$R^9$ or —S—$R^9$;
$R^9$ is acetyl, C$_{1-6}$-alkyl, C$_{2-4}$alkenyl, C$_{2-4}$alkynyl or a fully or partially unsaturated 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$;

each $R^{10}$, independently, is H, halo, haloalkyl, CN, OH, $NO_2$, $NH_2$, $SF_5$, acetyl, —C(O)NHCH$_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl, dioxolyl, —NHC(O)$R^{11}$— or —C(O)NH$R^{11}$—, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or oxetan-3yl; and $R^{11}$ is $C_{1-6}$alkyl, $C_{1-6}$alkoxyl or $C_{3-6}$cycloalkyl.

20. The compound according to claim 19, or a stereoisomer or pharmaceutically acceptable salt thereof, wherein
$A^4$ is $CR^4$;
$A^5$ is $CR^5$;
$A^6$ is $CR^6$; and
$A^8$ is $CR^8$;
each $R^1$, independently, is H, F, $CH_2F$ or $CH_3$;
$R^2$ is $CH_3$, $CH_2F$ or $CHF_2$;
$R^7$ is —NH—C(=O)—$R^9$;
or $R^7$ is

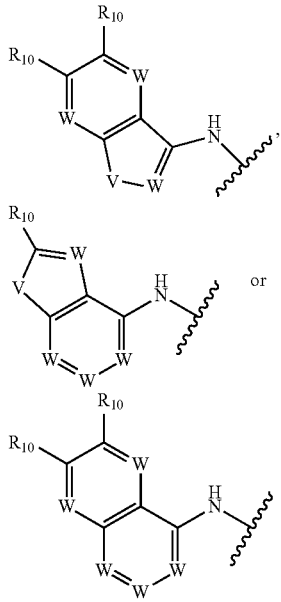

wherein V is $NR^{10}$, O or S; and
each W, independently, is CH, CF, CCl or N.

21. The compound according to claim 19, or a tautomer or pharmaceutically acceptable salt thereof, wherein $R^7$ is —NH—C(=O)—$R^9$.

22. The compound according to claim 19, or a stereoisomer, tautomer or pharmaceutically acceptable salt thereof, having a Formula III-A

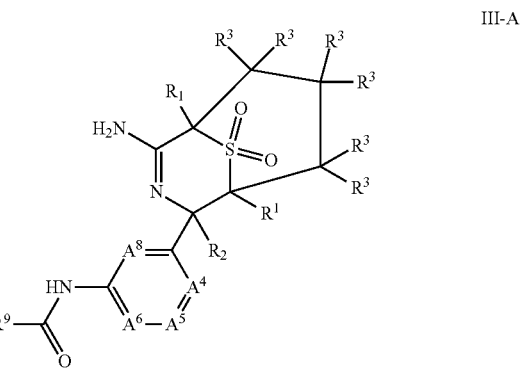

wherein
$A^4$ is $CR^4$;
$A^5$ is $CR^5$ or N;
$A^6$ is $CR^6$;
$A^8$ is $CR^8$;
each $R^1$, independently, is H, F, Cl, $CF_3$, $CH_3$, $CH_2CH_3$, CN, $CH_2F$ or $CHF_2$;
$R^2$ is $CH_3$, $CH_2F$ or $CHF_2$;
each $R^3$, independently, is H, F, Cl, $CF_3$, $OCF_3$, $CH_3$, $CH_2CH_3$, CN, OH, $OCH_3$, $CH_2OCH_2F$ or $CH_2OCHF_2$;
each of $R^4$, $R^5$, $R^6$ and $R^8$, independently, is H, F, Cl, $CF_3$, $OCF_3$, $CH_3$, $CH_2CH_3$, CN, OH, $OCH_3$, $SCH_3$, $NHCH_3$ or $C(O)CH_3$;
$R^9$ is acetyl, $C_{1-6}$-alkyl, $C_{2-4}$alkenyl, $C_{2-4}$alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, imidazo-pyridyl, cyclopropyl, cyclobutyl, cyclopentyl and cyclohexyl, wherein the $C_{1-6}$-alkyl, $C_{2-4}$alkenyl, $C_{2-4}$alkynyl and ring are optionally substituted, independently, with 1-5 substituents of $R^{10}$; and each $R^{10}$, independently, is H, halo, haloalkyl, CN, OH, $NO_2$, $NH_2$, $SF_5$, acetyl, —C(O)NHCH$_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl, oxetan-3yl or a ring selected from oxazolyl, isoxazolyl, pyrazolyl, thiazolyl, isothiazolyl or oxadiazolyl wherein the ring is optionally substituted independently with 1-5 substituents of F, Cl, CN or $CH_3$.

23. The compound according to claim 22, or a stereoisomer, tautomer or pharmaceutically acceptable salt thereof, wherein
$A^4$ is $CR^4$;
$A^5$ is $CR^5$ or N;
$A^6$ is $CR^6$;
$A^8$ is $CR^8$; wherein each of $R^4$, $R^5$, $R^6$ and $R^8$, independently, is H, F, Cl, $CF_3$, $OCF_3$, $CH_3$, CN or $OCH_3$;
each $R^1$, independently, is H, F, $CH_3$, $CF_3$, $CF_2H$ or $CH_2F$;
$R^2$ is $CH_3$, $CH_2F$ or $CHF_2$;
each $R^3$, independently, is H, F, $CH_3$, $C_2H_5$, $CH_2F$, $CF_2H$, $CF_3$ or $CH_2CF_3$;
$R^9$ is a ring selected from phenyl, pyridyl, pyrimidyl, pyrazinyl, pyridazinyl, pyrazolyl, isoxazolyl, thiazolyl, furanyl, thienyl or pyrrolyl, wherein the ring is optionally substituted, independently, with 1-5 substituents of $R^{10}$; and
each $R^{10}$, independently, is H, F, Cl, Br, CN, OH, $NO_2$, $NH_2$, acetyl, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy or 2-butynyloxy, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy and 2-butynyloxy is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-propynyloxy, 2-butynyloxy, isobutyl, sec-butyl, tert-butyl, $C_{1-3}$alkylamino-, $C_{1-3}$dialkylamino, $C_{1-3}$thioalkoxyl oxetan-3yl or a ring selected from oxazolyl, isoxazolyl, pyrazolyl, thiazolyl, isothiazolyl or oxadiazolyl wherein the ring is optionally substituted independently with 1-5 substituents of F, Cl, CN or $CH_3$.

24. The compound according to claim 19, or a stereoisomer, tautomer or pharmaceutically acceptable salt thereof, having a Formula III-B:

III-B wherein
$A^4$ is $CR^4$;
$A^5$ is $CR^5$ or N;
$A^6$ is $CR^6$;
A is $CR^8$;
each $R^1$, independently, is H, F, Cl, $CF_3$, $CH_3$, $CH_2CH_3$, CN, $CH_2F$ or $CHF_2$;
$R^2$ is $CH_3$, $CH_2F$ or $CHF_2$;
each $R^3$, independently, is H, F, Cl, $CF_3$, $OCF_3$, $CH_3$, $CH_2CH_3$, CN, OH, $OCH_3$, $CH_2OCH_2F$ or $CH_2OCHF_2$;
each of $R^4$, $R^5$, $R^6$ and $R^8$, independently, is H, F, Cl, $CF_3$, $OCF_3$, $CH_3$, $CH_2CH_3$, CN, OH, $OCH_3$, $SCH_3$, $NHCH_3$ or $C(O)CH_3$;
each W, independently, is CH, CF, CCl or N; and
each $R^{10}$, independently, is H, halo, haloalkyl, CN, OH, $NO_2$, $NH_2$, $SF_5$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy, 2-butynyloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or a ring selected from oxazolyl, isoxazolyl, pyrazolyl, thiazolyl, isothiazolyl or oxadiazolyl wherein the ring is optionally substituted independently with 1-5 substituents of F, Cl, CN or $CH_3$.

25. The compound according to claim 24, or a stereoisomer, tautomer or pharmaceutically acceptable salt thereof, wherein
$A^4$ is $CR^4$;
$A^5$ is $CR^5$ or N;
$A^6$ is $CR^6$;
$A^8$ is $CR^8$; wherein each of $R^4$, $R^5$, $R^6$ and $R^8$, independently, is H, F, Cl, $CF_3$, $OCF_3$, $CH_3$, CN or $OCH_3$;
each $R^1$, independently, is H, F, $CH_3$, $CF_3$, $CF_2H$ or $CH_2F$;
$R^2$ is $CH_3$, $CH_2F$ or $CHF_2$;
each $R^3$, independently, is H, F, $CH_3$, $C_2H_5$, $CH_2F$, $CF_2H$, $CF_3$ or $CH_2CF_3$;
each W, independently, is CH, CF or N, provided no more than 3 W's are N; and
each $R^{10}$, independently, is H, F, Cl, Br, CN, OH, $NO_2$, $NH_2$, acetyl, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy or 2-butynyloxy, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propynyloxy and 2-butynyloxy is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-propynyloxy, 2-butynyloxy, isobutyl, sec-butyl, tert-butyl, $C_{1-3}$alkylamino-, $C_{1-3}$dialkylamino, $C_{1-3}$thioalkoxyl oxetan-3yl or a ring selected from oxazolyl, isoxazolyl, pyrazolyl, thiazolyl, isothiazolyl or oxadiazolyl wherein the ring is optionally substituted independently with 1-5 substituents of F, Cl, CN or $CH_3$.

26. The compound of claim 1, or a stereoisomer, tautomer or pharmaceutically acceptable salt thereof, selected from

219
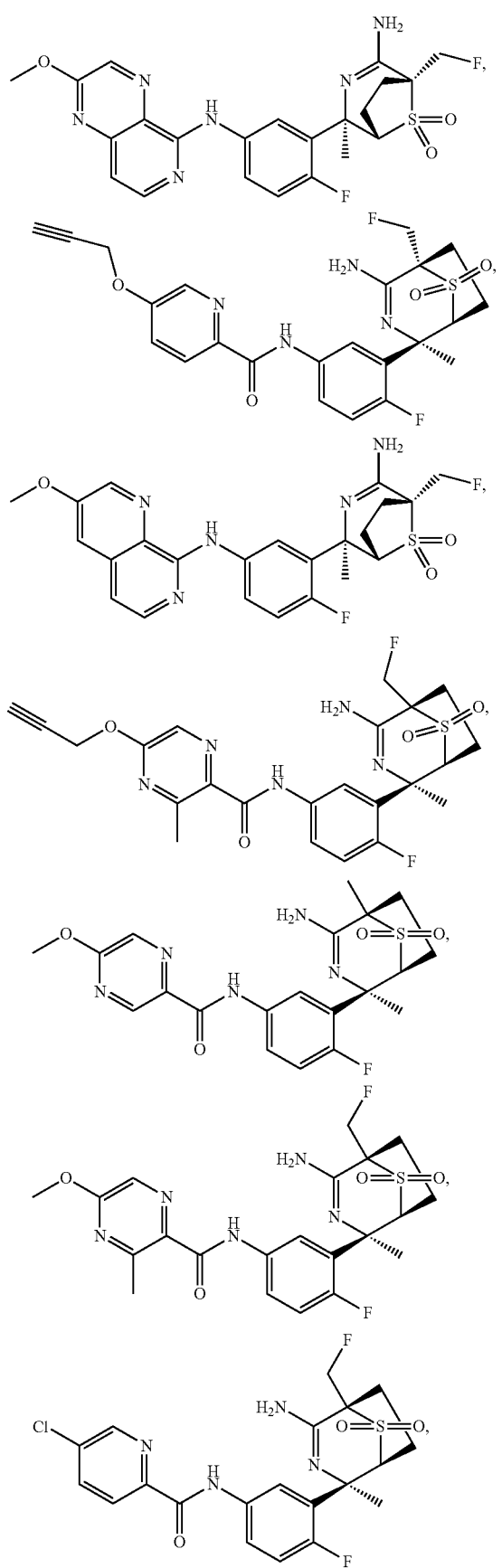
220
-continued
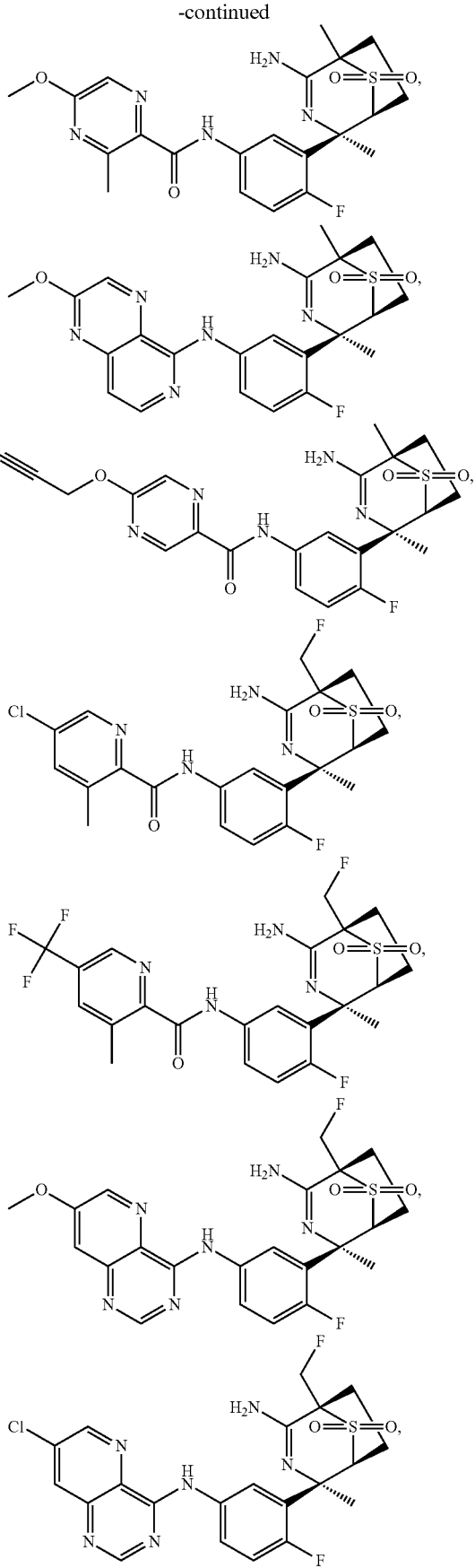

-continued

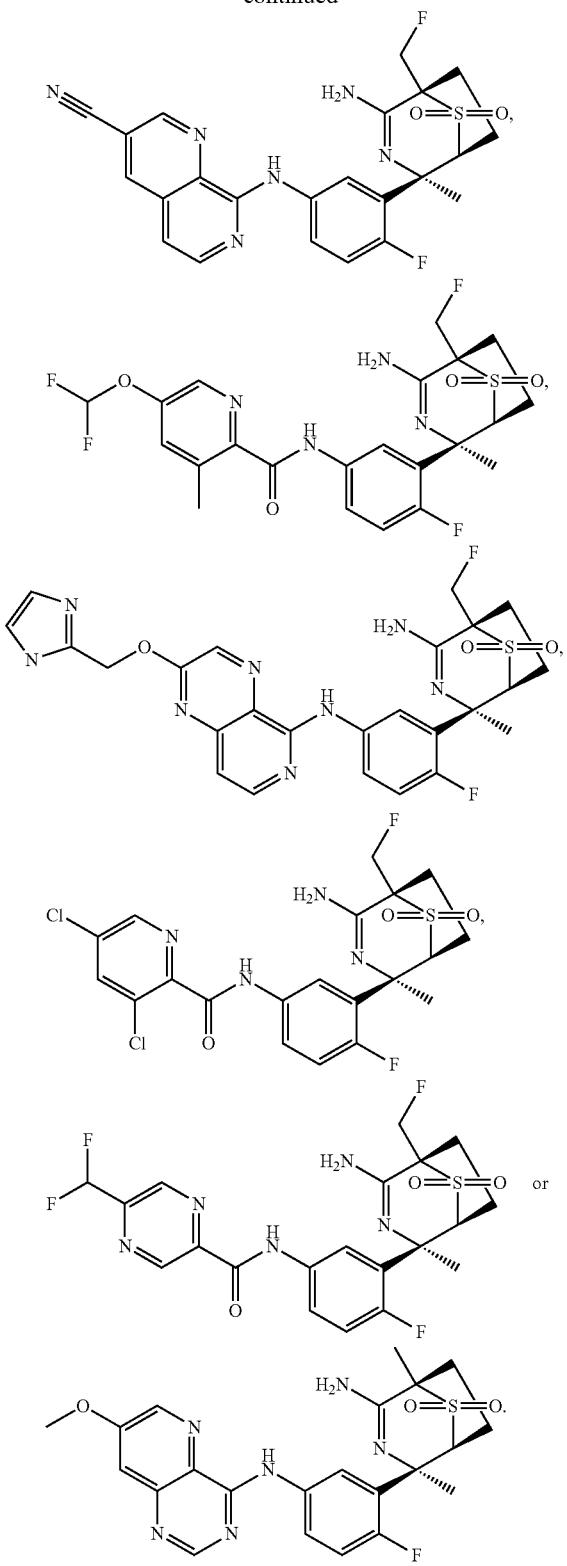

27. The compound of claim 1, or a stereoisomer, tautomer or pharmaceutically acceptable salt thereof, selected from N-(3-((1R,2R,5R)-4-amino-2-methyl-9,9-dioxido-9-thia-3-azabicyclo[3.3.1]non-3-en-2-yl)-4-fluorophenyl)-5-chloro-3-methyl-2-pyridinecarboxamide;

N-(3-((1R,2R,5R)-4-amino-2-methyl-9,9-dioxido-9-thia-3-azabicyclo[3.3.1]non-3-en-2-yl)-4-fluorophenyl)-5-(difluoromethoxy)-3-methyl-2-pyridinecarboxamide;

N-(3-((1S,2R,5S)-4-amino-2-methyl-9,9-dioxido-9-thia-3-azabicyclo[3.3.1]non-3-en-2-yl)-4-fluorophenyl)-5-chloro-3-methyl-2-pyridinecarboxamide;

N-(3-((1R,2R,5R)-4-amino-2-methyl-9,9-dioxido-9-thia-3-azabicyclo[3.3.1]non-3-en-2-yl)-4-fluorophenyl)-2-methoxypyrido[3,4-b]pyrazin-5-amine;

N-(3-((1S,2R,5S)-4-amino-2,5-dimethyl-9,9-dioxido-9-thia-3-azabicyclo[3.3.1]non-3-en-2-yl)-4-fluorophenyl)-2-methoxypyrido[3,4-b]pyrazin-5-amine;

N-(3-((1R,2R,5S)-4-amino-2,5-dimethyl-9,9-dioxido-9-thia-3-azabicyclo[3.3.1]non-3-en-2-yl)-4-fluorophenyl)-2-methoxypyrido[3,4-b]pyrazin-5-amine;

N-(3-((1S,2R,5R)-4-amino-2,5-dimethyl-9,9-dioxido-9-thia-3-azabicyclo[3.3.1]non-3-en-2-yl)-4-fluorophenyl)-5-chloro-3-methyl-2-pyridinecarboxamide;

N-(3-((1R,2R,5S)-4-amino-2,5-dimethyl-9,9-dioxido-9-thia-3-azabicyclo[3.3.1]non-3-en-2-yl)-4-fluorophenyl)-5-chloro-3-methyl-2-pyridinecarboxamide;

N-(3-((1S,2R,5R)-4-amino-2,5-dimethyl-9,9-dioxido-9-thia-3-azabicyclo[3.3.1]non-3-en-2-yl)-4-fluorophenyl)-5-(difluoromethoxy)-3-methyl-2-pyridinecarboxamide;

N-(3-((1R,2R,5S)-4-amino-2,5-dimethyl-9,9-dioxido-9-thia-3-azabicyclo[3.3.1]non-3-en-2-yl)-4-fluorophenyl)-5-(difluoromethoxy)-3-methyl-2-pyridinecarboxamide;

N-(3-((1S,2R,5R)-4-amino-1-fluoro-2,5-dimethyl-9,9-dioxido-9-thia-3-azabicyclo[3.3.1]non-3-en-2-yl)-4-fluorophenyl)-5-chloro-3-methyl-2-pyridinecarboxamide;

N-(3-((1S,2R,5R)-4-amino-1-fluoro-2,5-dimethyl-9,9-dioxido-9-thia-3-azabicyclo[3.3.1]non-3-en-2-yl)-4-fluorophenyl)-5-(difluoromethoxy)-3-methyl-2-pyridinecarboxamide;

N-(3-((1R,2R,5S)-4-amino-1-fluoro-2,5-dimethyl-9,9-dioxido-9-thia-3-azabicyclo[3.3.1]non-3-en-2-yl)-4-fluorophenyl)-5-chloro-3-methyl-2-pyridinecarboxamide;

N-(3-((1R,2R,5S)-4-amino-1-fluoro-2,5-dimethyl-9,9-dioxido-9-thia-3-azabicyclo[3.3.1]non-3-en-2-yl)-4-fluorophenyl)-5-(difluoromethoxy)-3-methyl-2-pyridinecarboxamide;

N-(3-((1S,2R,5R)-4-amino-1,2,5-trimethyl-9,9-dioxido-9-thia-3-azabicyclo[3.3.1]non-3-en-2-yl)-4-fluorophenyl)-5-chloro-3-methyl-2-pyridinecarboxamide;

N-(3-((1R,2R,5S)-4-amino-1,2,5-trimethyl-9,9-dioxido-9-thia-3-azabicyclo[3.3.1]non-3-en-2-yl)-4-fluorophenyl)-5-chloro-3-methyl-2-pyridinecarboxamide;

N-(3-((1S,2R,5R)-4-amino-1,2,5-trimethyl-9,9-dioxido-9-thia-3-azabicyclo[3.3.1]non-3-en-2-yl)-4-fluorophenyl)-5-(difluoromethoxy)-3-methyl-2-pyridinecarboxamide;

N-(3-((1R,2R,5S)-4-amino-1,2,5-trimethyl-9,9-dioxido-9-thia-3-azabicyclo[3.3.1]non-3-en-2-yl)-4-fluorophenyl)-5-(difluoromethoxy)-3-methyl-2-pyridinecarboxamide;

N-(3-((1S,2R,5R)-4-amino-1,2,5-trimethyl-9,9-dioxido-9-thia-3-azabicyclo[3.3.1]non-3-en-2-yl)-4-fluorophenyl)-5-methoxy-2-pyrazinecarboxamide; and N-(3-((1R,2R,5S)-4-amino-1,2,5-trimethyl-9,9-dioxido-9-thia-3-azabicyclo[3.3.1]non-3-en-2-yl)-4-fluorophenyl)-5-methoxy-2-pyrazinecarboxamide.

28. A pharmaceutical composition comprising a compound according to claim 1 and a pharmaceutically acceptable excipient.

29. A method of reducing beta amyloid peptide levels in the cerebral spinal fluid of a subject, the method comprising administering to the subject a dose effective amount of the compound of claim 1.

30. A method of treating Alzheimer's disease, cognitive impairment or a combination thereof in a subject, the method comprising administering to the subject a dose effective amount of the compound of claim 1.

31. A method of treating a neurological disorder selected from the group consisting of mild cognitive impairment, Down's syndrome, Hereditary cerebral hemorrhage with dutch-type amyloidosis, cerebral amyloid angiopathy, degenerative dementia, dementia associated with Parkinson's disease, dementia associated with supranuclear palsy, dementia associated with cortical basal degeneration, diffuse lewy body type of Alzheimer's disease or a combination thereof in a subject, the method comprising administering to the subject a dose effective amount of the compound of claim 1.

32. A process for preparing a compound according to claim 1, the process comprising the step of reacting a compound 20

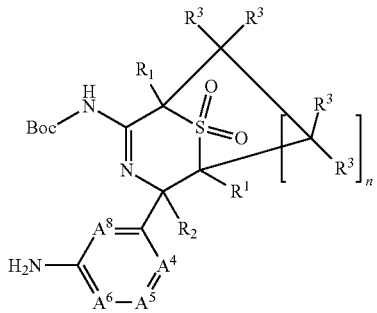

wherein $A^4$, $A^5$, $A^6$, $A^8$, $R^1$, $R^2$, $R^3$ and n of compound 20 are as defined in claim 1, with a compound having the structure or $R^9$—C(=O)OH in the presence of an acid activating agent or $R^9$—Cl in the presence of acid, wherein $R^9$ is as defined in claim 1 to prepare the compound according to claim 1.

* * * * *